(12) United States Patent
Simmen et al.

(10) Patent No.: US 7,659,245 B2
(45) Date of Patent: Feb. 9, 2010

(54) MACROCYLIC INHIBITORS OF HEPATITIS C VIRUS

(75) Inventors: Kenneth Alan Simmen, Tervuren (BE); Herman Augustinus De Kock, Arendonk (BE); Pierre Jean-Marie Bernard Raboisson, Sterrebeek (BE); Lili Hu, Mechelen (BE); Karin Charlotta Lindquist, Huddinge (SE); Mats Stefan Lindström, Huddinge (SE); Anna Karin Gertrud Linnea Belfrage, Huddinge (SE); Horst Jürgen Wähling, Huddinge (SE); Karl Magnus Nilsson, Huddinge (SE); Bengt Bertil Samuelsson, Huddinge (SE); Åsa Annica Kristina Rosenquist, Huddinge (SE); Sven Crister Sahlberg, Huddinge (SE); Hans Kristian Wallberg, Huddinge (SE); Pia Cecilia Kahnberg, Huddinge (SE); Björn Olof Classon, Huddinge (SE)

(73) Assignee: Tibotec Pharmaceuticals Ltd (IE)

( * ) Notice: Subject to any disclaimer, the term of this patent is extended or adjusted under 35 U.S.C. 154(b) by 65 days.

(21) Appl. No.: 11/995,900

(22) PCT Filed: Jul. 28, 2006

(86) PCT No.: PCT/EP2006/064822

§ 371 (c)(1),
(2), (4) Date: Jan. 16, 2008

(87) PCT Pub. No.: WO2007/014927

PCT Pub. Date: Feb. 8, 2007

(65) Prior Publication Data

US 2009/0118312 A1 May 7, 2009

(30) Foreign Application Priority Data

Jul. 29, 2005 (EP) .................... 05107057
Apr. 25, 2006 (EP) .................... 06113097

(51) Int. Cl.
*A61K 38/00* (2006.01)
(52) U.S. Cl. .................................................. 514/9
(58) Field of Classification Search ............... None
See application file for complete search history.

(56) References Cited

U.S. PATENT DOCUMENTS

2004/0180815 A1* 9/2004 Nakajima et al. ............ 514/10

FOREIGN PATENT DOCUMENTS

| WO | WO 00/09543 A2 | 2/2000 |
| WO | WO 02/59929 A1 | 10/2000 |
| WO | WO 03/053349 A2 | 7/2003 |
| WO | WO 03/087092 A2 | 10/2003 |
| WO | WO 03/099274 A1 | 12/2003 |
| WO | WO2004/072243 * | 8/2004 |

OTHER PUBLICATIONS

Brown, F., et al., Hydroxyacetophenone-Derived Antagonists of the Peptidoleukotrienes; J. Med. Chem., 1989, 32, pp. 807-826.
Dolby, L., et al., "Studies of the Synthesis of the B, C, and D Rings of Gibberellic Acid", in J. Org. Chem. 36 (1971) 1277-1285.

(Continued)

*Primary Examiner*—Cecilia Tsang
*Assistant Examiner*—Marcela M Cordero Garcia

(57) ABSTRACT

Compounds of the formula I:

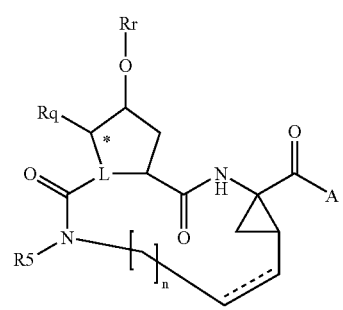

and N-oxides, salts, and stereoisomers thereof
wherein
A is $OR^1$, $NHS(=O)_pR^2$; wherein;
  $R^1$ is hydrogen, $C_1$-$C_6$alkyl, $C_0$-$C_3$alkylenecarbocyclyl, $C_0$-$C_3$alkylene-heterocyclyl;
  $R^2$ is $C_1$-$C_6$alkyl, $C_0$-$C_3$alkylenecarbocyclyl, $C_0$-$C_3$alkyleneheterocyclyl;
p is independently 1 or 2;
n is 3, 4, 5 or 6;
----denotes an optional double bond;
L is N or CRz;
  Rz is H or forms a double bond with the asterisked carbon;
Rq is H or when L is CRz, Rq can also be $C_1$-$C_6$alkyl;
Rr is quinazolinyl, optionally substituted with one two or three substituents each independently selected from $C_1$-$C_6$ alkyl, $C_1$-$C_6$alkoxy, hydroxyl, halo, halo$C_1$-$C_6$alkyl, amino, mono- or dialkylamino, mono- or dialkylaminocarbonyl, $C_1$-$C_6$alkyl-carbonylamino, $C_0$-$C_3$alkylenecarbocyclyl and $C_0$-$C_3$ alkyleneheterocyclyl;
$R^5$ is hydrogen, $C_1$-$C_6$alkyl, $C_1$-$C_6$alkoxy$C_1$-$C_6$alkyl or $C_3$-$C_7$cycloalkyl;
$R^6$ is hydrogen, $C_1$-$C_6$alkyl, $C_1$-$C_6$alkoxy, $C_0$-$C_3$alkylenecarbocyclyl, $C_0$-$C_3$alkylene-heterocyclyl, hydroxy, bromo, chloro or fluoro have utility in the treatment or prophylaxis of flaviviral infections such as HCV.

28 Claims, No Drawings

OTHER PUBLICATIONS

Goodman and Gillman's "The Pharmacological Basis of Therapeutics" Eighth Edition, McGraw-Hill, Inc., Health Professions Division, p. 1-20 (Title Page, Table of Contents), date: 1990.

Greene, "Protective Groups in Organic Chemistry", Wiley & Sons, New York (1999) and "The Peptides: Analysis, Synthesis, Biology", vol. 9, Academic Press, NY (1987) Title Page and Table of Contents.

Huang, et al., "Olefin Metathesis-Active Ruthenium Complexes Bearing a Nucleophilic Carbene Ligand" J. Am. Chem. Soc. 1999 121, p. 2674-2678.

Kingsbury, J., "A Recyclable Ru-Based Metathesis Catalyst", et al., J. Am. Chem. Soc. 1999, 121, p. 791-799.

Krchnak, V. et al., "Polymer-Supported Mitsunobu Ether Formation and its Use in Combinatorial Chemistry", Tetrahedron Letters, vol. 36, No. 35, p. 6193-6195, 1995.

Krieger, N., et al., "Enhancement of Hepatitis C Virus RNA Replication by Cell Culture-Adaptive Mutations", Journal of Virology, May 2001, pp. 4614-4624.

Lohmann, V., et al., "Replication of Subgenomic Hepatitis C Virus RNAs in a Hepatoma Cell Line", Science 285, 1999, pp. 110-113.

Miller, S., et al., "Application of Ring-Closing Metathesis to the Synthesis of Rigidified Amino Acids and Peptides", J. Am. Chem. Soc. 1996, 118, p. 9606-9614.

Mitsunobu, Synthesis, Jan. 1-28, (1981).

Rano, T. et al., "Solid Phase Synthesis of Aryl Ethers via the Mitsunobu Reaction", Tetrahedron Letters, vol. 36, No. 22, pp. 3789-3792, 1995.

Richter, L. et al, "A Surprising Observation about Mitsunobu Reactions in Solid Phase Synthesis", Tetrahedron Letters, vol. 35, No. 27, p. 4705-4706, 1994.

Smith, E.M., et al., "Synthesis and Pharmacological Activity of Anagiotensin converting Enzyme Inhibitors: N-(Mercaptoacy)-4-substituted-(S)-Prolines", J. Med. Chem. (1988), 31, 875-885.

* cited by examiner

MACROCYLIC INHIBITORS OF HEPATITIS C VIRUS

CROSS REFERENCE TO RELATED APPLICATIONS

This application claims priority to the benefits of the filing of Application Nos. EP 05107057.1 filed Jul. 29, 2005; EP 06113097.7 filed Apr. 25, 2006; and PCT/EP2006/064822 filed Jul. 28, 2006. The complete disclosures of the aforementioned related patent applications are hereby incorporated herein by reference for all purposes.

The present invention is concerned with macrocyclic compounds having inhibitory activity on the replication of the hepatitis C virus (HCV). It further concerns compositions comprising these compounds as active ingredients as well as processes for preparing these compounds and compositions.

Hepatitis C virus is the leading cause of chronic liver disease worldwide and has become a focus of considerable medical research. HCV is a member of the Flaviviridae family of viruses in the hepacivirus genus, and is closely related to the flavivirus genus, which includes a number of viruses implicated in human disease, such as dengue virus and yellow fever virus, and to the animal pestivirus family, which includes bovine viral diarrhea virus (BVDV). HCV is a positive-sense, single-stranded RNA virus, with a genome of around 9,600 bases. The genome comprises both 5' and 3' untranslated regions which adopt RNA secondary structures, and a central open reading frame that encodes a single polyprotein of around 3,010-3,030 amino acids. The polyprotein encodes ten gene products which are generated from the precursor polyprotein by an orchestrated series of co- and posttranslational endoproteolytic cleavages mediated by both host and viral proteases. The viral structural proteins include the core nucleocapsid protein, and two envelope glycoproteins E1 and E2. The non-structural (NS) proteins encode some essential viral enzymatic functions (helicase, polymerase, protease), as well as proteins of unknown function. Replication of the viral genome is mediated by an RNA-dependent RNA polymerase, encoded by non-structural protein 5b (NS5B). In addition to the polymerase, the viral helicase and protease functions, both encoded in the bifunctional NS3 protein, have been shown to be essential for replication of HCV RNA. In addition to the NS3 serine protease, HCV also encodes a metalloproteinase in the NS2 region.

Following the initial acute infection, a majority of infected individuals develop chronic hepatitis because HCV replicates preferentially in hepatocytes but is not directly cytopathic. In particular, the lack of a vigorous T-lymphocyte response and the high propensity of the virus to mutate appear to promote a high rate of chronic infection. Chronic hepatitis can progress to liver fibrosis leading to cirrhosis, end-stage liver disease, and HCC (hepatocellular carcinoma), making it the leading cause of liver transplantations.

There are 6 major HCV genotypes and more than 50 subtypes, which are differently distributed geographically. HCV type 1 is the predominant genotype in Europe and the US. The extensive genetic heterogeneity of HCV has important diagnostic and clinical implications, perhaps explaining difficulties in vaccine development and the lack of response to therapy.

Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades.

Current HCV therapies are based on (pegylated) interferon-alpha (IFN-α) in combination with ribavirin. This combination therapy yields a sustained virologic response in more than 40% of patients infected by genotype 1 viruses and about 80% of those infected by genotypes 2 and 3. Beside the limited efficacy on HCV type 1, this combination therapy has significant side effects and is poorly tolerated in many patients. Major side effects include influenza-like symptoms, hematologic abnormalities, and neuropsychiatric symptoms. Hence there is a need for more effective, convenient and better tolerated treatments.

Recently, two peptidomimetic HCV protease inhibitors have gained attention as clinical candidates, namely BILN-2061 disclosed in WO00/59929 and VX-950 disclosed in WO03/87092. A number of similar HCV protease inhibitors have also been disclosed in the academic and patent literature. It has already become apparent that the sustained administration of BILN-2061 or VX-950 selects HCV mutants which are resistant to the respective drug, so called drug escape mutants. These drug escape mutants have characteristic mutations in the HCV protease genome, notably D168V, D168A and/or A156S. Accordingly, additional drugs with different resistance patterns are required to provide failing patients with treatment options, and combination therapy with multiple drugs is likely to be the norm in the future, even for first line treatment.

Experience with HIV drugs, and HIV protease inhibitors in particular, has further emphasized that sub-optimal pharmacokinetics and complex dosage regimes quickly result in inadvertent compliance failures. This in turn means that the 24 hour trough concentration (minimum plasma concentration) for the respective drugs in an HIV regime frequently falls below the $IC_{90}$ or $ED_{90}$ threshold for large parts of the day. It is considered that a 24 hour trough level of at least the $IC_{50}$, and more realistically, the $IC_{90}$ or $ED_{90}$, is essential to slow down the development of drug escape mutants. Achieving the necessary pharmacokinetics and drug metabolism to allow such trough levels provides a stringent challenge to drug design. The strong peptidomimetic nature of prior art HCV protease inhibitors, with multiple peptide bonds poses pharmacokinetic hurdles to effective dosage regimes.

There is a need for HCV inhibitors which may overcome the disadvantages of current HCV therapy such as side effects, limited efficacy, the emerging of resistance, and compliance failures.

The present invention concerns inhibitors of HCV replication which exhibit at least one improved property in view of the compounds of the prior art compounds. In particular, the inhibitors of the present invention are superior in one or more of the following pharmacological related properties, i.e. potency, decreased cytotoxicity, improved pharmacokinetics, improved resistance profile, acceptable dosage and pill burden.

In addition, the compounds of the present invention have relatively low molecular weight and are typically easy to synthesize, starting from starting materials that are commercially available or readily available through art-known synthesis procedures.

The present invention concerns inhibitors of HCV replication, which can be represented by formula (I):

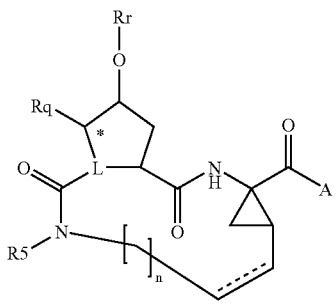

and N-oxides, salts, and stereoisomers thereof wherein

A is $OR^1$, $NHS(=O)_pR^2$; wherein;
  $R^1$ is hydrogen, $C_1$-$C_6$alkyl, $C_0$-$C_3$alkylenecarbocyclyl, $C_0$-$C_3$alkyleneheterocyclyl;
  $R^2$ is $C_1$-$C_6$alkyl, $C_0$-$C_3$alkylenecarbocyclyl, $C_0$-$C_3$alkyleneheterocyclyl;

p is independently 1 or 2;

n is 3, 4, 5 or 6;

-----denotes an optional double bond;

L is N or CRz;
  Rz is H or forms a double bond with the asterisked carbon;

Rq is H or when L is CRz, Rq can also be $C_1$-$C_6$alkyl;

Rr is quinazolinyl, optionally substituted with one two or three substituents each independently selected from $C_1$-$C_6$alkyl, $C_1$-$C_6$alkoxy, hydroxyl, halo, halo$C_1$-$C_6$alkyl, amino, mono- or dialkylamino, mono- or dialkylaminocarbonyl, $C_1$-$C_6$alkylcarbonyl-amino, $C_0$-$C_3$alkylenecarbocyclyl and $C_0$-$C_3$alkyleneheterocyclyl;

$R^5$ is hydrogen, $C_1$-$C_6$alkyl, $C_1$-$C_6$alkoxy$C_1$-$C_6$alkyl or $C_3$-$C_7$cycloalkyl; and wherein each $C_1$-$C_6$alkyl, $C_0$-$C_3$alkylenecarbocycyl or $C_0$-$C_3$alkyleneheterocyclyl is optionally substituted with 1 to 3 substituents independently selected from the group consisting of halo, oxo, nitrile, azido, nitro, $C_1$-$C_6$alkyl, $C_0$-$C_3$alkylenecarbocyclyl, $C_0$-$C_3$alkylene-heterocyclyl, $NH_2C(=O)$—, Y—NRaRb, Y—O—Rb, Y—C(=O)Rb, Y—(C=O)NRaRb, Y—NRaC(=O)Rb, Y—NHSO$_p$Rb, Y—S(=O)$_p$Rb and Y—S(=O)$_p$NRaRb, Y—C(=O)ORb, Y—NRaC(=O)ORb;
  Y is independently a bond or $C_1$-$C_3$alkylene;
  Ra is independently H, $C_1$-$C_6$alkoxy, $C_1$-$C_3$alkyl or;
  Rb is independently H, $C_1$-$C_6$alkyl, $C_1$-$C_6$alkoxy, $C_0$-$C_3$alkylenecarbocyclyl or $C_0$-$C_3$alkyleneheterocyclyl;
  or Ra and Rb together with the nitrogen to which they are attached join to form a heterocyclyl group.

The invention further relates to methods for the preparation of the compounds of formula (I), the prodrugs, N-oxides, addition salts, quaternary amines, metal complexes, and stereochemically isomeric forms thereof, its intermediates, and the use of the intermediates in the preparation of the compounds of formula (I).

The invention relates to the compounds of formula (I) per se, the prodrugs, N-oxides, addition salts, quaternary amines, metal complexes, and stereochemically isomeric forms thereof, for use as a medicament. The invention further relates to pharmaceutical compositions comprising the aforementioned compounds for administration to a subject suffering from HCV infection. The pharmaceutical compositions may comprise combinations of the aforementioned compounds with other anti-HCV agents.

The invention also relates to the use of a compound of formula (I), or a prodrug, N-oxide, addition salt, quaternary amine, metal complex, or stereochemically isomeric form thereof, for the manufacture of a medicament for inhibiting HCV replication. Or the invention relates to a method of inhibiting HCV replication in a warm-blooded animal said method comprising the administration of an effective amount of a compound of formula (I), or a prodrug, N-oxide, addition salt, quaternary amine, metal complex, or stereochemically isomeric form thereof.

The invention further envisions compounds of the formula I wherein represented by formula (It):

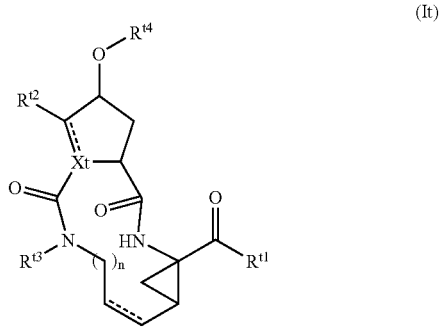

(It)

and the N-oxides, salts, and stereoisomers thereof, wherein
Xt is N, CH and where Xt bears a double bond it is C;
$Rt^1$ is —$ORt^5$, —NH—$SO_2Rt^6$;
$Rt^2$ is hydrogen, and where Xt is C or CH, $Rt^2$ may also be $C_{1-6}$alkyl;
$Rt^3$ is hydrogen, $C_{1-6}$alkyl, $C_{1-6}$alkoxy$C_{1-6}$alkyl, or $C_{3-7}$cycloalkyl;
$Rt^4$ is quinazolinyl optionally substituted with one, two or three substituents each independently selected from $C_{1-6}$alkyl, $C_{1-6}$alkoxy, hydroxy, halo, polyhalo-$C_{1-6}$alkyl, polyhalo$C_{1-6}$alkoxy, amino, mono- or di$C_{1-6}$alkylamino, mono- or di$C_{1-6}$alkylaminocarbonyl, $C_{1-6}$alkylcarbonyl-amino, aryl, and Het;
n is 3, 4, 5, or 6;

wherein each dashed line (represented by -----represents an optional double bond;
$Rt^5$ is hydrogen; aryl; Het; $C_{3-7}$cycloalkyl optionally substituted with $C_{1-6}$alkyl; or $C_{1-6}$alkyl optionally substituted with $C_{3-7}$cycloalkyl, aryl or with Het;
$Rt^6$ is aryl; Het; $C_{3-7}$cycloalkyl optionally substituted with $C_{1-6}$alkyl; or $C_{1-6}$alkyl optionally substituted with $C_{3-7}$cycloalkyl, aryl or with Het;
each aryl as a group or part of a group is phenyl optionally substituted with one, two or three substituents selected from halo, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, amino, mono- or di$C_{1-6}$alkylamino, azido, mercapto, polyhalo$C_{1-6}$alkyl, polyhalo$C_{1-6}$alkoxy, cyclopropyl, pyrrolidinyl, piperidinyl, piperazinyl, 4-$C_{1-6}$alkylpiperazinyl, 4-$C_{1-6}$alkylcarbonylpiperazinyl, and morpholinyl; and
each Het as a group or part of a group is a 5 or 6 membered saturated, partially unsaturated or completely unsaturated heterocyclic ring containing 1 to 4 heteroatoms each independently selected from nitrogen, oxygen and sulfur, and being optionally substituted with one, two or three substituents each independently selected from the group consisting of halo, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, amino, mono- or di$C_{1-6}$alkylamino, azido, mercapto, polyhalo$C_{1-6}$alkyl, polyhalo$C_{1-6}$alkoxy, cyclopropyl, pyrrolidinyl, piperidinyl, piperazinyl, 4-$C_{1-6}$alkyl-piperazinyl, 4-$C_{1-6}$alkylcarbonyl-piperazinyl, and morpholinyl.

It will be apparent that in the alternative embodiment of the invention in the paragraph immediately above, that $Rt^1$ broadly corresponds to A, $Rt^2$ broadly corresponds to Rq, $Rt^3$ broadly corresponds to $R^5$, X broadly corresponds to L, aryl is broadly speaking embraced by $C_0$-$C_3$alkylenecarbocyclyl where $C_0$-$C_3$alkylene is zero (ie a bond) and Het is broadly speaking embraced by $C_0$-$C_3$alkylheterocyclyl, where $C_0$-$C_3$alkylene is zero (ie a bond). The preferments expressed below for formula I apply even to the corresponding values in formula It and references to formula (I) shall be construed as including the corresponding compounds of formula (It).

As used in the foregoing and hereinafter, the following definitions apply unless otherwise noted.

The term halo is generic to fluoro, chloro, bromo and iodo.

The term "halo$C_{1-6}$alkyl" as a group or part of a group, e.g. in halo$C_{1-6}$alkoxy, is defined as mono- or polyhalo substituted $C_{1-6}$alkyl, in particular $C_{1-6}$alkyl substituted with up to one, two, three, four, five, six, or more halo atoms, such as methyl or ethyl with one or more fluoro atoms, for example, difluoromethyl, trifluoromethyl, trifluoroethyl. Preferred is trifluoromethyl. Also included are perfluoro$C_{1-6}$alkyl groups, which are $C_{1-6}$alkyl groups wherein all hydrogen atoms are replaced by fluoro atoms, e.g. pentafluoroethyl. In case more than one halogen atom is attached to an alkyl group within the definition of polyhalo$C_{1-6}$alkyl, the halogen atoms may be the same or different.

As used herein "$C_{1-4}$alkyl" as a group or part of a group defines straight or branched chain saturated hydrocarbon radicals having from 1 to 4 carbon atoms such as for example methyl, ethyl, 1-propyl, 2-propyl, 1-butyl, 2-butyl, 2-methyl-1-propyl; "$C_{1-6}$alkyl" encompasses $C_{1-4}$alkyl radicals and the higher homologues thereof having 5 or 6 carbon atoms such as, for example, 1-pentyl, 2-pentyl, 3-pentyl, 1-hexyl, 2-hexyl, 2-methyl-1-butyl, 2-methyl-1-pentyl, 2-ethyl-1-butyl, 3-methyl-2-pentyl, and the like. Of interest amongst $C_{1-6}$alkyl is $C_{1-4}$alkyl.

The term "$C_{2-6}$alkenyl" as a group or part of a group defines straight and branched chained hydrocarbon radicals having saturated carbon-carbon bonds and at least one double bond, and having from 2 to 6 carbon atoms, such as, for example, ethenyl (or vinyl), 1-propenyl, 2-propenyl (or allyl), 1-butenyl, 2-butenyl, 3-butenyl, 2-methyl-2-propenyl, 2-pentenyl, 3-pentenyl, 2-hexenyl, 3-hexenyl, 4-hexenyl, 2-methyl-2-butenyl, 2-methyl-2-pentenyl and the like. Of interest amongst $C_{2-6}$alkenyl is $C_{2-4}$alkenyl.

The term "$C_{2-6}$alkynyl" as a group or part of a group defines straight and branched chained hydrocarbon radicals having saturated carbon-carbon bonds and at least one triple bond, and having from 2 to 6 carbon atoms, such as, for example, ethynyl, 1-propynyl, 2-propynyl, 1-butynyl, 2-butynyl, 3-butynyl, 2-pentynyl, 3-pentynyl, 2-hexynyl, 3-hexynyl and the like. Of interest amongst $C_{2-6}$alkynyl is $C_{2-4}$alkynyl.

$C_{3-7}$cycloalkyl is generic to cyclopropyl, cyclobutyl, cyclopentyl, cyclohexyl and cycloheptyl.

$C_{0-3}$alkylene defines a bond ($C_0$) or bivalent straight and branched chain saturated hydrocarbon radicals having from 1 to 3 carbon atoms such as, for example, methylene, ethylene, 1,3-propanediyl, 1,2-propanediyl, and the like, especially methylene.

$C_{1-6}$alkoxy means $C_{1-6}$alkyloxy wherein $C_{1-6}$alkyl is as defined above.

As used herein before, the term (=O) or oxo forms a carbonyl moiety when attached to a carbon atom, a sulfoxide moiety when attached to a sulfur atom and a sulfonyl moiety when two of said terms are attached to a sulfur atom. Whenever a ring or ring system is substituted with an oxo group, the carbon atom to which the oxo is linked is a saturated carbon.

'Amino' unless the context suggests otherwise, includes $NH_2$, $NHC_1$-$C_6$alkyl or $N(C_1$-$C_6$-alkyl$)_2$, wherein in the amino definitions each $C_1$-$C_6$alkyl is especially $C_1$-$C_3$alkyl variants, or saturated cyclic amines such as pyrrolidinyl, piperidinyl, piperazinyl, 4-$C_1$-$C_6$alkylpiperazinyl, such as 4-methylpiperazinyl, 4-$C_1$-$C_6$alkyl-carbonylpiperazinyl and morpholinyl.

'Amido' includes C(=O)$NH_2$, and alkylamido, such as C(=O)NH$C_1$-$C_6$alkyl, C(=O)N($C_1$-$C_6$alkyl$)_2$ especially C(=O)NH$C_1$-$C_3$alkyl, C(=O)N($C_1$-$C_3$alkyl$)_2$ or —NH(C=O)$C_1$-$C_6$alkyl, for example —NHC(=O)CH$C(CH_3)_3$, including —NH(C=O)$C_1$-$C_3$alkyl.

'$C_0$-$C_3$alkylenearyl' as applied herein is meant to include an aryl moiety such as a phenyl, naphthyl or phenyl fused to a $C_3$-$C_7$cycloalkyl (for example indanyl), which aryl is directly bonded (i.e. $C_0$) or through an intermediate methyl, ethyl, or propyl group as defined for $C_1$-$C_3$alkylene above. Unless otherwise indicated the aryl and/or its fused cycloalkyl moiety is optionally substituted with 1-3 substituents selected from halo, hydroxy, nitro, cyano, carboxy, $C_1$-$C_6$alkyl, $C_1$-$C_6$alkoxy, $C_1$-$C_6$alkoxy$C_1$-$C_6$alkyl, $C_1$-$C_6$alkanoyl, amino, azido, oxo, mercapto, nitro $C_0$-$C_3$alkylenecarbocyclyl, $C_0$-$C_3$alkyleneheterocyclyl, it being understood that heterocyclic and carbocyclic moieties in the $C_0$-$C_3$alkylenecarbocyclyl or $C_0$-$C_3$alkyleneheterocyclyl substituent may itself be substituted as provided herein but typically not with a further $C_0$-$C_3$alkylene-carbocyclyl or $C_0$-$C_3$alkyleneheterocyclyl. "Aryl" has the corresponding meaning, i.e. where the $C_0$-$C_3$alkyl linkage is absent.

'$C_0$-$C_3$alkylene$C_3$-$C_7$cycloalkyl' as applied herein is meant to include a $C_3$-$C_7$cycloalkyl group such as cyclopropyl, cyclobutyl, cyclopentyl, cyclohexyl or cycloheptyl, which cycloalkyl is directly bonded (i.e. $C_0$alkyl) or through an intermediate methyl, ethyl, propyl or isopropyl group as defined for $C_1$-$C_3$alkylene above. The cycloalkyl group may contain an unsaturated bond. Unless otherwise indicated the cycloalkyl moiety is optionally substituted with 1-3 substituents selected from halo, hydroxy, nitro, cyano, carboxy, $C_1$-$C_6$alkyl, $C_1$-$C_6$alkoxy, $C_1$-$C_6$alkoxy$C_1$-$C_6$alkyl, $C_1$-$C_6$alkanoyl, amino, azido, oxo, mercapto, nitro $C_0$-$C_3$alkylcarbocyclyl, $C_0$-$C_3$alkylheterocyclyl, it being understood that heterocyclic and carbocyclic moieties in the $C_0$-$C_3$alkylenecarbocyclyl or $C_0$-$C_3$alkyleneheterocyclyl substituent may itself be substituted as provided herein but typically not with a further $C_0$-$C_3$alkylenecarbocyclyl or $C_0$-$C_3$alkyleneheterocyclyl.

'$C_0$-$C_3$alkylcarbocyclyl' as applied herein is meant to include $C_0$-$C_3$alkylaryl and $C_0$-$C_3$alkyl$C_3$-$C_7$cycloalkyl. Unless otherwise indicated the aryl or cycloalkyl group is optionally substituted with 1-3 substituents selected from halo, hydroxy, nitro, cyano, carboxy, $C_1$-$C_6$alkyl, $C_1$-$C_6$alkoxy, $C_1$-$C_6$alkoxy$C_1$-$C_6$alkyl, $C_1$-$C_6$alkanoyl, amino, azido, oxo, mercapto, nitro, $C_0$-$C_3$alkylcarbocyclyl and/or $C_0$-$C_3$alkylheterocyclyl, it being understood that heterocyclic and carbocyclic moieties in the $C_0$-$C_3$alkylene-carbocyclyl or $C_0$-$C_3$alkyleneheterocyclyl substituent may itself be substituted as provided herein but typically not with a further $C_0$-$C_3$alkylenecarbocyclyl or $C_0$-$C_3$alkyleneheterocyclyl. "Carbocyclyl" has the corresponding meaning, i.e. where the $C_0$-$C_3$alkyl linkage is absent '$C_0$-$C_3$alkyleneheterocycylyl' as applied herein is meant to include a monocyclic, saturated or unsaturated, heteroatom-containing ring such as piperidinyl, morpholinyl, piperazinyl, pyrazolyl, imidazolyl, oxazolyl, isoxazolyl, thiazinolyl, isothiazinolyl, thiazolyl, oxadiazolyl, 1,2,3-triazolyl, 1,2,4-triazolyl, tetrazolyl, furanyl, thienyl, pyridyl, pyrimidyl, pyridazinyl, or any of such groups fused to a phenyl ring, such as quinolinyl, benzimidazolyl, benzoxazolyl, benzisoxazolyl, benzothiazinolyl, benzisothiazinolyl, benzothiazolyl, benzoxadiazolyl, benzo-1,2,3-triazolyl, benzo-1,2,4-triazolyl, benzotetrazolyl, benzofuranyl, benzothienyl, benzopyridyl, benzopyrimidyl, benzopyridazinyl, benzopyrazolyl etc, which ring is bonded directly i.e. ($C_0$), or through an intermediate methyl, ethyl, propyl, or isopropyl group as defined for $C_1$-$C_3$alkylene above. Any such non-saturated rings having an aromatic character may be referred to as heteroaryl herein. Unless otherwise indicated the hetero ring and/or its fused phenyl moiety is optionally substituted with 1-3 substituents selected from halo, hydroxy, nitro, cyano, carboxy, $C_1$-$C_6$alkyl, $C_1$-$C_6$alkoxy, $C_1$-$C_6$alkoxy-$C_1$-$C_6$alkyl, $C_1$-$C_6$alkanoyl, amino, azido, oxo, mercapto, nitro, $C_0$-$C_3$alkylcarbocyclyl, $C_0$-$C_3$alkylheterocyclyl. "Heterocyclyl" and "Heteroaryl" have the corresponding meaning, i.e. where the $C_0$-$C_3$alkyl linkage is absent.

Typically heterocyclyl and carbocyclyl moieties within the scope of the above definitions are thus a monocyclic ring with 5 or especially 6 ring atoms, or a bicyclic ring structure comprising a 6 membered ring fused to a 4, 5 or 6 membered ring.

Typical such groups include $C_3$-$C_8$cycloalkyl, phenyl, benzyl, tetrahydronaphthyl, indenyl, indanyl, heterocyclyl such as from azepanyl, azocanyl, pyrrolidinyl, piperidinyl, morpholinyl, thiomorpholinyl, piperazinyl, indolinyl, pyranyl, tetrahydro-pyranyl, tetrahydrothiopyranyl, thiopyranyl, furanyl, tetrahydrofuranyl, thienyl, pyrrolyl, oxazolyl, isoxazolyl, thiazolyl, imidazolyl, pyridinyl, pyrimidinyl, pyrazinyl, pyridazinyl, tetrazolyl, pyrazolyl, indolyl, benzofuranyl, benzothienyl, benzimidazolyl, benzthiazolyl, benzoxazolyl, benzisoxazolyl, quinolinyl, tetrahydroquinolinyl, isoquinolinyl, tetrahydroisoquinolinyl, quinazolinyl, tetrahydroquinazolinyl and quinoxalinyl, any of which may be optionally substituted as defined herein.

The saturated heterocycle moiety thus includes radicals such as pyrrolinyl, pyrrolidinyl, pyrazolinyl, pyrazolidinyl, piperidinyl, morpholinyl, thiomorpholinyl, pyranyl, thiopyranyl, piperazinyl, indolinyl, azetidinyl, tetrahydropyranyl, tetrahydrothio-pyranyl, tetrahydrofuranyl, hexahydropyrimidinyl, hexahydropyridazinyl, 1,4,5,6-tetrahydropyrimidinylamine, dihydro-oxazolyl, 1,2-thiazinanyl-1,1-dioxide, 1,2,6-thiadiazinanyl-1,1-dioxide, isothiazolidinyl-1,1-dioxide and imidazolidinyl-2,4-dione, whereas the unsaturated heterocycle include radicals with an aromatic character such as furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl. In each case the heterocycle may be condensed with a phenyl ring to form a bicyclic ring system.

The radical Het is a heterocycle as specified in this specification and claims. Examples of Het comprise, for example, pyrrolidinyl, piperidinyl, morpholinyl, thiomorpholinyl, piperazinyl, pyrrolyl, pyrazolyl, imidazolyl, oxazolyl, isoxazolyl, thiazinolyl, isothiazinolyl, thiazolyl, isothiazolyl, oxadiazolyl, thiadiazolyl, triazolyl (including 1,2,3-triazolyl, 1,2,4-triazolyl), tetrazolyl, furanyl, thienyl, pyridyl, pyrimidyl, pyridazinyl, pyrazolyl, triazinyl, and the like. Of interest amongst the Het radicals are those which are non-saturated, in particular those having an aromatic character. Of further interest are those Het radicals having one or two nitrogens.

Each of the Het radicals mentioned above may be optionally substituted with the number and kind of substituents mentioned in the definitions of the compounds of formula (I), (It) or any of the subgroups of compounds of formula (I). Some of the Het radicals mentioned in this and the following paragraph may be substituted with one, two or three hydroxy substituents. Such hydroxy substituted rings may occur as their tautomeric forms bearing keto groups. For example a 3-hydroxypyridazine moiety can occur in its tautomeric form 2H-pyridazin-3-one.

It should be noted that the radical positions on any molecular moiety used in the definitions may be anywhere on such moiety as long as it is chemically stable.

Radicals used in the definitions of the variables include all possible isomers unless otherwise indicated. For instance pyridyl includes 2-pyridyl, 3-pyridyl and 4-pyridyl; pentyl includes 1-pentyl, 2-pentyl and 3-pentyl.

When any variable occurs more than one time in any constituent, each definition is independent.

Whenever used hereinafter, the term "compounds of formula (I)", or "the present compounds" or similar terms, it is meant to include the compounds of formula (I), their prodrugs, N-oxides, addition salts, quaternary amines, metal complexes, and stereochemically isomeric forms. One embodiment comprises the compounds of formula (I) or any subgroup of compounds of formula (I) specified herein, as well as the N-oxides, salts, as the possible stereoisomeric forms thereof. Another embodiment comprises the compounds of formula (I) or any subgroup of compounds of formula (I) specified herein, as well as the salts as the possible stereoisomeric forms thereof.

The compounds of formula (I) have several centers of chirality and exist as stereochemically isomeric forms. The term "stereochemically isomeric forms" as used herein defines all the possible compounds made up of the same atoms bonded by the same sequence of bonds but having different three-dimensional structures which are not interchangeable, which the compounds of formula (I) may possess.

With reference to the instances where (R) or (S) is used to designate the absolute configuration of a chiral atom within a substituent, the designation is done taking into consideration the whole compound and not the substituent in isolation.

Unless otherwise mentioned or indicated, the chemical designation of a compound encompasses the mixture of all possible stereochemically isomeric forms, which said compound may possess. Said mixture may contain all diastereomers and/or enantiomers of the basic molecular structure of said compound. All stereochemically isomeric forms of the compounds of the present invention both in pure form or mixed with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphorsulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of the compounds of formula (I) can be obtained separately by conventional methods. Appropriate physical separation methods that may advantageously be employed are, for example, selective crystallization and chromatography, e.g. column chromatography.

For some of the compounds of formula (I), their prodrugs, N-oxides, salts, solvates, quaternary amines, or metal complexes, and the intermediates used in the preparation thereof, the absolute stereochemical configuration was not experimentally determined.

A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

The term "prodrug" as used throughout this text means the pharmacologically acceptable derivatives such as esters, amides and phosphates, such that the resulting in vivo biotransformation product of the derivative is the active drug as defined in the compounds of formula (I). The reference by Goodman and Gilman (The Pharmacological Basis of Therapeutics, 8$^{th}$ ed, McGraw-Hill, Int. Ed. 1992, "Biotransformation of Drugs", p 13-15) describing prodrugs generally is hereby incorporated. Prodrugs preferably have excellent aqueous solubility, increased bioavailability and are readily metabolized into the active inhibitors in vivo. Prodrugs of a compound of the present invention may be prepared by modifying functional groups present in the compound in such a way that the modifications are cleaved, either by routine manipulation or in vivo, to the parent compound.

Preferred pharmaceutically acceptable ester prodrugs that are hydrolysable in vivo and are derived from those compounds of formula (I) having a hydroxy or a carboxyl groups. An in vivo hydrolysable ester is an ester, which is hydrolysed in the human or animal body to produce the parent acid or alcohol. Suitable pharmaceutically acceptable esters for carboxy include $C_{1-6}$alkoxymethyl esters for example methoxy-methyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyl-oxyethyl which may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxy-methoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

For therapeutic use, salts of the compounds of formula (I) are those wherein the counter-ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I) as well as the salts thereof, are able to form. Such solvates are for example hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several nitrogen atoms are oxidized to the so-called N-oxide.

It will be appreciated that the compounds of formula (I) may have metal binding, chelating, complex forming properties and therefore may exist as metal complexes or metal chelates. Such metalated derivatives of the compounds of formula (I) are intended to be included within the scope of the present invention.

Some of the compounds of formula (I) may also exist in their tautomeric form. Such forms although not explicitly indicated in the above formula are intended to be included within the scope of the present invention.

As mentioned above, the compounds of formula (I) have several asymmetric centers. In order to more efficiently refer to each of these asymmetric centers, the numbering system as indicated in the following structural formula will be used.

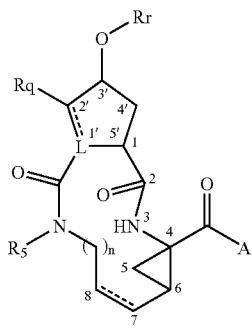
(I)

Asymmetric centers are present at positions 1, 4 and 6 of the macrocycle as well as at the carbon atom 3' in the 5-membered ring, carbon atom 2' when the Rq substituent is $C_{1-6}$alkyl, and at carbon atom 1' when L is CH. Each of these asymmetric centers can occur in their R or S configuration.

The stereochemistry at position 1 preferably corresponds to that of an L-amino acid configuration, i.e. that of L-proline.

When L is CH, the 2 carbonyls borne by the cyclopentane ring are preferably trans as depicted below.

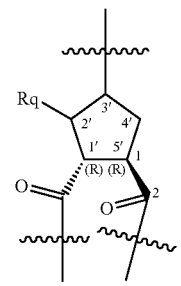

The structure of formula (I) includes a cyclopropyl group as represented in the P1 fragment below:

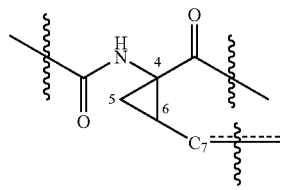

wherein $C_7$ represents the carbon at position 7 and carbons at position 4 and 6 are asymmetric carbon atoms of the cyclopropane ring.

Notwithstanding other possible asymmetric centers at other segments of the compounds of the invention, the presence of these two asymmetric centers means that the compounds can exist as mixtures of diastereomers, such as the diastereomers of compounds of formula (I) wherein the carbon at position 7 is configured either syn to the carbonyl or syn to the amide as shown below.

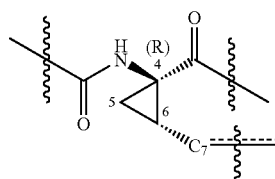

C7 syn to carbonyl

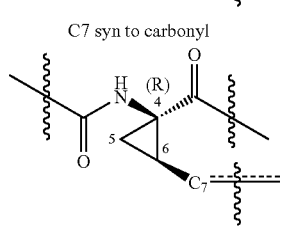

C7 syn to amide

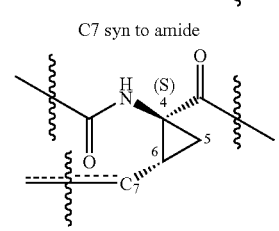

C7 syn to carbonyl

-continued

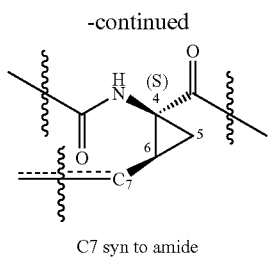

C7 syn to amide

The structure of formula (I) may include as well a proline residue (when L is N). Preferred are the compounds of formula (I) wherein the substituent at the 1 (or 5') position and the substituent —O—Rr (at position 3') are in a trans configuration. Of particular interest are the compounds of formula (I) wherein position 1 has the configuration corresponding to L-proline and the —O—Rr substituent is in a trans configuration in respect of position 1. Preferably the compounds of formula (I) have the stereochemistry as indicated in the structures of formulae (I-a) and (I-b) below:

(I-a)
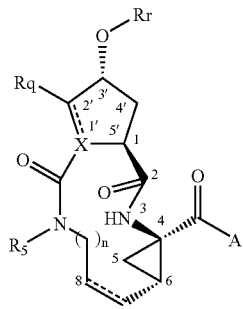

(I-b)
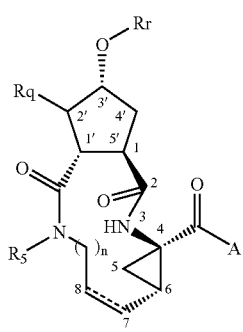

One embodiment of the present invention concerns compounds of formula (I) or of formula (I-a) or of any subgroup of compounds of formula (I), wherein one or more of the following conditions apply:

(a) Rq is hydrogen;

(b) L is nitrogen;

(c) a double bond is present between carbon atoms 7 and 8.

One embodiment of the present invention concerns compounds of formula (I) or of formulae (I-a), (I-b), or of any subgroup of compounds of formula (I), wherein one or more of the following conditions apply:

(a) Rq is hydrogen;

(b) X is CH;

(c) a double bond is present between carbon atoms 7 and 8.

One embodiment of the present invention comprises compounds comprising the partial structure:

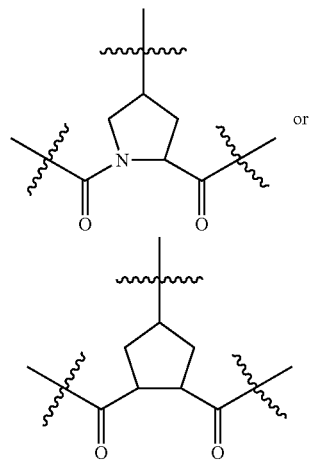

Particular subgroups of compounds of formula (I) are those represented by the following structural formulae:

(I-c)
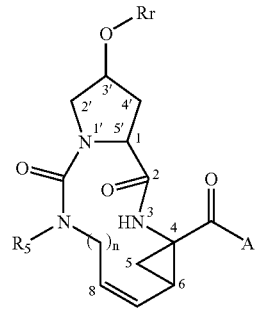

(I-d)
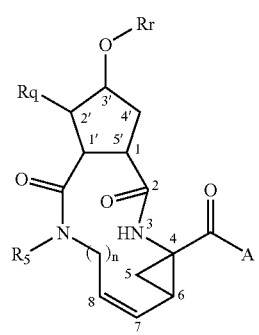

Amongst the compounds of formula (I-c) and (I-d), those having the stereochemical configuration of the compounds of formulae (I-a), and (I-b), respectively, are of particular interest.

The double bond between carbon atoms 7 and 8 in the compounds of formula (I), or in any subgroup of compounds of formula (I), may be in a cis or in a trans configuration. Preferably the double bond between carbon atoms 7 and 8 is in a cis configuration, as depicted in formulae (I-c) and (I-d).

The double bond between carbon atoms 7 and 8 in the compounds of formula (I), or in any subgroup of compounds of formula (I), may be in a cis or in a trans configuration. Preferably the double bond between carbon atoms 7 and 8 is in a cis configuration, as depicted in formulae (I-c) and (I-d).

In (I-a), (I-b), (I-c) and (I-d), where applicable, A, L, n, Rr, Rq, $R^5$ are as specified in the definitions of the compounds of formula (I) or of any of the subgroups of compounds of formula (I) specified herein.

It is to be understood that the above defined subgroups of compounds of formulae (I-a), (I-b), (I-c) or (I-d), as well as any other subgroup defined herein, are meant to also comprise any prodrugs, N-oxides, addition salts, quaternary amines, metal complexes and stereochemically isomeric forms of such compounds.

When n is 2, the moiety —$CH_2$— bracketed by "n" corresponds to a ethanediyl in the compounds of formula (I) or in any subgroup of compounds of formula (I). When n is 3, the moiety —$CH_2$— bracketed by "n" corresponds to a propanediyl in the compounds of formula (I) or in any subgroup of compounds of formula (I). When n is 4, the moiety —$CH_2$-bracketed by "n" corresponds to a butanediyl in the compounds of formula (I) or in any subgroup of compounds of formula (I). When n is 5, the moiety —$CH_2$— bracketed by "n" corresponds to a pentanediyl in the compounds of formula (I) or in any subgroup of compounds of formula (I). When n is 6, the moiety —$CH_2$— bracketed by "n" corresponds to a hexanediyl in the compounds of formula (I) or in any subgroup of compounds of formula (I). Particular subgroups of the compounds of formula (I) are those compounds wherein n is 4 or 5.

Embodiments of the invention are compounds of formula (I) or any of the subgroups of compounds of formula (I) wherein (a) A is —$OR^1$, in particular wherein $R^1$ is $C_{1-6}$alkyl, such as methyl, ethyl, or tert-butyl and most preferably where $R^1$ is hydrogen; or (b) A is —$NHS(=O)_2R^2$, in particular wherein $R^2$ is $C_1$-$C_6$alkyl optionally substituted with $C_3$-$C_7$cycloalkyl, $C_3$-$C_7$cycloalkyl optionally substituted with $C_1$-$C_6$alkyl or aryl, e.g. wherein $R^2$ is methyl, cyclopropyl or phenyl. For example $R^2$ can be 1-methylcyclopropyl.

Further embodiments of the invention are compounds of formula (I) or any of the subgroups of compounds of formula (I) wherein (a) Rq is hydrogen; L is CH or N;
(b) Rq is methyl, L is C and the dashed line represents a double bond.

Further embodiments of the invention are compounds of formula (I) or any of the subgroups of compounds of formula (I) wherein (a) $R^5$ is hydrogen;
(c) $R^5$ is $C_1$-$C_6$alkyl;
(d) $R^5$ is $C_1$-$C_6$alkoxy$C_1$-$C_6$alkyl or $C_3$-$C_7$cycloalkyl.

Preferred embodiments of the invention are compounds of formula (I) or any of the subgroups of compounds of formula (I) wherein $R^5$ is hydrogen, or $C_{1-6}$alkyl, more preferably hydrogen or methyl.

Embodiments of the invention are compounds of formula (I) or any of the subgroups of compounds of formula (I) wherein Rr is quinazolin-4-yl. Typically, the Rr quinazolin-4-yl is optionally mono, di, or tri substituted, for example with $C_1$-$C_6$alkyl, $C_1$-$C_6$alkoxy, hydroxy, halo, trifluoromethyl, mono- or di$C_1$-$C_6$alkylamino, mono- or di$C_1$-$C_6$alkylaminocarbonyl, aryl, heteroaryl or heterocyclyl, where aryl heteroaryl or heterocyclyl are each, independently, optionally substituted with halo, $C_1$-$C_6$alkyl, $C_1$-$C_6$alkoxy, polyhalo$C_1$-$C_6$alkoxy, amino, mono- or di$C_1$-$C_6$alkylamino, cyclopropyl, pyrrolidinyl, piperidinyl, piperazinyl, N-methyl-piperazinyl or morpholinyl.

Quinazoline embodiments of Rr include a radical (f-1):

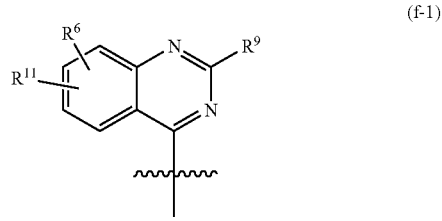

or in particular a radical (f-1-a):

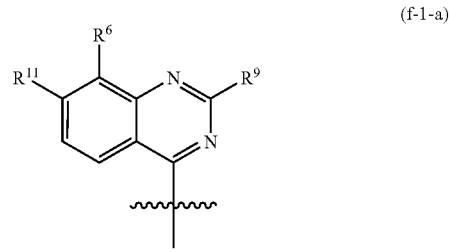

wherein $R^9$, $R^6$ and $R^{11}$ have the meanings stated for the substituents of Rr or $R^{r4}$ wherein specifically $R^9$ is $C_3$-$C_7$cycloalkyl, aryl or Het, any of which is optionally substituted with one, two or three (in particular with one) $R^{10}$; wherein $R^{10}$ is hydrogen, $C_1$-$C_6$alkyl, $C_3$-$C_7$cycloalkyl, aryl, Het (preferably mono- or disubstituted with $C_1$-$C_6$alkyl), pyrrolidinyl, piperidinyl, piperazinyl, 4-methyl-piperazinyl, thiomorpholinyl or morpholinyl, aminocarbonyl, mono or di $C_1$-$C_6$alkylaminocarbonyl; wherein the piperidinyl, morpholinyl or thiomorpholinyl may be optionally substituted with one or two $C_1$-$C_6$alkyl radicals; or $R^9$ is $C_1$-$C_6$alkoxy;

$R^6$ is hydrogen, halogen, $C_1$-$C_6$alkyl, especially methyl, $C_3$-$C_7$cycloalkyl, aryl, Het, halo, in particular bromo, chloro or fluoro;

$R^{11}$ is hydrogen or $C_1$-$C_6$alkoxy;

Favoured embodiments of $R^9$ for quinazolines include aryl or Het, especially wherein $R^9$ is phenyl, pyridyl, thiazolyl, oxazolyl or pyrrazolyl either of which is optionally substituted with one, two or three (in particular with one) $R^{10}$ as defined.

A further alternative embodiment of $R^9$ is alkoxy, especially ethoxy and isopropoxy.

Embodiments of $R^{10}$ for quinazolines include hydrogen, methyl, ethyl, isopropyl, tert-butyl, alkoxy such as methoxy, halo (including dihalo, such as difluoro), pyrrolidinyl, piperidinyl, piperazinyl, 4-$C_1$-$C_6$alkylpiperazinyl (e.g. 4-methylpiperazinyl), thiomorpholinyl or morpholinyl, $C_{1-6}$alkylamino, ($C_1$-$C_6$alkyl)$_2$amino, aminocarbonyl, mono or di$C_{1-6}$alkylaminocarbonyl, or $C_3$-$C_7$cycloalkyl (in particular cyclopropyl).

Preferred $R^9$ embodiments for quinazolines include phenyl substituted with one or two $R^{10}$ groups such as hydrogen, methyl, ethyl, isopropyl, tert-butyl, alkoxy such as methoxy, saturated monocyclic amino, $C_{1-6}$alkylamino, $(C_{1-6}$alkyl$)_2$-amino or $C_{1-6}$alkyl-amido or halo (in particular fluoro) especially when $R^6$ is hydrogen, methyl or bromo.

Preferably the phenyl substituent is in the para position. Specially favoured structures for $R^9$ according to this embodiment are phenyl, p-methoxyphenyl and p-fluorophenyl.

Additional configurations for $R^9$ in the quinazloyl radical specified under (f-1) or (f-1-a) includes any of radicals:

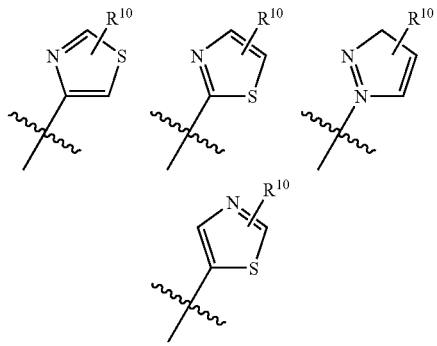

wherein $R^{10}$ is as defined above or in particular hydrogen, $C_1$-$C_6$alkyl (such as methyl, ethyl, isopropyl, tert-butyl), pyrrolidinyl, piperidinyl, piperazinyl, 4-$C_1$-$C_6$alkyl-piperazinyl, N-methylpiperazinyl, thiomorpholinyl or morpholinyl, $C_1$-$C_6$alkylamino, $(C_1$-$C_6$alkyl$)_2$-amino or aminocarbonyl, mono or di$C_1$-$C_6$alkylaminocarbonyl.

$R^9$ for quinazolines may include

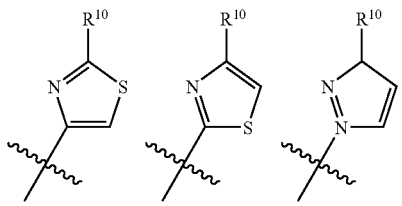

wherein $R^{10}$ is hydrogen, $C_{1-6}$alkyl (such as methyl, ethyl, isopropyl, tert-butyl), $C_1$-$C_6$alkylamino, $(C_1$-$C_6$alkyl$)_2$ amino, $C_1$-$C_6$alkylamido, morpholinyl, thiomorpholinyl or piperidin-1-yl, the morpholine or piperidine being optionally substituted with one or two $C_1$-$C_6$alkyl groups.

Embodiments of $R^6$ for quinazolines include $C_{1-6}$alkyl, in particular methyl, halo (e.g. bromo, chloro fluoro) especially bromo.

Embodiments of $R^{11}$ for quinazolines include hydrogen, $C_{1-6}$alkyloxy (in particular methoxy).

Specific embodiments of the compounds of formula (I) or any other of the subgroups of formula (I) are those wherein Rr is:

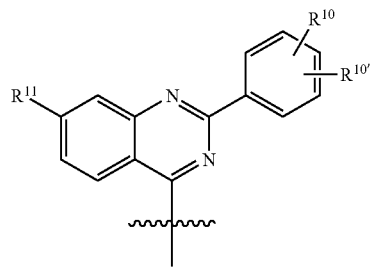

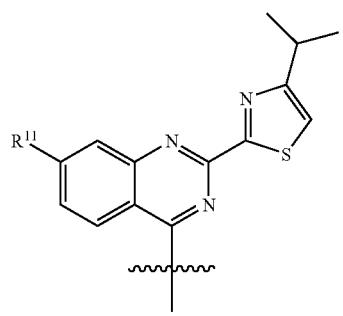

wherein $R^{10}$, $R^{10'}$, and $R^{11}$ are as specified above and in particular $R^{11}$ is hydrogen or $C_{1-6}$alkoxy (e.g. methoxy) and $R^{10}$ and $R^{10'}$, are particularly hydrogen, methoxy or halo such as fluoro or difluoro. Conveniently, when $R^{10}$ or $R^{10'}$ is not hydrogen, it is in the para position of the phenyl ring.

Further favoured structures are compounds of formula (I) or any other of the subgroups of formula (I) wherein Rr is:

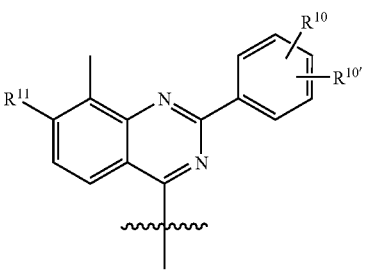

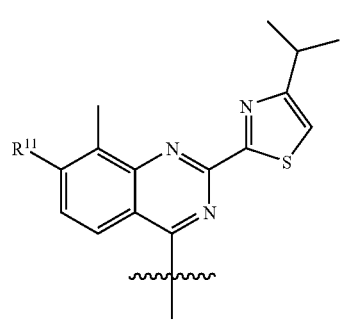

wherein $R^{10}$, $R^{10'}$, and $R^{11}$ are as specified above and in particular $R^{11}$ is hydrogen or $C_{1-6}$alkoxy (e.g. methoxy) and $R^{10}$ and $R^{10'}$, are particularly hydrogen, methoxy or halo such as fluoro or difluoro. Conveniently $R^{10}$ or $R^{10'}$ is in the para position of the phenyl ring.

Particularly favoured compounds of this embodiment are those wherein Rr is according to formulae (f-4), (f-5) or (f-6)

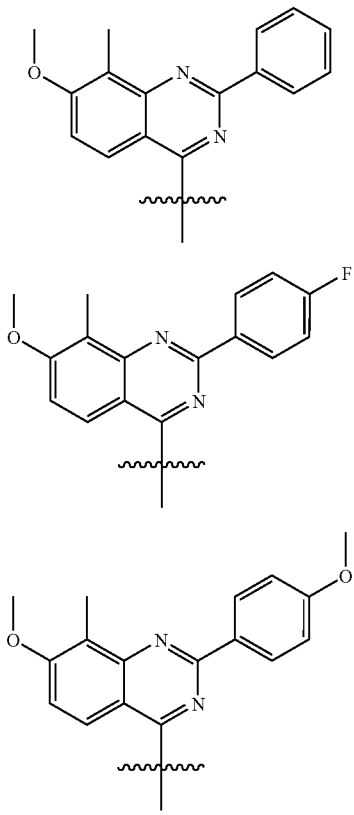

(f-4)

(f-5)

(f-6)

Compounds of the invention are prepared as generally described below and in detail in the experimental part. A convenient intermediate to compounds of formula (I) wherein Rr is an 8-methyl substituted quinazolinyl derivative is the tri-substituted aniline of formula (II):

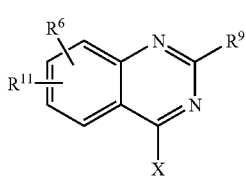

(II)

which aniline derivative constitutes a further aspect of the present invention.

Further useful intermediates for the preparation of compounds of formulae (I) are quinazolinyl derivatives having the general formula (III)

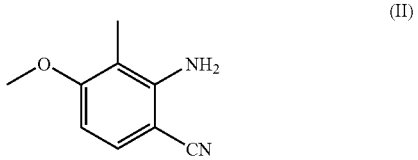

(III)

and in particular formula (III-a),

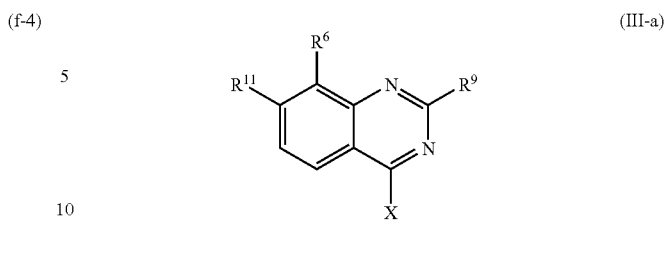

(III-a)

wherein X is OH or a leaving group such as a halide like chloride, bromide or iodide or a derivative of sulphonic acid such as a tosylate, triflate, mesylate or the like, Preferably X is OH. $R^6$, $R^9$ and $R^{11}$ are as defined above for compounds of formulae (f-1) and (f-1-a). The compounds (III) and (IIIa) are a new compounds and constitutes a further aspect of the present invention.

The various embodiments described above for the quinazolinyl moiety applies also to the compounds of formulae (III) and (IIIa).

Preferred $R^9$ embodiments for compounds of formula (III) and (IIIa) include pyridyl and phenyl optionally substituted with one or two $R^{10}$ groups such as hydrogen, methyl, ethyl, isopropyl, tert-butyl, saturated monocyclic amino, $C_1$-$C_6$alkylamino, $(C_1$-$C_6$alkyl$)_2$amino or $C_1$-$C_6$alkylamido or halo (in particular fluoro) especially when $R^6$ is hydrogen, methyl or bromo. Preferably the substituent is in the para position of the phenyl ring. A favoured structure for $R^9$ is parafluorophenyl.

Specific embodiments of the compounds of formula (III) are those having the structure indicated in formula (III-2) and (III-3):

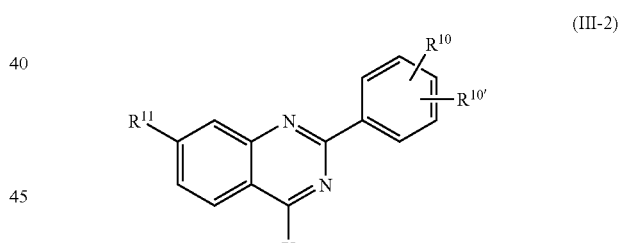

(III-2)

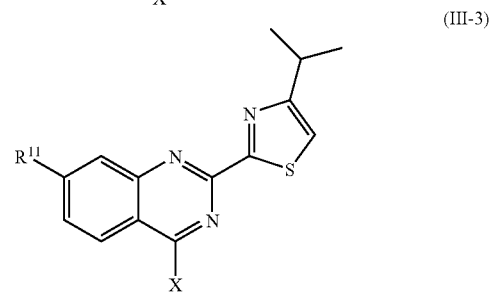

(III-3)

wherein X, $R^{10}$, $R^{10'}$, and $R^{11}$ are as specified above and in particular $R^{11}$ is hydrogen or $C_{1-6}$alkoxy (e.g. methoxy) and $R^{10}$ or $R^{10'}$ are particularly hydrogen, methoxy or halo such as fluoro or difluoro. Conveniently $R^{10}$ or $R^{10'}$ is in the para position of the phenyl ring.

Further favoured structures for compounds of formula (III) are those according to formula (III-2-Me) and (III-3-Me):

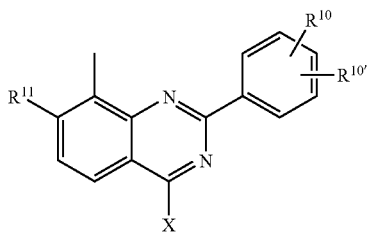
(III-2-Me)

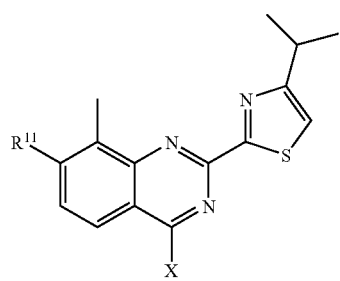
(III-3-Me)

wherein X, $R^{10}$, $R^{10'}$, and $R^{11}$ are as specified above and in particular $R^{11}$ is hydrogen or $C_{1-6}$alkoxy (e.g. methoxy) and $R^{10}$ or $R^{10'}$ is particularly hydrogen, methoxy or halo such as fluoro or difluoro. Conveniently $R^{10}$ or $R^{10'}$ is in the para position of the phenyl ring.

Particularly favoured compounds of formula (III) are those having the formulae (III-4) or (III-5):

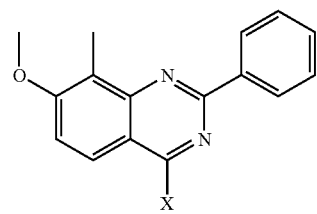
(III-4)

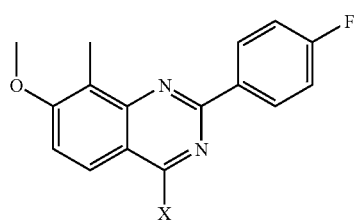
(III-5)

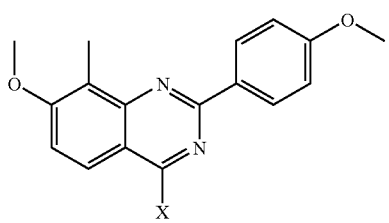
(III-6)

wherein X is as described above.

Embodiments of the invention are compounds of formula (I) or any of the subgroups of compounds of formula (I) wherein Rr is quinazolin-4-yl optionally mono, di, or tri substituted with methyl, ethyl, isopropyl, tert-butyl (or t.butyl), methoxy, trifluoromethyl, trifluoromethoxy, fluoro, chloro, bromo, mono- or di$C_1$-$C_6$alkylamino, mono- or di$C_1$-$C_6$alkylaminocarbonyl, phenyl, methoxyphenyl, cyanophenyl, halophenyl, pyridyl, $C_1$-$C_4$alkylpyridyl, pyrimidinyl, morpholinyl, piperazinyl, $C_1$-$C_4$alkylpiperazinyl, pyrrolidinyl, pyrazolyl, $C_1$-$C_4$alkylpyrazolyl, thiazolyl, $C_1$-$C_4$alkylthiazolyl, cyclopropyl-thiazolyl, or mono- or di$C_{1-4}$alkylaminothiazolyl.

Embodiments of the invention are compounds of formula (I) or any of the subgroups of compounds of formula (I) wherein Rr is:

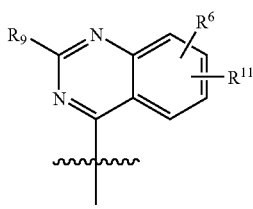

wherein $R^9$ is hydrogen, halo, $C_1$-$C_6$alkyl, $C_1$-$C_6$alkoxy, mono- or $C_1$-$C_6$alkylamino, amino, aryl, heteroaryl or heterocyclyl, said aryl or heteroaryl or heterocyclyl being each, independently, optionally substituted with one or two $C_{1-6}$alkyl, $C_1$-$C_6$alkoxy, polyhalo$C_1$-$C_6$alkoxy, halo, amino, mono- or di$C_{1-C6}$alkylamino; and each $R^6$ and $R^{11'}$ are, independently, hydrogen, $C_{1-6}$alkyl, $C_{1-6}$alkoxy, mono- or di$C_{1-6}$alkylamino, mono- or di$C_{1-6}$alkylaminocarbonyl, hydroxy, halo, trifluoromethyl, aryl, heteroaryl or heterocycylyl; said aryl, heteroaryl or heterocycylyl being each, independently, optionally substituted with $C_1$-$C_6$alkyl, $C_1$-$C_6$alkoxy, polyhalo$C_1$-$C_6$alkoxy, amino, saturated cyclic amino, mono- or di$C_1$-$C_6$alkylamino.

Embodiments of the invention are compounds of formula (I) or any of the subgroups of compounds of formula (I) wherein $R^9$ is selected from the group consisting of:

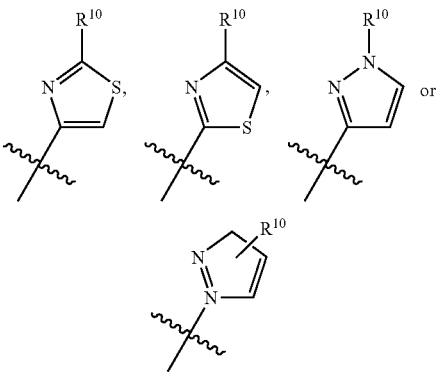

wherein $R^{10}$ is, each independently, hydrogen, halo, $C_1$-$C_6$alkyl, amino, saturated cyclic amino, or mono- or di-$C_1$-$C_6$alkylamino.

Embodiments of the invention are compounds of formula (I) or any of the subgroups of compounds of formula (I) wherein Rr is:

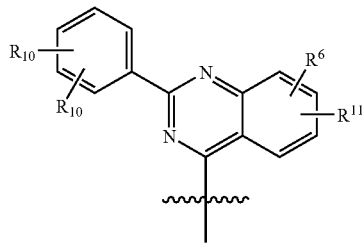

wherein $R^6$ and $R^{11}$ are, independently, hydrogen, $C_1$-$C_6$alkyl, $C_1$-$C_6$alkoxy, mono- or di$C_1$-$C_6$alkylamino, mono- or di$C_1$-$C_6$alkylaminocarbonyl, hydroxy, halo, trifluoro-methyl, aryl, heteroaryl or heterocyclyl; and $R^{10}$ is independently hydrogen, $C_1$-$C_6$alkyl, $C_1$-$C_6$alkoxy, or halo.

Further embodiments of the invention are compounds of formula (I) or any of the subgroups of compounds of formula (I) wherein Rr is:

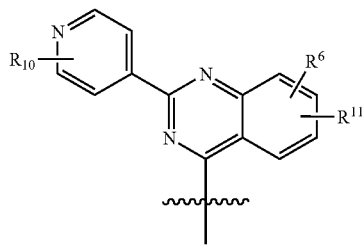

wherein $R^6$ and $R^{11}$ are, independently, hydrogen, $C_1$-$C_6$alkyl, $C_1$-$C_6$alkoxy, mono- or di$C_1$-$C_6$alkylamino, mono- or di$C_{1-6}$alkylaminocarbonyl, hydroxy, halo, trifluoro-methyl, aryl or Het; and $R^{10}$ is hydrogen, $C_{1-6}$alkyl, $C_1$-$C_6$alkoxy, or halo.

Embodiments of the invention are compounds of formula (I) or any of the subgroups of compounds of formula (I) wherein Rr is:

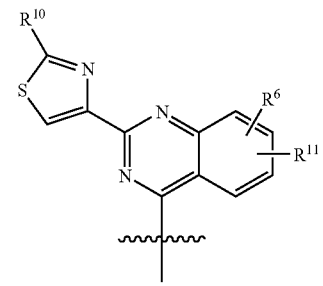

wherein $R^6$ and $R^{11}$ are, independently, hydrogen, $C_1$-$C_6$alkyl, $C_1$-$C_6$alkoxy, mono- or di$C_1$-$C_6$alkylamino, mono- or di$C_1$-$C_6$alkylaminocarbonyl, hydroxy, halo, trifluoromethyl; preferably $R^{4b}$ is $C_1$-$C_6$alkoxy, most preferably methoxy; and $R^{10}$ is hydrogen, $C_1$-$C_6$alkyl, amino, mono- or di$C_1$-$C_6$alkylamino, pyrrolidinyl, piperidinyl, piperazinyl, N-methyl-piperazinyl, or morpholinyl.

Embodiments of the invention are compounds of formula (I) or any of the subgroups of compounds of formula (I) wherein $R^4$ is:

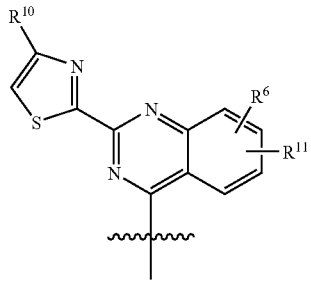

wherein $R^6$ and $R^{11}$ are, independently, hydrogen, $C_1$-$C_6$alkyl, $C_1$-$C_6$alkoxy, mono- or di$C_1$-$C_6$alkylamino, mono- or di$C_1$-$C_6$alkylaminocarbonyl, hydroxy, halo, trifluoromethyl; preferably $R^{4b}$ is $C_{1-6}$alkoxy, most preferably methoxy, halo, or $C_{1-3}$alkyl; and $R^{10}$ is hydrogen, $C_1$-$C_6$alkyl, amino, mono- or di$C_1$-$C_6$alkylamino, pyrrolidinyl, piperidinyl, piperazinyl, N-methyl-piperazinyl, or morpholinyl.

Embodiments of the invention are compounds of formula (I) or any of the subgroups of compounds of formula (I) wherein Rr is:

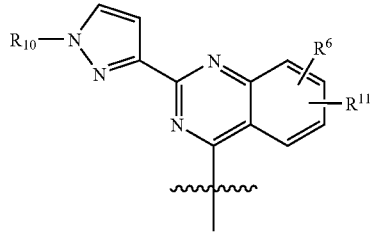

wherein $R^6$ and $R^{11}$ are, independently, hydrogen, $C_1$-$C_6$alkyl, $C_1$-$C_6$alkoxy, mono- or di$C_1$-$C_6$alkylamino, mono- or di$C_1$-$C_6$alkylaminocarbonyl, hydroxy, halo, trifluoro-methyl; preferably $R^{4b}$ is $C_1$-$C_6$alkoxy, most preferably methoxy, halo, or $C_1$-$C_3$alkyl; and $R^{10}$ is hydrogen, $C_1$-$C_6$alkyl, amino, mono- or di$C_1$-$C_6$alkylamino, pyrrolidinyl, piperidinyl, piperazinyl, N-methyl-piperazinyl, or morpholinyl.

Embodiments of the invention are compounds of formula (I) or any of the subgroups of compounds of formula (I) wherein Rr is:

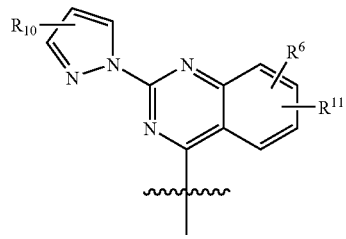

wherein $R^6$ and $R^{11}$ are, independently, hydrogen, $C_1$-$C_6$alkyl, $C_{1-6}$alkoxy, mono- or di$C_1$-$C_6$alkylamino, mono- or di$C_1$-$C_6$alkylaminocarbonyl, hydroxy, halo, trifluoro-methyl; preferably $R^{4b}$ is $C_1$-$C_6$alkoxy, most preferably methoxy, halo, or $C_1$-$C_3$alkyl; and $R^{4i}$ is hydrogen, $C_1$-$C_6$alkyl, amino, mono- or di$C_{1-6}$alkylamino, pyrrolidinyl, piperidinyl, piperazinyl, N-methyl-piperazinyl, or morpholinyl.

Preferred embodiments of the invention are compounds of formula (I) or any of the subgroups of compounds of formula (I) wherein Rr is:

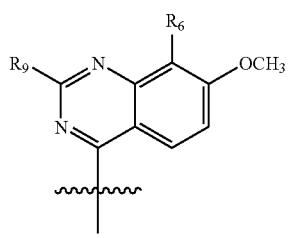

wherein $R^9$ is as defined in any of the groups or subgroups of compounds of formula (I); and $R^6$ is hydrogen, halo, or trifluoromethyl.

Further embodiments of the invention are compounds of formula (I) or any of the subgroups of compounds of formula (I) wherein $R^4$ is:

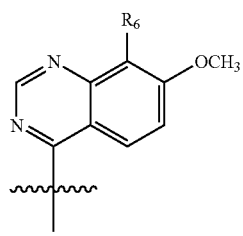

wherein $R^6$ is hydrogen, halo, or trifluoromethyl.

Other embodiments of the invention include those wherein $R^9$ is

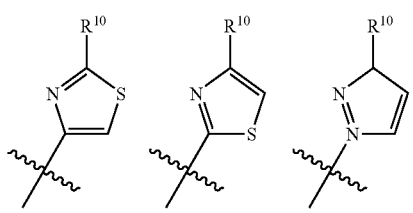

wherein $R^{10}$ is hydrogen, methyl, ethyl, isopropyl, tert-butyl, $C_1$-$C_3$alkylamino, ($C_1$-$C_3$alkyl)$_2$amino, ($C_1$-$C_6$alkyl)amido morpholin-4-yl, piperidin-1-yl, the morpholine and piperidine optionally substituted with $C_1$-$C_3$alkyl.

Other embodiments of the invention include those wherein Rr is

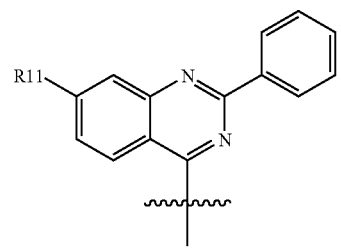

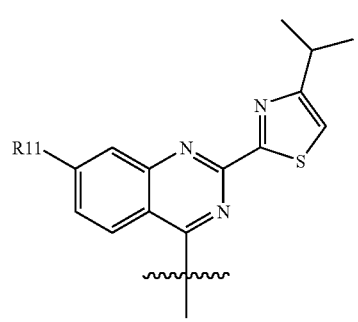

wherein $R^{11}$ is H or methoxy.

The compounds of formula (I-c) and (I-d) having a double bond in the macrocycle (i.e. between carbon atoms 7 and 8; represented by formula (I-d), (I-e), and (I-f) herebelow), consist of three building blocks P1, P2, P3. For chemistry purposes, building block P2 of compounds of formula (I-d) and (I-e) incorporates the carbonyl group attached to the position 1'.

The linking of building blocks P1 with P2 and P2 with P3 involves forming an amide bond. The linking of blocks P1 and P3 involves double bond formation. The linking of building blocks P1, P2 and P3 to prepare compounds (I-c) or (I-d) can be done in any given sequence. The last steps obviously involve a cyclization whereby the macrocycle is formed.

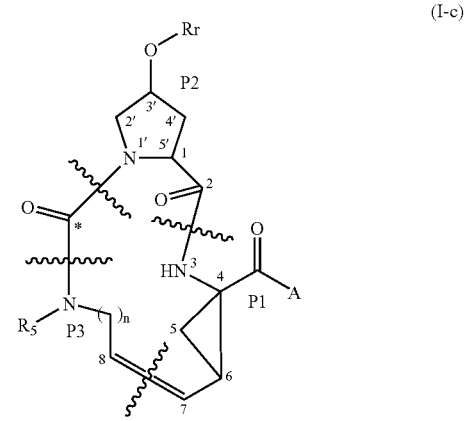

(I-c)

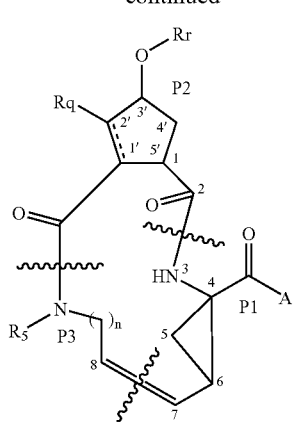

(I-d)

In a preferred embodiment, compounds (I-c) are prepared by first forming the amide bonds and subsequent forming the double bond linkage between P3 and P1 with concomitant cyclization to the macrocycle.

Alternatively, in compound of formula (I-c), a first amide bond between building blocks P2 and P1 is formed, followed by coupling of the P3 building block, and a subsequent amide bond formation between P3 and P2 with concomitant ring closure. Yet another alternative synthetic methodology is the formation of an amide bond between building blocks P2 and P3, followed by the coupling of building block P1 to P3, and a last amide bond formation between P1 and P2 with concomitant ring closure.

It should be noted that in compounds of formula (I-c), the amide bond formation between blocks P2 and P3 may be accomplished at two different positions of the urea motif. A first amide bond encompasses the nitrogen of the pyrrolidine ring and the adjacent carbonyl (marked with an asterisk). An alternative second amide bond formation involves the reaction of the asterisked carbonyl with a —NHR³ group. Both amide bond formations between building blocks P2 and P3 are feasible.

Compounds of formulae (I-d) can be prepared by linking P1 to P2 or vice versa, followed by the formation of the second amide bond between P3 and P2 building blocks with concomitant cyclization to the macrocycle.

Alternatively, in compound of formulae (I-d), building block P1-P3 may as well be synthesized prior its coupling to building block P2. This building block P1-P3 can be realised by a metathesis reaction, Wittig reaction, or the like, which is followed by two amide bonds formation with building block P2, and concomitant ring closure.

The individual building blocks can first be prepared and subsequently coupled together or alternatively, precursors of the building blocks can be coupled together and modified at a later stage to the desired molecular composition.

The functionalities in each of the building blocks may be protected to avoid side reactions.

The formation of amide bonds can be carried out using standard procedures such as those used for coupling amino acids in peptide synthesis. The latter involves the dehydrative coupling of a carboxyl group of one reactant with an amino group of the other reactant to form a linking amide bond. The amide bond formation may be performed by reacting the starting materials in the presence of a coupling agent or by converting the carboxyl functionality into an active form such as an active ester or an acyl chloride. General descriptions of such coupling reactions and the reagents used therein can be found in general textbooks on peptide chemistry, for example, M. Bodanszky, "Peptide Chemistry", 2nd rev ed., Springer-Verlag, Berlin, Germany, (1993), hereafter simply referred to as Bodanszky, the contents of which are hereby incorporated by reference.

Examples of coupling reactions with amide bond formation include the azide method, mixed carbonic-carboxylic acid anhydride (isobutyl chloroformate) method, the carbodiimide (dicyclohexylcarbodiimide, diisopropylcarbodiimide, or water-soluble carbodiimide such as N-ethyl-N'-[(3-dimethylamino)propyl]carbodiimide) method, the active ester (p-nitrophenyl ester, N-hydroxysuccinic imido ester) method, the Woodward reagent K-method, the carbonyldiimidazole method, the phosphorus reagents or oxidation-reduction methods. Some of these methods can be enhanced by adding suitable catalysts, e.g. in the carbodiimide method by adding 1-hydroxybenzo-triazole or 4-DMAP. Further coupling agents are (benzotriazol-1-yloxy)tris-(dimethyl-amino) phosphonium hexafluorophosphate, either by itself or in the presence of 1-hydroxybenzotriazole or 4-DMAP; or 2-(1H-benzotriazol-1-yl)-N,N,N',N'-tetra-methyluronium tetrafluoroborate. or 0-(7-azabenzotrizol-1-yl)-N,N,N',N'-tetramethyl-uronium hexafluorophosphate. These coupling reactions can be performed in either solution (liquid phase) or solid phase.

The coupling reaction preferably are conducted in an inert solvent, such as halogenated hydrocarbons, e.g. dichloromethane, chloroform, dipolar aprotic solvents such as acetonitrile, dimethylformamide, dimethylacetamide, ethers such as tetrahydrofuran.

In many instances the coupling reactions are done in the presence of a suitable base such as a tertiary amine, e.g. triethylamine, diisopropylethylamine (DIPEA), N-methylmorpholine, N-methylpyrrolidine or 4-DMAP. The reaction temperature may range between 0° C. and 50° C. and the reaction time may range between 15 min and 24 h.

The functional groups in the building blocks that are linked together may be protected to avoid formation of undesired bonds. Appropriate protecting groups that can be used are listed for example in Greene, "Protective Groups in Organic Chemistry", John Wiley & Sons, New York (1981) and "The Peptides: Analysis, Synthesis, Biology", Vol. 3, Academic Press, New York (1981), hereafter referred to simply as Greene, the disclosures of which are hereby incorporated by reference.

Carboxyl groups can be protected as an ester that can be cleaved to give the carboxylic acid. Protecting groups that can be used include 1) alkyl esters such as methyl, trimethylsilyl and tert-butyl; 2) aralkyl esters such as benzyl and substituted benzyl; or 3) esters that can be cleaved by mild base or mild reductive means such as trichloroethyl and phenacyl esters.

Amino groups can be protected by a variety of N-protecting groups, such as: 1) acyl groups such as formyl, trifluoroacetyl, phthalyl, and p-toluenesulfonyl; 2) aromatic carbamate groups such as benzyloxycarbonyl (Cbz or Z) and substituted benzyloxy-carbonyls, and 9-fluorenylmethyloxycarbonyl (Fmoc); 3) aliphatic carbamate groups such as tert-butyloxycarbonyl (Boc), ethoxycarbonyl, diisopropylmethoxy-carbonyl, and allyloxycarbonyl; 4) cyclic alkyl carbamate groups such as cyclopentyl-oxy-carbonyl and adamantyloxycarbonyl; 5) alkyl groups such as triphenylmethyl and benzyl; 6) trialkylsilyl such as trimethylsilyl; and 7) thiol containing groups such as phenylthiocarbonyl and dithiasuccinoyl. Interesting amino protecting groups are Boc and Fmoc.

Preferably the α-amino protecting group is cleaved off prior to the next coupling step. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethyl-formamide. When the Fmoc group is used, the reagents of choice are piperidine or substituted piperidine in dimethylformamide, but any secondary amine can be used. The deprotection is carried out at a temperature between 0° C. and room temperature, usually around 20-22° C.

Other functional groups that can interfere undesirably in reactions during the synthetic procedure, for example during coupling reactions of the building blocks, may also be protected. For example hydroxyl groups may be protected by protecting groups such as those listed i.a. in Greene, "Protective Groups in Organic Chemistry", John Wiley & Sons, New York (1981). Hydroxy protecting groups comprise substituted methyl ethers, for example methoxymethyl, benzyloxymethyl, 2-methoxyethoxymethyl, 2-(trimethylsilyl) ethoxymethyl, t-butyl and other lower alkyl ethers, such as isopropyl, ethyl and especially methyl, benzyl and triphenylmethyl; tetrahydropyranyl ethers; substituted ethyl ethers, for example, 2,2,2-trichloroethyl; silyl ethers, for example, trimethylsilyl, t-butyldimethylsilyl and t-butyldiphenylsilyl; and esters prepared by reacting the hydroxyl group with a carboxylic acid, for example, acetate, propionate, benzoate and the like.

Further amino groups may be protected by protecting groups that can be cleaved off selectively. For example, when Boc is used as the α-amino protecting group, the following side chain protecting groups are suitable: p-toluenesulfonyl (tosyl) moieties can be used to protect further amino groups; benzyl (Bn) ethers can be used to protect hydroxy groups; and benzyl esters can be used to protect further carboxyl groups. Or when Fmoc is chosen for the α-amino protection, usually tert-butyl based protecting groups are acceptable. For instance, Boc can be used for further amino groups; tert-butyl ethers for hydroxyl groups; and tert-butyl esters for further carboxyl groups.

Any of the protecting groups may be removed at any stage of the synthesis procedure but preferably, the protecting groups of any of the functionalities not involved in the reaction steps are removed after completion of the build-up of the macrocycle. Removal of the protecting groups can be done in whatever manner is dictated by the choice of protecting groups, which manners are well known to those skilled in the art.

The building blocks P1, P2 and P3 for compounds (I-c) and (I-d) can be prepared starting from art-known intermediates. A number of such syntheses are described hereafter in more detail.

Synthesis of P2 Building Blocks

The P2 building blocks contain either a pyrrolidine, a cyclopentane, or a cyclopentene moiety substituted with a group —O—Rr. The Rr group can be coupled to any of these rings at any convenient stage of the synthesis of compounds according to the present invention. One approach is to first couple the Rr group to the appropriate ring and subsequently add the other desired building blocks, i.e. P1 and P3, followed by the macrocycle formation. Another approach is to couple the building blocks P2, bearing no Rr substituent, and P1, and to add the Rr group either before or after the macrocycle formation.

Synthesis and Introduction of the P2 Substituent

The desired quinazoline group on the cyclic P2 scaffold can be introduced by various methods at any convenient stage of the synthesis. Scheme 1 exemplifies the introduction of a P2 substituent by way of a Mitsunobu reaction. Mitsunobu, 1981, Synthesis, January, 1-28; Rano et al., Tetrahedron Lett., 1995, 36, 22, 3779-3792; Krchnak et al., Tetrahedron Lett., 1995, 36, 5, 6193-6196; Richter et al., Tetrahedron Lett., 1994, 35, 27, 4705-4706).

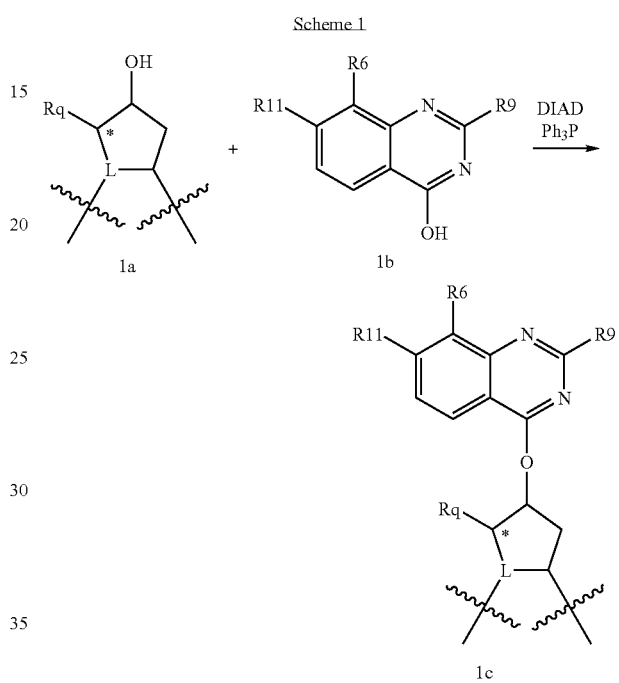

Scheme 1

Treatment of the appropriate cyclic hydroxy substituted P2 scaffold (1a) with the desired quinazolinol (1b) in the presence of triphenylphosphine and an activating agent like diethyl azodicarboxylate (DEAD), diisopropyl azodicarboxylate (DIAD) or the like, provides the alkylated compound (1c). The hydroxy group of the cyclic scaffold (1a) may alternatively be transformed into any other suitable leaving group such as a derivative of sulfonic acid like a tosylate, mesylate or triflate or the like by subjection of the alcohol to the appropriate sulfonylating conditions, like treatment with the anhydride or halide of the desired acid in a solvent like pyridine or using the desired sulfonic acid and triphenyl phosphine in the presence of DEAD in a solvent like toluene, or the hydroxy group can be converted to a halide by treatment of the alcohol with a suitable halogenating agent, for example the bromide can be prepared by using a reagent such as phosphorus tribromide or the like. The achieved leaving group can then be replaced by a desired quinazolinol to give the alkylated derivative (1c)

A reversed strategy can alternatively be used wherein the hydroxy compound (1a) is used as nucleophile and is treated with a base such as sodium hydride or potassium t-butoxide or the like, in a solvent like dimethylformamide (DMF) followed by reaction of the resulting alkoxide with an alkylating agent Q-Lg, wherein Lg is a suitable leaving group such as a halide like chloride, bromide or iodide or a derivative of sulfonic acid or the like and Q is a quinazoline derivative, provides the desired substituted derivative. An example applied to a proline derivative is described by E. M. Smith et al. in J. Med. Chem. (1988), 31, 875-885.

It will be apparent that the above methods to introduce the quinazoline group to the cyclic P2 scaffold can be performed at any convenient stage of the synthesis of compounds according to the present invention. For example the $R^8$ substituent can be introduced to a suitable cyclic scaffold prior to introduction of the other components of the compound or a hydroxy protected cyclic scaffold can be used throughout the synthesis and the quinazoline group introduced as the last step of the synthesis.

An example of the synthesis of substituted quinazoline derivatives is shown in Scheme 2.

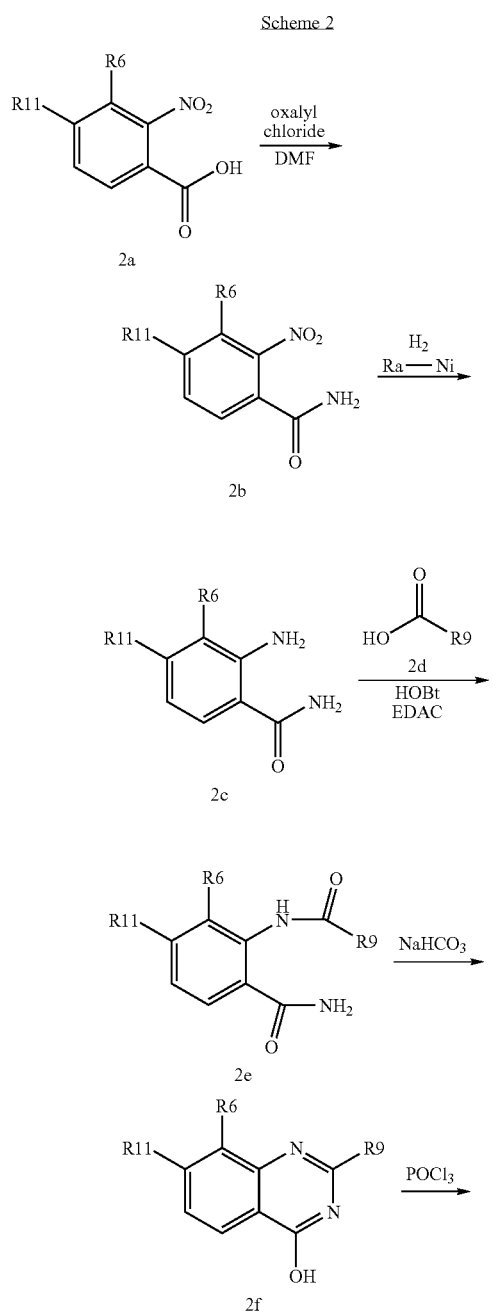

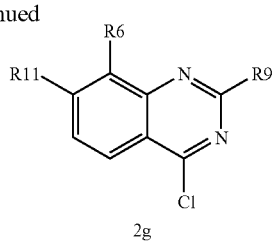

Transformation of a nitro substituted benzoic acid derivative (2a) to the corresponding benzamide for example by subjection of the acid to Vilsmeyer conditions followed by reduction of the nitro group using conditions like catalytic hydrogenation over Raney-nickel gives the corresponding amine (2c). The afforded amine can subsequently be coupled to a heterocyclic carboxylic acid (2d) under peptide coupling conditions, such as with HOBt and EDAC or any other suitable coupling agents well known in the art. Ring closure and dehydration can thereafter be effected by treatment with a base such as sodium hydrogen carbonate which provides quinazoline derivative (2f). The quinazoline derivative (2f) can be coupled to the hydroxy group of a P2 scaffold in a Mitsunobu reaction as described above, or the hydroxy group of the quinazoline can be displaced by a suitable leaving group such as a halide like chloride, bromide or iodide, by treatment of quinazoline (2f) with an appropriate halogenating agent for example phosphoryl chloride or the like.

8-Methyl quinazoline derivatives may also be achieved from an alternative tri-substituted intermediate acid or amide, prepared as illustrated in scheme 2A.

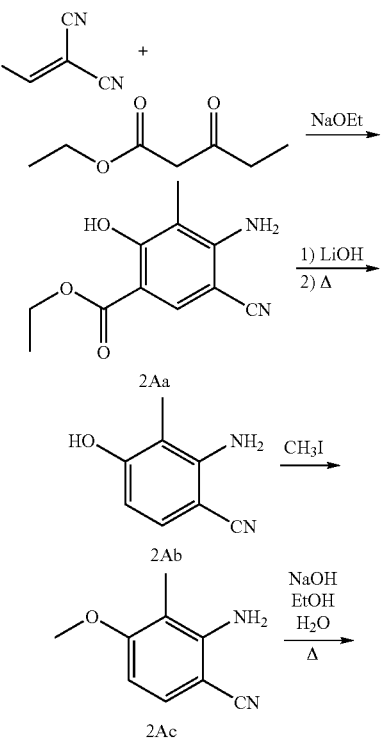

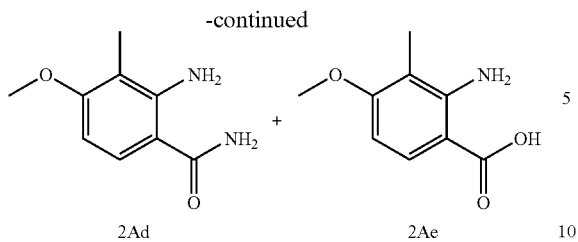

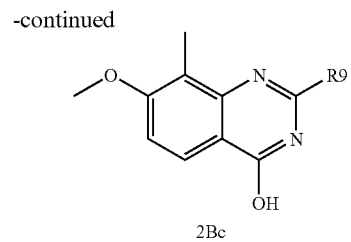

Condensation of ethylpropionyl acetate and ethoxymethylenemalonnitrile in the presence of a suitable base, preferably ethoxide such as sodium ethoxide in for example ethanol provides the tetra-substituted benzoic acid derivative (2Aa). Hydrolysis of the ethyl ester effected by treatment with a base such as lithium hydroxide followed by a decarboxylation step achieved by heating the afforded acid then gives the tri substituted phenol derivative (2Ab). Alkylation of the hydroxy function using for instance methyl iodide in the presence of a base such as potassium carbonate or the like provides the corresponding alkoxy derivative (2Ac). The tri-substituted amide (2Ad) can subsequently be obtained together with the corresponding acid (2Ae) by hydrolysis of the cyano group effected by heating a solution of the cyano derivative in for instance water and ethanol in the presence of a base like sodium hydroxide.

The amide (2Ad) can then be reacted with a desired acid under peptide coupling conditions as described in scheme 2 to give the 8-methyl substituted quinazolinol and, if desired, further reacted to the corresponding 4-halo derivative.

The acid (2Ae) achieved in scheme 2A may also be used for the preparation of 8-methyl substituted quinazoline derivatives, which is illustrated in scheme 2B.

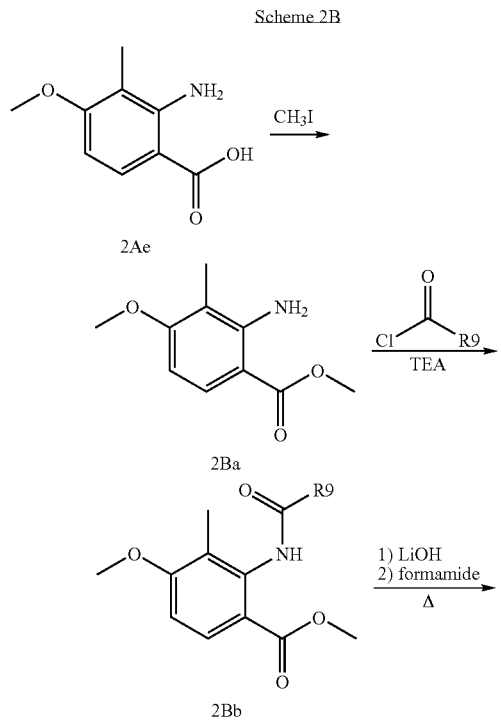

Protection of the acid function of the acid (2Ae), for example as the methyl ester, can be effected by subjecting the acid to alkylation conditions such as treatment with methyl iodide in the presence of a base such as potassium carbonate. The amino function of the afforded ester derivative can then be coupled with a desired acid using any conventional peptide coupling technique such as using the acid chloride in the presence of a base such as triethylamine or the like, which gives the amide (2Bb). Hydrolysis of the methyl ester by treatment with a base like lithium hydroxide followed by heating of the afforded acid in the presence of formamide yields the quinazolinol (2Bc). As described above, the quinazolinol can be further reacted to give the corresponding 4-halo derivative.

A variety of carboxylic acids with the general structure (2d) can be used in Scheme 2. These acids are available either commercially or in the literature. An example of the preparation of 2-(substituted)-amino-carboxy-aminothiazole derivatives, following the procedure by Berdikhina et al. Chem. Heterocycl. Compd. (Engl. Transl.) (1991), 427-433, is shown below.

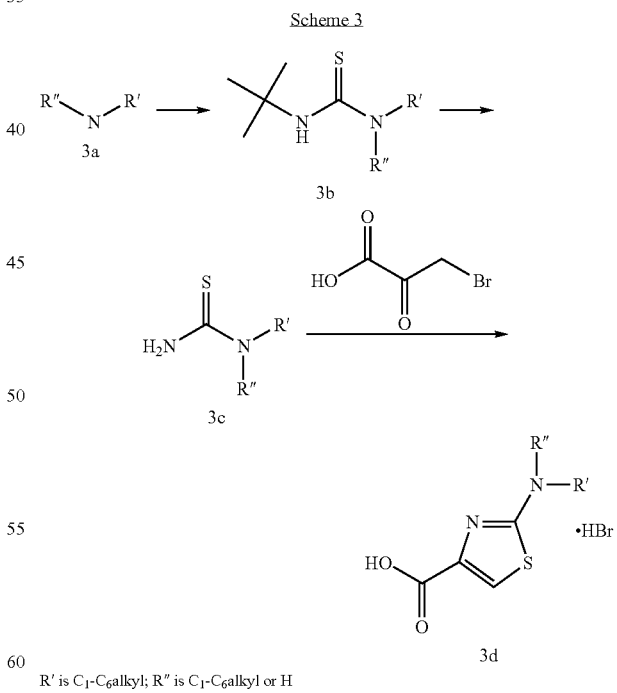

Thiourea (3c) with different alkyl substituents R' and R" can be formed by reaction of the appropriate amine (3a) with tert-butylisothiocyanate in the presence of a base like diisopropylethylamine in a solvent like dichloromethane followed by removal of the tert-butyl group under acidic conditions. Alternatively, thiourea (3c) can be formed by reaction of the amine (3a) with thiocarbonyldiimidazole and subsequently with a saturated solution of ammonia in methanol. Subsequent condensation of the afforded thiourea derivative (3c) with 3-bromopyruvic acid provides the acid (3d).

4-Substituted thiazole-2-carboxylic acids to be used in the reaction with the amine 2c in scheme 2 can be prepared as illustrated in scheme 4.

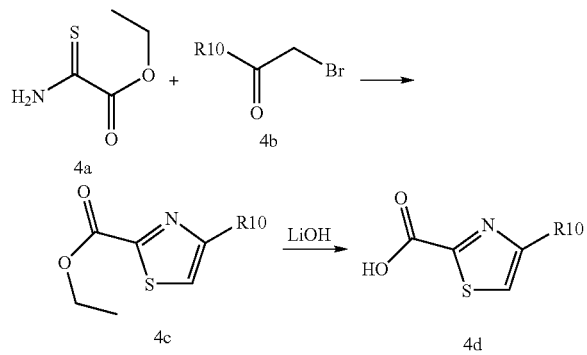

Condensation of ethyl thiooxamate (4a) with a desired α-bromoketon (4b) followed by ester hydrolysis effected by treatment with a base such as lithium hydroxide provides the thiazole carboxylic acid (4d). α-Bromoketons (4b) are commercially available or they can be prepared by α-bromination of the corresponding keton according to known procedures.

Synthesis and Introduction of P1 Building Blocks.

Amino acids useful for the preparation of P1 fragments are available either commercially or in the literature, see for example WO 00/09543 and WO00/59929. Scheme 5 shows an example of the preparation of a sulfonamide derivative to be used as a P1 fragment.

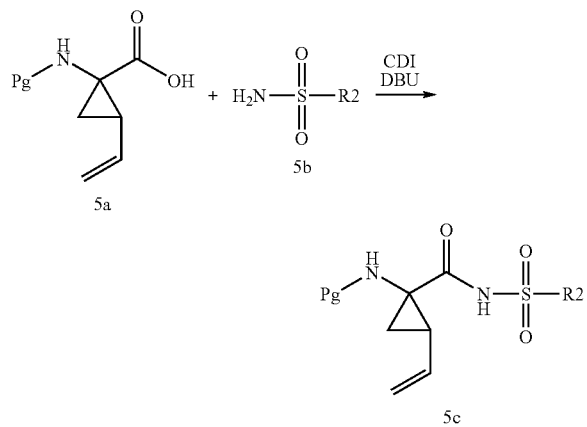

The sulfonamide group can be introduced on a suitably protected amino acid (6a) by treatment of the amino acid with a coupling agent, for example N,N'-carbonyl-diimidazole (CDI) or the like, in a solvent like THF followed by reaction with the desired sulfonamide (5b) in the presence of a strong base such as 1,8-diazabicyclo-[5.4.0]undec-7-ene (DBU). Alternatively the amino acid can be treated with the desired sulfonamide (5b) in the presence of a base like diisopropyl ethylamine followed by treatment with a coupling agent like PyBOP® to effect the introduction of the sulfonamide group. Removal of the amino protecting group by standard methods and subsequent coupling to a P2 moiety or precursor thereof.

P1 building blocks for the preparation of compounds according to general formula I wherein A is an ester can be prepared for example by reacting amino acid (5a) with the appropriate amine or alcohol under standard conditions for ester formation.

A general example of the coupling of a P1 building block to the acid function of the P2 scaffold is shown in scheme 7.

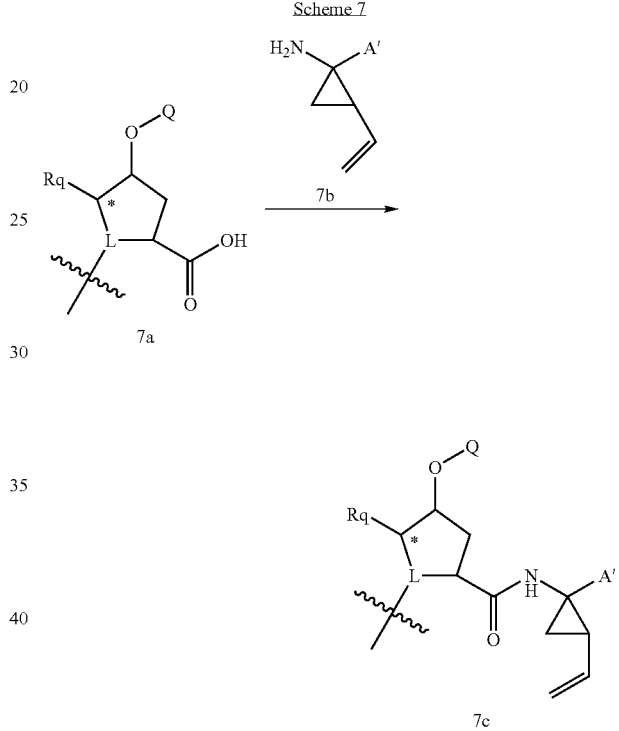

Q is a quinazoline derivative or a hydroxy protecting group
A' is a protected carboxylic acid or a substituted amide Coupling of the P1 building block (7b), prepared as described above, to the acid function of the P2 moiety using standard methods for amide bond formation, like using a coupling agent as HATU in the presence of a base such as diisopropylamine in a solvent like dimethylformamide, gives the amide (7c).

Alternatively, the sulfonamide group can be introduced at a later stage of the synthesis, for example as the last step. In this case A' in scheme 7 is an appropriately protected carboxylic acid, for example a methyl ester, and appropriately deprotected, for example with aqueous lithium hydroxide, prior to coupling of the sulfonamide group.

Introduction of a Urea Linked ω-Unsaturated Alkyl Chain to a Heterocyclic P2 Scaffold The alkyl chain linked via a urea functionality to the P2 scaffold, can be introduced as depicted in scheme 10.

Scheme 10

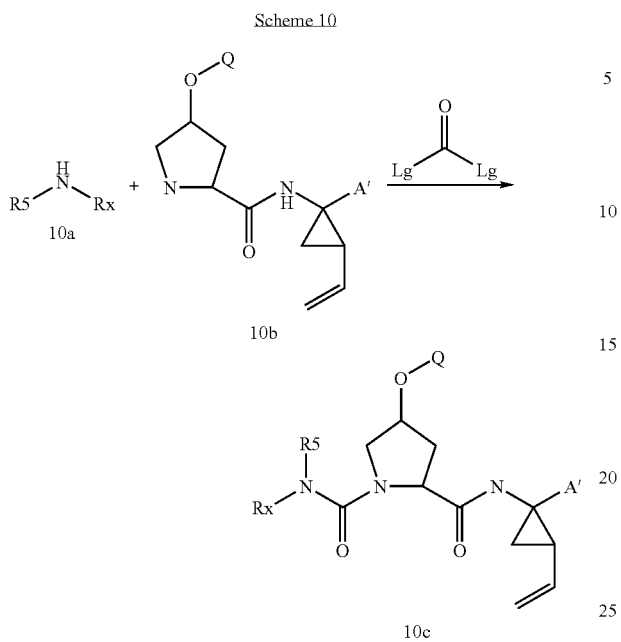

Q is a quinazoline derivative or a hydroxy protecting group;
Rx is an ω-unsaturated 5-8 membered alkyl chain;
A' is a protected carboxylic acid or a substituted amide.

Reaction of hydrazine derivative (10a) with a formylating agent such as p-nitrophenyl chloroformate, carbonyl diimidazole, phosgene or the like in the presence of a base like sodium hydrogen carbonate followed by addition of the P2 building block provides the urea derivative (10c).

Suitably alkenylamines to be used in scheme 10 can be prepared for example by alkylation of a desired tert-butylcarbamate, a general example is shown in scheme 11.

Scheme 11

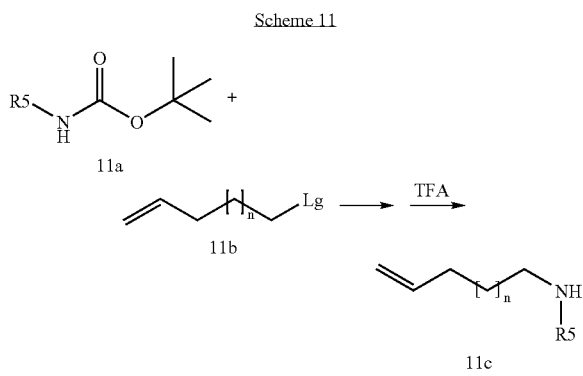

n is 1, 2, 3 or 4

Reaction of a desired amine, R5-$NH_2$, with tert-butyl dicarbonate provides the boc protected amine (11a). Alkylation of the afforded carbamate with an ω-unsaturated alkylating agent (11b) such as an alkenylhalide for example the bromide or chloride followed by removal of the boc group using standard conditions such as treatment with a solution of TFA in a solvent like dichloromethane provides the free amine (11c).

The A or $Rt^1$ group can be connected to the P1 building block at any stage of the synthesis, i.e. before or after the cyclization, or before or after the cyclization and reduction as described herein above. The compounds of formula (I) wherein A or $Rt^1$ represents —$NHSO_2R^2$, said compounds being represented by formula (I-k-1), can be prepared by linking the A or $Rt^1$ group to P1 by forming an amide bond between both moieties. Similarly, the compounds of formula (I) wherein A or $Rt^1$ represents —$OR^1$, i.e. compounds (I-k-2), can be prepared by linking the A or $Rt^1$ group to P1 by forming an ester bond. In one embodiment, the —$OR^1$ groups are introduced in the last step of the synthesis of the compounds (I) as outlined in the following reaction schemes wherein G represents a group:

(a)

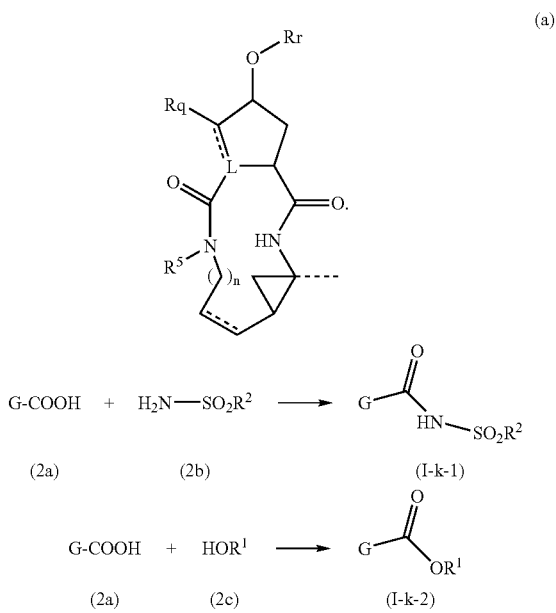

Intermediate (2a) can be coupled with the amine (2b) by an amide forming reaction such as any of the procedures for the formation of an amide bond described hereinafter. In particular, (2a) may be treated with a coupling agent, for example N,N'-carbonyl-diimidazole (CDI), EEDQ, IIDQ, EDCI or benzotriazol-1-yl-oxy-tris-pyrrolidino-phosphonium hexafluorophosphate (commercially available as PyBOP®), in a solvent such as an ether, e.g. THF, or a halogenated hydrocarbon, e.g. dichloromethane, chloroform, dichloroethane, and reacted with the desired sulfonamide (2b), preferably after reacting (2a) with the coupling agent. The reactions of (2a) with (2b) preferably are conducted in the presence of a base, for example a trialkylamine such as triethyl-amine or diisopropylethylamine, or 1,8-diazabicycle[5.4.0]undec-7-ene (DBU). Intermediate (2a) can also be converted into an activated form, e.g. an activated form of general formula G-CO-Z, wherein Z represents halo, or the rest of an active ester, e.g. Z is an aryloxy group such as phenoxy, p.nitrophenoxy, pentafluorophenoxy, trichlorophenoxy, pentachlorophenoxy and the like; or Z can be the rest of a mixed anhydride. In one embodiment, G-CO—Z is an acid chloride (G-CO—Cl) or a mixed acid anhydride (G-CO—O—CO—R or G-CO—O—CO—OR, R in the latter being e.g. $C_{1-4}$alkyl, such as methyl, ethyl, propyl, i.propyl, butyl, t.butyl, i.butyl, or benzyl). The activated form G-CO-Z is reacted with the sulfonamide (2b).

The activation of the carboxylic acid in (2a) as described in the above reactions may lead to an internal cyclization reaction to an azalactone intermediate of formula

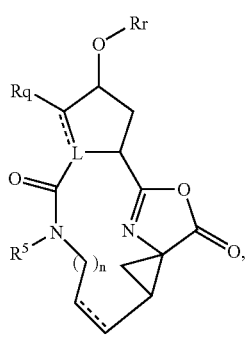

(2a-1)

wherein L, Rr, Rq, $R^5$, n are as specified above and wherein the stereogenic centers may have the stereochemical configuration as specified above, for example as in (I-a) or (I-b). The intermediates (2a-1) can be isolated from the reaction mixture, using conventional methodology, and the isolated intermediate (2a-1) is then reacted with (2b), or the reaction mixture containing (2a-1) can be reacted further with (2b) without isolation of (2a-1). In one embodiment, where the reaction with the coupling agent is conducted in a water-immiscible solvent, the reaction mixture containing (2a-1) may be washed with water or with slightly basic water in order to remove all water-soluble side products. The thus obtained washed solution may then be reacted with (2b) without additional purification steps. The isolation of intermediates (2a-1) on the other hand may provide certain advantages in that the isolated product, after optional further purification, may be reacted with (2b), giving rise to less side products and an easier work-up of the reaction.

Intermediate (2a) can be coupled with the alcohol (2c) by an ester forming reaction. For example, (2a) and (2c) are reacted together with removal of water either physically, e.g. by azeotropical water removal, or chemically by using a dehydrating agent. Intermediate (2a) can also be converted into an activated form G-CO—Z, such as the activated forms mentioned above, and subsequently reacted with the alcohol (2c). The ester forming reactions preferably are conducted in the presence of a base such as an alkali metal carbonate or hydrogen carbonate, e.g. sodium or potassium hydrogen carbonate, or a tertiary amine such as the amines mentioned herein in relation to the amide forming reactions, in particular a trialkylamine, e.g. triethylamine. Solvents that can be used in the ester forming reactions comprise ethers such as THF; halogenated hydrocarbons such as dichoromethane, $CH_2Cl_2$; hydrocarbons such as toluene; polar aprotic solvents such as DMF, DMSO, DMA; and the like solvents.

Synthesis of Compounds Containing a Carbocyclic P2 Unit

A typical route to compounds containing a saturated carbocyclic P2 scaffold i.e. L is CH in general formula 1, is shown in Scheme 14.

Scheme 14

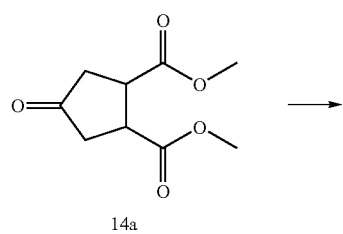

14a

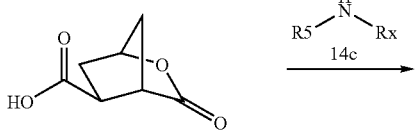

14b

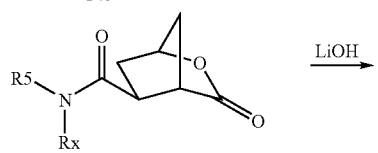

14d

14e

14f

Rx is an ω-unsaturated 5-8 membered alkyl chain;
A' is a protected carboxylic acid, substituted amide.

The saturated cycloalkyl scaffold (14b) can be prepared, for example, from 3,4-bis-(methoxycarbonyl)cyclopentanone (14a), described by Rosenquist et al. in Acta Chem. Scand. 46 (1992) 1127-1129 by reduction of the keto group with a reduction agent like sodium borohydride in a solvent like methanol followed by hydrolysis of the esters and finally ring closure in acetic anhydride in the presence of pyridine. The provided bicyclic acid (14b) can then be coupled to the amine function of the desired hydrazine derivative (14c) using conventional peptide coupling conditions like with HATU and diisopropyl amine in a solvent like dimethyl formamide to give (14d). Lactone opening of (14d) with for example lithium hydroxide provides the acid (14e) which subsequently can be coupled to the amino group of a P1 building block or a precursor of a desired P1 fragment (14f), using conventional peptide coupling conditions. Introduction of the $R^8$-group of the carbocycle can then be performed for example by a Mitsunobu reaction with the appropriate alcohol as described above or by any other suitable method previously described.

Scheme 15 shows an alternative route towards compounds of formula I comprising a saturated P2 scaffold where the building blocks are introduced in the reversed order, i.e. the P1 fragment is introduced before the hydrazine moiety.

Scheme 15

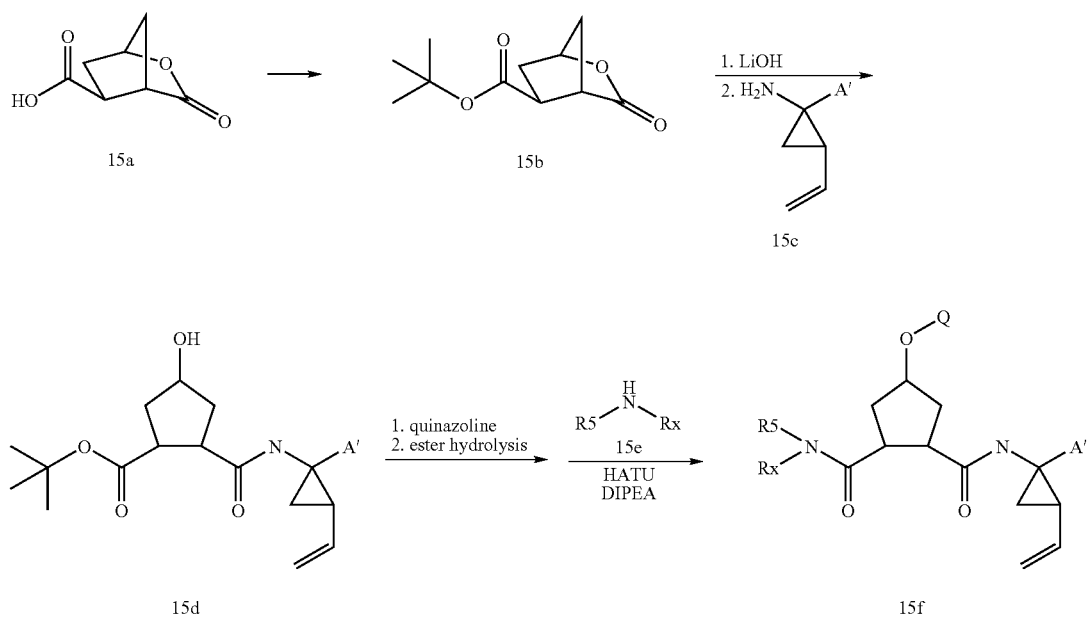

Q is a quinazoline derivative;
Rx is an ω-unsaturated 5 to 8 membered alkyl chain;
A' is a protected carboxylic acid, substituted amide.

Protection of the acid group of (15a) for example as the tert-butyl ester by treatment with di-tert-butyl dicarbonate in the presence of a base like dimethylaminopyridine and triethylamine in a solvent like dichloromethane provides ester (15b). Lactone opening using for example lithium hydroxide and subsequent coupling of a P1 building block (15c) as described in scheme 12 or directly by the amine group of the P1 fragment provides (15d). Introduction of the $R^8$-group as described above followed by removal of the acid protecting group by subjection of the ester to acidic conditions like trifluoroacetic acid and triethylsilane in a solvent like methylene chloride and finally coupling of the hydrazine moiety (15e) using the peptide coupling conditions as described above provides the hydrazide derivative (15f).

An unsaturated P2 scaffold useful for the preparation of compounds of formula I can be prepared as illustrated in scheme 16.

Scheme 16

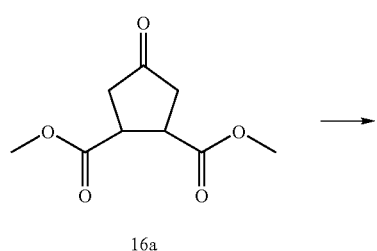

16a

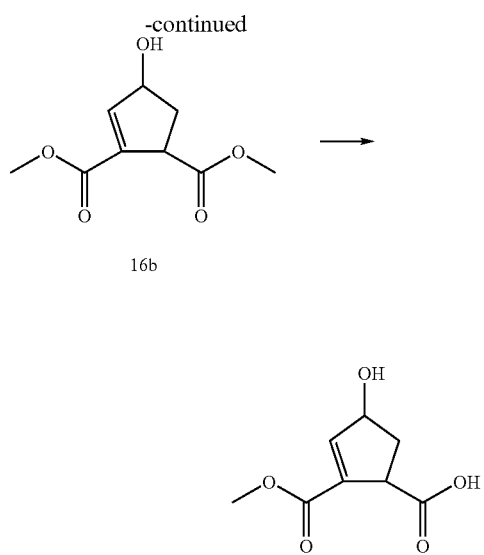

A bromination-elimination reaction of 3,4-bis(methoxycarbonyl)cyclopentanone (15a) as described by Dolby et al. in J. Org. Chem. 36 (1971) 1277-1285 followed by reduction of the keto functionality with a reduction agent like sodium borohydride provides the unsaturated hydroxy compound (15b). Selective ester hydrolysis using for example lithium hydroxide in a solvent like a mixture of dioxane and water provides hydroxy substituted monoester derivative (15c).

A P2 scaffold wherein Rq is other than hydrogen, such as a methyl, can be prepared as shown in scheme 17.

Scheme 17

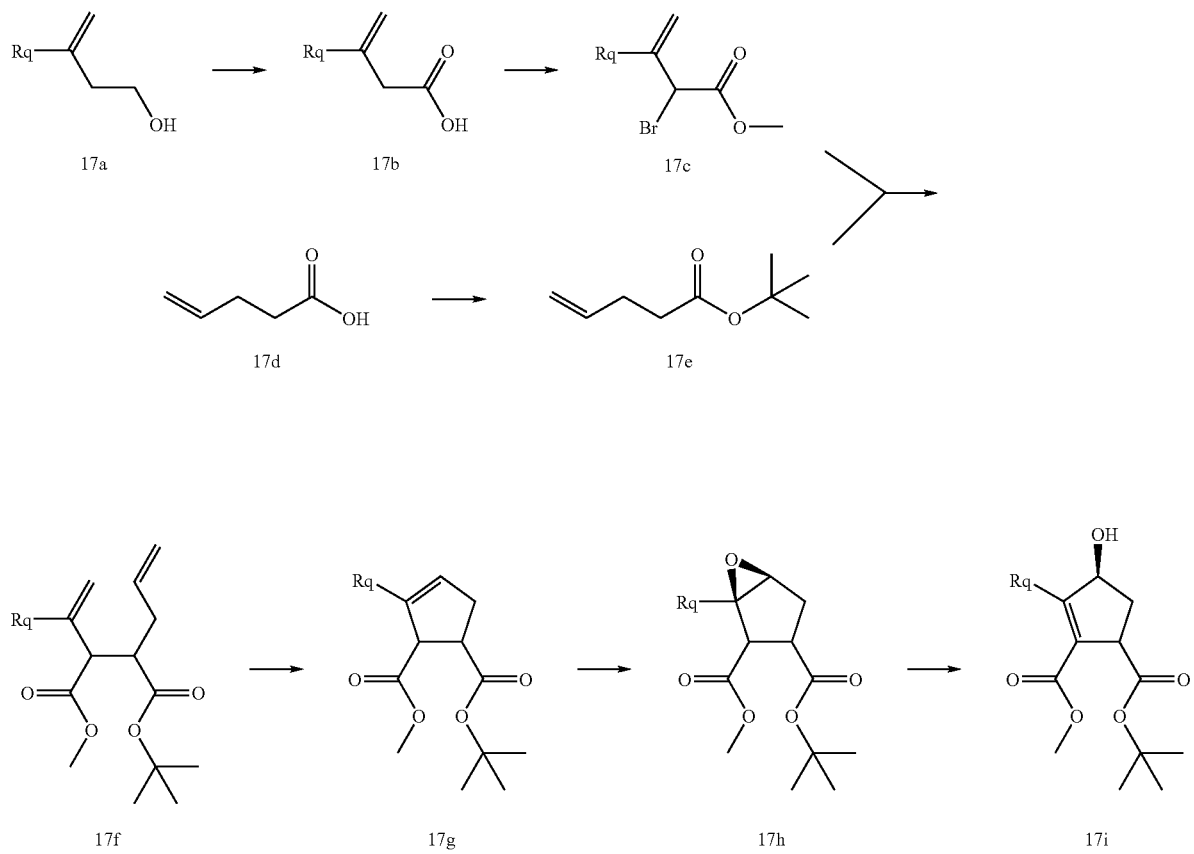

Oxidation of commercially available 3-methyl-3-buten-1-ol (17a) by the use of an oxidation agent like pyridinium chlorochromate followed by treatment with acetyl chloride, bromine and methanol provides the α-bromo ester (17c). The afforded ester (17c) can then be reacted with the enolate (17e), achieved for example by treatment of the corresponding tert-butyl ester with a base such as lithium diisopropyl amide in a solvent like tetrahydrofuran, to give the alkylated compound (17f). The tert-butyl ester (17e) can be prepared by treatment of the corresponding commercially available acid (17d) with di-tert-butyl dicarbonate in the presence of a base like dimethylamino-pyridine. Cyclisation of (17f) by an olefin metathesis reaction performed as described above provides cyclopentene derivative (17g). Stereoselective epoxidation of (17g) can be carried out using the Jacobsen asymmetric epoxidation method to furnish the epoxide (17h). Finally, addition of a base like DBN (1,5-diazabicyclo-[4.3.0]non-5-ene) yields the alcohol (17i). Optionally the double bond of compound (17i) can be reduced for example by catalytic hydrogenation using a catalyst like palladium on carbon which provides the corresponding saturated compound.

The afforded cyclic scaffolds can then be used, as described above, to complete the synthesis of compounds of formula 1. An example is shown in scheme 18.

Scheme 18

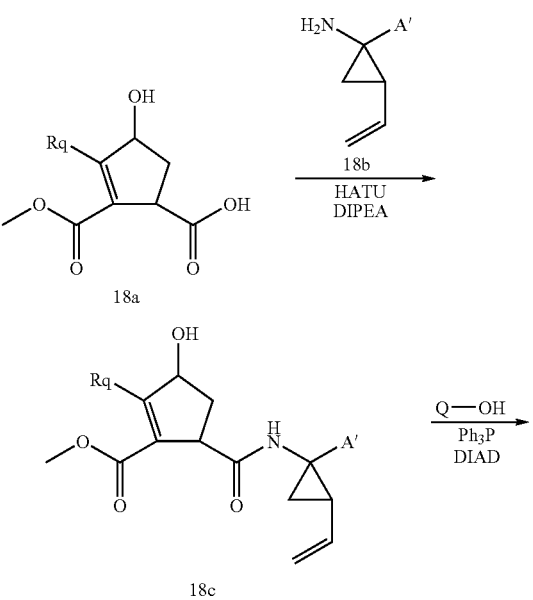

-continued

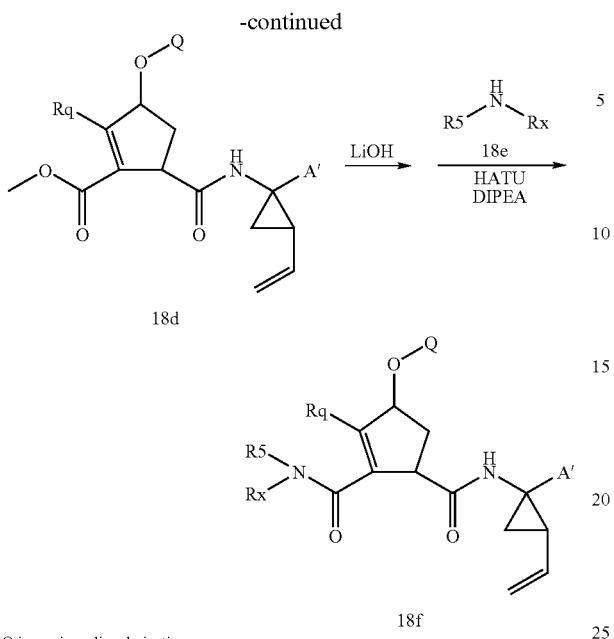

18d

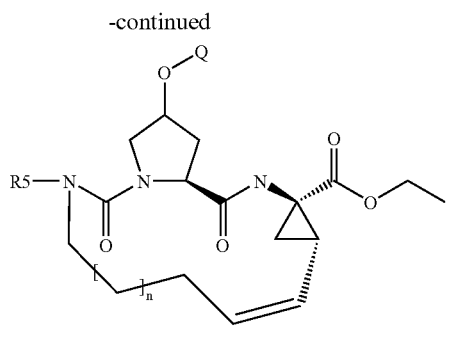

18f

Q is a quinazoline derivative;
Rq is an ω-unsaturated 5 to 8 membered alkyl chain;
A' is a protected carboxylic acid, substituted amide.

The amino group of a P1-building block or a suitable precursor thereof (18b) can be coupled to the acid of the cyclopentene derivative (18a) using standard amide coupling conditions such as using HATU in the presence of a base like diisopropyl phenylamine or the like, followed by introduction of the quinazoline group for example by Mitsunobu conditions as described above to provide (18d). Hydrolysis of the remaining ester and subsequent amide coupling of a desired ω-unsaturated amine (18e) optionally followed by manipulations of the P1 part provides cyclopentene containing compounds (18f) according to general formula I.

Macrocyclization

The macrocycle present in the compounds of the invention is typically formed by an olefin metathesis reaction (macrocyclization). The quinazoline group of the cyclic P2 scaffold can be introduced by any of the previously described strategies before or after formation of the macrocycle.

A typical route to macrocyclic urea compounds is shown in Scheme 19.

Scheme 19

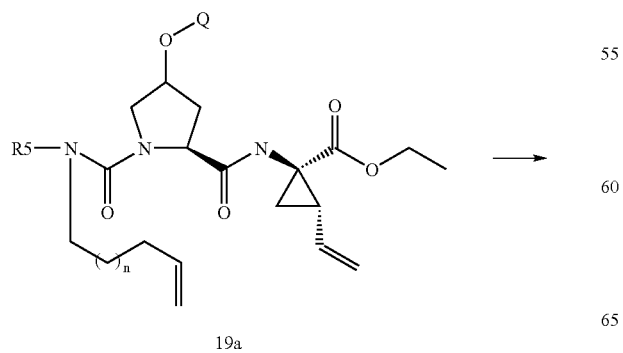

19a

-continued

19b

Q is a quinazoline derivative or a hydroxy protecting group
n = 1, 2, 3 or 4

Compound (19a) prepared as described above by using vinyl cyclopropyl glycine ethyl aster as P1 moiety can be transformed into a macrocyclic compound (19b) by performing an olefin metathesis reaction. A Ru-based catalyst such as the one reported by Miller, S. J., Blackwell, H. E.; Grubbs, R. H. J. Am. Chem. Soc. 118, (1996), 9606-9614, Kingsbury, J. S., Harrity, J. P. A., Bonitatebus, P. J., Hoveyda, A. H., J. Am. Chem. Soc. 121, (1999), 791-799 and Huang et al., J. Am. Chem. Soc. 121, (1999), 2674-2678 can be used to effect the metathesis reaction. It will also be recognized that catalysts containing other transition metals such as Mo can be used for this reaction. Optionally the double bond is reduced using standard hydrogenation methods well known in the art thus affording the corresponding saturated macrocyclic derivative.

The macrocyclisation described in Scheme 19 can also be applied to compounds comprising a saturated or unsaturated carbocyclic P2 scaffold as exemplified in scheme 20.

Scheme 20

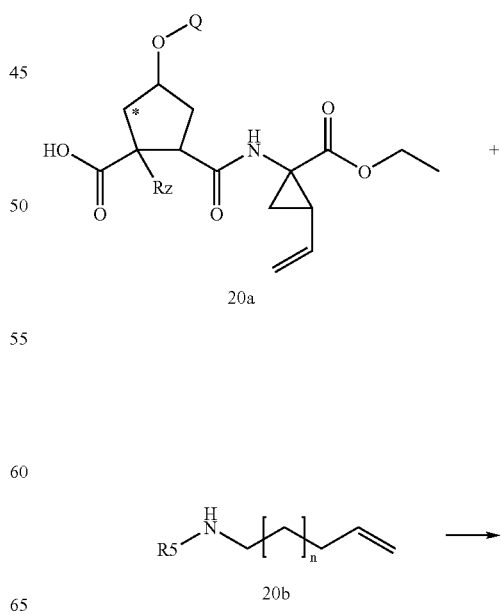

20a

20b

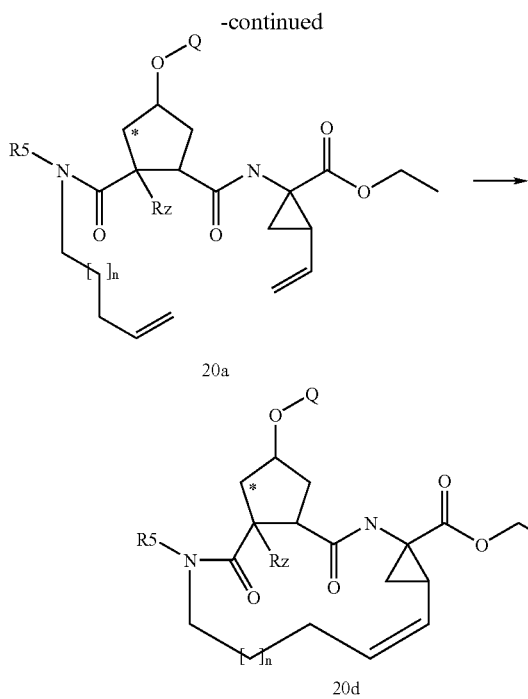

20a

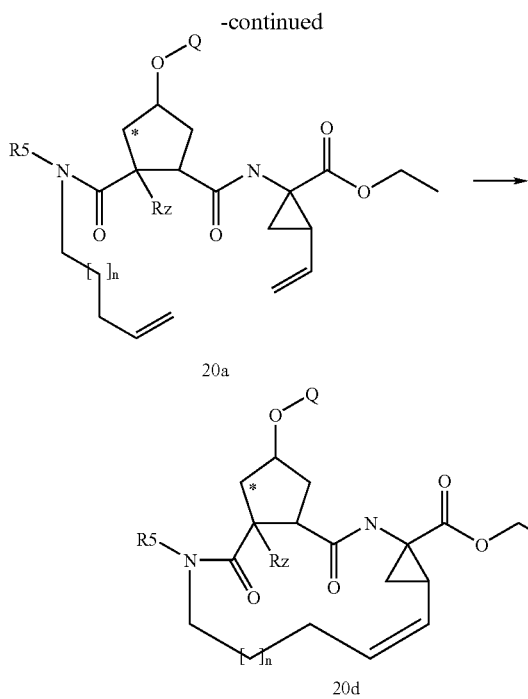

20d

Q is a quinazoline derivative or a hydroxy protecting group;
n is 1, 2, 3 or 4

Coupling of the hydrazine derivative (20b) to a P2-P1 building block (21a), prepared as desired in scheme 13 or 14, using standard peptide coupling conditions such as with HATU in the presence of a suitable base for instance diisopropylamine provides intermediate (20c). Ring closure of (20c) by an olefin metathesis reaction as described in scheme 18 gives the macrocyclic compound (20d).

When intermediates in the above described schemes contain a functional group(s), these are suitably protected where appropriate and subsequently deprotected by methods recognized by persons skilled in the art. For an extensive description see for example Bodanzky or Greene cited above.

Synthesis of the P3 Building Blocks

The P3 building blocks can be generated according to methodologies known to the skilled in the art. One of these methodologies is shown in Scheme 28 below and employs monoacylated amines, such as trifluoroacetamide or a Boc-protected amine.

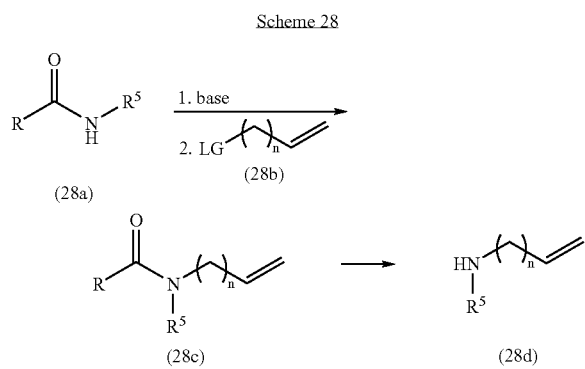

wherein R is t-butoxy, trifluoromethyl; $R^5$ and n are as defined in the present invention; and LG is a leaving group, such as a halogen.

The monoacylated amines (18a) are treated with a strong base such as sodium hydride and are subsequently reacted with a haloC$_{3-6}$alkenyl (28b) to form the corresponding protected amine (28c). Deprotection of (28c) affords building block P3 or (28d). Deprotection will depend on the functional group R, thus if R is t-butoxy, deprotection of the corresponding Boc-protected amine can be accomplished with an acidic treatment, e.g. trifluoroacetic acid. Alternatively, when R is for instance trifluoro-methyl, removal of the R group is accomplished with a base, e.g. sodium hydroxide.

Scheme 29 exemplifies yet another method for preparing a P3 building block.

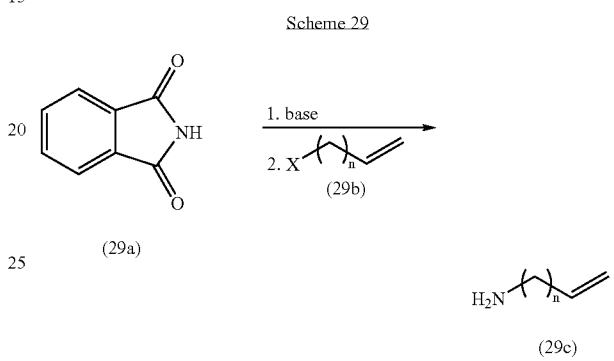

wherein X is halogen, n is as defined in the present invention

A Gabriel synthesis of primary C$_{3-6}$alkenylamines, which can be carried out by the treatment of a phthalimide (29a) with a base, such as potassium hydroxide, and a haloC$_{3-6}$alkenyl (29b), followed by the hydrolysis of the intermediate N-alkyl imide to generate a primary C$_{3-6}$alkenylamine (29c).

Coupling of the appropriate P3 building block to the P2-P1 moiety will be accomplished by forming an amide bond as explained herein.

Formation of the Macrocycle

Formation of the macrocycle can be carried out via an olefin metathesis reaction in the presence of a suitable metal catalyst such as e.g. the Ru-based catalyst reported by Miller, S. J., Blackwell, H. E.; Grubbs, R. H. J. Am. Chem. Soc. 118, (1996), 9606-9614, Kingsbury, J. S., Harrity, J. P. A., Bonitatebus, P. J., Hoveyda, A. H., J. Am. Chem. Soc. 121, (1999), 791-799 and Huang et al., J. Am. Chem. Soc. 121, (1999), 2674-2678, for example a Hoveyda-Grubbs catalyst. Air-stable ruthenium catalysts such as Bis(tricyclohexylphosphine)-3-phenyl-1H-inden-1-ylidene ruthenium chloride (Neolyst M1®) or Bis(tricyclohexylphosphine)[(phenylthio)methylene]ruthenium (IV) dichloride can be used for large-scale production. Also other catalysts containing other transition metals such as Mo can be used for this reaction.

The metathesis reactions may be conducted in a suitable solvent such as for example ethers, e.g. THF, dioxane; halogenated hydrocarbons, e.g. dichoromethane, CHCl$_3$, 1,2-dichloroethane and the like, hydrocarbons, e.g. toluene. In a preferred embodiment, the metathesis reaction is conducted in toluene. These reactions are conducted at increased temperatures under nitrogen atmosphere.

Optionally the double bond is reduced by standard hydrogenation methods well known in the art, e.g. with hydrogen in the presence of a noble metal catalyst such as Pd or Pt.

A number of specific synthesis routes to prepare the compounds of formula (I) or particular subgroups of compounds of formula (I) are outlined in the following schemes in somewhat more detail. In schemes 30-33.

Scheme 30
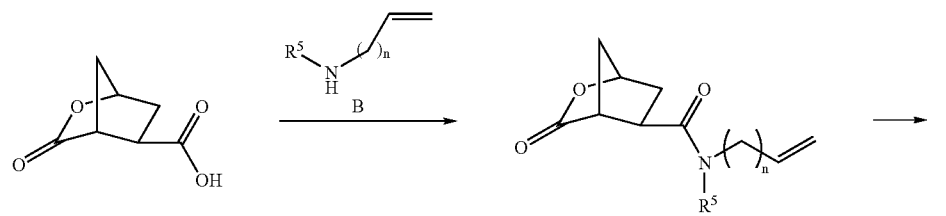
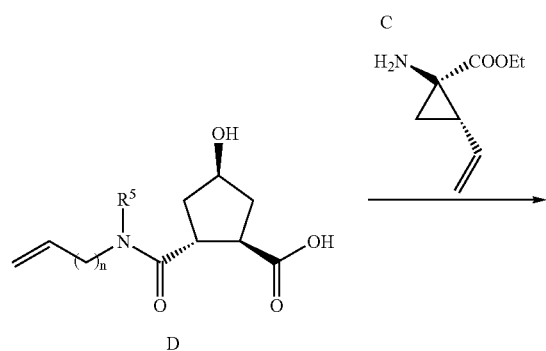
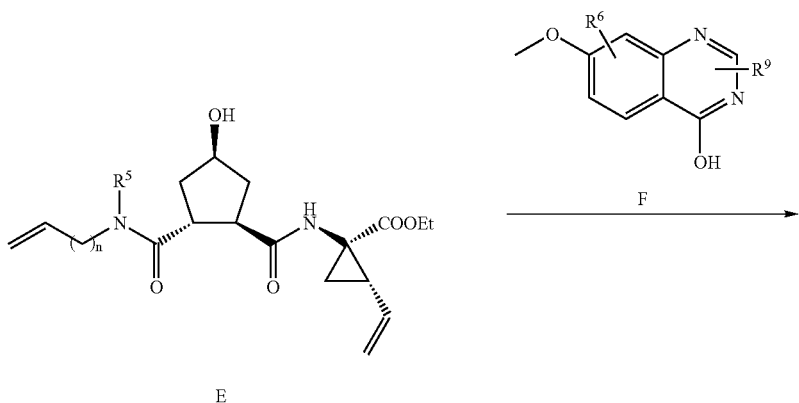
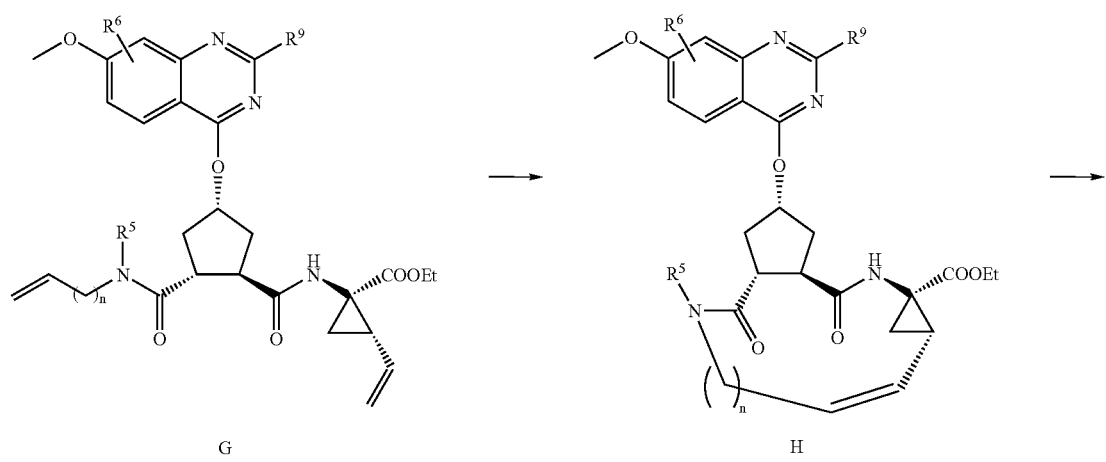

-continued

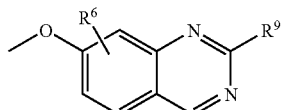
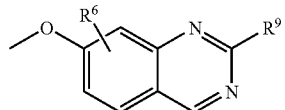

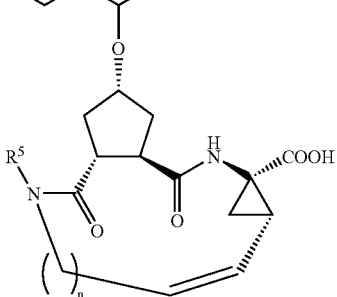
I

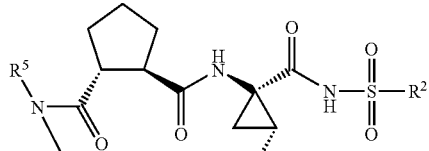
J

Compounds of the present invention can be synthesized, as shown in Scheme 30, from compounds of Formula A, B and F. The lactone A is coupled with an $C_{3-6}$alkenylamine of structure B, in the presence of peptide coupling agent, such as HATU or EDCI/HOAt in presence of a base, such as DIPEA, to form a compound of Formula C. The subsequent lactone opening and coupling with 1-(amino)-2-(vinyl)cyclopropane-carboxylic acid ethyl ester in the presence of peptide coupling agent, such as HATU or EDCI/HOAt in presence of a base, such as DIPEA, affords a compound of Formula E. Compounds E can be coupled to an quinazoline of Formula F using a Mitsunobu type reaction. The resulting diolefin G can be submitted to ring closure using an olefin metathesis catalyst, such as the Hoveyda-Grubbs catalysts, or Bis(tricyclohexyl-phosphine)[(phenylthio)methylene]rythenium (IV) dichloride, Bis(tricyclohexyl-phosphine)-3-phenyl-1H-inden-1-ylideneruthenium (IV) dichloride (Neolyst M1®), in an appropriate solvent such as 1,2-dichloroethane, dichloromethane or toluene, to form a compound of Formula H, which can be hydrolyzed to the corresponding acid of Formula I. The acid of formula I is coupled with $R^6SO_2NH_2$, in presence of peptide coupling agent, such as CDI or EDAC, and in presence of a base such as 1,8-diazabicyclo[5.4.0]undec-7-ene (DBU) or DMAP to provide a compound of Formula J.

Scheme 31

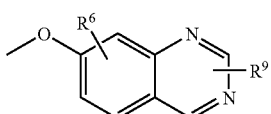

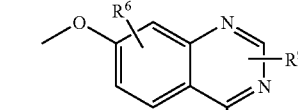

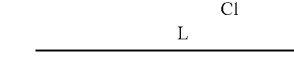
K

-continued

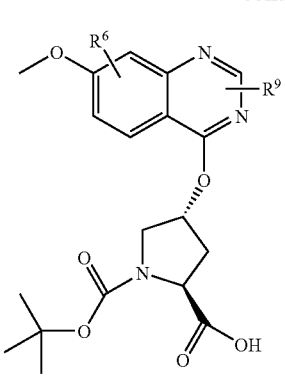
M

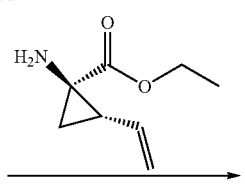

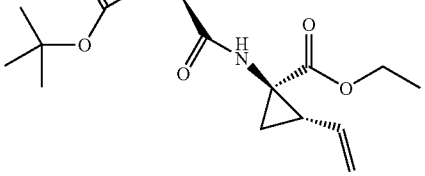
N

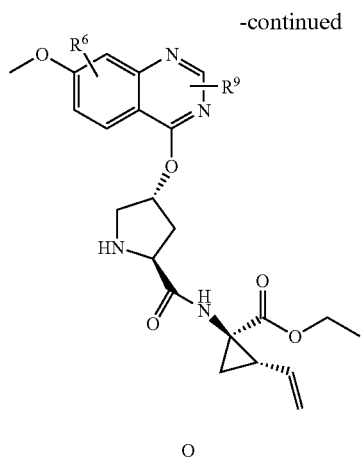

O

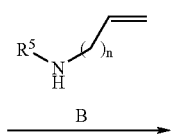

B

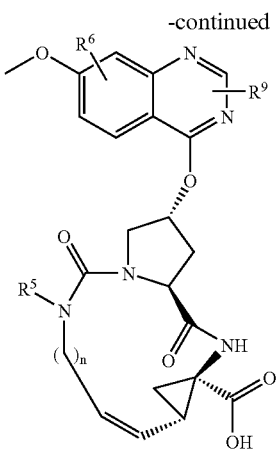

R

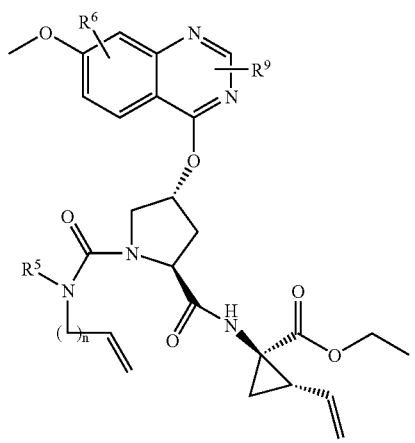

P

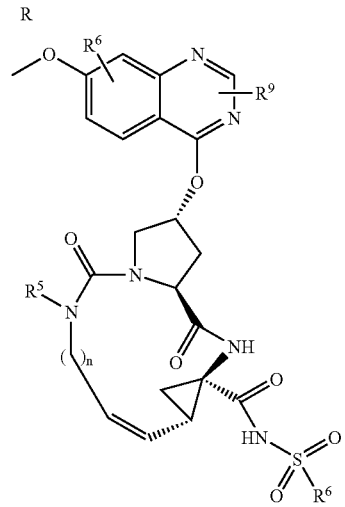

S

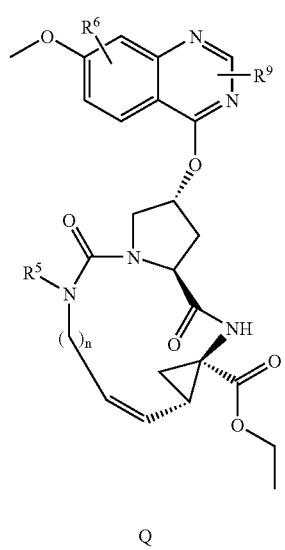

Q

In Scheme 31, a compound of Formula K is reacted with a chlorooquinazoline L in presence of a base, such as NaH or tBuOK, to form a compound of Formula M. The resulting acid M can be treated with 1-(amino)-2-(vinyl)cyclopropanecarboxylic acid ethyl ester or the corresponding tosylate in the presence of peptide coupling agent, such as HATU or EDCI/HOAt and in presence of a base, such as DIPEA, to give a product of Formula N. The deprotection of the Boc moiety of the compound of Formula N can be realized by treatment with an acid, such as TFA, in a solvent such as methylene chloride to provide the free amine of Formula O. Subsequently, the urea of Formula P can be prepared from the compound of Formula O by treatment with phosgene, or an equivalent of phosgene, and an amine of Formula B, in presence of a base, such as NaHCO$_3$. The resulting diolefin P can be submitted to ring closure using an olefin metathesis catalyst, such as the Hoveyda-Grubbs catalysts or Bis(tricyclohexyl-phosphine)[(phenylthio)-methylene]rythenium (IV) dichloride, Bis(tricyclohexyl-phosphine)-3-phenyl-1H-inden-1-ylideneruthenium (IV) dichloride (Neolyst M1®), in an appropriate solvent such as 1,2-dichloroethane, dichloromethane or toluene, to form a compound of Formula Q, which can be hydrolyzed to the corresponding acid of Formula R. The acid of formula R is coupled with $R^6SO_2NH_2$, in presence of peptide coupling agent, such as CDI or EDAC, and in presence of a base such as 1,8-diaza-bicyclo[5.4.0]undec-7-ene (DBU) or DMAP to provide a compound of Formula S.
An alternative method for the synthesis of compound of Formula Q is outlined in the Scheme 32 below.
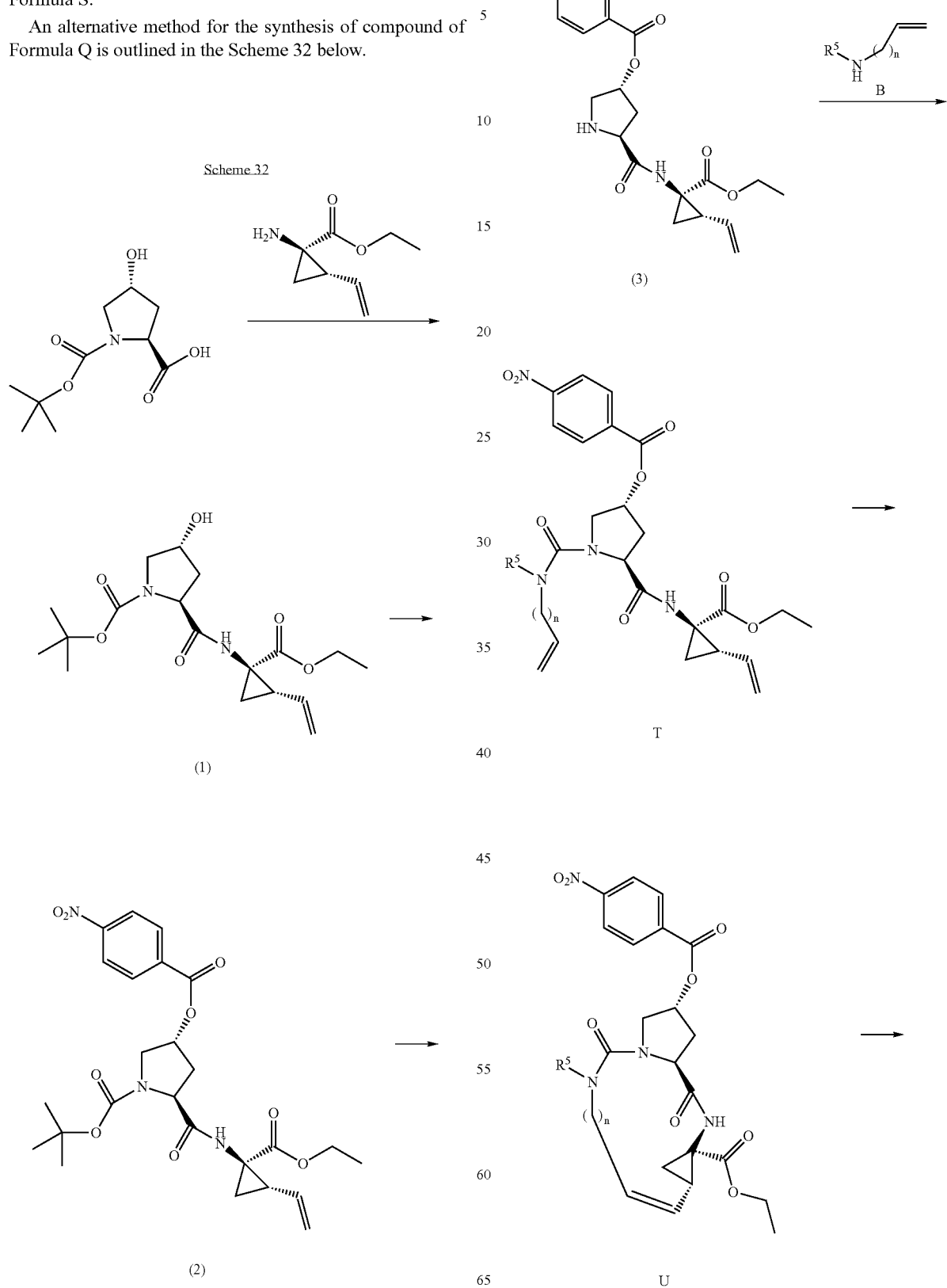

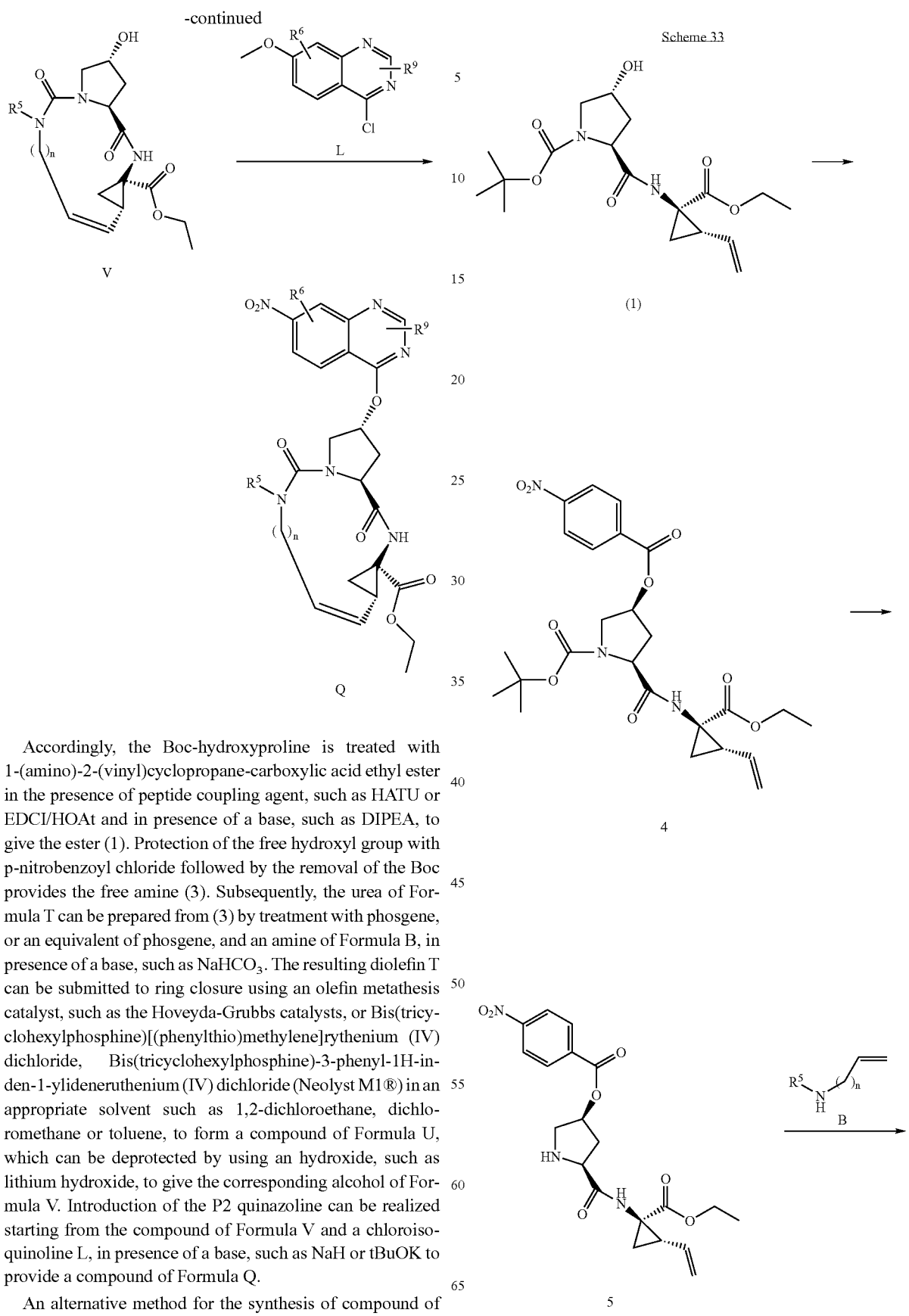

Accordingly, the Boc-hydroxyproline is treated with 1-(amino)-2-(vinyl)cyclopropane-carboxylic acid ethyl ester in the presence of peptide coupling agent, such as HATU or EDCI/HOAt and in presence of a base, such as DIPEA, to give the ester (1). Protection of the free hydroxyl group with p-nitrobenzoyl chloride followed by the removal of the Boc provides the free amine (3). Subsequently, the urea of Formula T can be prepared from (3) by treatment with phosgene, or an equivalent of phosgene, and an amine of Formula B, in presence of a base, such as $NaHCO_3$. The resulting diolefin T can be submitted to ring closure using an olefin metathesis catalyst, such as the Hoveyda-Grubbs catalysts, or Bis(tricyclohexylphosphine)[(phenylthio)methylene]rythenium (IV) dichloride, Bis(tricyclohexylphosphine)-3-phenyl-1H-inden-1-ylideneruthenium (IV) dichloride (Neolyst M1®) in an appropriate solvent such as 1,2-dichloroethane, dichloromethane or toluene, to form a compound of Formula U, which can be deprotected by using an hydroxide, such as lithium hydroxide, to give the corresponding alcohol of Formula V. Introduction of the P2 quinazoline can be realized starting from the compound of Formula V and a chloroisoquinoline L, in presence of a base, such as NaH or tBuOK to provide a compound of Formula Q.

An alternative method for the synthesis of compound of Formula Q is outlined in the Scheme 33 below.

-continued

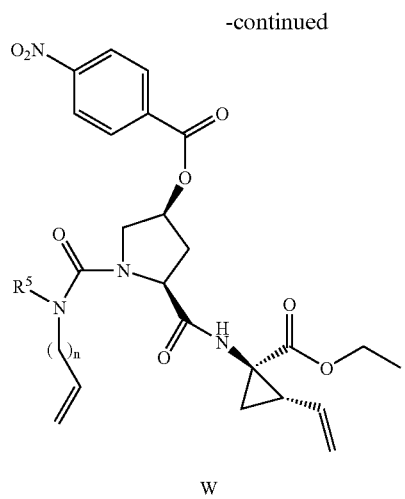

W

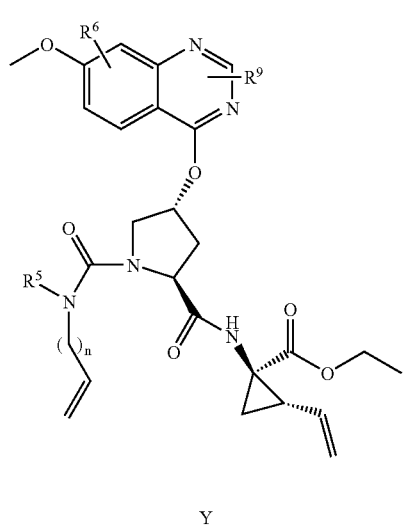

X

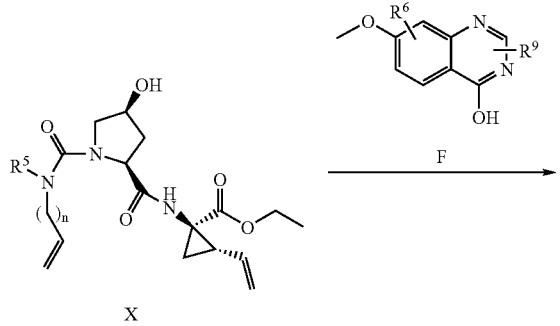

Y

-continued

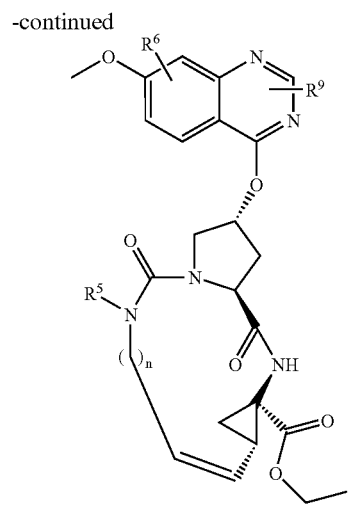

Q

Accordingly, the proline derivative (1) is protected with p-nitrobenzoic acid followed by the removal of the Boc to give free amine (5). Subsequently, the urea of Formula W can be prepared from (5) by treatment with phosgene, or an equivalent of phosgene, and an amine of Formula B, in presence of a base, such as $NaHCO_3$. The compound of Formula W can be deprotected by using an hydroxide, such as lithium hydroxide, to give the corresponding alcohol of Formula X. Introduction of the P2 isoquinoline can be realized starting from the compound of Formula X and a hydroxyisoquinoline F, using a Mitsunobu reaction, to provide a compound of Formula Y. The resulting diolefin Y can be submitted to ring closure using an olefin metathesis catalyst, such as the Hoveyda-Grubbs catalyst or the like, in an appropriate solvent such as 1,2-dichloroethane, dichloromethane or toluene, to form a compound of Formula Q.

In the above schemes 28-33 (only) $R^3$ corresponds to the present $R^5$, X corresponds to L, $R^{4a}$ corresponds to $R^9$, $R^{4b}$ and $R^{4b'}$ correspond to $R^6$ and $R^{11}$, $R^5$ corresponds to $R^1$ and $R^6$ corresponds to $R^2$, as defined above for the compounds of formula (I) or of any of the subgroups thereof.

The reactions of the schemes above may be conducted in a suitable solvent in the presence of a base such as an alkali metal carbonate or hydroxide, e.g. sodium, potassium or cesium carbonate; or an organic base such as a trialkylamine, e.g. triethylamine. Suitable solvents for this reaction are for example ethers, e.g. THF, dioxane; halogenated hydrocarbons, e.g. dichoromethane, $CHCl_3$, toluene, polar aprotic solvents such as DMF, DMSO, DMA and the like.

Compounds of formula (I) may be converted into each other following art-known functional group transformation reactions, comprising those described hereinafter.

A number of the intermediates used to prepare the compounds of formula (I) are known compounds or are analogs of known compounds, which can be prepared following modifications of art-known methodologies readily accessible to the skilled person. A number of preparations of intermediates are given hereafter in somewhat more detail.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) may be obtained as racemic mixtures of enantiomers which can be separated from one another following art-known resolution procedures. The racemic compounds of formula (I), which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound may be synthesized by stereospecific methods of preparation. These methods may advantageously employ enantiomerically pure starting materials.

In a further aspect, the present invention concerns a pharmaceutical composition comprising a therapeutically effective amount of a compound of formula (I) as specified herein, or a compound of any of the subgroups of compounds of formula (I) as specified herein, and a pharmaceutically acceptable carrier. A therapeutically effective amount in this context is an amount sufficient to prophylactically act against, to stabilize or to reduce viral infection, and in particular HCV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula (I), as specified herein, or of a compound of any of the subgroups of compounds of formula (I) as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) show antiviral properties. Viral infections and their associated diseases treatable using the compounds and methods of the present invention include those infections brought on by HCV and other pathogenic flaviviruses such as Yellow fever, Dengue fever (types 1-4), St. Louis encephalitis, Japanese encephalitis, Murray valley encephalitis, West Nile virus and Kunjin virus. The diseases associated with HCV include progressive liver fibrosis, inflammation and necrosis leading to cirrhosis, end-stage liver disease, and HCC; and for the other pathogenic flaviruses the diseases include yellow fever, dengue fever, hemorraghic fever and encephalitis. A number of the compounds of this invention moreover are active against mutated strains of HCV. Additionally, many of the compounds of this invention show a favorable pharmacokinetic profile and have attractive properties in terms of bioavailabilty, including an acceptable half-life, AUC (area under the curve) and peak values and lacking unfavourable phenomena such as insufficient quick onset and tissue retention.

The in vitro antiviral activity against HCV of the compounds of formula (I) was tested in a cellular HCV replicon system based on Lohmann et al. (1999) Science 285:110-113, with the further modifications described by Krieger et al. (2001) Journal of Virology 75: 4614-4624 (incorporated herein by reference), which is further exemplified in the examples section. This model, while not a complete infection model for HCV, is widely accepted as the most robust and efficient model of autonomous HCV RNA replication currently available. Compounds exhibiting anti-HCV activity in this cellular model are considered as candidates for further development in the treatment of HCV infections in mammals. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

Due to their antiviral properties, particularly their anti-HCV properties, the compounds of formula (I) or any subgroup thereof, their prodrugs, N-oxides, addition salts, quaternary amines, metal complexes and stereochemically isomeric forms, are useful in the treatment of individuals experiencing a viral infection, particularly a HCV infection, and for the prophylaxis of these infections. In general, the compounds of the present invention may be useful in the treatment of warm-blooded animals infected with viruses, in particular flaviviruses such as HCV.

The compounds of the present invention or any subgroup thereof may therefore be used as medicines. Said use as a medicine or method of treatment comprises the systemic administration to viral infected subjects or to subjects susceptible to viral infections of an amount effective to combat the conditions associated with the viral infection, in particular the HCV infection.

The present invention also relates to the use of the present compounds or any subgroup thereof in the manufacture of a medicament for the treatment or the prevention of viral infections, particularly HCV infection.

The present invention furthermore relates to a method of treating a warm-blooded animal infected by a virus, or being at risk of infection by a virus, in particular by HCV, said method comprising the administration of an anti-virally effective amount of a compound of formula (I), as specified herein, or of a compound of any of the subgroups of compounds of formula (I), as specified herein.

In general it is contemplated that an antiviral effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of previously known anti-HCV compound, such as, for instance, interferon-α (IFN-α), pegylated interferon-α and/or ribavirin, and a compound of formula (I) can be used as a medicine in a combination therapy. The term "combination therapy" relates to a product containing mandatory (a) a compound of formula (I), and (b) optionally another anti-HCV compound, as a combined preparation for simultaneous, separate or sequential use in treatment of HCV infections, in particular, in the treatment of infections with HCV. Thus, to combat or treat HCV infections, the compounds of formula (I) may be co-administered in combination with for instance, interferon-α (IFN-α), pegylated interferon-α and/or ribavirin, as well as therapeutics based on antibodies targeted against HCV epitopes, small interfering RNA (Si RNA), ribozymes, DNAzymes, antisense RNA, small molecule antagonists of for instance NS3 protease, NS3 helicase and NS5B polymerase.

Accordingly, the present invention relates to the use of a compound of formula (I) or any subgroup thereof as defined above for the manufacture of a medicament useful for inhibiting HCV activity in a mammal infected with HCV viruses, wherein said medicament is used in a combination therapy, said combination therapy preferably comprising a compound of formula (I) and (pegylated) IFN-α and/or ribavirin, and optionally an anti-HIV compound. For example in drugs prone to rapid metabolism by Cyp3A4, co-dosing with the HIV protease inhibitors such as ritonavir can allow lower dosage regimes to be administered.

EXAMPLES

The following examples are intended to illustrate the present invention and not to limit it thereto. Examples showing the preparation of building blocks are intended to be coupled to any other appropriate building block described herein and not simply the components shown in the exemplified end products of formula I.

Example 1

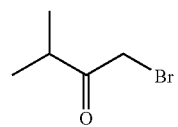

1-bromo-3-methylbutan-2-one (1)

To an ice cooled solution of 3-methyl-2-butanone (25.8 g, 300 mmol) in EtOH (250 ml) was added drop wise bromine (12.9 ml, 250 mmol) and the mixture was stirred for two hours in an ice bath. Petroleum ether (600 ml) was added. The organic phase was washed twice with water. The combined water phases was extracted twice with petroleum ether. The combined organic phases was washed twice with a cold sodium carbonate solution and with brine. The organic phase was dried over sodium sulfate and evaporated under reduced pressure (room temperature).

Yield: 50%.

Example 2

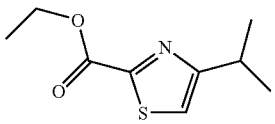

Ethyl 4-isoppropylthiazole-2-carboxylate (2)

To a boiling solution of ethyl thiooxamate (16.0 g, 120 mmol) in EtOH was added drop wise 1-bromo-3-methyl-2-butanone over a period of 15 minutes. The mixture was refluxed for 1.5 hours. The solution was added to 300 ml of ice water and basified with concentrated ammonia solution. The mixture was extracted twice with ethyl acetate. The organic phase was washed with brine, dried with sodium sulfate and evaporated under reduced pressure. The product was purified by column on chromatography silica gel eluted with hexane and 20% ethyl acetate. Yield: 15.2 g, 67%.

$^1$H-NMR-CDCl$_3$ 1.35 (d, 6H), 1.42 (t, 3H), 3.25 (m, 1H), 4.49 (m, 2H) 7.20 (s, 1H)

Example 3

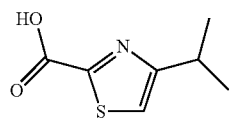

4-isopropylthiazole-2-carboxylic acid (3)

To a solution of ethyl 4-isopropylthiazole-2-carboxylate (9.1 g, 46 mmol) in THF (100 ml) and MeOH (30 ml) was added a solution of lithium hydroxide (1.16 g, 48.5 mmol) and the mixture was stirred for two days at room temperature. The mixture was acidified with 2M hydrochloric acid and extracted four times with diethyl ether. The organic phase was dried with sodium sulfate and evaporated under reduced pressure. Yield: 7.1 g, 90%.

Example 4

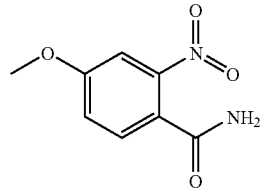

4-methoxy-2-nitro-benzamide (4)

To an ice cooled suspension of 4-methoxy-2-nitro-benzoic acid (14.1 g, 71.5 mmol) and some drops of DMF in DCM (150 ml) was added drop wise oxalyl chloride (19.0 g, 150 mmol) and the mixture was stirred for two hours at room temperature. The solvent was evaporated and water was added. The product was filtered of and washed with water and hexane. The product was dried in vacuum. Yield: 10 g, 71%.

Example 5

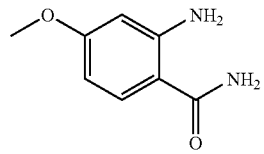

4-methoxy-2-amino-benzamide (5)

A suspension of 4-methoxy-2-nitro-benzamide (6.9 g, 35.1 mmol) in EtOH (200 ml) was hydrogenated with Raney-Ni (4.0 g) for two days at room temperature and 50 psi. The catalyst was filtered of and washed with DMF. The solvent was evaporated under reduced pressure. Yield: 5.6 g, 95%.

Example 6

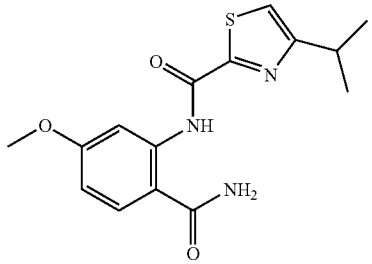

4-isopropylthiazole-2-carboxylic acid (2-carbamoyl-5-methoxy-phenyl)-amide (6)

To a cooled solution of 4-methoxy-2-aminobenzamide (5.6 g, 33.7 mmol), 4-isopropyl-thiazole-2-carboxlic acid (7.1 g, 42 mmol) and Hobt-hydrate (6.4 g, 42 mmol) in DMF (150 ml) was added EDAC (8.6 g, 45 mmol) and TEA (6.4 ml, 45 mmol) and the mixture was stirred overnight at room temperature. A 2.5% aqueous solution of citric acid (600 ml) was added and the mixture was extracted three times with ethyl acetate. The organic phase was washed with brine and saturated sodium hydrogencarbonate. The solution was dried over sodium sulfate and evaporated under reduced pressure.

Yield: 9.0 g, 91%.

Example 7

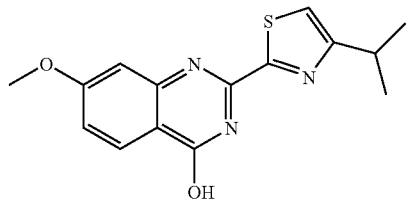

2-(4-isopopylthiazole-2-yl)-7-methoxy-quinazolin-4-ol (7)

A mixture of 4-isopropyl-2-carboxylic acid (2-carbamoyl-5-methoxy-phenyl)-amide (9.0 g, 28.2 mmol) and sodium carbonate (7.5 g, 71 mmol) in EtOH water 50/50 (300 ml) was refluxed for two hours. The mixture was cooled an acidified with citric acid and extracted four times with ethyl acetate. The organic phase was dried with sodium sulfate and evaporated under reduced pressure. The product was crystallisized from EtOH. Yield: 4.8 g, 60%.

$^1$H-NMR-DMSO-D$_6$ δ 1.30 (d, 6H), 3.10 (m, 1H), 3.90 (s, 3H), 7.10 (dd, 1H) 7.16 (d, 1H), 7.62 (d, 1H), 8.02 (d, 1H).

Example 8

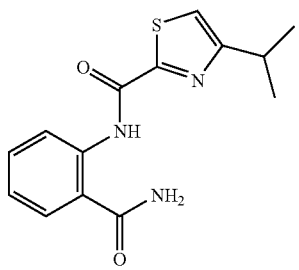

4-isopropylthiazole-2-carboxylic acid (2-carbamoyl-phenyl)-amide (8)

2-Aminobenzamide (2.04 g, 15 mmol) was reacted with 4-isopropylthiazole-2-carboxlic acid (2.5 g, 14.6 mmol) as described in example 6 which gave the title compound (2.4 g, 56%).

Example 9

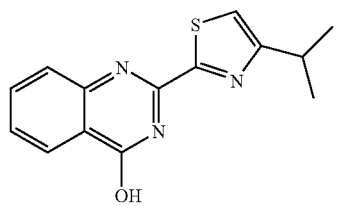

2-(4-isopopylthiazole-2-yl)-quinazolin-4-ol (9)

4-isopropylthiazole-2-carboxylic acid (2-carbamoyl-phenyl)-amide (2.4 g, 8.3 mmol) was treated according to the procedure described in example 7 which gave the title compound (1.7 g, 77%).

$^1$H-NMR CDCl$_3$ δ1.33 (d, 6H), 3.12 (m, 1H), 7.55 (t, 1H), 7.65 (s, 1H), 7.72 (d, 1H), 7.82 (t, 1H), 8.14 (d, 1H).

Example 10

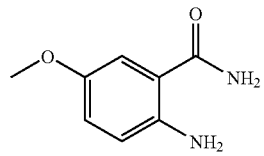

2-Amino-5-methoxy-benzamide (10)

Catalytic hydrogenation of 5-Methoxy-nitro-benzamide (3.6 g) over Raney-nickel gave the title compound (2.75 g, 90%).

Example 11

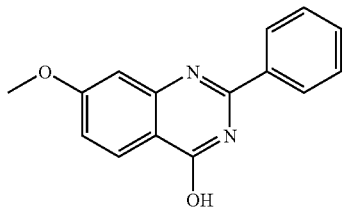

7-Methoxy-2-phenyl-quinazolin-4-ol (11)

Treatment of 2-amino-5-methoxy-benzamide according the procedure described by Raid J. Abdel-Jalil, Wolfgang Voelter and Muhammad Saeed in Tetrahedron Letters 45 (2004) 3475-3476 for the preparation of 2-phenyl-quinazoline 4-ol gave the title compound.

Example 12

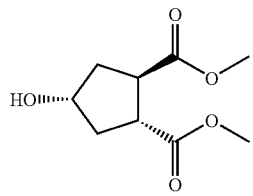

trans-(3R,4R)-Bis(methoxycarbonyl)cyclopentanol (12)

Sodium borohydride (1.11 g, 0.029 mol) was added to a stirred solution of (1R,2S)-4-oxo-cyclopentane 1,2-dicarboxylic acid dimethyl ester (4.88 g, 0.0244 mol) in methanol (300 mL) at 0° C. After 1 h the reaction was quenched with 90 mL brine, concentrated and extracted with ethyl acetate. The organic phases were pooled, dried, filtered and concentrated. The crude product was purified by flash column chromatography (toluene/ethyl acetate 1:1) which gave the title compound (3.73 g, 76%) as a yellow oil.

Example 13

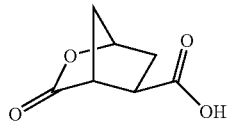

3-Oxo-2-oxa-bicyclo[2.2.1]heptane-5-carboxylic acid (13)

Sodium hydroxide (1M, 74 mL, 0.074 mol) was added to a stirred solution of 12 (3.73 g, 0.018 mol) in methanol (105 mL) at room temperature. After 4 h, the reaction mixture was neutralized with 3M HCl, evaporated and co-evaporated with toluene several times. Pyridine (75 mL) and Ac₂O (53 mL) were added and the reaction mixture was allowed to shake overnight at room temperature. The mixture was then co-evaporated with toluene and purified by flash column chromatography (ethyl acetate+1% acetic acid) which gave the title compound (2.51 g, 88%) as a yellow oil.

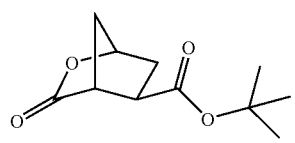

Example 14

3-Oxo-2-oxa-bicyclo[2.2.1]heptane-5-carboxylic acid tert-butyl ester (14)

DMAP (14 mg, 0.115 mmol) and Boc₂O (252 mg, 1.44 mmol) was added to a stirred solution of 13 (180 mg, 1.15 mmol) in 2 mL CH₂Cl₂ under inert argon atmosphere at 0° C. The reaction was allowed to warm to room temperature and was stirred overnight. The reaction mixture was concentrated and the crude product was purified by flash column chromatography (toluene/ethyl acetate gradient 15:1, 9:1, 6:1, 4:1, 2:1) which gave the title compound (124 mg, 51%) as white crystals.

$^1$H-NMR (300 MHz, CD₃OD) δ 1.45 (s, 9H), 1.90 (d, J=11.0 Hz, 1H), 2.10-2.19 (m, 3H), 2.76-2.83 (m, 1H), 3.10 (s, 1H), 4.99 (s, 1H); $^{13}$C-NMR (75.5 MHz, CD₃OD) δ 27.1, 33.0, 37.7, 40.8, 46.1, 81.1, 81.6, 172.0, 177.7.

Alternative method for the preparation of compound 14

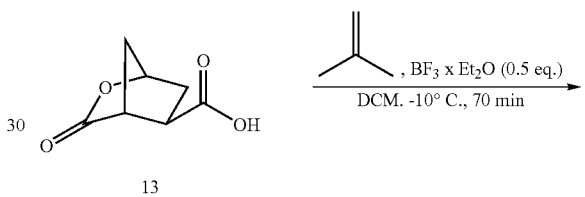

Compound 13 (13.9 g, 89 mmol) was dissolved in dichloromethane (200 ml) and then cooled to approximately −10° C. under nitrogen. Isobutylene was then bubbled into the solution until the total volume had increased to approximately 250 ml which gave a "cloudy solution". BF₃×Et₂O (5.6 ml, 44.5 mmol, 0.5 eq.) was added and the reaction mixture was kept at approximately −10° C. under nitrogen. After 10 min, a clear solution was obtained. The reaction was monitored by TLC (EtOAc-Toluene 3:2 acidified with a few drops of acetic acid and hexane-EtOAc 4:1, staining with basic permanganate solution). At 70 min only traces of compound 13 remained and aq. saturated NaHCO₃ (200 ml) was added to the reaction mixture, which was then stirred vigorously for 10 min. The organic layer was washed with saturated NaHCO₃ (3×200 ml) and brine (1×150 ml), then dried with sodium sulfite, filtered and concentrated into an oil containing small droplets. Upon addition of hexane to the residue the product crashed out. Addition of more hexane and heating to reflux gave a clear solution from which the product crystallized. The crystals were collected by filtration and was washed with hexane (rt), then air-dried for 72 h giving colourless needles (12.45 g, 58.7 mmol, 66% from first harvest)

Example 15

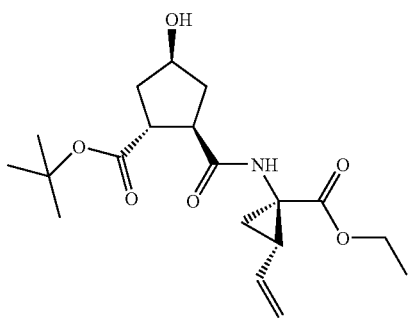

(1R,2R,4S)-2-((1R,2S)-1-Ethoxycarbonyl-2-vinyl-cyclopropylcarbamoyl)-4-hydroxy-cyclopentanecarboxylic acid tert-butyl ester (15)

Compound 14 (56 mg, 0.264 mmol) was dissolved in dioxane/water 1:1 (5 mL) and the mixture was cooled to 0° C. 1 M lithium hydroxide (0.52 mL, 0.520 mmol) was added and the mixture was stirred at 0° C. for 45 minutes, after which the mixture was neutralized with 1M hydrochloric acid and evaporated and coevaporated with toluene. The crystalline residue was dissolved in DMF (5 mL) and (1R,2S)-1-amino-2-vinyl-cyclopropane carboxylic acid ethyl ester hydrochloride (60 mg, 0.313 mmol) and diisopropylethylamine (DIEA) (138 µL, 0.792 mmol) were added and the solution was cooled to 0° C. HATU (120 mg, 0.316 mmol) was added and the mixture was stirred for 0.5 h at 0° C. and for an additional 2 h at room temperature. The mixture was then evaporated and extracted with EtOAc, washed with brine, dried, filtered and concentrated. Purification by flash column chromatography (toluene/EtOAc 1:1) provided the title compound (86 mg, 89%) as a colourless oil. The afforded oil was crystallised from ethyl acetate-hexane.

Example 16

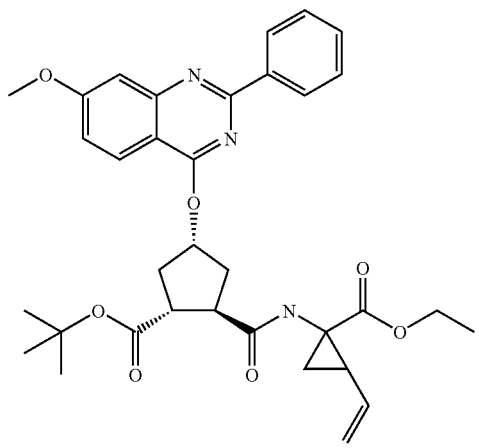

2-(1-Ethoxycarbonyl-2-vinyl-cyclopropylcarbamoyl)-4-(7-methoxy-2-phenyl-quinazolin-4-yloxy)-cyclopentanecarboxylic acid tert-butyl ester (16)

Compound 15 (700 mg, 1.9 mmol), 7-methoxy-2-phenyl-quinazolin-4-ol (670 mg, 2.66 mmol) and triphenyl phosphine (1245 mg, 4.75 mmol) were dissolved in THF (50 ml) and cooled to 0° C. Diisopropyl azidocarboxylate (960 mg, 4.75 mmol) was added slowly and the slurry was allowed to reach room temperature. After 12 h, the solvent was removed under reduced pressure and the residue taken up in ether and filtrated. Purification by column chromatography (SiO$_2$; 1% methanol in dichloromethane) gave the pure title compound (778 mg, 68%). MS (M+H)$^+$ 603.

Example 17

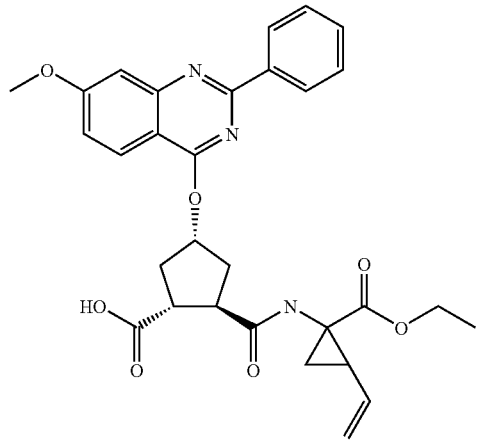

2-(1-Ethoxycarbonyl-2-vinyl-cyclopropylcarbamoyl)-4-(7-methoxy-2-phenyl-quinazolin-4-yloxy)-cyclopentanecarboxylic acid (17)

Compound 16 (780 mg, 1.29 mmol) was dissolved in dichloromethane (20 mL) and triethylsilane (0.4 mL). Trifluoromethanesulfonic acid was added dropwise at room temperature. The mixture was then left for 2 h at room temperature. Removal of the solvent gave pure title product (700 mg, 99%) MS (M+H)+ 546.

Example 18

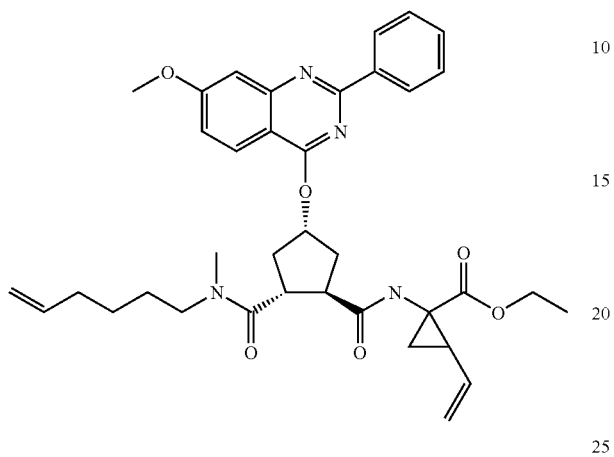

1-{[2-Hex-1-enyl-methyl-carbamoyl)-4-(7-methoxy-2-phenyl-quinazolin-4-yloxy)-cyclopentanecarbonyl]-amino}-2-vinyl-cyclopropanecarboxylicacid ethyl ester (18)

Compound 17 (700 mg, 1.28 mmol), N-methyl-1-hexen hydrochloride (291 mg, 1.94 mmol), diisopropyl ethylamine (750 mg, 5.8 mmol) and HATU (736 mg, 1.94 mmol) were dissolved in DMF (30 mL) and the mixture was stirred at room temperature over night. The solvent was removed and the residue was partitioned between dichloromethane and aqueous sodium bicarbonate. The organic phase was collected and the crude product was purified by column chromatography (silica gel, 2% methanol in dichloromethane→4% methanol in dichloromethane. Evaporation of the solvent gave pure title compound (700 mg, 85%). MS (M+H)+ 641.

Example 19

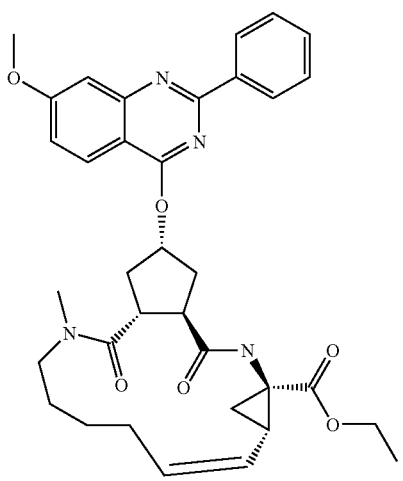

17-(7-Methoxy-2-phenyl-quinazolin-4-yloxy-13-methyl-2,14-dioxo-3,13-diazatricyclo[13.3.0.0*4,6*] octadec-7-ene-4-carboxylic acid ethyl ester (19s)

Compound 18 (700 mg, 1.1 mmol) and Hoveyda-Grubbs catalyst, 1$^{st}$ generation (55 mg, 0.091 mmol) were dissolved in degassed and dry 1,2-dichloroethane (1000 mL). The mixture was heated to reflux temperature over-night under argon atmosphere. Evaporation of the solvent and purification by column chromatography (silica gel; ether) gave 240 mg (40%) of pure title compound. MS (M+H)+ 613.

Example 20

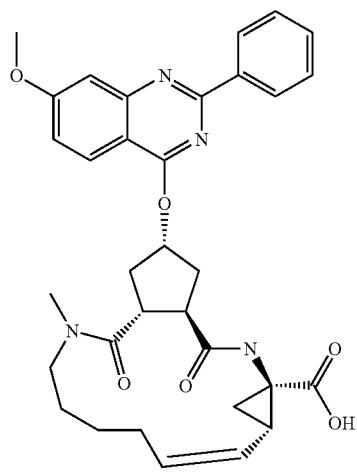

17-(7-Methoxy-2-phenyl-quinazolin-4-yloxy-13-methyl-2,14-dioxo-3,13-diazatricyclo[13.3.0.0*4,6*] octadec-7-ene-4-carboxylic acid (20)

Compound 19 (240 mg, 0.39 mmol) was dissolved in a 40 mL solvent mixture (THF 2:methanol 1:methanol 1). Aqueous lithium hydroxide (1.9 mL, 1M) was added and the reaction mixture was heated at 40° C. over-night. Purification by HPLC and column chromatography (silica gel, 5% methanol in dichloromethane) gave the title compound (75 mg, 33%). MS (M+H)+ 585.

Example 21

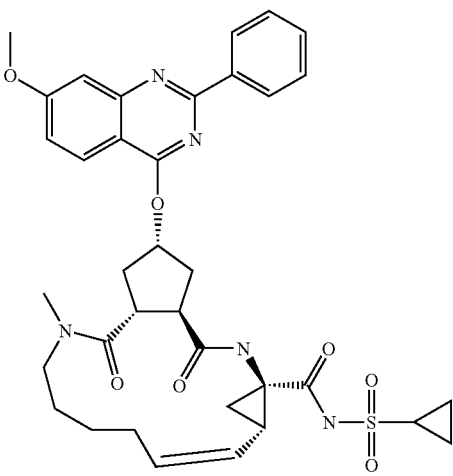

Cyclopropanesulfonic acid [17-(7-methoxy-2-phenyl-quinazolin-4-yloxy)-13-methyl-2,14-dioxo-3,13-diaza-tricyclo[13.3.0.0*4,6*]octadec-7-ene-4-carbonyl]-amide (21)

Compound 20 (75 mg, 0.13 mmol) and N,N,-carbonyldiimidazole (43 mg, 0.26 mmol) in THF (7 mL) were heated to reflux for 2 hours. Optionally, the formed azalactone can be isolated. DBU (29 µl), and cyclopropanesulfonamide, prepared as described in WO03/053349, (47 mg, 0.39 mmol) was then added and the mixture was stirred at 60° C. over-night. The reaction mixture was diluted with ethyl acetate (25 mL) and washed with 0.5 M citric acid. Purification by HPLC gave 30 mg pure title compound. MS (M+H)$^+$ 688.

Example 22

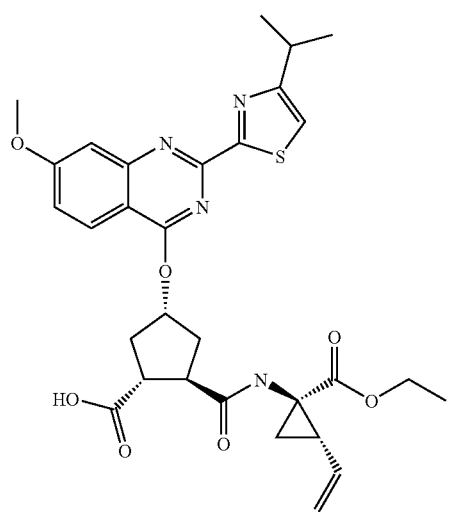

2-(1-Ethoxycarbonyl-2-vinyl-cyclopropylcarbamoyl)-4-[2-(4-isopropyl-thiazol-2-yl)-7-methoxy-quinazolin-4-yloxy]-cyclopentanecarboxylic acid (22)

Compound 15 (850.0 mg, 2.30 mmol), PPh$_3$ (1.60 g, 6 mmol), and the thiazole quinazoline 7 (820 mg, 2.72 mmol) were dissolved in THF (30 mL) in an ice bath. DIAD (1.18 ml, 6 mmol) was added dropwise. After stirring for 30 min, the mixture was stirred at RT for 2 days and then concentrated under vacuum. Flash column chromatography (silica, EtOAc—hexane) gave the Mitsunobu product. To a solution of this product (1.04 g, 1.60 mmol) and triethylsilane (460 mg, 4.00 mmol) in DCM (30 mL), TFA (30 mL) was added dropwise at RT. The mixture was stirred for 2 h at room temperature, evaporated under reduced pressure, and coevaporated twice with toluene. Flash column chromatography (silica, 94/6 DCM-MeOH) gave the title compound as a white solid (950 mg, 70%).

Example 23

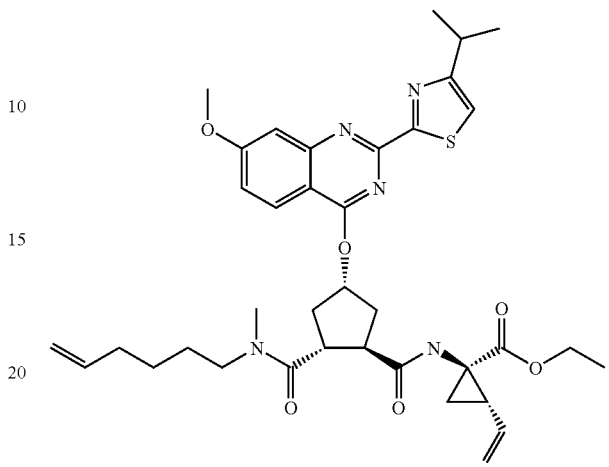

1-({2-Hex-5-enyl-methyl-carbamoyl)-4-[2-(4-isopropyl-thiazol-2-yl)-7-methoxy-quinazolin-4-yloxy]-cyclopentanecarbonyl}-amino)-2-vinyl-cyclopropanecarboxylic acid ethyl ester (23)

To a solution of the carboxylic acid 22 (1.60 mmol), N-methyl-5-hexenylamine HCl salt (360 mg, 2.40 mmol), and HATU (920 mg, 2.40 mmol) in 35 mL DMF, in an ice bath, was added DIEA (1.30 mL, 7.2 mmol) and stirred for 30 min. The mixture was stirred at RT for 3 h and then added to an saturated aqueous solution of sodium hydrogen-carbonate. The mixture was extracted three times with ethyl acetate. The organic phase was washed with brine, dried with sodium sulfate and evaporated under reduced pressure. The product was isolated by column chromatography on silica gel eluted with hexane-ethyl acetate (920 mg, 83%).

Example 24

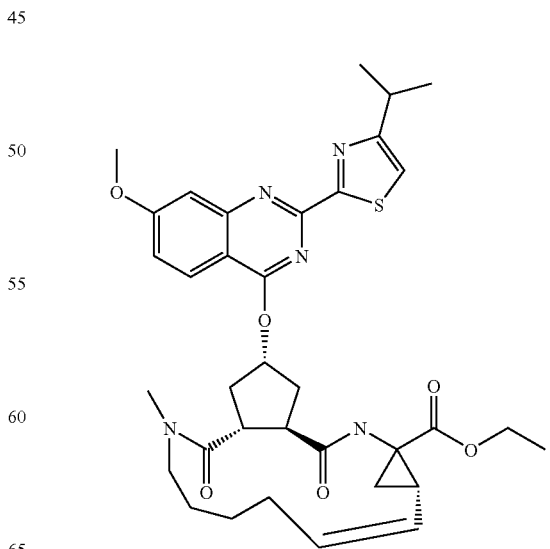

17-[2-(4-Isopropyl-thiazol-2-yl)-7-methoxy-quinazolin-4-yloxy]-13-methyl-2,14-dioxo-3,13-diaza-tricyclo[13.3.0.0*4,6*]octadec-7-ene-4-carboylic acid ethyl ester (24)

The diene 23 (900 mg) was dissolved in 900 mL DCE in a reflux setup. The system was successively evacuated and filled with argon 3×. Hoveyda-Grubbs $2^{nd}$ generation catalyst (90 mg) was added and the system was evacuated and filled with argon twice. The mixture was refluxed at 90° C. overnight, concentrated, and subjected to flash column chromatography (silica, EtOAc—hexane) to give the title compound as a gray-brown solid (380 mg, 46%). MS $(M+H)^+$ 662.

Example 25

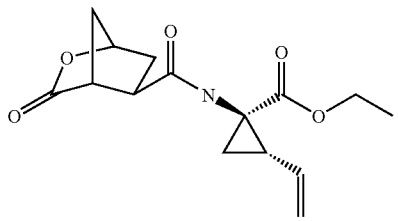

1-[(3-Oxo-2-oxa-bicyclo[2.2.1]heptane-5-carbonyl)-amino]-2-vinyl-cyclopropane carboxylic acid ethyl ester (25)

To a solution of 13 (857 mg, 5.5 mmol), in DMF (14 mL) and DCM (25 mL) at room temperature, was added the hydrochloride of 1-amino-2-vinyl-cyclopropanecarboxylic acid ethyl ester, prepared as described in WO03/099274, (1.15 g, 6.0 mmol), HATU (2.29 g, 6.0 mmol) and DIPEA (3.82 mL, 22 mmol). The reaction was stirred under $N_2$-atmosphere at ambient temperature for 1 h. LC/MS analysis showed complete conversion and the reaction mixture was concentrated in vacuo. The residue was redissolved in DCM (100 mL) and 0.1 M HCl (aq) and the phases were separated. The organic phase was washed with $NaHCO_3$ (aq) and brine, dried ($MgSO_4$) and filtered. Removal of the solvent in vacuo afforded the target compound (1.6 g, 99%). LC/MS>95%, m/z $(ESI^+)$=294 $(MH^+)$ Example 26

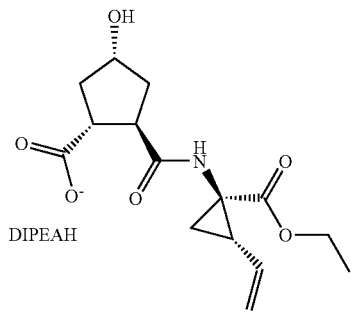

2-(1-Ethoxycarbonyl-2-vinyl-cyclopropylcarbamoyl)-4-hydroxy-cyclopentane carboxylic acid diisopropylethylamine salt (26)

To a solution of 25 (800 mg, 2.73 mmol) in water (15 mL) in a 20 mL microwave reaction vessel was added DIPEA (1.2 mL, 6.8 mmol) and a stirrbar. The reaction vessel was sealed and the immiscible slurry was shaken vigorously before insertion in the microwave cavity. After 1 min of pre-stirring, the reaction was irradiated for 40 min to a set temperature of 100° C. After cooling to 40° C., the transparent solution was concentrated in vacuo, and the residual brown oil co-evaporated 3× with MeCN to remove any residual water. The crude title compound, in the form of a DIPEA salt, was immediately taken forward to the next step. LC/MS>95%, m/z $(ESI^+)$=312 $(MH^+)$.

Example 27

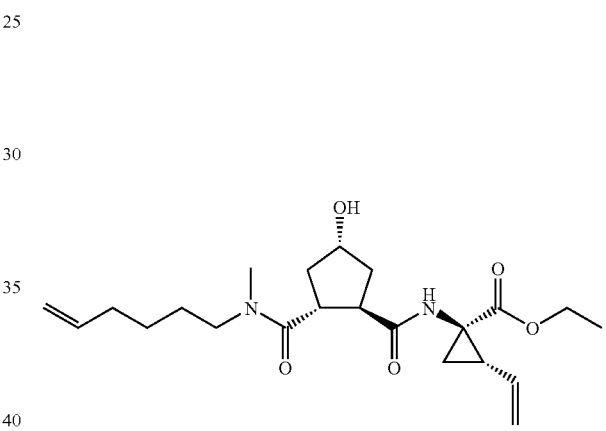

1-{[2-(Hex-5-enyl-methyl-carbamoyl)-4-hydroxy-cyclopentanecarbonyl]-amino}-2-inyl-cyclopropane carboxylic acid ethyl ester (27)

The crude compound 26 (5.5 mol) was dissolved in DCM (50 mL) and DMF (14 mL) followed by addition of HATU (2.09 g, 5.5 mmol), N-methyl-N-hex-5-enylamin (678 mg, 6.0 mmol) and DIPEA (3.08 mL, 17.5 mmol) at room temperature. The reaction was stirred at ambient temperature for 1 h. LC/MS analysis showed complete conversion of the starting materials and the reaction mixture was concentrated in vacuo. The residue was redissolved in EtOAc (100 mL) and the organic phase washed with 0.1 M HCl (aq), $K_2CO_3$ (aq) and brine, dried ($MgSO_4$) and filtered. Removal of the solvent in vacuo gave an oil which was purified by flash chromatography (Silica, EtOAc:MeOH) to afford the title compound (1.65 g, 74%). TLC(Silica): MeOH:EtOAc 5:95, $R_f$=0.5; LC/MS>95%, m/z (ESI$^+$)=407 (MH$^+$).

Example 28

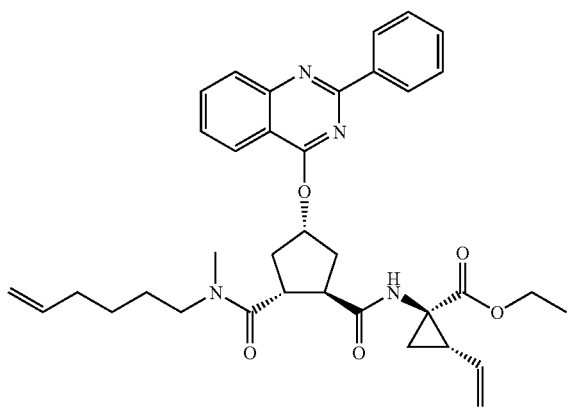

1-{[2-(Hex-5-enyl-methyl-carbamoyl)-4-(2-phenyl-quinazolin-4-yloxy)-cyclo-pentanecarbonyl]-amino}-2-vinyl-cyclopropanecarboxylic acid ethyl ester (28)

Compound 27 (0.15 g, 0.37 mmol) was dissolved in DMF and the solution was cooled to 0° C. NaH (60% in mineral oil, 0.04 g, 1.10 mmol) was added in one portion. After 0.5 h 4-chloro-2-phenylquinazoline (purchased from Aldrich) (0.98 g, 0.41 mmol) was added and after stirring at 0° C. for 0.5 h the reaction mixture was allowed to warm up to room temperature. After stirring at room temperature for 2 h, the reaction was quenched with citric acid (5%, aq) and extracted with EtOAc (3×20 mL). The combined organic phases were washed with citric acid (5%, aq, 2×20 mL), H$_2$O (2×20 mL). The organic phase was then dried over MgSO$_4$, filtered and evaporated. Purified by flash chromatography with DCM/MeOH to yield 166 mg of product (9)/hydrolysed product (48/52). This mixture was used in the next step.

Example 29

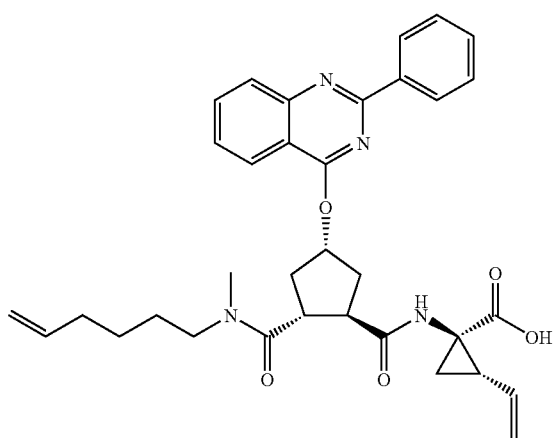

1-{[2-(Hex-5-enyl-methyl-carbamoyl)-4-(2-phenyl-quinazolin-4-yloxy)-cyclo-pentanecarbonyl]-amino}-2-vinyl-cyclopropanecarboxylic acid (29)

Compound 28 (0.17 g, 0.27 mmol) was dissolved in DMF (2.5 mL) and transferred to a microwave vial. LiOH (aq, 2 M, 8 mL) was added and the reaction was heated in the microwave at 130° C. for 1 h. Quenched the reaction with HCl (aq, 1M) to pH 1 and extracted with DCM (3×20 mL). Combined organic phases were washed with HCl (aq, 1M, 20 mL) and H$_2$O (3×30 mL). Water phase was back-extracted with DCM (2×30 mL). Organic phases were dried over MgSO$_4$, filtered and evaporated. Purified by flash chromatography (DCM/MeOH) to yield the title compound (0.08 g, 49%).

Example 30

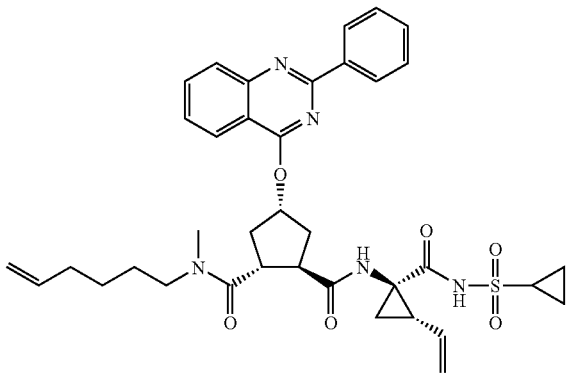

4-(2-Phenyl-quinazolin-4-yloxy)-cyclopentane-1,2-dicarboxylic acid 1-[(1 cyclo-propanesulfonecarbonyl-2-vinylcyclopropyl)-amide]2-(hex-5-enylmethylamide) (30)

Compound 29 (0.05 g, 80.70 μmol) was dissolved in DMF/DCM (1:3, 1200 μL) and transferred to a vial loaded with EDAC. The mixture was allowed to incubate for 10 min at room temperature. Addition of DMAP was followed by 20 min of incubation at room temperature. A mixture of cyclopropane sulfonamide, prepared as described in WO03/053349, (39.1 mg, 0.32 mmol) and DBU (49.1 mg, 0.32 mmol) in DCM/DMF (1:1, 800 μL) was added to the activated compound 10. The reaction mixture was heated in the microwave for 30 min at 100° C. After evaporation of solvents in vacuo the residue was redissolved in DCM. The organic phase was washed with HCl (1M, 3×20 mL). Water phase was then back-extracted with DCM (1×20 mL). Combined organic phases were washed with HCl (1M, aq), brine and water.

Dried the organic phase over MgSO₄ and evaporated. Dried in vacuo to yield the title compound (50 mg, 90%).

Example 31

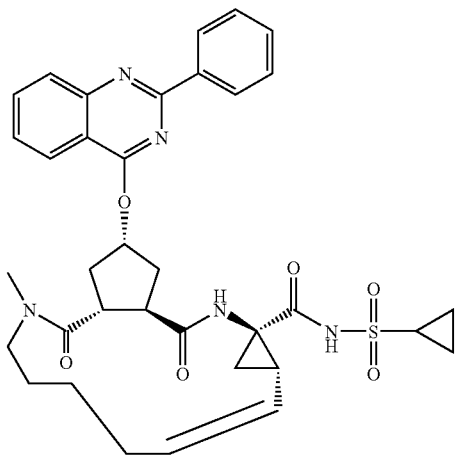

Cyclopropanesulfonic acid [13-methyl-2,14-dioxo-17-(2-phenylquinazolin-4-yl-oxy)3,13-diaza-tricyclo[13.3.0.0*4,6*]octadec-7-ene-4-carbonyl]amide (31)

A solution of compound 30 (0.02 g, 25.80 µmol) in dry DCE (15 mL) was added to a dry microwave vial loaded with Hoveyda Grubbs second generation catalyst (83.1 mg, 5.0 µmol). The solution was degassed with nitrogen gas before heated in the microwave for 10 min at 150° C. After evaporation of solvent, purification was done on prep-LC which gave the title compound (3.00 mg, 29%).

Example 32

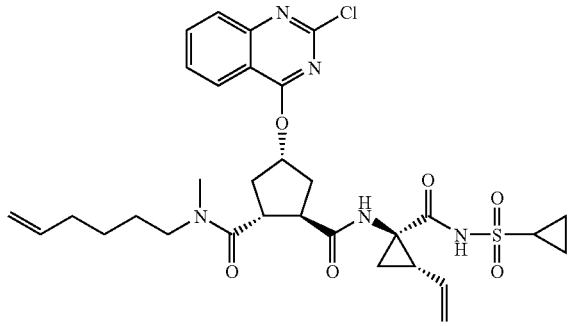

1-{[4-(2-Chloro-quinazolin-4-yloxy)-2-(hex-5-enyl-methyl-carbamoyl)-cyclo-pentanecarbonyl]-amino}-2-vinyl-cyclopropanecarboxylic acid ethyl ester (32)

Compound 27 (0.49 g, 1.21 mmol) was dissolved in DMF (1 mL) and transferred to a 20 mL microwave reaction vessel equipped with a magnetic stirring bar and aqueous LiOH (2 M, 10.5 mL) and was added. The reaction vessel was sealed and the immiscible slurry was shaken vigorously before insertion in the microwave cavity. The reaction was irradiated for 30 min to 130° C. The reaction mixture was cooled to 40° C. and the clear solution acidified to pH 2 with aqueous HCl (1 M, 24 mL) and extracted 3× with EtOAc (20 mL). The pooled org phases were washed with brine, dried (MgSO₄) and filtered. The solvent was removed in vacuo which gave the acid (0.41 g, 90%). The crude acid (410 mg, 1.09 mmol) was dissolved in DMF (1.5 mL) and DCM (4.5 mL) followed by addition of EDAC (417 mg, 2.18 mmol) at room temperature. The mixture was allowed to incubate with stirring at room temperature. After 10 min, DMAP (133 mg, 1.09 mmol) was added followed by another 20 min incubation at room temperature. Subsequently, a pre-mixed solution of cyclopropanesulfonic acid amide, prepared as described in WO03/053349, (527 mg, 4.36 mmol) and DBU (663 mg, 4.36 mmol) in DMF (2 mL) and DCM (2 mL) was added followed by heating in the microwave to 100° C. for 30 min. The resulting red solution was concentrated in vacuo and redissolved in EtOAc (20 mL). The organic phase was washed with 1 M HCl (aq) (3×10 mL) and brine (10 mL), dried (MgSO₄) and filtered. The solvent was removed in vacuo and the residue was purified by chromatography (silica, EtOAc:MeOH, 97.5:2.5) to give the sulphonamide derivative (0.40 g, 77%); LC/MS>95%, m/z (ESI⁺)=482 (MH⁺).

The sulfonamide derivative (0.33 g, 0.69 mmol) was dissolved in DMF (9 mL) and the solution was cooled to 0° C. NaH (60% in mineral oil, 0.04 g, 1.10 mmol) was added in portions. After 0.5 h 2,4-dichloro-quinazoline (0.15 g, 0.75 mmol) was added and after stirring at 0° C. for 1 h the reaction was allowed to warm up to room temperature. The reaction was quenched by addition of citric acid (5%, aq) and extracted with DCM (3×20 mL). The combined organic phases were washed with citric acid (5%, aq, 2×20 mL), H₂O (2×20 mL). The organic phase was then dried over MgSO₄, filtered and evaporated to yield the title compound (0.38 g, 79%).

Example 33

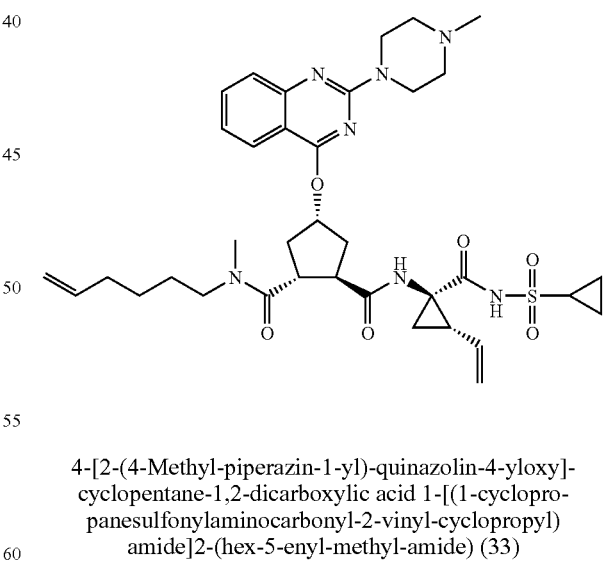

4-[2-(4-Methyl-piperazin-1-yl)-quinazolin-4-yloxy]-cyclopentane-1,2-dicarboxylic acid 1-[(1-cyclopropanesulfonylaminocarbonyl-2-vinyl-cyclopropyl)amide]2-(hex-5-enyl-methyl-amide) (33)

Compound 32 (0.03 g, 46.6 µmol) was loaded in a microwave vial together with 1-methyl-piperazine (0.5 mL). The mixture was heated neat for 10 min at 120° C. in the microwave system. The reaction was quenched by addition of citric acid (5%, aq) to pH 5 and extracted with DCM (15 mL×2). The combined organic phases were washed with citric acid (10 mL×3). Back-extracted water phase was washed with DCM (20 mL×2) and the combined organic phases were dried over Na$_2$SO$_4$, filtered and evaporated which gave the title compound (27 mg, 82%).

Example 34

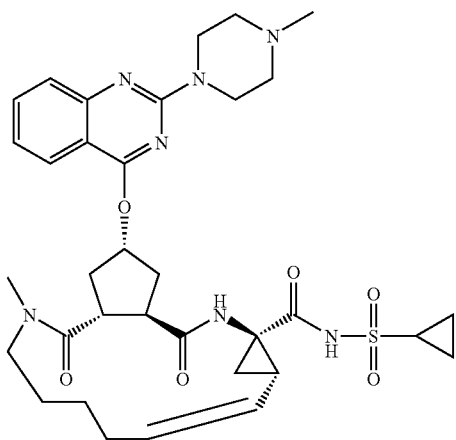

Cyclopropanesulfonic acid {13-methyl-17-[2-(4-methyl-piperazin-1-yl)quinazolin-4-yloxy]-2,14-dioxo-3,13-diaza-tricyclo[13.3.0.0*4,6*]octadec-7-ene4-carbonyl}-amide (34)

A solution of compound 33 (23.5 mg, 32.2 μmol) in dry DCE (20 mL) was added to two dry microwave vials each loaded with Hoveyda Grubbs second generation catalyst (2.6 mg, 4.2 μmol). The solution was degassed with nitrogen gas before heated in the microwave for 10 min at 150° C. The two batches were combined after heating and the solvents evaporated. Purification on prep-LC gave the title compound (5.00 mg, 22%).

Example 35

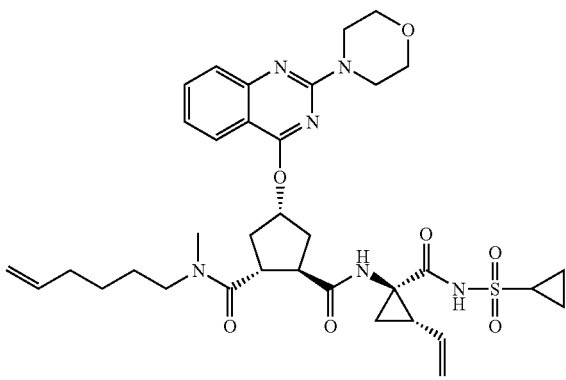

4-(2-Morpholin-4-yl-quinazolin-4-yloxy)-cyclopentane-1,2-dicarboxylic acid 1-[(1-cyclopropanesulfonylaminocarbonyl-2-vinyl-cyclopropyl)-amide]2-(hex-5-enyl-methyl-amide) (35)

Compound 32 (0.03 g, 46.6 μmol) was loaded in a microwave vial together with morpholine (0.5 mL). The mixture was heated neat for 10 min at 120° C. in the microwave system. To quench the reaction citric acid (5%, aq) was added to pH 5 and extracted with DCM (15 mL×2). The combined organic phases were washed with citric acid (10 mL×3). Back-extracted water phase was washed with DCM (20 mL×2) and the combined organic phases were dried over Na$_2$SO$_4$, filtered and evaporated which gave the title compound (17 mg, 52%).

Example 36

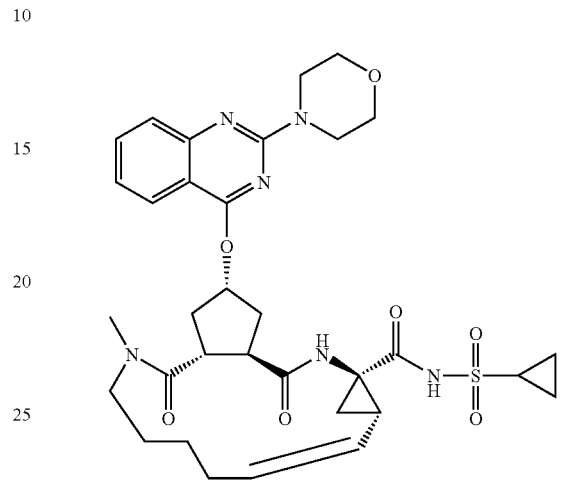

Cyclopropanesulfonic acid [13-methyl-17-(2-morpholin-4-yl-quinazolin-4-yloxy)-2,14-dioxo-3,13-diaza-tricyclo[13.3.0.0*4,6*]octadec-7-ene-4-carbonyl]-amide (36)

A solution of compound 35 (17 mg, 24.5 μmol) in dry DCE (15 mL) was added to a dry microwave vial loaded with Hoveyda Grubbs second generation catalyst (3.8 mg, 6.1 μmol). The solution was degassed with nitrogen gas before heated in the microwave for 10 min at 150° C. Evaporation of the solvents followed by purification on prep-LC gave the title compound (9.2 mg, 56%).

Example 37

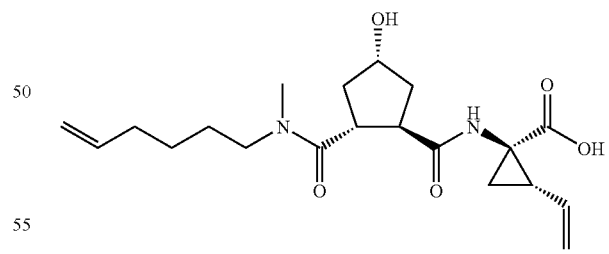

1-{[2-(Hex-5-enyl-methyl-carbamoyl)-4-hydroxy-cyclopentanecarbonyl]-amino}-2-vinyl-cyclopropanecarboxylic acid (37)

Compound 27 (493 mg, 1.21 mmol) was dissolved in DMF (1 mL) and transferred to a 20 mL microwave reaction vessel equipped with a magnetic stirring bar and aqueous LiOH (2 M, 10.5 mL) was added. The reaction vessel was sealed and the immiscible slurry was shaken vigorously before insertion in the microwave cavity. The reaction was irradiated for 30 min to 130° C. The reaction mixture was cooled to 40° C. and the clear solution was acidified to pH 2 with aqueous HCl (1 M, 24 mL) and extracted with EtOAc (3×20 mL). The pooled org phases were washed with brine, dried (MgSO$_4$) and filtered. The solvent was removed in vacuo to afford the title compound (410 mg, 90%). LC/MS>95%, m/z (ESI$^+$)=379 (MH$^+$).

Example 38

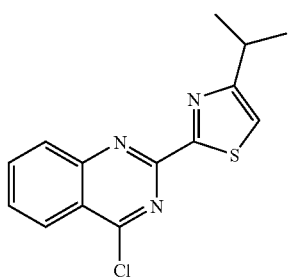

4-Chloro-2-(4-isopropyl-thiazol-2-yl)-quinazoline (38)

Compound 9 (100 mg, 0.37 mmol) was added to phosphorous oxychloride (2 mL) and heated to 100° C. for 2 h. The reaction mixture was then poured on ice with vigorous stirring and made basic with NaOH (aq). The resulting slurry was extracted with ether (3×20 mL) and the combined organic phases were dried (MgSO$_4$) and filtered. Removal of the solvent in vacuo afforded the title compound in quantitative yield. LC/MS>95%, m/z (ESI$^+$)=290 (MH$^+$).

Example 39

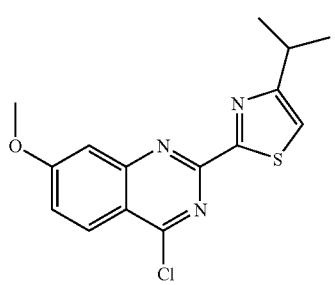

4-Chloro-2-(4-isopropyl-thiazol-2-yl)-7-methoxy-quinazoline (39)

Compound 7 (300 mg, 1 mmol) was added to phosphorous oxychloride (6 mL) and heated to 90° C. for 4 h. The reaction mixture was then poured on ice with vigorous stirring and made basic with NaOH (aq). The resulting slurry was extracted with ether (3×50 mL) and the combined organic phases were dried (MgSO$_4$) and filtered. Removal of the solvent in vacuo afforded the title compound in quantitative yield. LC/MS>95%, m/z (ESI$^+$)=320 (MH$^+$).

Example 40

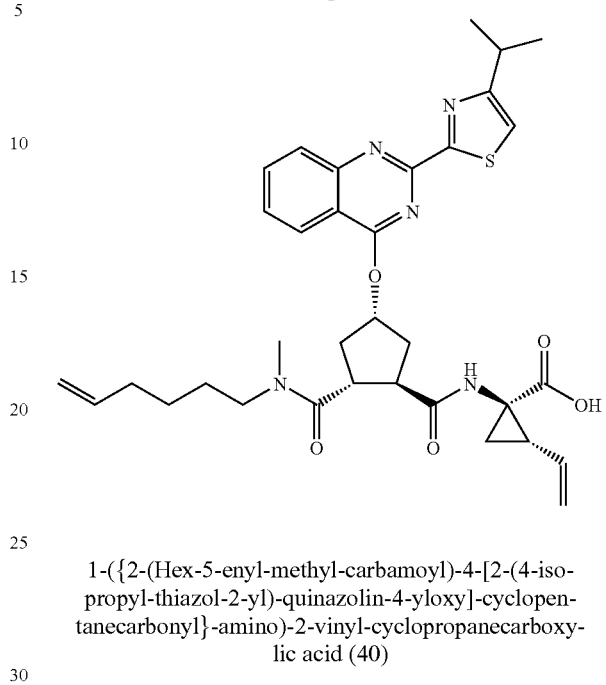

1-({2-(Hex-5-enyl-methyl-carbamoyl)-4-[2-(4-isopropyl-thiazol-2-yl)-quinazolin-4-yloxy]-cyclopentanecarbonyl}-amino)-2-vinyl-cyclopropanecarboxylic acid (40)

Compound 37 (26 mg, 70 μmol) was dissolved in THF (3 mL, dried with mol. siev.). To this solution was added NaH (60% in oil, 8.2 mg, 210 μmol) and the reaction was incubated for 10 min at ambient temperature. To the reaction mixture was then added compound 39 (17.6 mg, 61 μmol) followed by incubation at ambient temperature for 16 h. To the reaction was then added 0.1 M HCl (aq) and EtOAc, the phases separated and the aqueous phase extracted with another portion of EtOAc. The pooled organic phases were dried (MgSO4), filtered and concentrated in vacuo which gave a crude product which was further purified by flash-chromatography (Silica; DCM:MeOH) to afford the title compound (30 mg, 78%). LC/MS>95%, m/z (ESI$^+$)=632 (MH$^+$).

Example 41

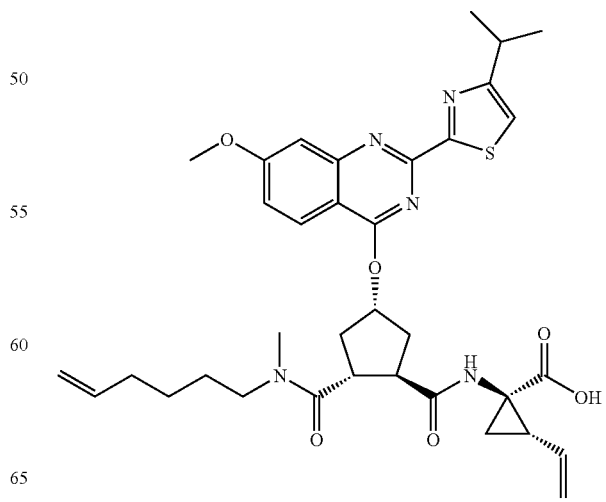

1-({2-(Hex-5-enyl-methyl-carbamoyl)-4-[2-(4-isopropyl-thiazol-2-yl)-7-methoxy-quinazolin-4-yloxy]-cyclopentanecarbonyl}-amino)-2-vinyl-cyclopropanecarboxylic acid (41)

The procedure described in example 40 was followed but with the use of quinazoline derivative 38 instead of 39 which gave the title compound. LC/MS>95%, m/z (ESI$^+$)=662 (MH$^+$).

Example 42

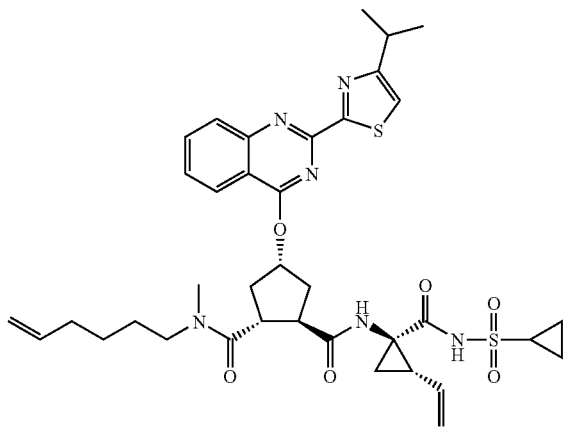

4-[2-(4-Isopropyl-thiazol-2-yl)-quinazolin-4-yloxy]-cyclopentane-1,2-dicarboxylic acid 1-[(1-cyclopropanesulfonylaminocarbonyl-2-vinyl-cyclopropyl)-amide]2-(hex-5-enyl-methyl-amide) (42)

Compound 40 (25 mg, 0.0395 mmol) was dissolved in DMF:DCM (1:4, 700 µL), followed by the addition of EDAC (15.2 mg, 0.079 mmol) at 25° C. The mixture was incubated for 10 minutes, followed by the addition of DMAP (4.8 mg, 0.0395 mmol) and another additional 20 minutes of incubation. A pre-mixed solution of cyclo-propylsulfonamide, prepared as described in WO03/053349, (19.3 mg, 0.158 mmol) and DBU (23.8 µL, 0.158 mmol) in DCM:DMF (1:1, 200 µL) was added, followed by heating in the microwave to 100° C. for 30 min. The resulting red solution was concentrated in vacuo which gave a crude product which was further purified by Prep LCMS to afford compound MS-103-156 (19 mg, 65%), m/z (ESI$^+$)=735.28 (MH$^+$).

Example 43

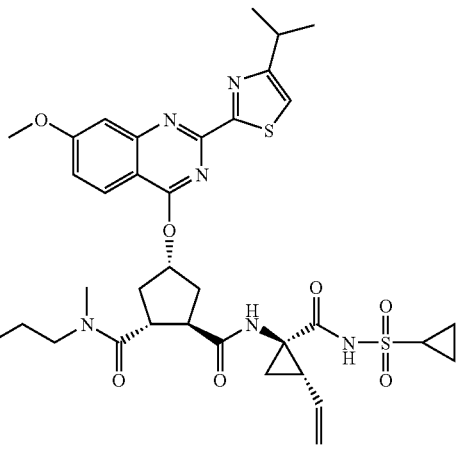

4-[2-(4-Isopropyl-thiazol-2-yl)-7-methoxy-quinazolin-4-yloxy]-cyclopentane-1,2-dicarboxylic acid 1-[(1-cyclopropanesulfonylaminocarbonyl-2-vinyl-cyclopropyl)-amide]2-(hex-5-enyl-methyl-amide) (43)

The procedure described in example 42 was followed but with the use of compound 41 instead of compound 40, which gave the title compound (12.3 mg, 36%), m/z (ESI$^+$)=765.28 (MH$^+$).

Example 44

Cyclopropanesulfonic acid {17-[2-(4-isopropyl-thiazol-2-yl)-quinazolin-4-yloxy-]-13-methyl-2,14-dioxo-3,13-diaza-tricyclo[13.3.0.0*4,6*]octadec-7-ene-4-carbonyl}-amide (44)

Compound 42 (14.9 mg, 0.02 mmol) was dissolved in dry DCE (8 mL) under nitrogen, followed by the addition of Hoveyda-Grubbs catalyst second generation (3.17 mg, 0.005 mmol) dissolved in dry DCE (4 mL). The mixture was microwave heated to 15° C. for 10 minutes and then concentrated in vacuo which gave a crude product which was purified by Prep LCMS to afford the title compound (9 mg, 64%), m/z (ESI$^+$)=707.27 (MH$^+$).

Example 45

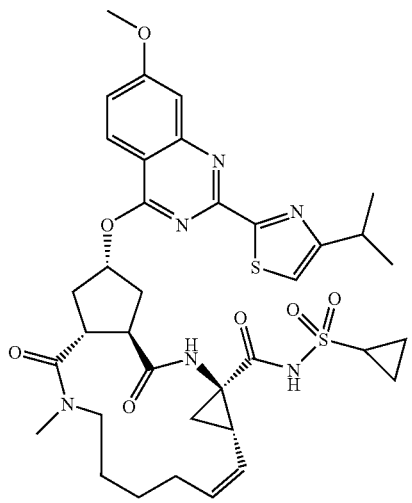

Cyclopropanesulfonic acid {17-[2-(4-isopropyl-thiazol-2-yl)-7-methoxy-quinazolin-4-yloxy]-13-methyl-2,14-dioxo-3,13-diaza-tricyclo[13.3.0.0*4,6*]octadec-7-ene-4-carbonyl}-amide (45)

The procedure described in Example 44 was followed but with the use of compound 43 (12.3 mg, 0.016 mmol) instead of compound 42, which gave the title compound (4.7 mg, 40%), m/z (ESI$^+$)=737.11 (MH$^+$).

Example 46

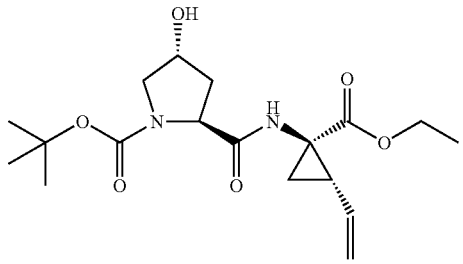

2-(1-Ethoxycarbonyl-2-vinyl-cyclopropylcarbamoyl)-4-hydroxy-pyrrolidine-1-carboxylic acid tert-butyl ester (46)

Boc-protected proline (4 g, 17.3 mmol), HATU (6.9 g, 18.2 mmol) and 1-amino-2-vinyl-cyclopropanecarboxylic acid ethyl ester prepared as described in WO03/099274, (3.5 g, 18.3 mmol) were dissolved in DMF (60 ml) and cooled to 0° on an ice-bath. Diisopropylethyl amine (DIPEA) (6 ml) was added. The ice-bath was removed and the mixture was left at ambient temperature over-night. Dichloromethane (~80 ml) was then added and the organic phase was washed with aqueous sodium hydrogen carbonate, citric acid, water, brine and dried over sodium sulfate. Purification by flash chromatography (ether→7% methanol in ether) gave pure title compound (6.13 g, 96%)

Example 47

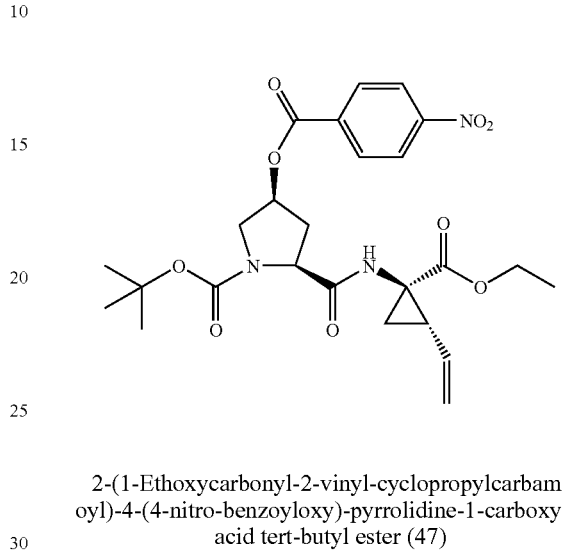

2-(1-Ethoxycarbonyl-2-vinyl-cyclopropylcarbamoyl)-4-(4-nitro-benzoyloxy)-pyrrolidine-1-carboxylic acid tert-butyl ester (47)

Compound 46 (6.13 g, 16.6 mmol), 4-nitrobenzoic acid (4.17 g, 25 mmol) and PPh$_3$ (6.55 g, 25 mmol) was dissolved in THF (130 ml). The solution was cooled to ~0° and diisopropyl azidocarboxylate (5.1 g, 25 mmol) was added slowly. The cooling was then removed and the mixture was left overnight at ambient condition. Aqueous sodium hydrogen carbonate (60 ml) was added and the mixture was extracted with dichloro-methane. Purification by flash chromatography (pentane-ether, 2:1→pentane-ether, 1:2→2% methanol in ether) gave pure title compound (6.2 g, 72%).

Example 48

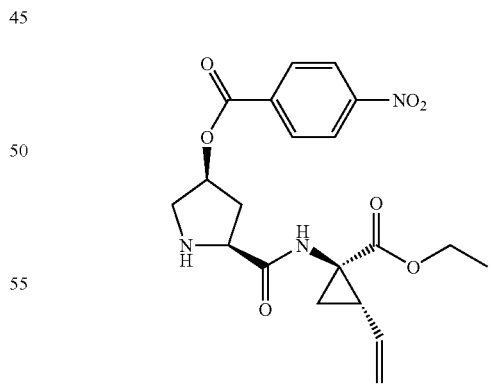

4-Nitro-benzoic acid 5-(1-ethoxycarbonyl-2-vinyl-cyclopropylcarbamoyl)-pyrrolidin-3-yl ester (48)

Compound 47 (6.2 g, 12 mmol) was dissolved in an ice-cold mixture of trifluoro-methanesulfonic acid 33% in dichloromethane. The ice-bath was then removed and the mixture was left at room temperature for ~1.5 h. The solvent was evaporated and 0.25 M sodium carbonate added and the mixture was extracted with dichloromethane. Evaporation gave the title compound (4.8 g, 95%) as a yellowish powder.

Example 49

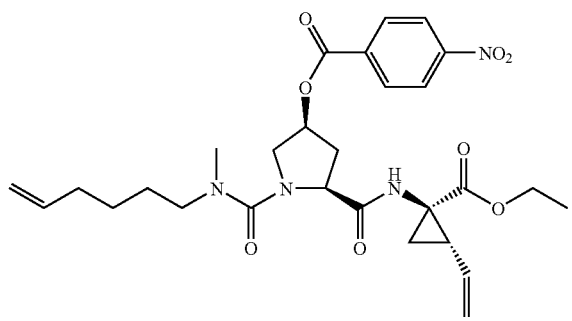

4-Nitro-benzoic acid 5-(1-ethoxycarbonyl-2-vinyl-cyclopropylcarbamoyl)-1-(hex-5-enyl-methyl-carbamoyl)-pyrrolidin-3-yl ester (49)

Compound 48 (4.5 g, 10.8 mmol) was dissolved in THF (160 ml). A tablespoon of sodium hydrogen carbonate was added followed by phosgene (11.3 ml, 20% in toluene). The mixture was stirred vigorously for 1 h. The mixture is filtrated and re-dissolved in dichloromethane (160 ml). Sodium hydrogen carbonate (~a tablespoon) was added followed by the amine hydrochloride (2.9 g, 21.6 mmol). The reaction was the left in room temperature over night. Purification by flash chromatography (ether→3% methanol in ether) gave pure title compound (5.48 g, 91%),

Example 50

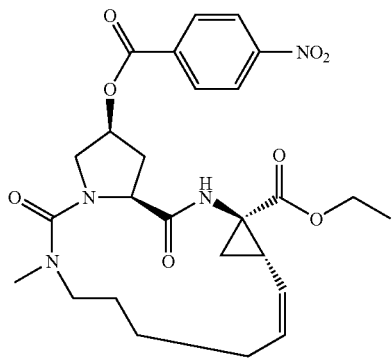

13-Methyl-17-(4-nitro-benzoyloxy)-2,14-dioxo-3,13,15-triaza-tricyclo[13.3.0.0*4,6*]-octadec-7-ene-4-carboxylic acid ethyl ester (50)

Compound 49 (850 mg, 1.53 mmol) was dissolved in 1.51 degassed and dried 1,2-di-chloroethane and refluxed under argon atmosphere over night. Scavenger (MP-TMT, P/N 800470 from Argonaut technologies, ~½ teaspoon) was added and the mixture was stirred for 2 h, filtrated and concentrated by reduced pressure. The crude product was crystallized from dichloromethane/n-hexane to yield the title compound (600 mg, 74%).

Example 51

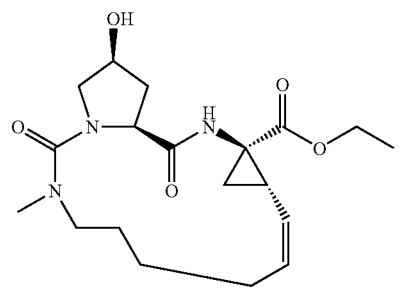

17-Hydroxy-13-methyl-2,14-dioxo-3,13,15-triaza-tricyclo[13.3.0.0*4,6*]octadec-7-ene-4-carboxylic acid ethyl ester (51)

Compound 50 (200 mg, 0.38 mmol) was dissolved in a mixture of methanol/THF/water, 1:2:1, (20 ml) and cooled on ice-bath. Lithium hydroxide (1.9 ml, 1M) was added slowly. The mixture was stirred for 4 h at 0° C., then neutralized with aqueous acetic acid (20 ml) and extracted with dichloromethane. The organic phase was washed with bicarbonate, water, brine and dried over magnesium sulfate. Purification by chromatography (2% methanol in dichloromethane→4%) gave the title compound as a greyish powder (80%).

Example 52

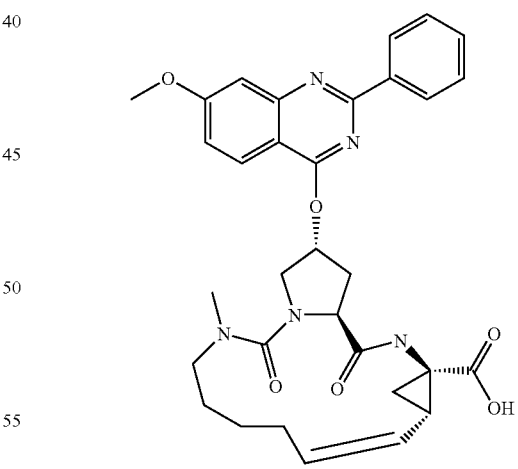

17-(7-Methoxy-2-phenyl-quinazolin-4-yloxy-13-methyl-2,14-dioxo-3,13,15-triaza-tricyclo [13.3.0.0*4,6*]octadec-7-ene-4-carboxylic acid (52)

Compound 51 (220 mg, 0.58 mmol), compound 11 (220 mg, 0.87 mmol) and triphenyl-phosphine (228 mg, 0.87 mmol) were suspended in dry THF (20 mL) and cooled to 0° C. Diisopropyl azidocarboxylate (176 mg, 0.87 mmol) was added dropwise. After the addition the reaction mixture was allowed to reach room temperature and left over-night. The solvent was removed and aqueous sodium hydrogen carbonate was added and the mixture was extracted with dichloromethane. The organic phase was collected and the solvent removed. The crude product obtained was dissolved in a 10 mL mixture of THF/methanol/water (2:1:1). Aqueous lithium hydroxide (1 mL, 1M) was added and the mixture was heated to 50° C. over-night. Water (20 mL) was then added and the volume reduced to half Aqueous lithium hydroxide (1 mL, 1M) was added and the aqueous phase was washed with several portions of dichloromethane. The water phase was then acidified with citric acid and extracted with dichloromethane. Evaporation of the solvent and purification by HPLC gave pure title compound (79 mg, 23%). M+H⁺ 586.

Example 53

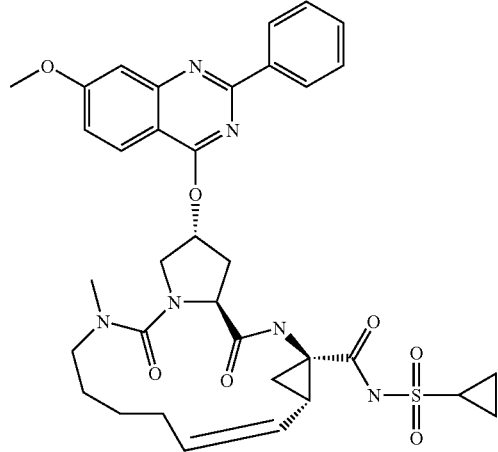

Cyclopropanesulfonic acid [17-(7-methoxy-2-phenyl-quinazolin-4-yloxy)-13-methyl-2,14-dioxo-3,13,15-triaza-tricyclo[13.3.0.0*4,6*]octadec-7-ene-4-carbonyl]-amide (53)

Compound 52 (79 mg, 0.13 mmol) and N,N-carbonyldiimidazole (33 mg, 0.2 mmol) were dissolved in THF (5 mL) in a sealed microwave tube under nitrogen atmosphere. The mixture was heated to 100° C. for 10 min and then left to cool down. A mixture of DBU (62 mg, 0.4 mmol) and cyclopropanesulfonamide (45 mg, 0.4 mmol) in THF (5 mL) were added. Heating was then continued at 100° C. for 60 min. After cooling, the solvent was removed and the residue dissolved in ethyl acetate. The organic phase was washed with 0.5 M citric acid. Purification by HPLC gave pure title compound (29 mg, 32%). MS (M+H)⁺ 689.

Example 54

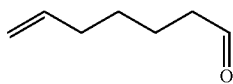

Hept-6-enal (54)

To a solution of hept-6-en-1-ol (1 mL, 7.44 mmol) and N-methylmorpholine N-oxide (1.308 g, 11.17 mmol) in DCM (17 mL) was added ground molecular sieves (3.5 g, 4 Å). The mixture was stirred for 10 min at room temperature under nitrogen atmosphere before tetrapropylammonium perruthenate (TPAP) (131 mg, 0.37 mmol) was added. After stirring for additional 2.5 h the solution was filtered through celite. The solvent was then carefully evaporated and the remaining liquid was purified by flash column chromatography (DCM) to give the volatile title compound (620 mg, 74%) as an oil.

Example 55

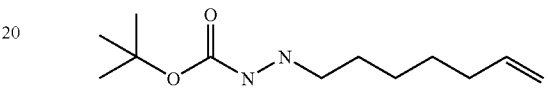

N'-Hept-6-en-(E)-ylidene-hydrazinecarboxylic acid tert-butyl ester (55)

To a solution of 54 (68 mg, 0.610 mmol) and tert-butyl carbazate (81 mg, 0.613 mmol) in MeOH (5 mL) was added ground molecular sieves (115 mg, 3 Å). The mixture was stirred for 3 h after which it was filtered through celite and evaporated. The residue was dissolved in dry THF (3 mL) and AcOH (3 mL). NaBH₃CN (95 mg, 1.51 mmol) was added and the solution was stirred over night. The reaction mixture was diluted with saturated NaHCO₃ solution (6 mL) and EtOAc (6 mL). The organic phase was washed with brine, saturated NaHCO₃, brine, dried over MgSO₄ and evaporated. The cyanoborane adduct was hydrolyzed by treatment with MeOH (3 mL) and 2 M NaOH (1.9 mL). The mixture was stirred for 2 h and the MeOH was evaporated. H₂O (5 mL) and DCM (5 mL) were added and the water phase was extracted three times with DCM. The combined organic phases were dried and evaporated. Purification by flash column chromatography (toluene/ethyl acetate 9:1 with 1% triethylamine and toluene/ethyl acetate 6:1 with 1% triethylamine) provided the title compound (85 mg, 61%) as an oil.

Example 56

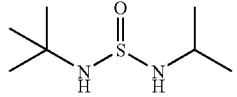

N-(tert-Butyl)-N'-isopropylthiourea (56)

To a solution of tert-butylisothiocyanate (5.0 mL, 39 mmol) in CH₂Cl₂ (200 mL) were added isopropylamine (4.0 mL, 47 mmol) and diisopropylethylamine (DIEA) (6.8 mL, 39 mmol), and the mixture was stirred at rt for 2 h. The reaction mixture was diluted with EtOAc, washed with 10% citric acid (2×), saturated NaHCO₃ (2×), H₂O (2×), and brine (1×). The organic layer was dried (MgSO₄) and evaporated to yield compound 94 (3.3 g, 52%) as a white solid which was used without further purification.

Example 57

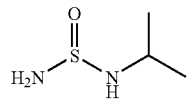

N-Isopropylthiourea (57)

Compound 56 (3.3 g, 20 mmol) was dissolved in conc. HCl (45 mL) and the solution was refluxed for 40 min. The mixture was allowed to cool to rt and then cooled in an ice bath and basified to pH 9.5 with solid and saturated NaHCO$_3$, after which the product was extracted into EtOAc (3×). The combined organic phases were washed with H$_2$O (2×) and brine (1×), dried (MgSO$_4$), and evaporated to yield crude title compound (2.1 g, 90%) which was used without further purification.

Example 58

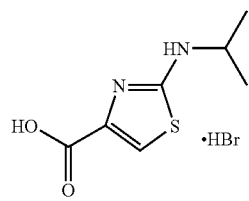

2-(Isopropylamino)-1,3-thiazole-4-carboxylic acid hydrobromide (58)

A suspension of compound 57 (2.1 g, 18 mmol) and 3-bromopyruvic acid (3.0 g, 18 mmol) in dioxane (180 mL) was heated to 80° C. Upon reaching 80° C. the mixture became clear, and soon thereafter the product started to precipitate as a white solid. After 2 h of heating, the reaction mixture was cooled to rt and the precipitate was filtered off and collected. This yielded pure title compound (4.4 g, 94%).

Example 59

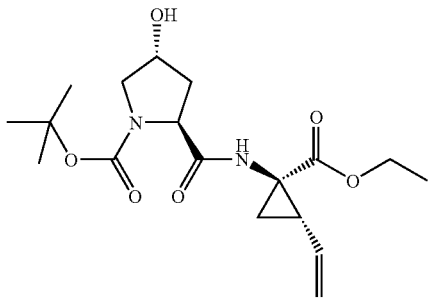

(2S,4R)-2-((1S 2R)1-Ethoxycarbonyl-2-vinyl-cyclopropylcarbamoyl)-4-hydroxy-pyrrolidine-1-carboxylic acid tert.butyl ester (59)

A solution of HATU (6 g), diisopropylethylamine (6.8 mL), (1R,2S)-1-amino-2-vinyl-cyclopropanecarboxylic acid ethyl ester (1.5 g) and BOC-L-hydroxyproline (1.6 g) in dichloromethane was stirred for 1 hrs. The mixture was extracted with DCM-NaHCO$_3$ (aq) dried and concentrated. HPLC purity ca 90% (M+H)$^+$ 369.1.

Example 60

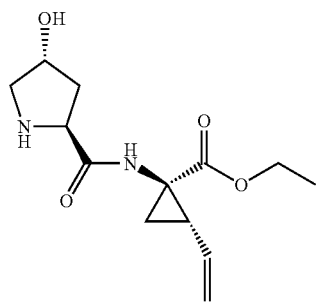

(1S,2R)-1-[(2S,4R)-(4-Hydroxy-pyrrolidine-2-carbonyl)-amino]-2-vinyl-cyclopropane-carboxylic acid ethyl ester (60)

Compound 59 was kept in 30% trifluoroacetic acid in dichloromethane and 1% MeOH for 2 hrs before it was concentrated to dryness. The residue was re-dissolved in dichloromethane and during stirring 1N NaOH was added to pH 10-11. The organic layer was separated and concentrated which gave 1.6 g of the title compound. HPLC purity ca. 90% (M+H)$^+$ 269.1.

Example 61

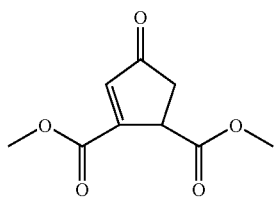

(Rac)-4-oxocyclopent-2-ene-1,2-dicarboxylic acid dimethyl ester (61)

(1R,2S)-4-oxo-cyclopentane-1,2-dicarboxylic acid dimethyl ester (4.8 g, 23.8 mmol) and CuBr$_2$ (11.9 g, 53.2 mmol) were dissolved in dry THF (70 mL) and the mixture was refluxed for two hours at 90° C. The formed CuBr was filtrated off and the organic phase was concentrated. CaCO$_3$ (2.7 g, 27.2 mmol) and DMF (70 mL) were added and the mixture was held at 100° C. for one hour. The dark brown mixture was poured over ice (35 g) and the formed precipitate was filtrated off. The aqueous layer was extracted with ethyl acetate (1×300 mL+3×150 mL). The organic phases were dried, filtrated and concentrated. Purification by flash chromatography (toluene/EtOAc 9:1) gave 2 (2.1 g, 45%) as yellow crystals

Example 62

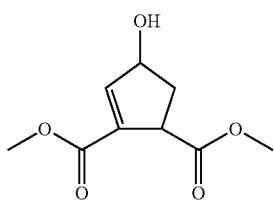

((1S,4R) & (1R,4S))-4-hydroxy-cyclopent-2-ene-1,
2-dicarboxylic acid dimethyl ester (62)

To a cold solution (−30° C.) of compound 61 (3.18 g, 16.1 mmol) dissolved in MeOH (23 mL), NaBH$_4$ (0.66 g, 17.5 mmol) was added. After nine minutes the excess of NaBH$_4$ was destroyed by adding brine (80 mL). The mixture was concentrated and extracted with ethyl acetate (4×80 mL). The organic phases were dried, filtrated and concentrated which gave the title compound (3.0 g, 92%) as a yellow oil.

Example 63

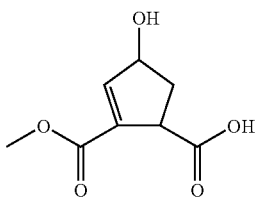

(1S,4R) & (1R,4S)-4-hydroxy-cyclopent-2-ene-1,2-
dicarboxylic acid 2-methyl ester (63)

To an ice-cold solution of 62 (3.4 g, 22 mmol) dissolved in dioxane and water (1:1, 110 mL), LiOH (0.52 g, 22 mmol) was added. After two and a half hours the mixture was co-evaporated with toluene and methanol. Purification by flash chromatography (toluene/Ethyl acetate 3:1+1% HOAc) gave the title compound (1.0 g, 27%) as yellow-white crystals.

$^1$H-NMR (300 MHz, CD$_3$OD): δ 1.78-1.89 (m, 1H), 2.70-2.84 (m, 1H), 3.56-3.71 (m, 1H), 3.76 (s, 3H), 4.81-4.90 (m, 1H), 6.76-6.81 (m, 1H); $^{13}$C-NMR (75.5 MHz, CDCl$_3$): δ 38.0, 48.0, 52.4, 75.7, 137.0, 146.2, 165.0 178.4.

Example 64

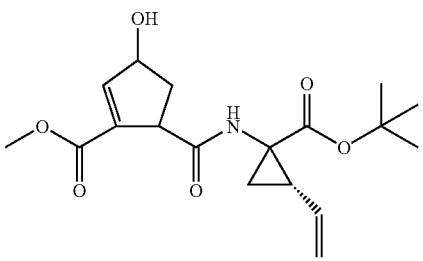

((3S,5R) & (3R,5S))-5-((1R,2S)-1-tert-Butoxycarbo-
nyl-2-vinyl-cyclopropylcarbamoyl)-3-hydroxy-cy-
clopent-1-enecarboxylic acid methyl ester (64)

Reaction of compound 63 (50 mg, 37 mmol) with (1R,2S)-1-amino-2-vinyl-cyclo-propane carboxylic acid tert-butyl ester according to the method described for the preparation of 59 provided the title compound as a slightly yellow oil (50 mg, 38%).

$^1$H-NMR (300 MHz, CDCl$_3$): δ [(1.38 & 1.42) s, 9H], 1.75-1.83 (m, 1H), 2.00-2.21 (m, 3H), 3.55-3.63 (m, 1H), [(3.77 & 3.82) s, 3H], 4.20-4.38 (m, 1H), 4.65-4.80 (m, 1H), 5.13-5.20 (m, 1H), 5.22-5.38 (m, 1H), 5.60-5.82 (m, 1H), 6.95-6.96 (m, 2H).

Example 65

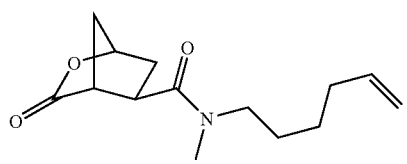

3-Oxo-2-oxa-bicyclo[2.2.1]heptane-5-carboxylic
acid hex-5-enyl-methylamide (65)

To HATU (2.17 g, 5.7 mmol) and N-methyl hex-5-eny-lamine hydrochloride (6.47 mmol) in 5 mL DMF, under argon in an ice bath, were added 1R,4R,5R-3-oxo-2-oxa-bicyclo[2.2.1]heptane-5-carboxylic acid (835.6 mg, 5.35 mmol) in 11 mL DMF followed by DIEA (2.80 mL, 16 mmol). After stirring for 40 min, the mixture was stirred at rt for 5 h. The solvent was evaporated, the residue dissolved in EtOAc (70 mL) and washed with saturated NaHCO$_3$ (10 mL). The aqueous phase was extracted with EtOAc (2×25 mL). The organic phases were combined, washed with saturated NaCl (20 mL), dried over Na$_2$SO$_4$, and evaporated. Flash column chromatography (150 g silica gel, 2/1 EtOAc-petroleum ether (PE),

Example 66

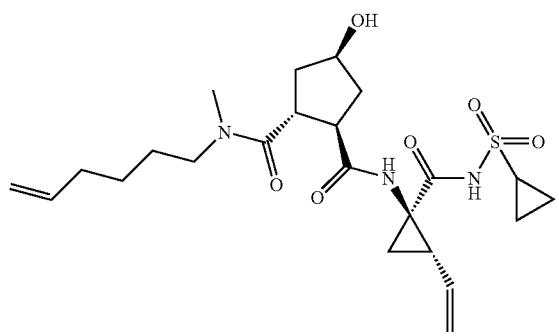

4-Hydroxycyclopentane-1,2-dicarboxylic acid 1-[(1-cyclopropanesulfonylaminocarbonyl-2-vinylcyclopropyl)-amide]2-(hex-5-enyl-methylamide) (66)

LiOH solution (0.15M, 53 mL, 8 mmol) was added to the lactone amide 65 (996 mg, 3.96 mmol) in an ice bath and stirred for 1 h. The mixture was acidified to pH 2-3 with 1N HCl and evaporated, co-evaporated with toluene several times, and dried under vacuum overnight. (1R,2S)-cyclopropanesulfonic acid (1-amino-2-vinyl-cyclopropane-carbonyl) amide hydrochloride (4.21 mmol) and HATU (1.78 g, 4.68 mmol) were added. The mixture was cooled in an ice bath under argon, DMF (25 mL) and then DIEA (2.0 mL, 11.5 mmol) were added. After stirring for 30 min, the mixture was stirred at rt for 3 h. After evaporation of solvent, the residue was dissolved in EtOAc (120 mL), washed successively with 0.5 N HCl (20 mL) and saturated NaCl (2×20 mL), and dried over $Na_2SO_4$. Flash column chromatography (200 g YMC silica gel, 2-4% MeOH in $CH_2Cl_2$ gave white solids (1.25 g, 66%).

Example 67

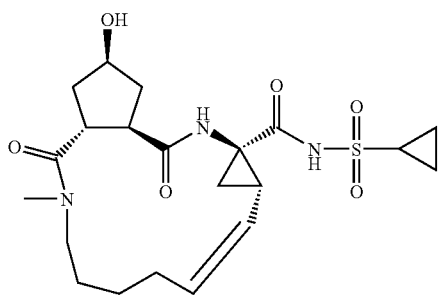

Cyclopropanesulfonic acid (17-hydroxy-13-methyl-2,14-dioxo-3,13-diazatricyclo-[13.3.0.0*4,6*]octadec-7-ene-4-carbonyl)-amide (67)

The cyclopentanol 66 (52.0 mg, 0.108 mmol) was dissolved in 19 mL 1,2-dichloroethane (bubbled with argon prior to use). The Hoveyda-Grubbs $2^{nd}$ generation catalyst (6.62 mg, 10 mole %) was dissolved in DCE (2×0.5 mL) and added. The green solution was bubbled with Ar for 1 min. Aliquots (4 mL each) were transferred into five 2 to 5-mL microwave tubes. To the last tube was added 0.8 mL rinsing with solvent. Each tube was heated by microwave (rt to 160° C. in 5 min). All aliquots were combined and the solvent evaporated. Flash column chromatography (silica gel, 3→7% MeOH in $CH_2Cl_2$) gave 24.39 mg solids (Rf 0.28 in 10% MeOH—$CH_2Cl_2$ with two spots). The solids were combined with a 9.66-mg sample and subjected to a second chromatography (2→8% MeOH in EtOAc) to give cream solids (23 mg) with 80% of the desired compound (26% yield).

Example 68

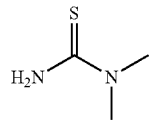

N,N-Dimethyl-thiourea (68)

Dimethylamine (2M in THF, 27.5 mL, 55 mmol) was added to a stirred solution of thiocarbonyldiimidazole (10 g, 56.1 mmol) in dry THF (50 mL). The reaction mixture turned clear by addition and was stirred at 50° C. for 2 hrs. After the reaction mixture had reached rt, it was evaporated on silica and purified by flash chromatography (MeOH:DCM 2:98). The solvent was removed by rotary evaporation and the remaining product dried with high vacuum before it was added to a solution of MeOH (125 mL) saturated with $NH_3$. The reaction mixture was stirred for 60 hrs until TLC indicated complete consumption of the starting material and LC-MS showed the product peak. The product precipitated while removing the solvent by rotary evaporation. The remaining solvent was diluted with diethyl ether and the white crystals were filtered off and dried to give a yield of 1.16 g (20%). The remaining oil was purified by flash chromatography (MeOH:DCM 5:95) and another 1.87 g (32%) was obtained.

Example 69

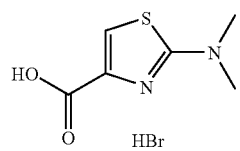

2-Dimethylamino-thiazole-4-carboxylic acid *HBr (69)

3-Bromopuruvic acid (2.94 g, 17.6 mmol) was added to a stirred solution of N,N-di-methyl-thiourea (1.87 g, 17.6 mmol) in dry THF (60 mL). The reaction mixture was stirred at rt for 4 hrs. The precipitate that had formed was filtered off, washed with cold THF and dried on high vacuum. LC-MS showed the product peak. The title compound was obtained as a white solid (2.64 g, 59%).

Example 70

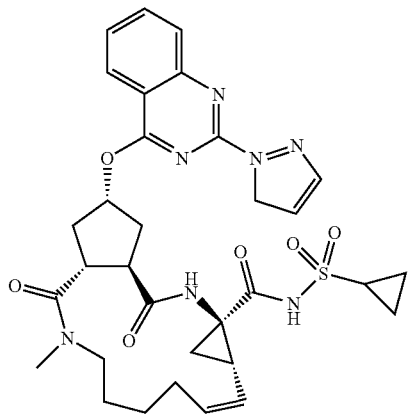

Cyclopropanesulfonic acid {13-methyl-2,14-dioxo-17-[2-(5H-pyrazol-1-yl)-quinazolin-4-yloxy]-3,13-diaza-tricyclo[13.3.0.0*4,6*]octadec-7-ene-4-carbonyl-amide (70)

The title compound is synthesized analogously to the above using 2-pyrazoline in the procedure of Example 33.

Example 71

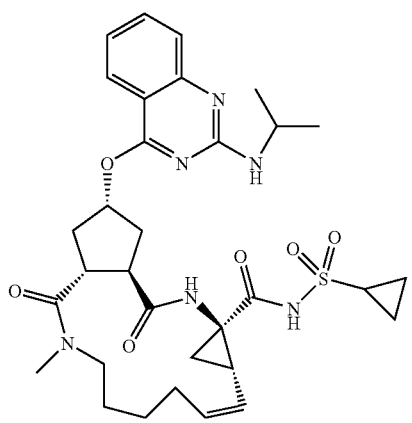

Cyclopropanesulfonic acid [17-(2-isopropylamino-quinazolin-4-yloxy)-13-methyl-2,14-dioxo-3,13-diaza-tricyclo[13.3.0.0*4,6*]octadec-7-ene-4-carbonyl]-amide (71)

The above compound is synthesized analogously to the above using isopropylamine in the procedure of Example 33.

Example 72

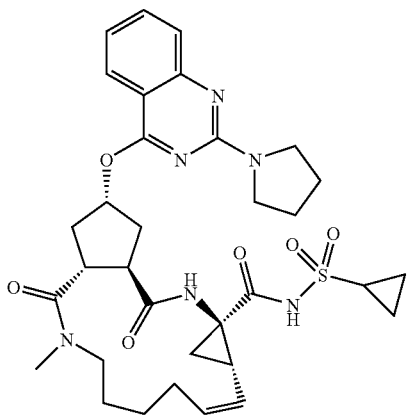

Cyclopropanesulfonic acid [13-methyl-2,14-dioxo-17-[2-pyrrolidin-1-yl)-quinazolin-4-yloxy]-3,13-diaza-tricyclo[13.3.0.0*4,6*]octadec-7-ene-4-carbonyl]-amide (72)

The above compound was synthesized analogously to the above using pyrrolidine in the procedure of Example 33

Example 73

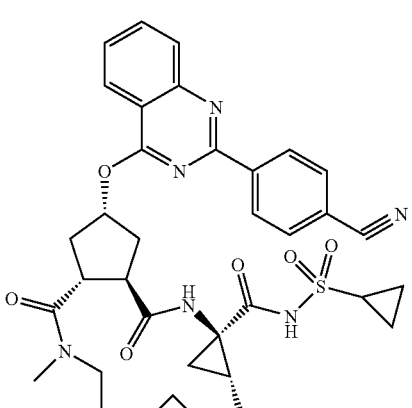

Cyclopropanesulfonic acid {17-[2-(4-cyano-phenyl)-quinazolin-4-yloxy]-13-methyl-2,14-dioxo-3,13-diaza-tricyclo[13.3.0.0*4,6*]octadec-7-ene-4-carbonyl}-amide (73)

The above compound is synthesized analogously to the above using 4-cyanobenzoic acid in Examples 6 and 7.

Example 74

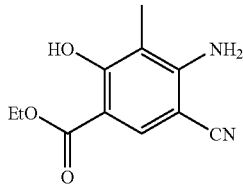

4-Amino-5-cyano-2-hydroxy-3-methylbenzoic acid ethyl ester (74)

To a solution of sodium ethoxide (1.3 L) (freshly prepared by addition of sodium metal (7.9 g, 0.35 mol) to ethanol (1.3 L)) at 0° C. was added ethylpropionyl acetate (25 g, 0.17 mol) and the solution was stirred at RT for 1 h. To the above solution was added ethoxymethylene malononitrile (21 g, 0.17 mol) at RT and the reaction mixture was refluxed at 80° C. for 2 h. The reaction mixture was cooled, neutralized to pH=7 by addition of 1.5 N HCl and concentrated under vacuum. The obtained residue was diluted with water (100 mL) and filtered. The solid was washed with water and dried under vacuum at 50° C. to give the crude product (27 g). The crude solid was washed with 5% ethyl acetate in pet. ether which gave pure title compound (22.5 g, 59%).

Example 75

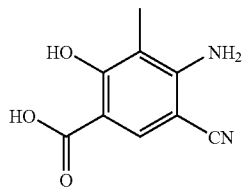

4-Amino-5-cyano-2-hydroxy-3-methylbenzoic acid (75)

To a solution of LiOH×H$_2$O (8.4 g, 0.2 mol) in ethanol/water (1:1, 300 mL) was added compound 74 (22 g, 0.1 mol) at RT and the reaction mixture was refluxed at 80° C. for 4 h. The reaction mixture was concentrated under vacuum, the obtained residue was diluted with water (100 mL), washed with pet. ether/ethyl acetate (1:1, 2×200 mL). The aqueous layer was separated, acidified to pH=5 using 1.5N HCl and the obtained solid product was filtered off. The aqueous layer was further extracted with ethyl acetate (2×300 mL), dried and concentrated to give more product. The combined products was washed with 5% ethyl acetate in pet. ether to give the pure title compound (19 g, >95%).

Example 76

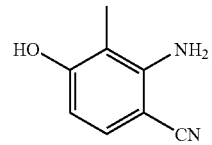

2-Amino-4-hydroxy-3-methylbenzonitrile (76)

A mixture of compound 75 (19 g, 0.1 mol) in quinoline (50 mL) was heated to 170° C. for 2 h (until effervescence ceased). The reaction mixture was cooled to RT and aqueous NaOH solution was added (1M, 500 mL) followed by pet. ether (500 mL). The reaction mixture was stirred for 15 min and the aqueous layer was separated. The aqueous layer was further washed with pet. ether (2×300 mL) to remove quinoline completely. The aqueous layer was acidified with 1.5N HCl to pH=5, the solid was filtered off and dried under vacuum. The obtained solid was further washed with 5% ethyl acetate in pet. ether to give pure title compound (12 g, 82%).

Example 77

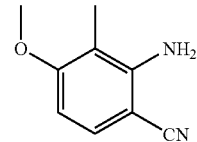

2-Amino-4-methoxy-3-methylbenzonitrile (77)

A mixture of compound 76 (12 g, 0.08 mol), K$_2$CO$_3$ (11 g, 0.08 mol) in dry DMF (200 mL) was stirred for 15 min at RT. To this was added MeI (13.6 g, 0.096 mol) and the mixture was stirred for 4 h at RT. The reaction mixture was diluted with water (800 mL), extracted with 30% ethyl acetate in pet. ether (3×300 mL). The combined organic layers were washed with water and brine, dried and concentrated to give a crude product. The crude product was washed with pet. ether to give pure title compound (12 g, 93%).

Example 78

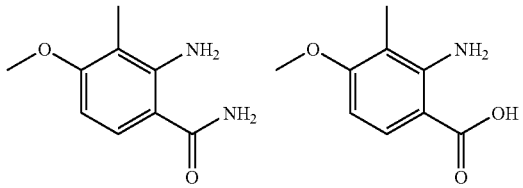

2-Amino-4-methoxy-3-methyl-benzamide and (78-amide) and 2-Amino-4-methoxy-3-methyl-bencoic acid (78-acid)

A mixture of 2-amino-4-methoxy-3-methyl-benzonitrile (9.4 g, 58 mmol) in EtOH (150 ml) and 2M sodium hydroxide solution (150 ml) was refluxed for 8 hours. The mixture was diluted with water and extracted three times with a mixture of ethyl acetate-THF (9:1). The organic phase was washed with water, dried with sodium sulfate and evaporated under reduced pressure. The product was crystallised from diethyl ether which gave the title amide (5.6 g, 58%).

$^1$H-NMR dmso-d6 δ 7.6 (br s, 1H), 7.44 (d, 1H), 6.82 (br s, 1H), 6.42 (s, 2H), 6.20 (d, 1H), 3.78 (s, 3H), 1.84 (s, 3H).

The combined water phases were acidified with citric acid and extracted three times with ethyl acetate, dried with sodium sulfate and evaporated under reduced pressure which gave the title acid (3.2 g, 30%).

$^1$H-NMR dmso-d6 δ 7.60 (d, 1H), 6.32 (d, 1H), 3.78 (s, 3H), 1.90 (s, 3H)

Example 79

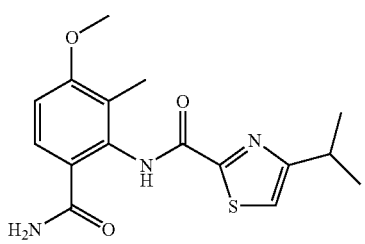

4-Isopropylthiazole-2-carboxylic acid (6-carbamoyl-3-methoxy-2-methyl-phenyl)-amide (79)

To a stirred mixture of 2-amino-4-methoxy-3-methyl-benzamide (2.0 g, 11 mmol), 4-isopropyl-thiazole-2-carboxylic acid (2.4 g, 14 mmol) and Hobt-hydrate (2.2 g, 14 mmol) in dry DMF (80 ml) was added EDAC (2.88 g, 15 mmol) and TEA (2.1 ml, 15 mmol) and the mixture was stirred overnight. A 5% aqueous solution of citric acid was added and the mixture was extracted three times with ethyl acetate. The organic phase was washed with saturated sodium hydrogen carbonate solution (two times) and brine, dried with sodium sulfate and evaporated under reduced pressure which gave the title compound (3.1 g).

Example 80

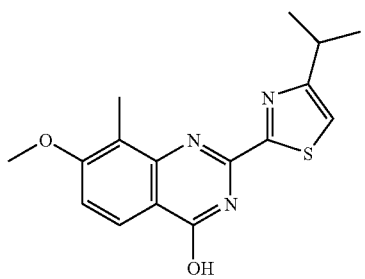

2-(4-Isopropylthiazol-2-yl)-7-methoxy-8-methylquinazolin-4-ol (80)

The above amide (79) (3.0 g, 9 mmol) was refluxed for three hours in a mixture of sodium carbonate (2.4 g, 22.5 mmol) in EtOH (70 ml) and water (70 ml). The mixture was acidified with 5% citric acid and extracted three times with a mixture of ethyl acetate-THF (4:1). The organic phase was dried with sodium sulfate and evaporated under reduced pressure. The product was purified by column chromatography on silica gel eluted with DCM containing 3% MeOH which gave the title compound (1.95 g).

$^1$H-NMR dmso-d6 δ 12 (s, 1H), 8.0 (d, 1H), 7.60 (s, 1H), 7.32 (d, 1H), 3.96 (s, 3H) 2.40 (s, 3H).

Example 81

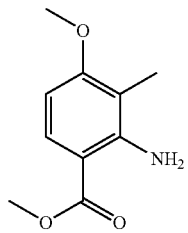

2-Amino-4-methoxy-3-methylbenzoic acid methyl ester (81)

To a solution of 2-amino-4-methoxy-3-methyl benzoic acid (3.1 g, 17.1 mmol) in dry DMF (40 ml) was added potassium carbonate (2.4 g, 17.1 mmol) and the mixture was stirred at room temperature for 30 minutes. Methyl iodide (3.1 g, 22 mmol) was added and the mixture was stirred for three hours at room temperature. A 5% aqueous solution of citric acid was added and the mixture was extracted three times with ethyl acetate. The organic phase was washed with water, dried with sodium sulfate and evaporated under reduced pressure. The product was isolated by column chromatography on silica gel eluted with hexane-ethyl acetate which gave the title compound (2.75 g).

Example 82

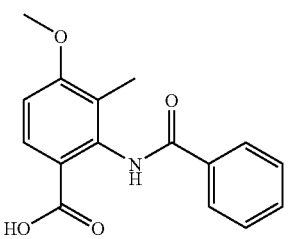

2-Benzoylamino-4-methoxy-3-methylbenzoic acid methyl ester (82)

To an ice cold solution of the above ester (81) (1.5 g, 7.68 mmol) and TEA (2 ml) in dry DCM (30 ml) was added benzoyl chloride (1.4 g, 10 mmol) and the mixture was stirred for four hours at room temperature. Benzoyl chloride (0.14 g, 1 mmol) was added and the mixture was stirred for one hour more at room temperature. A 5% aqueous solution of citric acid was added and the mixture was extracted three times with ethyl acetate. The organic phase was washed with a saturated aqueous solution of sodium hydrogen carbonate and brine, dried with sodium sulfate and evaporated under reduced pressure. The product was purified by column chromatography on silica gel with eluted with hexane-ethyl acetate which gave the title compound (1.6 g).

Example 83

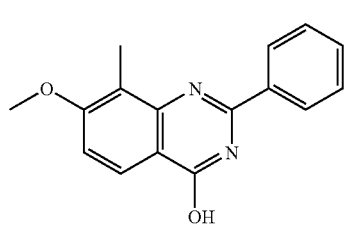

7-Methoxy-8-methyl-2-phenylquinazolin-4-ol (83)

A mixture of the above acid (82) (1.5 g, 5 mmol) in EtOH (6 ml) and 1 m LiOH solution (6 ml) was stirred for two hours at 60° C. A 5% aqueous solution of citric acid was added and the mixture was extracted three times with ethyl acetate. The organic phase was dried with sodium sulfate and evaporated under reduced pressure. The residue was stirred with formamide for five hours at 150° C. The formamide was distilled off under reduced pressure and the product was purified by column chromatography on silica gel eluted with hexane-ethyl acetate which gave the title compound (1.2 g).

$^1$H-NMR δ 12.40 (s, 1H), 8.21 (m, 2H), 8.02 (d, 1H), 7.50 (m, 3H), 7.22 (d, 1H) 3.96 (d, 3H), 2.47 (d, 3H).

Example 84

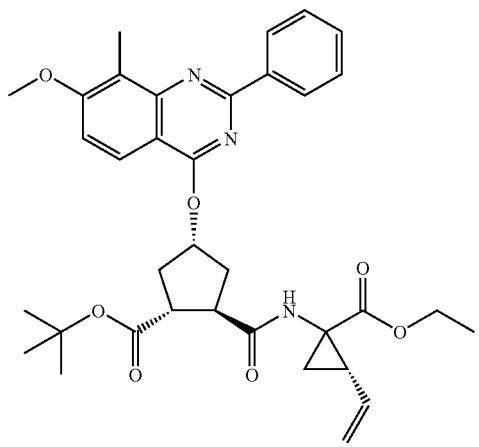

2-(1-Ethoxycarbonyl-2-vinylcyclopropylcarbamoyl)-4-(7-methoxy-8-methyl-2-phenyl-quinazolin-4-yloxy)-cyclopentanecarboxylic acid tert-butyl ester (84)

Quinazolinol derivative (83) (480 mg, 1.8 mmol) was coupled to compound 15 (0.55 mg, 1.5 mmol) as described in example 16, which gave the title compound (700 mg, 75%)
MS (M+H$^+$) 616.

Example 85

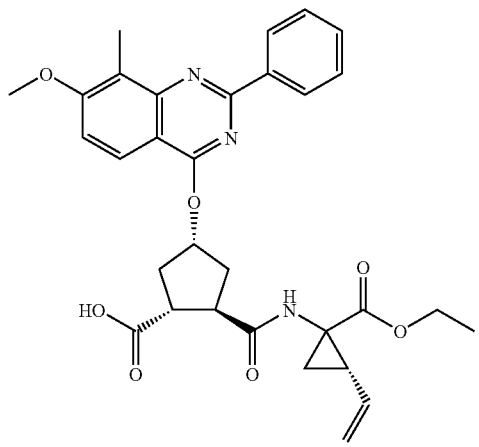

2-(1-Ethoxycarbonyl-2-vinyl-cyclopropylcarbamoyl)-4-(7-methoxy-8-methyl-2-phenyl-quinazolin-4-yloxy)-cyclopentanecarboxylic acid (85)

Compound 84 (0.68 mg) was treated as described in example 17, which gave the title compound (620 mg, 100%).

Example 86

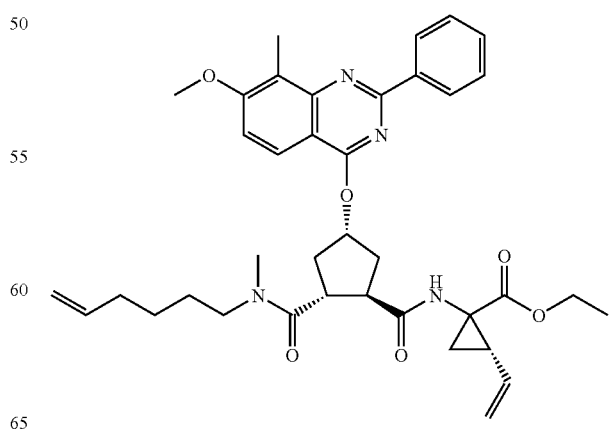

1-{[2-Hex-5-enyl-methyl-carbamoyl)-4-(7-methoxy-8-methyl-2-phenyl-quinazolin-4-yloxy)-cyclopentanecarbonyl]-amino}-2-vinyl-cyclopropanecarboxylic acid ethyl ester (86)

N-methyl-1-hexenylamine (192 mg, 1.7 mmol) was coupled to compound 85 (615 mg, 1.1 mmol) as described in example 18, which gave the title compound (490 mg, 68%).
MS (M+H⁺) 655.

Example 87

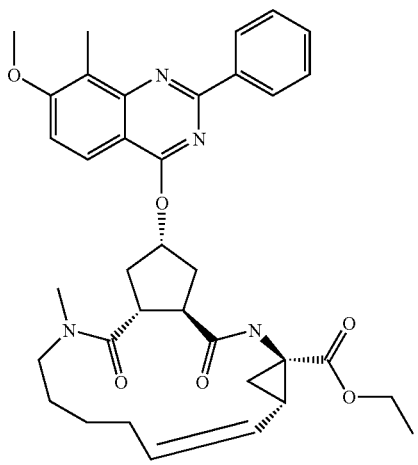

17-(7-Methoxy-8-methyl-2-phenyl-quinazolin-4-yloxy)-13-methyl-2,14-dioxo-3,13-diaza-tricyclo[13.3.0.0*4,6*]octadec-7-ene-4-carboxylic acid ethyl ester (87)

A ring closing metathesis reaction of compound 86 (480 mg, 0.73 mmol) was performed as described in example 19, which gave the title compound (290 mg, 46%).
MS (M+H⁺) 627.

Example 88

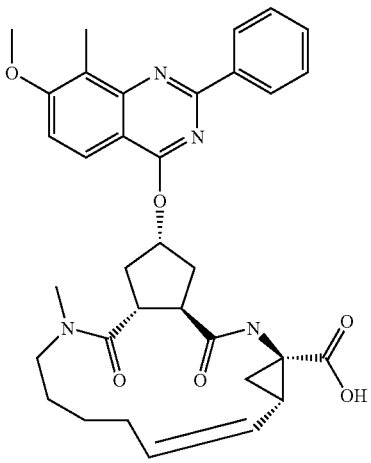

17-(7-Methoxy-8-methyl-2-phenyl-quinazolin-4-yloxy)-13-methyl-2,14-dioxo-3,13-diaza-tricyclo[13.3.0.0*4,6*]octaedec-7-ene-4-carboxylic acid (88)

The ethyl ester of compound 87 (280 mg, 0.45 mmol) was hydrolyzed as described in example 20, which gave the title compound (210 mg, 78%).
MS (M+H⁺) 599.

Example 89

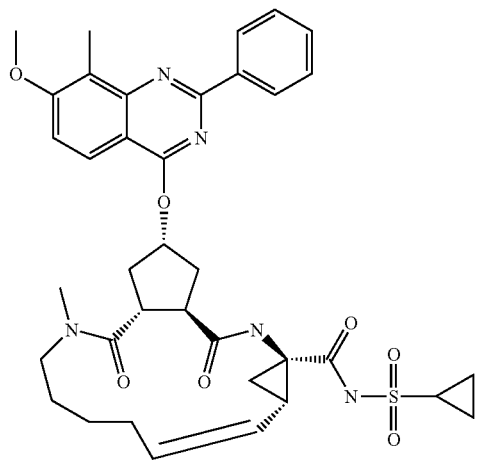

Cyclopropanesulfonic acid [17-(7-methoxy-8-methyl-2-phenyl-quinazolin-4-yloxy)-13-methyl-2,14-dioxo-3,13-diaza-tricyclo[13.3.0.0*4,6*]octadec-7-ene-4-carbnyl]-amide (89)

Cyclopropanesulfonamide (202 mg) was coupled to the acid 88 (200 mg) as described in example 21, which gave the title compound (100 mg, 42%).
MS (M+H⁺) 702.

Example 90

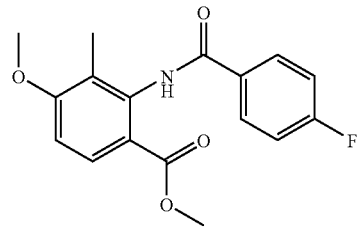

2-(4-Fluoro-benzoylamino)-4-methoxy-3-methyl-benzoic acid methyl ester (90)

4-Fluoro benzoic acid (700 mg, 5 mmol) was dissolved in dichloromethane (20 ml) and pyridine (2 ml). 2-Amino-4-methoxy-3-methyl-benzoic acid methyl ester (81) (878 mg, 4.5 mmol) was added and the mixture was refluxed for 5 h. Water was added and the mixture was extracted with dichloromethane. The organic phase was dried, filtered and evaporated and the afforded residue was purified by column chromatography on silica gel, eluted with ether-pentane 1:1 which gave pure title compound (870 mg, 61%). MS (M+H$^+$) 318.

Example 91

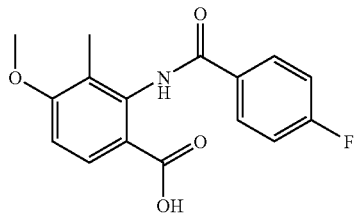

2-(4-Fluoro-benzoylamino)-4-methoxy-3-methyl-benzoic acid (91)

LiOH (1M, 4 mL) was added to a solution of 2-(4-fluoro-benzoylamino)-4-methoxy-3-methyl-benzoic acid methyl ester (90) (870 mg, 2.7 mmol), in tetrahydrofuran (15 ml), water (7.5 ml) and methanol (7.5 ml). The mixture was heated to 50° C. for 4 h. Water (30 ml) was then added and the volume reduced to half. Acidification with acetic acid followed by filtration gave pure title compound (830 mg, 100%).

MS (M+H$^+$) 304.

Example 92

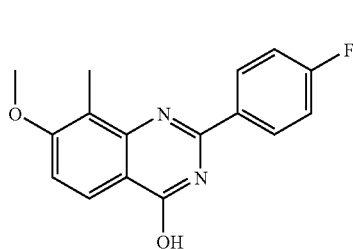

2-(4-Fluoro-phenyl)-7-methoxy-8-methyl-quinazolin-4-ol (92)

2-(4-Fluoro-benzoylamino)-4-methoxy-3-methyl-benzoic acid (91) (830 mg, 2.7 mmol) was heated to 150° C. in formamide (20 ml) for 4 h. The excess formamide was removed by distillation. Water was added and the precipitated product was filtered of to give pure title compound (642 mg, 83%).

MS (M+H$^+$) 285.

Example 93

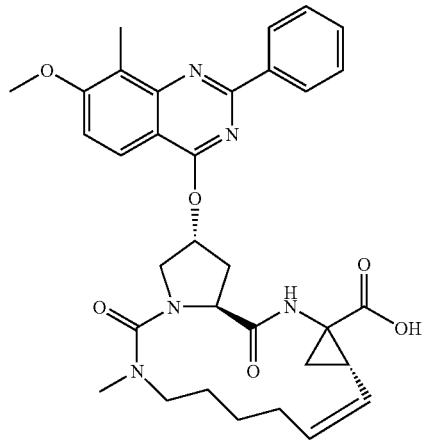

17-(7-Methoxy-8-methyl-2-phenyl-quinazolin-4-yloxy)-13-methyl-2,14-dioxo-3,13,15-triaza-tricyclo [13.3.0.0*4,6*]octadec-7-ene-4-carboxylic acid (93)

Quinazolinol derivative (83) (449 mg, 1.7 mmol) was coupled to compound 51 (400 mg, 1.1 mmol) followed by hydrolysis of the ethyl ester as described in example 52, which gave the title compound (112 mg, 17%).

MS (M+H$^+$) 600.

Example 94

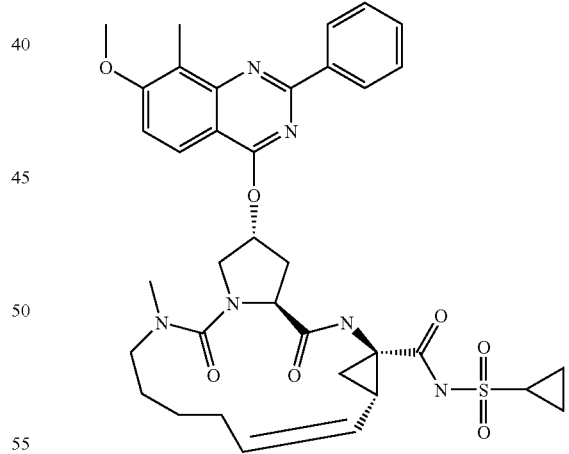

Cyclopropanesulfonic acid [17-(7-methoxy-8-methyl-2-phenyl-quinazolin-4-yloxy)-13-methyl-2,14-dioxo-3,13,15-triaza-tricyclo[13.3.0.0*4,6*]octadec-7-ene-4-carbonyl]-amide (94)

Cyclopropanesulfoneamide (115 mg, 0.95 mmol) was coupled to the acid 93 (112 mg, 0.19 mmol) as described in example 53, which gave the title compound (25 mg, 19%).

MS (M+H$^+$) 703.

Example 95

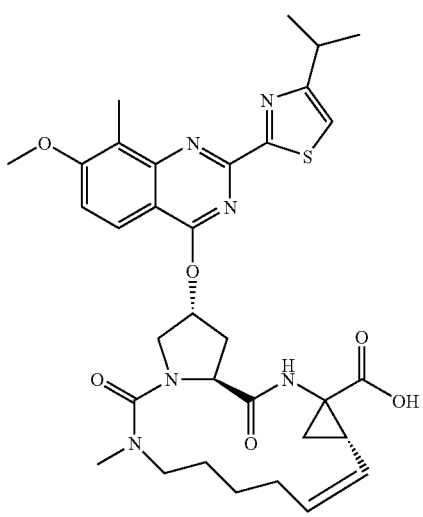

17-[2-(4-Isopropyl-thiazol-2-yl)-7-methoxy-8-methyl-quinazolin-4-yloxy]-13-methyl-2,14-dioxo-3,13,15-triaza-tricyclo[13.3.0.0*4,6*]octadec-7-ene-4-carboxylic acid (95)

Quinazolinol derivative (98) (141 mg, 0.5 mmol) was coupled to compound 51 (170 mg, 0.45 mmol) followed by hydrolysis of the ethyl ester as described in example 52, which gave the title compound (125 mg, 45%).

MS (M+H⁺) 618.

Example 96

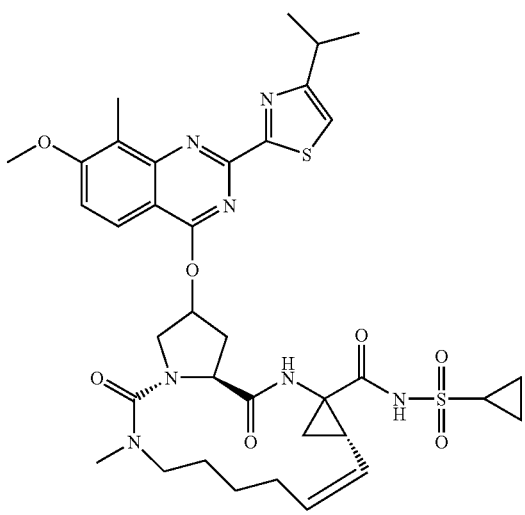

Cyclopropanesulfonic acid {17-[2-(4-isopropyl-thiazol-2-yl-(7-methoxy-8-methyl-quinazolin-4-yloxy)-13-methyl-2,14-dioxo-3,13,15-triaza-tricyclo[13.3.0.0*4,6*]-octadec-7-ene-4-carbonyl}-amide (96)

Cyclopropanesulfoneamide (61 mg, 0.5 mmol) was coupled to the acid 95 (125 mg, 0.2 mmol) as described in example 53, which gave the title compound (52 mg, 36%).

MS (M+H⁺) 721.

Example 97

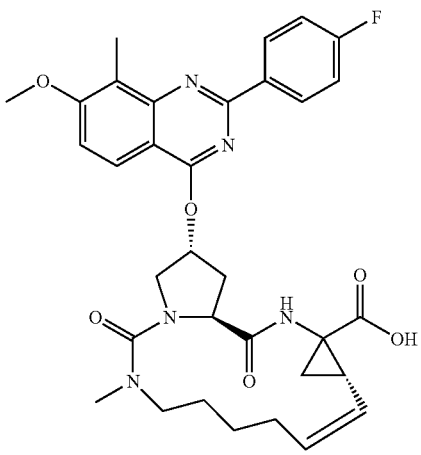

17-[2-(4-Fluoro-phenyl)-7-methoxy-8-methyl-quinazolin-4-yloxy]-13-methyl-2,14-dioxo-3,13,15-triaza-tricyclo[13.3.0.0*4,6*]octadec-7-ene-4-carboxylic acid (97)

Quinazolinol derivative (92) (141 mg, 0.5 mmol) was coupled to compound 51 (170 mg, 0.45 mmol) as described in example 52, which gave the crude ethyl ester of the title compound. The crude ester was purified by flash chromatography on silica gel eluted with 5→15% MeOH in diethyl ether, the afforded residue was dissolved in dichloromethane and filtered to remove traces of silica, which gave the ethyl ester of the title compound (135 mg, 46%). The ethyl ester was then hydrolyzed as described in example 52, which gave the title compound (125 mg, 100%)

MS (M+H)⁺ 618.3.

Example 98

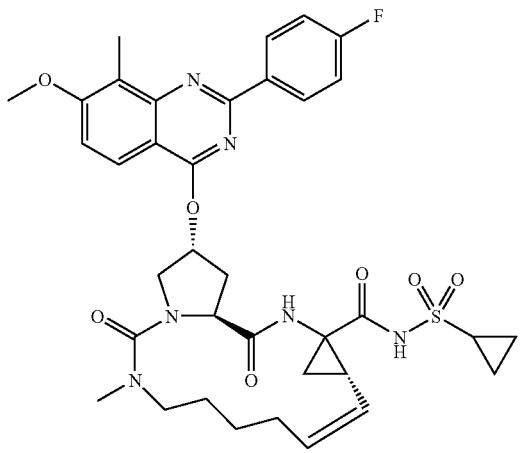

Cyclopropanesulfonic acid {17-[2-(4-fluoro-phenyl-(7-methoxy-8-methyl-quinazolin-4-yloxy)-13-methyl-2,14-dioxo-3,13,15-triaza-tricyclo[13.3.0.0*4, 6*]octadec-7-ene-4-carbonyl}-amide (98)

Cyclopropanesulfoneamide (61 mg, 0.5 mmol) was coupled to the acid 97 (125 mg, 0.2 mmol) as described in example 53, which gave the title compound (52 mg, 36%).
MS (M+H$^+$) 721.

Example 99

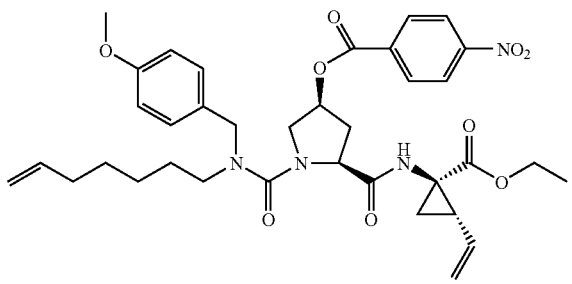

4-Nitro-benzoic acid 5-(1-ethoxycarbonyl-2-vinyl-cyclopropylcarbamoyl)-1-[hept-6-enyl-(4-methoxy-benzyl)-carbamoyl]-pyrrolidin-3-yl ester (99)

To a solution of compound 48 (4.5 g, 10.8 mmol) in THF (160 mL) were added NaHCO$_3$ (1 tablespoon) and phosgene in toluene (1.93 M, 11.5 mL, 22 mmol). The mixture was vigorously stirred for 1 h at room temperature, and then filtered and evaporated. The residue was dissolved in CH$_2$Cl$_2$ (160 mL), and NaHCO$_3$ (1 tablespoon) and hept-5-enyl-(p-methoxybenzyl)-amine (4.3 g, 18.5 mmol) were added. After stirring overnight at room temperature the reaction mixture was filtered and evaporated to dryness. Flash column chromatography on silica gel (EtOAc:toluene 25:75→40:60) gave the title compound (6.59 g, 90%) as a light brown syrup.

Example 100

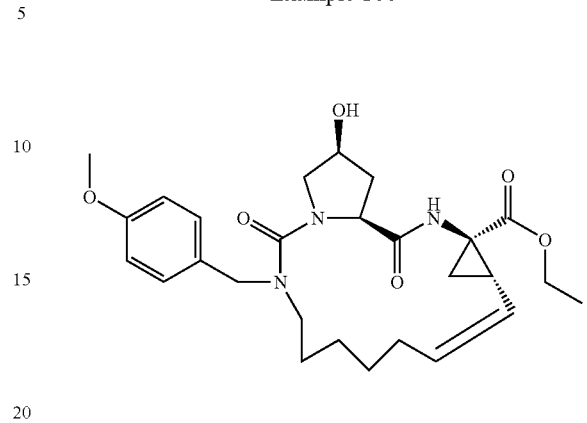

18-Hydroxy-14-(4-methoxy-benzyl)-2,15-dioxo-3, 14,16-triaza-tricyclo[14.3.0.0*4,6]-nonadec-7-ene-4-caroxylic acid ethyl ester (100)

Compound 99 (1 g, 1.48 mmol) was dissolved in 1,2-dichloroethane (2 l). The mixture was degassed for 15 min using a stream of argon. Hoveyda-Grubbs catalyst (II) (50 mg, 5 mol %) was added and the mixture was refluxed for 4 h. The solvent was evaporated and the crude ester was dissolved in tetrahydrofuran (100 ml), methanol (50 ml) and water (50 ml). The mixture was cooled 0° C. on ice-bath. Aqueous lithium hydroxide (20 ml, 1M) was added and the mixture was stirred at 0° C. for 4 h. The volume was then doubled with water and the mixture acidified with acetic acid. Extraction (dichloromethane) followed by flash chromatography (methanol 1→5% in ether) gave pure title compound (450 mg, 61%).
MS (M+H)$^+$ 500.

Example 101

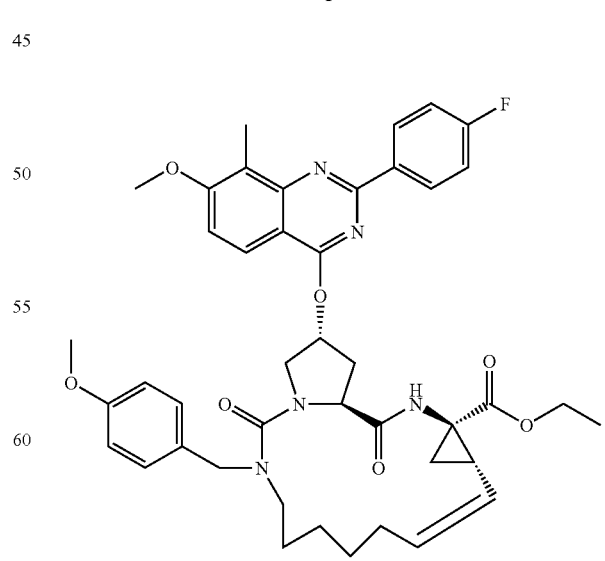

18-[2-(4-Fluoro-phenyl)-7-methoxy-8-methyl-quinazolin-4-yloxy]-14-(4-methoxy-benzyl)-2,15-dioxo-3,14,16-triaza-tricyclo[14.3.0.0*4,6*]nona-dec-7-ene-4-carboxylic acid ethyl ester (101)

Quinazolinol derivative (92) (125 mg, 0.44 mmol) was coupled to compound 100 (200 mg, 0.4 mmol) as described in example 52. The afforded crude product was purified by flash chromatography on silica gel eluted with 1% MeOH in diethyl ether, which gave the title compound (240 mg, 78%).
MS (M+H)+ 766.3.

Example 102

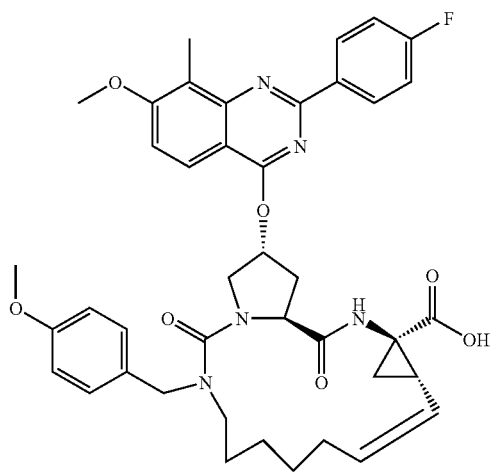

18-[2-(4-Fluoro-phenyl)-7-methoxy-8-methyl-quinazolin-4-yloxy]-14-(4-methoxy-benzyl)-2,15-dioxo-3,14,16-triaza-tricyclo[14.3.0.0*4,6*]nona-dec-7-ene-4-carboxylic acid (102)

The ethyl ester of compound 101 (240 mg, 0.31 mmol) was hydrolyzed as described in example 20, which gave the title compound (200 mg, 86%).
MS (M+H+) 738.

Example 103

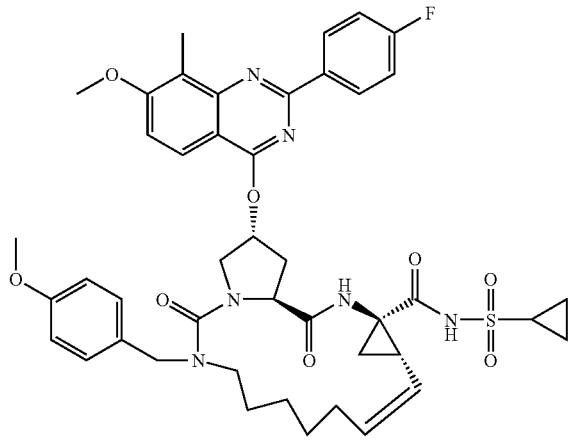

Cyclopropanesulfonic acid [18-[2-(4-fluoro-phenyl)-7-methoxy-8-methyl-quinazolin-4-yloxy]-14-(4-methoxy-benzyl)-2,15-dioxo-3,14,16-triaza-tricyclo[14.3.0.0*4,6*]nonadec-7-ene-4-carboyl]-amide (103)

Cyclopropanesulfonamide (99 mg, 0.8 mmol) was coupled to the acid 102 (200 mg. 0.27 mmol) as described in example 21. Purification by HPLC gave the title compound (75 mg, 33%).
MS (M−H)− 839.

Example 104

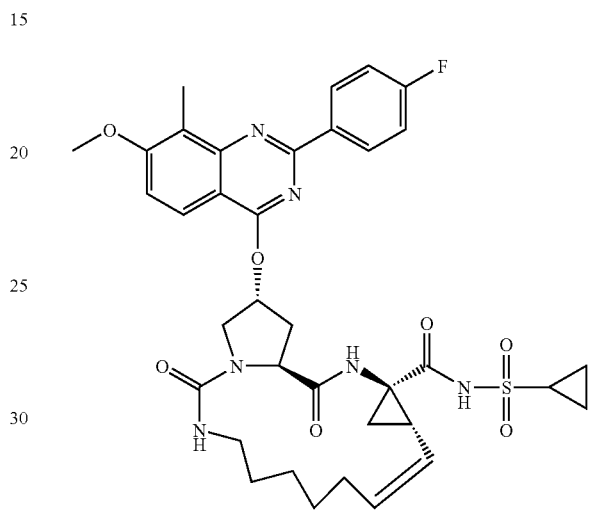

Cyclopropanesulfonic acid {18-[2-(4-fluoro-phenyl)-7-methoxy-8-methyl-quinazolin-4-yloxy]-2,15-di-oxo-3,14,16-triaza-tricyclo[14.3.0.0*4,6*]nonadec-7-ene-4-carbonyl}-amide (104)

Compound 103 (75 mg, 0.09 mmol) was stirred for 2 h in a mixture of dichloro-methane-trifluoroacetic acid; 2:1. Evaporation and purification by HPLC gave pure title compound (25 mg, 38%).
MS (M−H)− 719.0.

Example 105

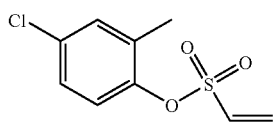

Ethenesulfonic acid 4-chloro-2-methylphenyl ester (105)

To a stirred mixture of 4-chloro-2-methylphenol (24.7 g, 173 mmol) in acetone (10 ml), dichloroethane (25 ml) and water (45 ml) at 0-5° C. was added drop wise simultaneously 2-chloro-1-ethane sulfonyl chloride (28.2 g, 173 mmol) and a solution of 25% sodium hydroxide (60 g) during approximately one hour. The mixture was stirred for one hour at S and for one hour at room temperature. Water was added and the mixture was extracted twice with DCM. The organic phase was dried with sodium sulphate, filtered and evaporated under reduced pressure. The residue was purified by column chromatography on silica gel eluted with hexane-ethyl acetate which gave the title compound (33.4 g, 83%).

Example 106

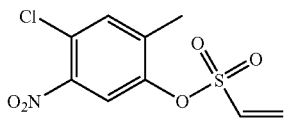

Ethenesulfonic acid 4-chloro-2-methyl-5-nitrophenyl ester (106)

Compound 105 (33.2 g, 142 mmol) was dissolved in cold concentrated sulphuric acid (70 ml) and 98% nitric acid (9.8 g) was added drop wise while cooling to keep the temperature below 10° C. The mixture was stirred for one hour at about 5° C. The mixture was added to ice water and extracted three times with ethyl acetate. The organic phase was washed twice with brine, dried with sodium sulphate and evaporated under reduced pressure. The product was isolated by column chromatography on silica gel eluted with hexane-ethyl acetate.
Yield: 30 g=75%

Example 107

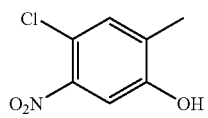

4-Chloro-2-methyl-5-nitrophenol (107)

A solution of compound 106 (27.8 g, 100 mmol) and potassium carbonate (27.6 g, 200 mmol) in ethanol water 1/1 (600 ml) was refluxed for one hour. Citric acid (5%) was added and the mixture was extracted three times with DCM. The organic phase was dried with sodium sulphate and evaporated under reduced pressure which gave the title compound (19 g, 100%).
$^1$H-NMR CDCl$_3$ δ 2.30 (s, 3H), 7.24 (s, 1H), 7.40 (s, 1H).

Example 108

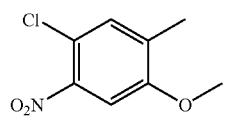

1-Chloro-4-methoxy-5-methyl-2-nitrobenzene (108)

To a stirred solution of 4-chloro-2-methyl-5-nitrophenol (18.8 g, 100 mmol) in DMF (200 ml) was added potassium carbonate (13.8 g, 100 mmol) and methyl iodide (21.3 g, 150 mmol). The mixture was stirred for about two hours at room temperature. 5% Citric acid was added and the mixture was extracted three times with ethyl acetate. The organic phase was washed with brine, dried with sodium sulphate and evaporated under reduced pressure which gave the title compound (20 G, 100%).

Example 109

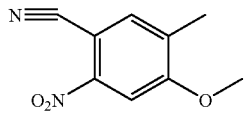

4-Methoxy-5-methyl-2-nitro-benzonitrile (109)

A mixture compound 108 (20 g, 100 mmol) and copper cyanide (11.25 g, 125 mmol) in n-methyl-pyrrolidone-2 (60 ml) was stirred for 20 h at 140-150° C. The mixture was diluted with ethyl acetate filtered and washed four times with water. The organic phase was dried with sodium sulphate and evaporated under reduced pressure. The residue was purified by column chromatography on silica gel eluted with hexane-ethyl acetate which gave the title compound (8 g, 41%).
$^1$H-NMR CDCl$_3$ δ 2.38 (s, 3H), 4.00 (s, 3H), 7.61 (s, 1H), 7.73 (s, 1H)

Example 110

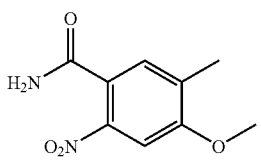

4-Methoxy-5-methyl-2-nitrobenzamide (110)

To a mixture of 4-methoxy-5-methyl-2-nitro-benzonitrile (8 g, 40 mmol) and water (50 ml) was added concentrated sulphuric acid (65 ml) and the mixture was stirred for 2.5 hours at 100-110° C. The mixture was allowed to stay overnight, filtered, washed with water and dried which gave the title compound (7 g, 83%).

Example 111

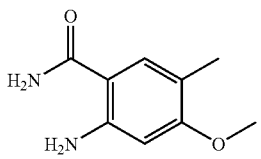

4-Methoxy-5-methyl-2-amino-benzamide (111)

Compound 110 (7.0 g, 33.3 mmol) was hydrogenated in EtOH (200 ml) and raney-ni (5.0 g) overnight at room temperature at 50 psi. The catalyst was filtered off and washed with dioxane and ethanol. The solvent was removed under vacuo and the product was isolated by column chromatography on silica gel eluted with dichloromethane and 3% methanol. Yield: 3.4 g=56%.

Example 112

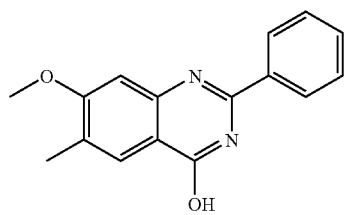

7-Methoxy-6-methyl-2-phenyl-quinazoline-4-ol (112)

To a mixture of compound III (1.8 g, 10 mmol), benzoic acid (1.46 g, 12 mmol) and hobt-hydrate (1.87 g, 12 mmol) in dry DMF (60 ml) was added EDAC (2.4 g, 12.5 mmol) and TEA (1.75 ml, 12.5 mmol) and the mixture was stirred at room temperature for 60 h. 5% Citric acid was added and the mixture was evaporated three times with ethyl acetate. The organic phase was washed with brine and saturated sodium hydrogen carbonate solution. The organic phase was dried with sodium sulphate and evaporated under reduced pressure. The residue was refluxed for two hours with sodium carbonate (2.65 g, 25 mmol) in 100 ml ethanol-water 1/1.5% Citric acid was added and the mixture was extracted three times with ethyl acetate including 10% THF. Silica gel was added, the solvent was evaporated and the product was purified by column chromatography on silica gel eluted with hexane-ethyl acetate.

Yield: 1.3 g=50%

$^1$H-NMR dmso-d$_6$ δ 2.21 (s, 3H), 3.96 (s, 3H), 7.17 (s, 1H), 7.58 (m, 3H), 7.82 (s, 1H), 8.18 (m, 2H).

Example 113

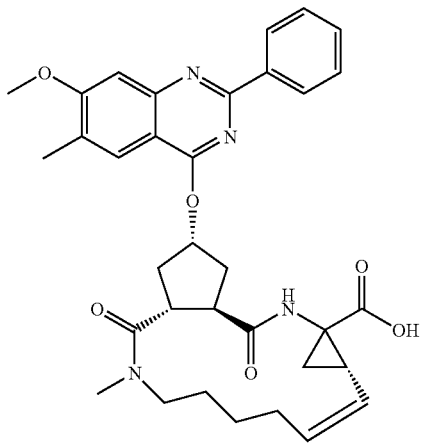

17-(7-Methoxy-6-methyl-2-phenyl-quinazolin-4-yloxy)-13-methyl-2,14-dioxo-3,13,15-triaza-tricyclo[13.3.0.0*4,6*]octadec-7-ene-4-carboxylic acid (113)

Quinazolinol derivative (112) (480 mg, 1.8 mmol) was coupled to compound 15 (550 mg, 1.5 mmol) as described in example 16, followed by removal of the boc group as described in example 17, coupling of N-methyl-1-hexenylamine as described in example 18, a ring closing metathesis reaction as described in example 19 and hydrolysis of the ethyl ester as described in example 52, which gave the title compound (290 mg, 30%).

MS (M+H)$^+$ 599.

Example 114

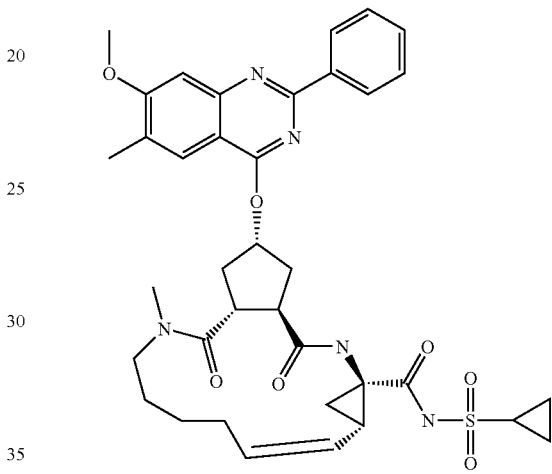

Cyclopropanesulfonic acid [17-(7-methoxy-6-methyl-2-phenyl-quinazolin-4-yloxy)-13-methyl-2,14-dioxo-3,13,15-triaza-tricyclo[13.3.0.0*4,6*]octadec-7-ene-4-carbonyl]-amide (114)

Cyclopropanesulfoneamide (202 mg, 1.67 mmol) was coupled to the acid 113 (200 mg, 0.33 mmol) as described in example 89, which gave the title compound (90 mg, 38%).

MS (M+H)$^+$ 702.

Example 115

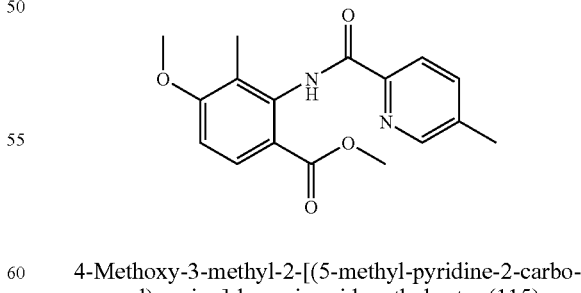

4-Methoxy-3-methyl-2-[(5-methyl-pyridine-2-carbonyl)-amino]-benzoic acid methyl ester (115)

2-Amino-4-methoxy-3-methyl-benzoic acid methyl ester (400 mg, 2 mmol) and 5-methyl-pyridine-2-carboxylic acid (280 mmol, 2 mmol) where dissolved in dichloro-methane (8 ml) and pyridine (1 ml). Phosphorous oxychloride (0.37 ml) was added while cooling on ice-bath. The mixture was left at 0° C. for 1 h then allowed to attain room temperature. Aqueous sodium hydroxide (20 ml, 1M) was added and the mixture were extracted with dichloromethane. Purification by column chromatography on silica gel (ether-pentane 1:1) gave pure title compound (410 mg, 65%). MS (M−H)+ 315.1

Example 116

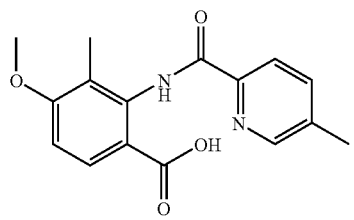

4-Methoxy-3-methyl-2-[(5-methyl-pyridine-2-carbonyl)-amino]-benzoic acid (116)

Compound 115 (620 mg, 1.9 mmol) was hydrolyzed by the procedure described in Example 91, which gave pure title compound (590 mg, 100%).

MS (M−H)+ 301.1.

Example 117

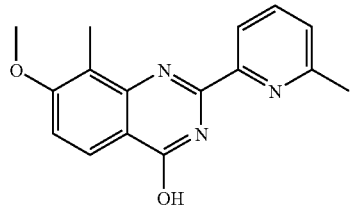

7-Methoxy-8-methyl-2-(6-methyl-pyridin-2-yl)-quinazolin-4-ol (117)

Compound 116 was heated in formamide at 150° C. for 5-6 h. Water was then added and the precipitated product was filtrated off to give pure title compound (397 mg, 71%). MS (M−H)+ 282.1

Example 118

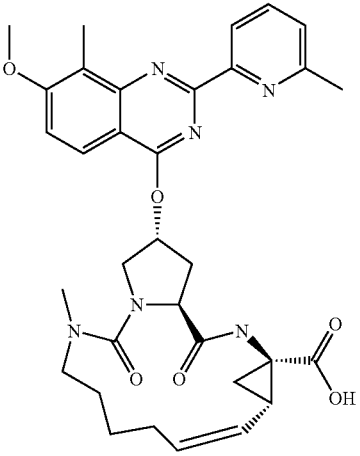

17-[7-Methoxy-8-methyl-2-(6-methyl-pyridin-2-yl)-quinazolin-4-yloxy]-13-methyl-2,14-dioxo-3,13,15-triaza-tricyclo[13.3.0.0*4,6*]octadec-7-ene-4-carboxylic acid (118)

Quinazolinol derivative (117) (198 mg, 0.7 mmol) was coupled to compound 51 (268 mg, 0.7 mmol) followed by hydrolysis of the ethyl ester as described in example 52 which gave the title compound (50 mg, 10%).

MS (M+H)+ 615.3.

Example 119

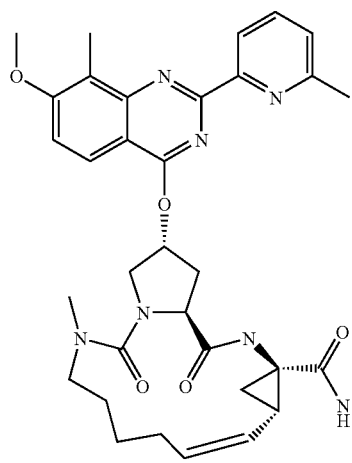

Cyclopropanesulfonic acid {17-[7-methoxy-8-methyl-2-(6-methyl-pyridin-2-yl)-quinazolin-4-yloxy]-13-methyl-2,14-dioxo-3,13,15-triazatricyclo[13.3.0.0*4,6*]octadec-7-ene-4-carbonyl}-amide (119)

Compound 118 (50 mg, 0.08 mmol) was reacted with cyclopropanesulfonic acid amide (44 mg, 0.36 mmol) according to the procedure described in Example 53 which gave the title compound (13 mg, 22%). MS (M−H)+ 718.2

Example 120

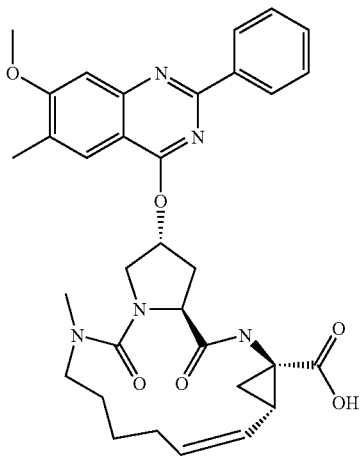

17-(7-Methoxy-6-methyl-2-phenyl-quinazolin-4-yloxy)-13-methyl-2,14-dioxo-3,13,15-triaza-tricyclo[13.3.0.0*4,6*]octadec-7-ene-4-carboxylic acid (120)

Quinazolinol derivative 112 (200 mg, 0.53 mmol) was coupled to compound 51 (268 mg, 0.7 mmol) followed by hydrolysis of the ethyl ester as described in example 52 which gave the title compound (36 mg, 11%). MS (M−H)+ 600.

Example 121

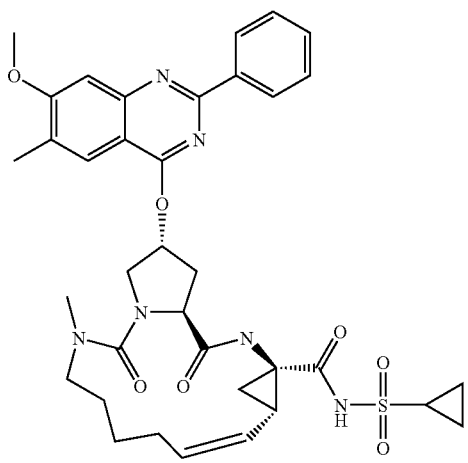

Cyclopropanesulfonic acid [17-(7-methoxy-6-methyl-2-phenyl-quinazolin-4-yloxy)-13-methyl-2,14-dioxo-3,13,15-triaza-tricyclo[13.3.0.0*4,6*]octadec-7-ene-4-carbonyl]-amide (121)

Reaction of the acid 120 (36 mg, 0.06 mmol) with cyclopropanesulfonic acid amide according to the procedure described in Example 53, gave the title compound (8 mg, 19%). MS (M−H)+ 703.

General Procedure for the Preparation of Substituted quinazolin-4-ols

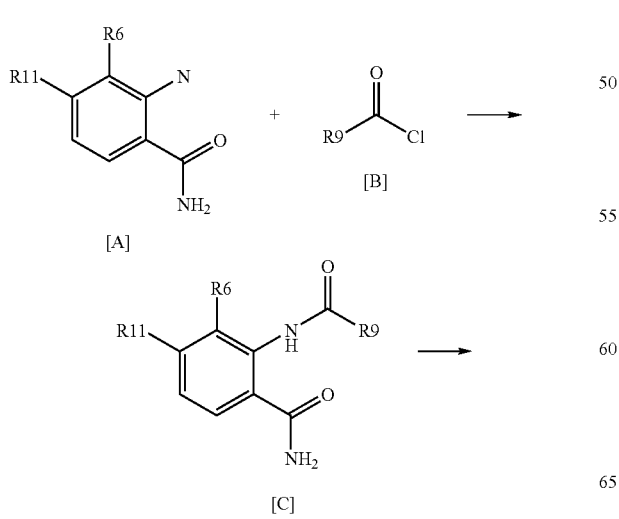

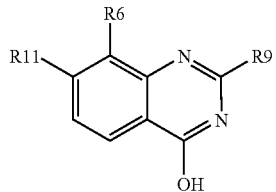

To a suspension of a substituted 2-amino-benzamide [A] (1 eq) in dry THF (60 ml) was added pyridine (2 eq) and the mixture was cooled to 5° C. The acid chloride [B] (1.25 eq) was added slowly and the mixture was stirred at room temperature overnight. The mixture was evaporated under reduced pressure and then suspended in water. The compound was left in the water for some hours, filtered and washed with cold water and diethyl ether. The product [C] was dried under vacuum. Yield: 90-100%.

When the acid chloride [B] used was a nicotinyl chloride hydrochloride, then 2.5 eq of pyridine was used and the mixture was stirred for 2-3 days at room temperature instead of over night.

The formed amide [C] (1 eq) was added to a suspension of sodium carbonate (2.5 eq) in a 1:1 mixture of water and EtOH and the mixture was refluxed for two hours. The EtOH was removed under reduced pressure, a solution of 5% citric acid was added and the mixture was allowed to stay overnight. The product [D] was isolated by filtration, then washed with water and diethyl ether and dried under vacuum.

Example 122

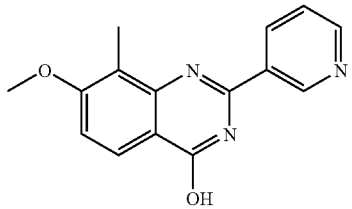

7-Methoxy-8-methyl-2-pyridin-3yl-quinazolin-4-ol (122)

The general procedure described above was followed using 2-amino-4-methoxy-3-methyl benzamide as benzamide derivative and nicotinyl chloride hydrochloride as acid chloride, which gave the title compound (2.5 g, 92%), [M+H] =268.

Example 123

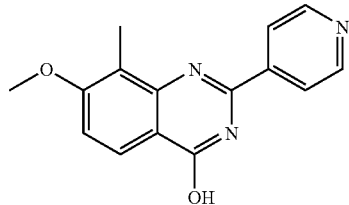

7-Methoxy-8-methyl-2-pyridin-4-yl-quinazolin-4-ol (123)

The general procedure described above was followed using 2-amino-4-methoxy-3-methyl benzamide as benzamide derivative and isonicotinoyl chloride hydrochloride as acid chloride, which gave the title compound (1.6 g, 60%), [M+H] =268.

Example 124

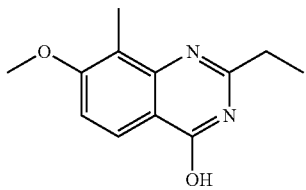

7-Methoxy-8-methyl-2-ethyl-quinazolin-4-ol (124)

The general procedure described above was followed using 2-amino-4-methoxy-3-methyl benzamide as benzamide derivative and acetic acid chloride as acid chloride [B], which gave the title compound (2.2 g, 100%).

$^1$H-NMR DMSO-D$_6$ δ 1.2 (m, 3H), 2.38 (s, 3H), 2.6 (m, 2H), 3.90 (s, 3H), 7.18 (d, 2H), 7.96 (d, 2H), 11.88 (s, 1H).

Example 125

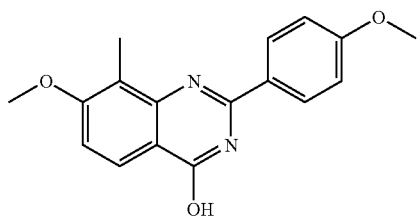

7-Methoxy-8-methyl-2-(4-methoxyphenyl)-quiazolin-4-ol (125)

The general procedure described above was followed using 2-amino-4-methoxy-3-methyl benzamide as benzamide derivative [A] and 4-methoxybenzoic acid chloride as acid chloride [B], which gave the title compound (5.5 g, 92%).

$^1$H-NMR DMSO-D$_6$ δ 2.38 (s, 3H), 3.82 (s, 3H), 3.92 (s, 3H), 7.04 (d, 2H), 7.20 (d, 1H), 8.00 (d, 1H), 8.20 (d, 2H), 12.18 (s, 1H).

Example 126

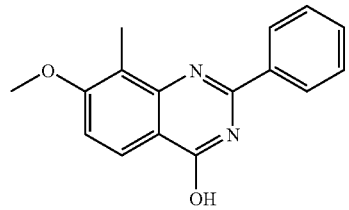

8-Methoxy-2-phenyl-quinazolin-4-ol (126)

The general procedure described above was followed using 2-amino-4-methoxy-3-methyl benzamide as benzamide derivative [A] and benzoyl chloride as acid chloride [B], which gave the title compound (2.0 g, 80%), [M+H]=253.

$^1$H-NMR DMSO-D$_6$ δ 3.97 (s, 3H), 7.39-7.72 (m, 6H), 8.19 (m, 2H), 12.48 (s, 1H).

Example 127

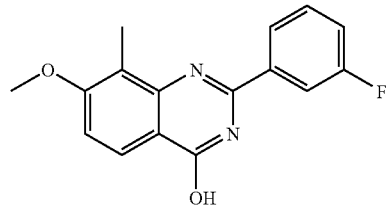

2-(3-Fluoro-phenyl)-7-methoxy-8-methyl-quinazolin-4-ol (127)

The general procedure described above was followed using 2-amino-4-methoxy-3-methyl benzamide as benzamide derivative [A] and 3-fluoro-benzoyl chloride as acid chloride [B], which gave the title compound (2.1 g, 73%), [M+H]=271.

Example 128

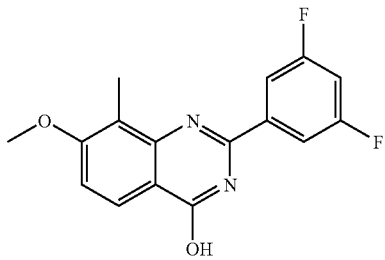

2-(3,5-Difluoro-phenyl)-7-methoxy-8-methyl-quinazolin-4-ol (128)

The general procedure described above was followed using 2-amino-4-methoxy-3-methyl benzamide as benzamide derivative [A] and 3,5-difluoro-benzoyl chloride as acid chloride [B], which gave the title compound (2.1 g, 85%), [M+H]=303.

Example 129

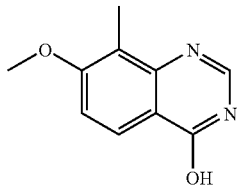

7-Methoxy-8-methyl-quinazolin-4-ol (129)

The title compound was formed as a biproduct when the ring closing reaction, step [B] to [C], in the general procedure was performed in DMF rather than in EtOH.

Example 130

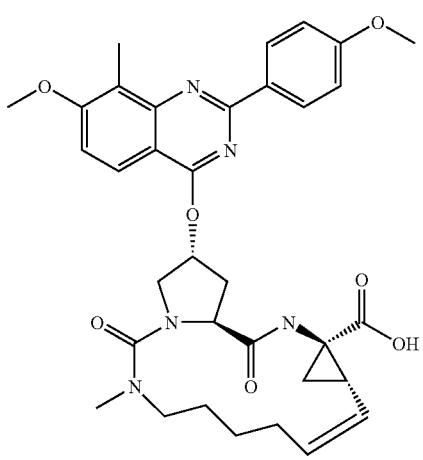

17-[7-Methoxy-2-(4-methoxy-phenyl)-8-methyl-quinazolin-4-yloxy]-13-methyl-2,14-dioxo-3,13,15-triaza-tricyclo[13.3.0.0*4,6*]octadec-7-ene-4-carboxylic acid (130)

Quinazolinol derivative (125) (281 mg, 0.949 mmol) was coupled to alcohol 51 (300 mg, 0.791 mmol) followed by hydrolysis of the ethyl ester as described in example 52 which gave the title compound (185 mg, 47%). MS (M+H)=630

Example 131

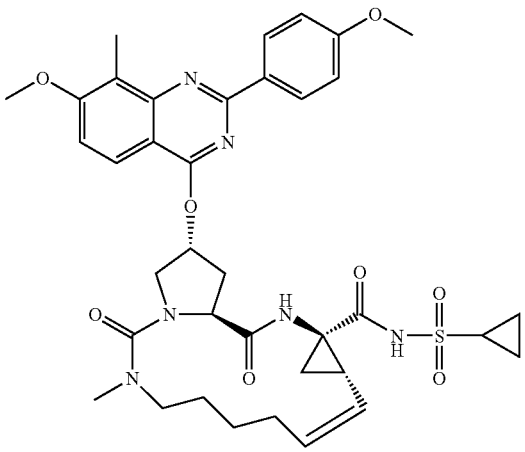

Cyclopropanesulfonic acid {17-[7-methoxy-2-(4-methoxy-phenyl)-8-methyl-quinazolin-4-yloxy]-13-methyl-2,14-dioxo-3,13,15-triaza-tricyclo[13.3.0.0*4,6*]-octadec-7-ene-4-carbonyl}-amide (131)

The acid (130) (70 mg, 0.111 mmol) was dissolved in DCM (2 ml). EDAC (26 mg, 0.133 mmol) was added and the mixture was stirred at room temperature over night. Cyclopropanesulfonic acid amide (15 mg, 0.122 mmol) and DBU (35 µl, 0.233 mmol) was added and the reaction mixture was stirred at room temperature over night. 5% Citric acid was added to the reaction mixture, and the mixture was extracted with brine, dried over $Na_2SO_4$ and purified by column chromatography (DCM/MeOH 20:1) to give the title compound (29 mg, 36%). MS (M+H)=733

Example 132

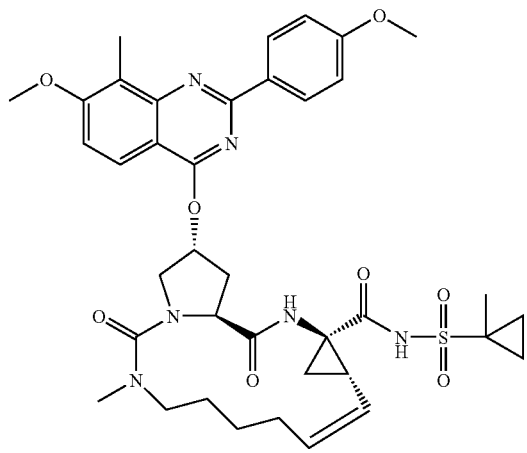

1-Methyl-cyclopropanesulfonic acid {17-[7-methoxy-2-(4-methoxy-phenyl)-8-methyl-quinazolin-4-yloxy]-13-methyl-2,14-dioxo-3,13,15-triaza-tricyclo[13.3.0.0*4,6*]octadec-7-ene-4-carbonyl}-amide (132)

The acid (130) (35 mg, 0.056 mmol) was dissolved in DCM (2 ml). EDAC (13 mg, 0.067 mmol) was added and the mixture was stirred at room temperature over night. Methyl-cyclopropanesulfonic acid amide (8.2 mg, 0.061 mmol) and DBU (18 µl, 0.117 mmol) was added and the reaction mixture was stirred at room temperature over night. 5% Citric acid was added to the reaction mixture, and the mixture was extracted with brine, dried over $Na_2SO_4$ and purified by HPLC to give the title compound (9 mg, 22%). MS (M+H)=747.

Example 133

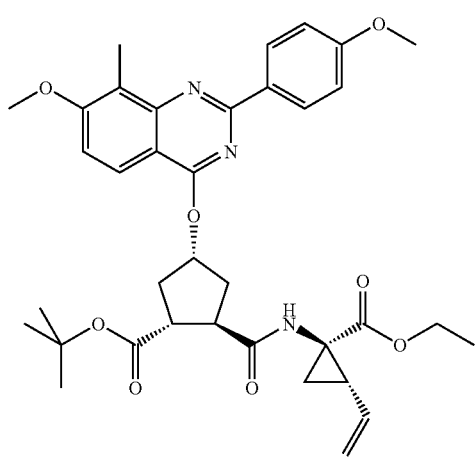

2-(1-Ethoxycarbonyl-2-vinyl-cyclopropylcarbamoyl)-4-[7-methoxy-2-(4-methoxy-phenyl)-8-methyl-quinazolin-4-yloxy]-cyclopentanecarboxylic acid tert-butyl ester (133)

The alcohol 15 (550 mg, 1.5 mmol), quinazolinol 125 (533 mg, 1.8 mmol) and triphenyl phosphine (990 mg, 3.75 mmol) were dissolved in THF (40 ml) and cooled to 0° C. Diisopropyl azidocarboxylate (0.74 ml, 3.75 mmol) was added slowly and the slurry was allowed to reach room temperature. After 12 h, the solvent was removed under reduced pressure and the residue was taken up in ether and filtrated. Purification by column chromatography ($SiO_2$; Toluene/EtOAc 9:1→4:1) gave the title compound (919 mg, 95%). MS (M+H)$^+$ 646.

Example 134

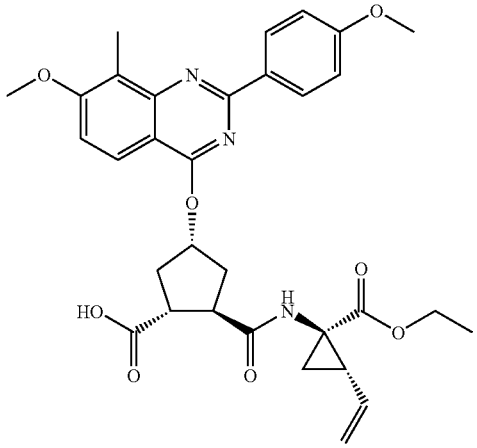

2-(1-Ethoxycarbonyl-2-vinyl-cyclopropylcarbamoyl)-4-[7-methoxy-2-(4-methoxy-phenyl)-8-methyl-quinazolin-4-yloxy]-cyclopentanecarboxylic acid (134)

Compound 133 (915 mg, 1.417 mmol) was dissolved in dichloromethane (20 mL) and triethylsilane (0.56 mL). TFA (20 ml) was added dropwise at room temperature and the mixture was left for 3 h at room temperature. Removal of the solvent gave the title compound (737 mg, 88%) MS (M+H)+ 590.

Example 135

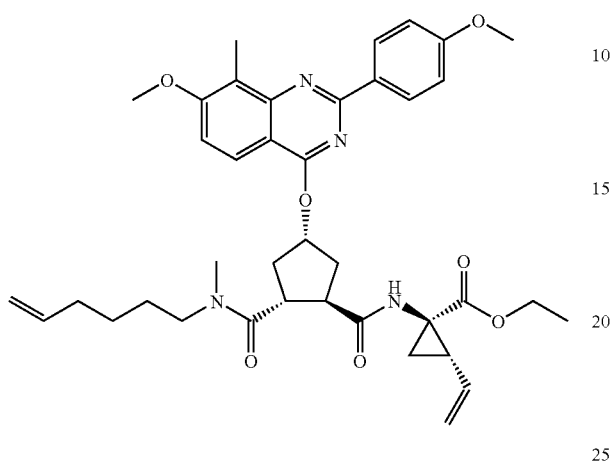

1-({2-(Hex-5-enyl-methyl-carbamoyl)-4-[7-methoxy-2-(4-methoxy-phenyl)-8-methyl-quinazolin-4-yloxy]-cyclopentanecarbonyl}-amino)-2-vinyl-cyclopropanecarboxylic acid ethyl ester (135)

The acid 134 (723 mg, 1.227 mmol) was dissolved in DMF (25 mL). Diisopropyl ethylamine (633 mg, 4.91 mmol) was added and the reaction mixture was placed on an ice-bath. N-methyl-1-hexen hydrochloride (266 mg, 1.78 mmol) and HATU (676 mg, 1.78 mmol) were added and the mixture was stirred at room temperature for 1 h. The solvent was removed and the residue was partitioned between EtOAc and aqueous sodium bicarbonate. The organic phase was collected and the crude product was purified by column chromatography (silica gel, Heptane/EtOAc 80:20→50:50). Evaporation of the solvent gave the title compound (585 mg, 70%). MS (M+H)+ 685.

Example 136

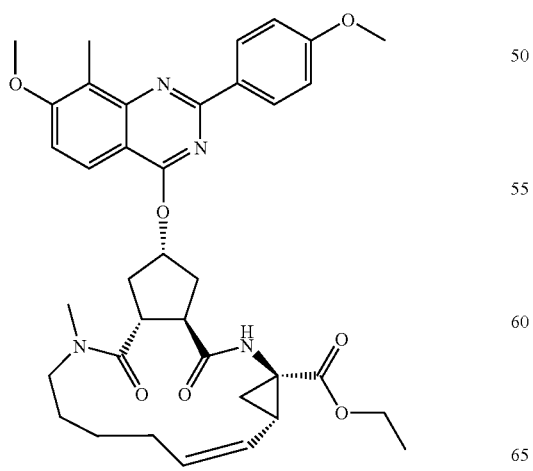

17-[7-Methoxy-2-(4-methoxy-phenyl)-8-methyl-quinazolin-4-yloxy]-13-methyl-2,14-dioxo-3,13-diaza-tricyclo[13.3.0.0*4,6*]octadec-7-ene-4-carboxylic acid ethyl ester (136)

The diene 135 (585 mg, 0.854 mmol) and Hoveyda-Grubbs catalyst, IInd generation (50 mg) were dissolved in degassed and dry 1,2-dichloroethane (500 mL). The mixture was heated to reflux temperature over-night under argon atmosphere. Evaporation of the solvent and purification by column chromatography (silica gel; Heptane/EtOAc 70:30) gave the title compound (420 mg, 75%). MS (M+H)+ 658.

Example 137

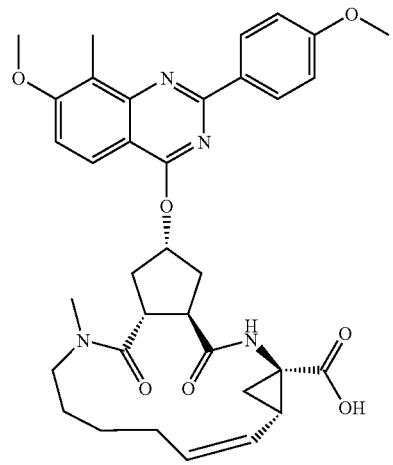

17-[7-Methoxy-2-(4-methoxy-phenyl)-8-methyl-quinazolin-4-yloxy]-13-methyl-2,14-dioxo-3,13-diaza-tricyclo[13.3.0.0*4,6*]octadec-7-ene-4-carboxylic acid (137)

Compound 136 (420 mg, 0.639 mmol) was dissolved in a 96 mL solvent mixture (THF 2:methanol 1:water 1). Aqueous lithium hydroxide (6.4 mL, 1M) was added and the reaction mixture was heated at 50° C. over-night. Purification by column chromatography (silica gel, 5% methanol in dichloromethane) gave the title compound (230 mg, 57%). MS (M+H)+ 629.

Example 138

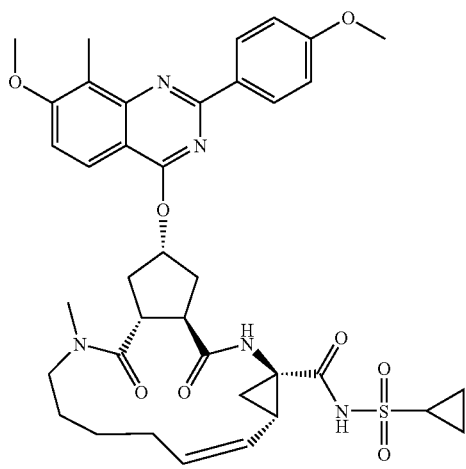

Cyclopropanesulfonic acid {17-[7-methoxy-2-(4-methoxy-phenyl)-8-methyl-quinazolin-4-yloxy]-13-methyl-2,14-dioxo-3,13-diaza-tricyclo[13.3.0.0*4,6*]octadec-7-ene-4-carbonyl}-amide (138)

The acid 137 (130 mg, 0.207 mmol) and N,N,-carbonyldiimidazole (43 mg, 0.26 mmol) in THF (7 mL) were heated to reflux for 2 hours. DBU (29 µl), and cyclopropanesulfonamide, prepared as described in WO03/053349, (28 mg, 0.23 mmol) was then added and the mixture was stirred at 60° C. over-night. The reaction mixture was diluted with ethyl acetate (25 mL) and washed with 0.5 M citric acid. Purification by HPLC gave 30 mg of the title compound. MS (M+H)+ 732.

Example 139

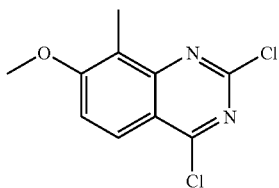

2,4-Dichloro-7-methoxy-8-methylquinazoline (139)

Trichloromethyl chloroformate (3.60 mL, 29.8 mmol) was added under nitrogen to a solution of 6-cyano-3-methoxy-2-methylaniline (77) (3.2 g, 19.7 mmol) in acetonitrile (0.809 g, 19.7 mmol). The resulting reaction mixture was heated in a sealed tube at 130° C. After 12 h, the reaction mixture was successively cooled down to room temperature, partitioned between ice-cooled water and EtOAc, dried (Na$_2$SO$_4$) and evaporated. Purification by column chromatography (gradient EtOAc/CH$_2$Cl$_2$, 1:9 to 1:1) afforded the title compound (3.17 g, 85%) as an orange solid: m/z=243 (M+H)+.

Example 140

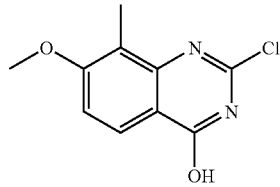

2-Chloro-4-hydroxy-7-methoxy-8-methylquinazoline (140)

A solution of NaOH (1.58 g, 39.6 mmol) in water (40 mL) was added to 2,4-dichloro-7-methoxy-8-methylquinazoline (139) (3.2 g, 13.05 mmol) in THF (20 mL). The resulting mixture was heated at 40° C. for 24 h. Then, the reaction mixture was cooled to room temperature, THF was evaporated and additional water (30 mL) was added. The precipitate was filtered off. Then, the pH of the filtrate was adjusted to 5 with AcOH to give a solid which was subsequently filtered off and successively washed with water and isopropylether to give the title compound (2.91 g, 99%) as a yellowish powder: m/z=225 (M+H)+.

Example 141

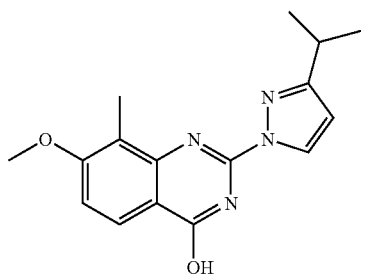

4-Hydroxy-2-(3-isopropylpyrazol-1-yl)-7-methoxy-8-methylquinazoline (141)

A mixture of 2-chloro-4-hydroxy-7-methoxy-8-methylquinazoline (140) (502 mg, 2.23 mmol) and 3-isopropylpyrazole (500 mg, 4.55 mmol) was heated at 155° C. for 10 min. Then, the reaction mixture was successively cooled down to room temperature, partitioned between CH$_2$Cl$_2$ and water, dried (Na$_2$SO$_4$) and evaporated. The residue was tritu-

Example 142

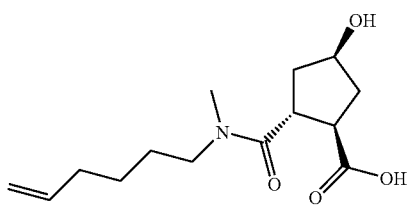

2-(Hex-5-enyl-methyl-carbamoyl)-4-hydroxy-cyclopentanecarboxylic acid (142)

A solution of LiOH (105 mg in 4 mL, of water) was added at 0° C. to the lactone amide (65). After 1 h, the conversion was completed (HPLC). The mixture was acidified to pH 2-3 with 1N HCl, extracted with EtOAc, dried (MgSO$_4$), evaporated, co-evaporated with toluene several times, and dried under high vacuum overnight to give the title compound (520 mg, 88%), m/z=270 (M+H)$^+$.

Example 143

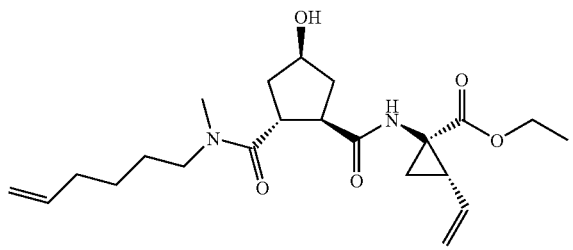

1-{[2-(Hex-5-enyl-methyl-carbamoyl)-4-hydroxy-cyclopentanecarbonyl]-amino}-2-vinyl-cyclopropanecarboxylic acid ethyl ester (143)

1-(Amino)-2-(vinyl)cyclopropanecarboxylic acid ethyl ester hydrochloride (4.92 g, 31.7 mmol) and HATU (12.6 g, 33.2 mmol) were added to the acid (142) (8.14 g, 30.2 mmol). The mixture was cooled in an ice bath under argon, and then DMF (100 mL) and DIPEA (12.5 mL, 11.5 mmol) were added. After 30 min at 0° C., the solution was stirred at room temperature for an additional 3 h. Then, the reaction mixture was partitioned between EtOAc and water, washed successively with 0.5 N HCl (20 mL) and saturated NaCl (2×20 mL), and dried (Na$_2$SO$_4$). Purification by flash chromatography (EtOAc/CH$_2$Cl$_2$/Petroleum ether, 1:1:1) afforded the title compound (7.41, g 60%) as a colorless oil, m/z=407 (M+H)$^+$.

rated in ether and filtered to give the title compound (422 mg, 63%) as white needles: m/z=299 (M+H)$^+$.

Example 144

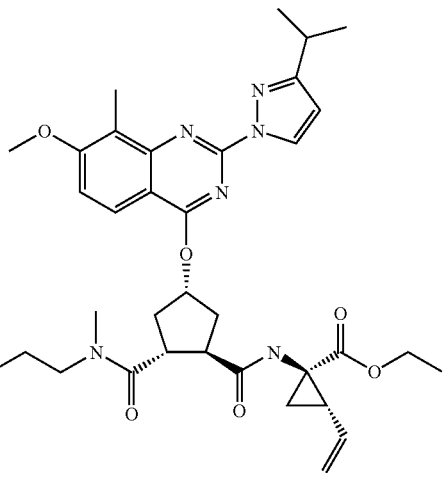

1-({2-(Hex-5-enyl-methyl-carbamoyl)-4-[2-(3-isopropyl-pyrazol-1-yl)-7-methoxy-8-methyl-quinazolin-4-yloxy]-cyclopentanecarbonyl}-amino)-2-vinyl-cyclopropane-carboxylic acid ethyl ester (144)

DIAD (280 µL, 1.42 mmol) was added at −20° C. under nitrogen atmosphere to a solution of the alcohol (143) (367 mg, 0.90 mmol), 4-hydroxy-2-(3-isopropylpyrazol-1-yl)-7-methoxy-8-methylquinazoline (141) (270 mg, 0.90 mmol) and triphenyl-phosphine (288 mg, 1.42 mmol) in dry DMF (35 mL). After 2 h, the solution was warmed up to room temperature. After 12 h, the reaction mixture was partitioned between ice-cold water and ether, organic layer was dried (Na$_2$SO$_4$) and evaporated. The residue was purified by column chromatography (gradient AcOEt/CH$_2$Cl$_2$, 1:9 to 10:0) to give the title compound (230 mg, 34%), m/z=687 (M+H)$^+$.

Example 145

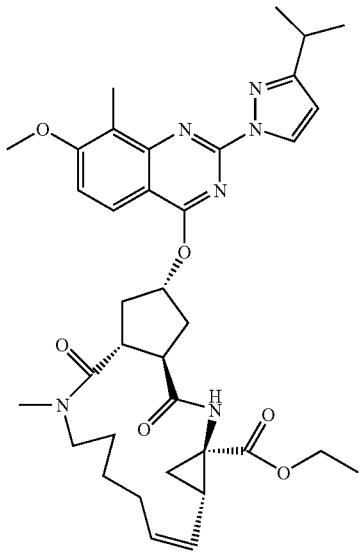

17-[2-(3-Isopropyl-pyrazol-1-yl)-7-methoxy-8-methyl-quinazolin-4-yloxy]-13-methyl-2,14-dioxo-3,13-diaza-tricyclo[13.3.0.0*4,6*]octadec-7-ene-4-carboxylic acid ethyl ester (145)

A solution of the diene (144) (230 mg, 0.335 mmol) and Hoveyda-Grubbs 1st generation catalyst (60.8 mg, 0.101 mmol) in dried and degassed 1,2-dichloroethane (230 mL) was heated at 80° C. under nitrogen for 18 h. Then, the solvent was evaporated and the residue purified by silica gel chromatography (ether) to give the target compound, m/z=659 (M+H)+.

Example 146

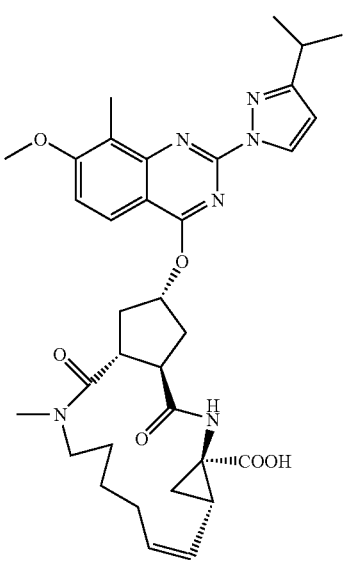

17-[2-(3-isopropylpyrazol-1-yl)-7-methoxy-8-methylquinazolin-4-yloxy]-13-methyl-2,14-dioxo-3,13-diazatricyclo[13.3.0.0^{4,6}]octadec-7-ene-4-carboxylic acid (146)

A solution of lithium hydroxide hydrate (796 mg, 18.6 mmol) in water (10 mL) was added to a stirred solution of the ester (145) (346 mg, 0.526 mmol) in THF (30 mL). After 5 days at room temperature, the reaction mixture was concentrated under vacuum. The pH was adjusted to 4 with 1N HCl and the resulting solution was successively extracted with AcOEt, washed with brine, dried (Na$_2$SO$_4$) and evaporated. The residue was purified by column chromatography (CH$_2$Cl$_2$/MeOH, 97.5:2.5) then triturated in isopropylether to give the title compound as a solid, m/z=631 (M+H)+.

Example 147

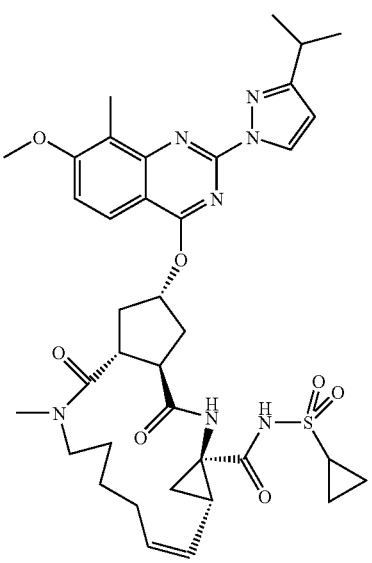

N-[17-[2-(3-isopropylpyrazol-1-yl)-7-methoxy-8-methylquinazolin-4-yloxy]-13-methyl-2,14-dioxo-3,13-diazatricyclo[13.3.0.0^{4,6}]octadec-7-ene-4-carbonyl](cyclo-propyl)sulfonamide (147)

A solution of the acid (146) (53 mg, 0.084 mmol), and carbonyldiimidazole (29.4 mg, 0.181 mmol) in dry THF (10 mL) was stirred at reflux under nitrogen for 2 h. The reaction mixture was cooled to room temperature and cyclopropylsulfonamide (50.3 mg, 0.415 mmol) and DBU (34.1 mg, 0.224 mmol) were added. This solution was heated at 50° C. for 15 h. Then, the reaction mixture was cooled down at room temperature and concentrated under reduced pressure. The residue was partitioned between AcOEt and diluted HCl, the organic layer was washed with brine, dried (Na$_2$SO$_4$) and evaporated. Purification by flash chromatography (EtOAc/CH$_2$Cl$_2$, 2:8) provided the desired product which was subsequently dissolved in a minimum of ethanol and diluted with water. Filtration of the precipitate afforded the title compound (14.8 mg, 24%) as a white powder, m/z=734 (M+H)+.

$^1$H NMR (CDCl$_3$): 0.96-2.05 (m, 20H), 2.20-2.80 (m, 10H), 2.90-3.60 (m, 4H), 3.99 (s, 3H), 4.60 (t, J=12 Hz, 1H), 5.04 (t, J=10 Hz, 1H), 5.65 (m, 1H), 5.94 (m, 1H), 6.20-6.60 (m, 2H), 7.12 (d, J=8.8 Hz, 1H), 7.95 (d, J=8.8 Hz, 1H), 8.56 (s, 1H), 10.9 (broad s, 1H).

Example 148

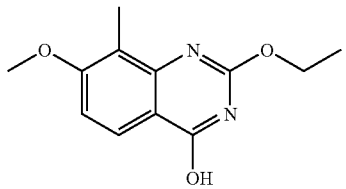

2-Ethoxy-4-hydroxy-7-methoxy-8-methylquinazoline (148)

The quinazolinol (140) (530 mg, 2.36 mmol) was added in small portions to freshly prepared EtONa (740 mg of Na added in 20 mL EtOH). The resulting solution was heated to reflux and after 24 h, the reaction mixture was cooled down to room temperature and evaporated. The residue was re-dissolved in water (10 mL) and the pH of the resulting solution was adjusted to 5 with AcOH. The precipitate was collected by filtration, washed with ice-cooled water and dried to give the title compound (534 mg, 96.6%) as a white solid, m/z=235 (M+H)$^+$.

Example 149

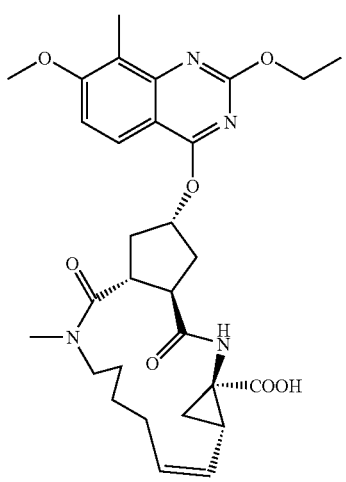

17-[2-Ethoxy-7-methoxy-8-methylquinazolin-4-yloxy]-13-methyl-2,14-dioxo-3,13-diazatricyclo[13.3.0.0$^{4,6}$]octadec-7-ene-4-carboxylic acid (149)

Reaction of the quinazolinol (148) and the alcohol (143) according to the procedure described in examples 144-146, gave the title compound m/z=567 (M+H)$^+$.

Example 150

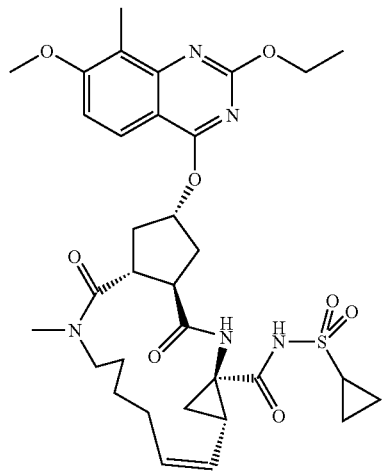

N-[17-[2-Ethoxy-7-methoxy-8-methylquinazolin-4-yloxy]-13-methyl-2,14-dioxo-3,13-diazatricyclo[13.3.0.0$^{4,6}$]octadec-7-ene-4-carbonyl](cyclopropyl)sulfonamide (150)

The acid (149) was reacted with cyclopropylsulfonamide according to the procedure described in example 147, which gave the title compound, m/z=670 (M+H)$^+$.

$^1$H NMR (CDCl$_3$):

Example 151

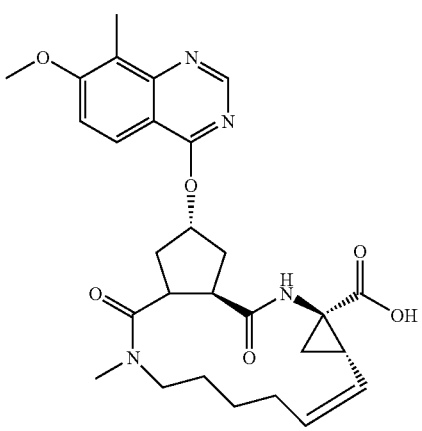

17-(7-Methoxy-8-methyl-quinazolin-4-yloxy)-13-methyl-2,14-dioxo-3,13,15-triaza-tricyclo[13.3.0.0*4,6*]octadec-7-ene-4-carboxylic acid (126)

Quinazolinol derivative (126) (460 mg, 2.4 mmol) was coupled to the alcohol 15 (740 mg, 2 mmol) as described in example 16, followed by removal of the boc group as described in example 17, coupling of N-methyl-1-hexenylamine as described in example 18, a ring closing metathesis reaction as described in example 19 and hydrolysis of the ethyl ester as described in example 52, which gave the title compound (82 mg, 8%), MS (M+H) 523.

Example 152

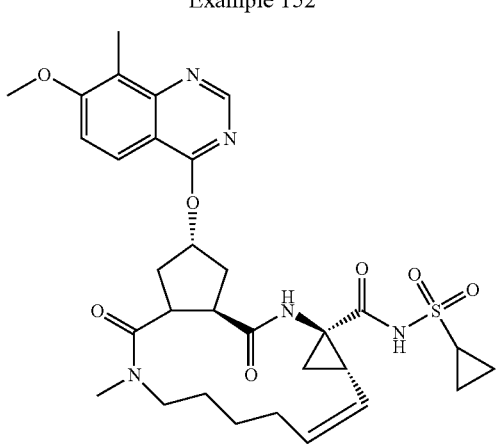

Cyclopropanesulfonic acid [17-(7-methoxy-8-methyl-quinazolin-4-yloxy)-13-methyl-2,14-dioxo-3,13,15-triaza-tricyclo[13.3.0.0*4,6*]octadec-7-ene-4-carbonyl]-amide (152)

A solution of the acid (151) (81 mg, 0.155 mmol) and EDC (40 mg, 0.21 mmol) in dry DCM (2 ml) was stirred at room temperature overnight. Cyclopropylsulfonamide (48 mg, 0.4 mmol) and DBU (76 mg, 0.5 mmol) was added and the mixture was stirred at room temperature for 6 hours. 5% Citric acid was added and the mixture was extracted three times with ethyl acetate. The organic phase was washed with 5% citric acid and brine, dried with sodium sulphate and evaporated under reduced pressure. The residue was purified by column chromatography on silica gel eluted with ether-methanol which gave the title compound (32 mg, 31%), MS (M+H) 626.

Example 153

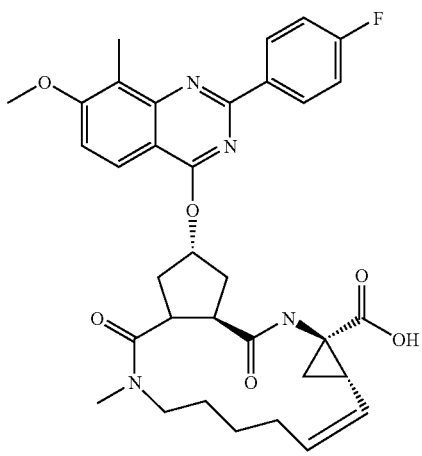

17-[2-(4-Fluoro-phenyl)-7-methoxy-8-methyl-quinazolin-4-yloxy]-13-methyl-2,14-dioxo-3,13,15-triaza-tricyclo[13.3.0.0*4,6*]octadec-7-ene-4-carboxylic acid (153)

Quinazolinol derivative (92) (520 mg, 1.8 mmol) was coupled to the alcohol 15 (550 mg, 1.5 mmol) as described in example 16, followed by removal of the boc group as described in example 17, coupling of N-methyl-1-hexenylamine as described in example 18, a ring closing metathesis reaction as described in example 19 and hydrolysis of the ethyl ester as described in example 52, which gave the title compound (185 mg, 20%), MS (M+H) 617.

Example 154

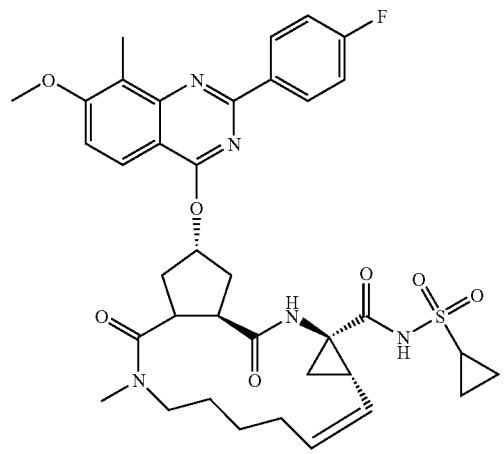

Cyclopropanesulfonic acid {17-[2-(4-fluoro-phenyl)-7-methoxy-8-methyl-quinazolin-4-yloxy]-13-methyl-2,14-dioxo-3,13,15-triaza-tricyclo[13.3.0.0*4,6*]octadec-7-ene-4-carbonyl}-amide (154)

A solution of the acid (153) (92 mg, 0.15 mmol) and EDC (38 mg, 0.2 mmol) in dry DCM (2 ml) was stirred at room temperature overnight. Cyclopropylsulfonamide (48 mg, 0.4 mmol) and DBU (76 mg, 0.5 mmol) was added and the mixture was stirred at room temperature for 6 hours. 5% Citric acid was added and the mixture was extracted three times with ethyl acetate. The organic phase was washed with 5% citric acid and brine, dried with sodium sulphate and evaporated under reduced pressure. The residue was purified by column chromatography on silica gel eluted with ether-methanol which gave the title compound (70 mg, 65%), MS (M+H) 720.

Example 155

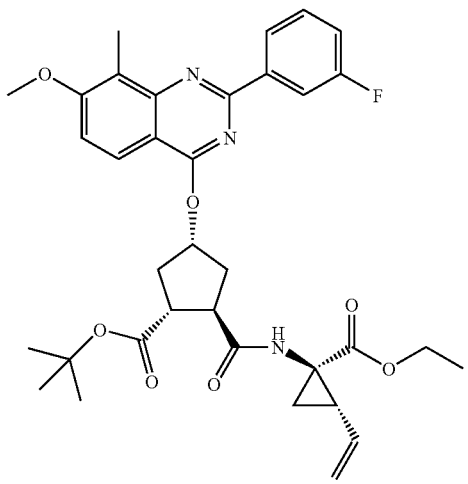

2-(1-Ethoxycarbonyl-2-vinyl-cyclopropylcarbamoyl)-4-[2-(3-fluoro-phenyl)-7-methoxy-8-methyl-quinazolin-4-yloxy]-cyclopentanecarboxylic acid tert-butyl ester (155)

PPh$_3$ (787 mg, 3.0 mmol) was added to a stirred solution of the alcohol 15 (550 mg, 1.5 mmol) and the quinazolinol 127 (430 mg, 1.5 mmol) in a mixture of dry THF (40 mL) and dry DMF 10 mL. The reaction mixture was put under inert atmosphere (N$_2$) at room temperature and DIAD (591 µL, 3.0 mmol) was added. The reaction mixture was stirred for 18 h whereafter the solvents were evaporated. The residue was dissolved in CHCl$_3$ and washed with brine in a separatory funnel. The organic phase was dried with Na$_2$SO$_4$, evaporated on silica and purified by flash chromatography (heptane:ethyl acetate 2:1 to 1:1) which gave the title compound as a white-beige solid (896 mg, 94%), LRMS (M+H) 634.

Example 156

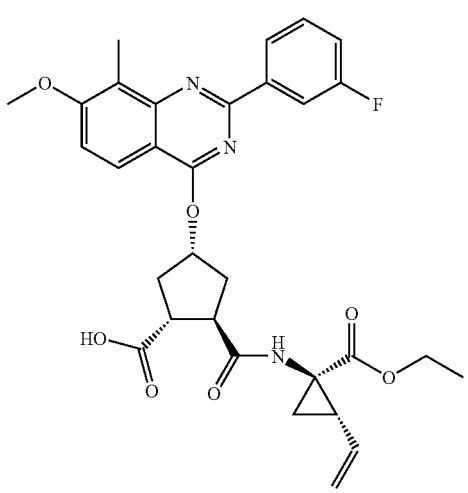

2-(1-Ethoxycarbonyl-2-vinyl-cyclopropylcarbamoyl)-4-[2-(3-fluoro-phenyl)-7-methoxy-8-methyl-quinazolin-4-yloxy]-cyclopentanecarboxylic acid (156)

Compound 155 (0.896 g, 1.41 mmol) was dissolved in a mixture of DCM (30 mL), TFA (10 mL), a few drops of TES and a drop of H$_2$O. The reaction was stirred for 30 minutes followed by removal of solvent by evaporation. The crude residue was partitioned between CHCl$_3$ and saturated NaHCO$_3$ (aq). The organic phase was dried (Na$_2$SO$_4$) and evaporated which gave the compound (0.81 g, 99%) as a white solid.

LRMS (M+H) 578.

Example 157

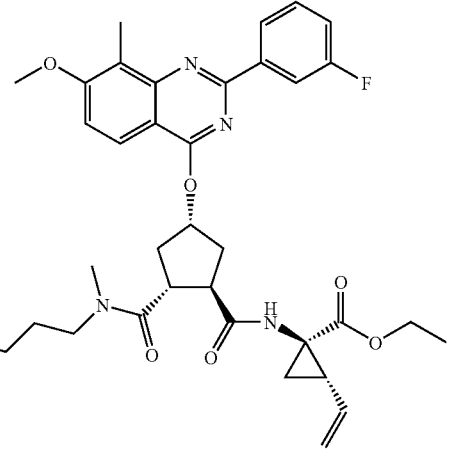

1-{[4-[2-(3-Fluoro-phenyl)-7-methoxy-8-methyl-quinazolin-4-yloxy]-2-(hex-5-enyl-methyl-carbamoyl)-cyclopentanecarbonyl]-amino}-2-vinyl-cyclopropanecarboxylic acid ethyl ester (157)

Compound 156 (0.81 g, 1.40 mmol) and hex-5-enyl-methyl-amine hydrochloride (272 mg, 1.82 mmol) was dissolved in dry DMF (50 mL). DIEA (975 µL, 5.6 mmol) was added and the reaction flask was placed in an ice bath. After 10 minutes HATU (559 mg, 1.47 mmol) was added to the solution. The reaction flask was allowed to reach room temperature and the stirring was continued for 3 hrs before the solvent was removed by evaporation. The crude product was extracted with CHCl$_3$ and washed with saturated NaHCO$_3$ (aq). The organic phase was dried (Na$_2$SO$_4$), evaporated on silica and purified to by flash chromatography (heptane:ethyl acetate 1:1) to give the title compound (0.716 g, 76%), LRMS (M+H) 673.

Example 158

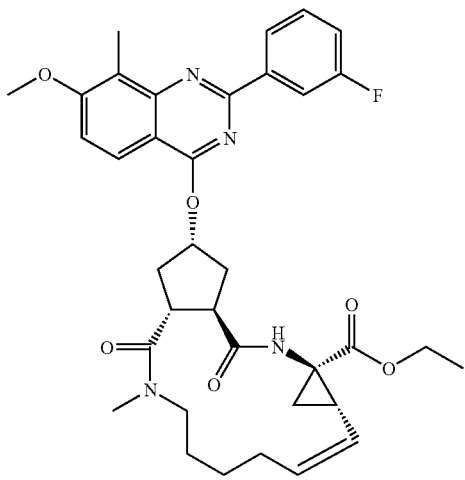

17-[2-(3-Fluoro-phenyl)-7-methoxy-8-methyl-quinazolin-4-yloxy]-13-methyl-2,14-dioxo-3,13-diaza-tricyclo[13.3.0.0*4,6*]octadec-7-ene-4-carboxylic acid ethyl ester (158)

The diene 157 (0.70 g, 1.041 mmol) was dissolved in dry DCE (0.7 L). The solution was put under inert atmosphere ($N_2$) and catalyst (Hoveyda Grubbs $2^{nd}$ generation, 70 mg, 0.113 mmol) was added to the solution. The reaction mixture was refluxed for 16 h, cooled to room temperature and evaporated on silica by rotary evaporation. The product was purified by flash chromatography (heptane:ethyl acetate 1:1) which gave the title compound (0.466 g, 70%), LRMS (M+H) 645.

Example 159

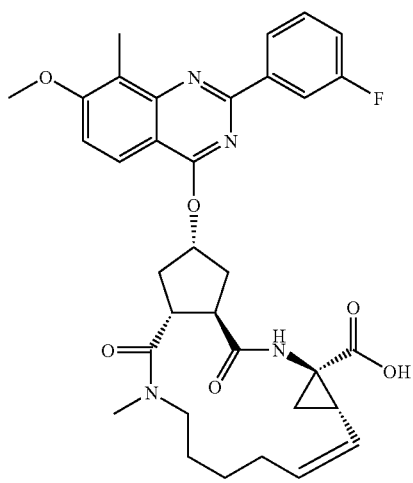

17-[2-(3-Fluoro-phenyl)-7-methoxy-8-methyl-quinazolin-4-yloxy]-13-methyl-2,14-dioxo-3,13-diaza-tricyclo[13.3.0.0*4,6*]octadec-7-ene-4-carboxylic acid (159)

The ethyl ester 158 (460 mg, 0.713 mmol) was dissolved in THF:MeOH:$H_2O$ (2:1:1, 100 mL) and LiOH (1M) (7.13 mL mg, 7.13 mmol) was added to the solution. The reaction was heated to 50° C. for 16 hrs. THF and MeOH was then removed by rotary evaporation and the remaining solution was acidified with 20 mL 10% citric acid (aq). The water phase was extracted with $CHCl_3$ (3×50 mL) and the organic phase was washed with brine. The organic phase was dried with $Na_2SO_4$, filtered and concentrated by rotary evaporation. The product was obtained as a white solid (0.363 g, 82%), LRMS (M+H) 617.

Example 160

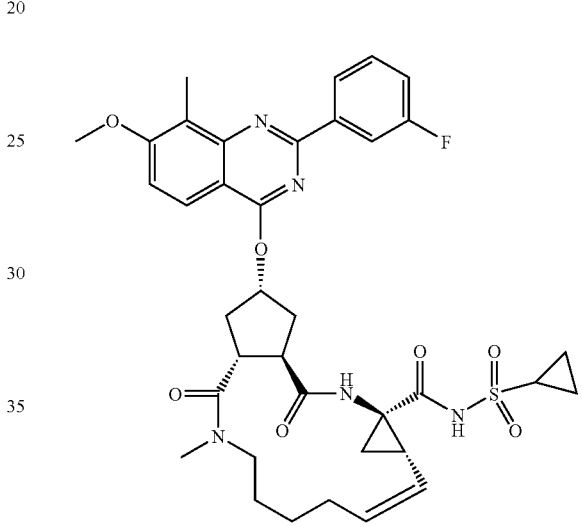

Cyclopropanesulfonic acid {17-[2-(3-fluoro-phenyl)-7-methoxy-8-methyl-quinazolin-4-yloxy]-13-methyl-2,14-dioxo-3,13-diaza-tricyclo[13.3.0.0*4,6*] octadec-7-ene-4-carbonyl}-amide (160)

A mixture of the acid 159 (200 mg, 0.324 mmol) and CDI (105 mg, 0.649 mmol) in dry THF (12 mL) was heated at reflux for 2 h under $N_2$. The reaction mixture was cooled 50° C. and a pre-mixed solution of cyclopropyl sulfonamide (118 mg, 0.973 mmol) and DBU (138 μL, 0.908 mmol) in 2 ml of dry THF was added to the reaction mixture. The reaction was stirred at 50° C. for 18 h. The solution was pored in a separatory funnel and acidified with approx. 20 mL citric acid 10% (aq). Additional brine (20 mL) and EtOAc (40 mL) was added. The mixture was extracted with EtOAc and washed with brine, thereafter dried with $Na_2SO_4$, filtered and the solvent was removed by rotary evaporation. The crude product was purified by HPLC on an Ace-5 C8 column (100×21.2 mm) with a gradient going from 35 to 60% acetonitrile (0.1% TFA) in $H_2O$ (0.1% TFA) over 8 minutes. The title compound was obtained as a white solid (144 mg, 62%), LRMS (M+H) 720.

$^{13}C$ NMR ($CDCl_3$, 500 MHz) δ 6.1, 6.6, 9.6, 21.1, 24.1, 25.8, 27.8, 31.0, 32.4, 34.3, 34.9, 35.8, 44.8, 44.8, 47.5, 48.3, 56.2, 109.6, 112.3, 115.3*, 115.4*, 117.6*, 117.8*, 120.9, 122.4, 124.2, 124.3, 129.9*, 130.0*, 132.9, 140.7, 149.8, 158.2, 161.3, 162.0, 166.3, 168.2, 173.6, 179.6. (*=carbon dublets).

141.0*, 141.0*, 151.4, 157.9, 160.8, 162.2, 166.1, 167.9, 173.4, 180.4. (*=carbon dublets).

Example 161

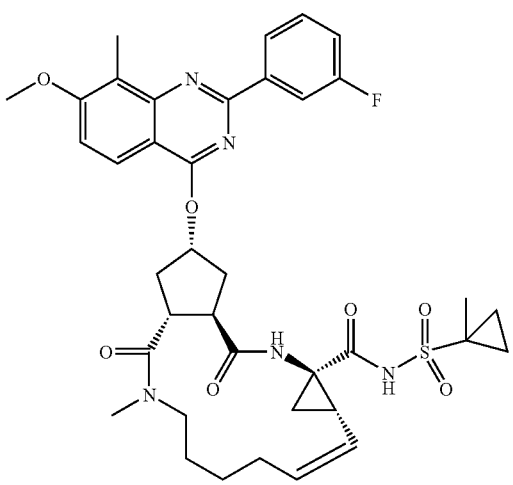

1-Methyl-cyclopropanesulfonic acid {17-[2-(3-fluoro-phenyl)-7-methoxy-8-methyl-quinazolin-4-yloxy]-13-methyl-2,14-dioxo-3,13-diazatricyclo[13.3.0.0*4,6*]octadec-7-ene-4-carbonyl}-amide (161)

A mixture of the acid 159 (100 mg, 0.162 mmol) and CDI (53 mg, 0.325 mmol) in dry THF (7 mL) was heated at reflux for 2 h under $N_2$. The reaction mixture was cooled 50° C. and a pre-mixed solution of methyl-cyclopropyl sulfonamide (66 mg, 0.486 mmol) and DBU (69 µL, 0.454 mmol) in dry THF (1 ml) was added to the reaction mixture. The reaction was stirred at 50° C. for 18 h. The solvent was evaporated and the residue was dissolved in $CHCl_3$ and washed with citric acid (10% aq). The organic phase was dried with $Na_2SO_4$, filtered and the solvent was removed by rotary evaporation. The crude product was purified by HPLC on an Ace-5 C8 column (100× 21.2 mm) with a gradient going from 35 to 60% acetonitrile (0.1% TFA) in $H_2O$ (0.1% TFA) over 8 minutes. The product was obtained as a white solid (23 mg, 19%). LRMS (M+H) 734.

$^{13}C$ NMR (CDCl$_3$, 500 MHz) δ 9.6, 12.5, 14.4, 18.2, 22.3, 23.9, 25.9, 27.5, 32.4, 34.1, 35.2, 35.9, 36.3, 44.3, 44.9, 47.4, 48.1, 56.1, 76.7, 109.8, 112.0, 115.0*, 115.2*, 117.1*, 117.3*, 121.8, 122.0, 124.0, 124.9, 129.9*, 129.9*, 132.7,

Example 162

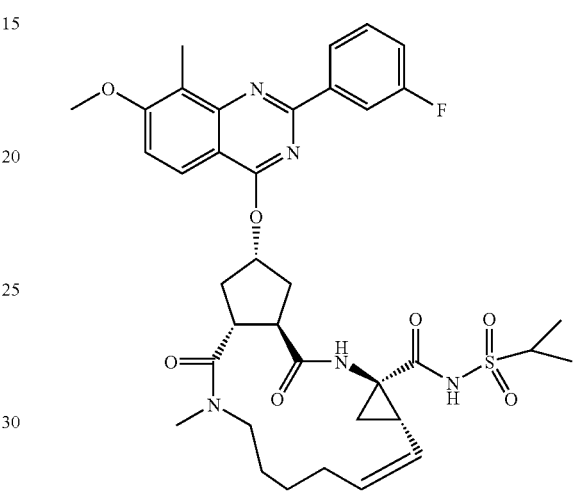

Propane-2-sulfonic acid {17-[2-(3-fluoro-phenyl)-7-methoxy-8-methyl-quinazolin-4-yloxy]-13-methyl-2,14-dioxo-3,13-diazatricyclo[13.3.0.0*4,6*]octadec-7-ene-4-carbonyl}-amide (162)

A mixture of the acid 159 (71 mg, 0.115 mmol) and CDI (37 mg, 0.228 mmol) in dry THF (10 mL) was heated at reflux for 2 h under $N_2$. The reaction mixture was cooled 50° C. and a pre-mixed solution of methyl-cyclopropyl sulfonamide (43 mg, 0.349 mmol) and DBU (49 µL, 0.322 mmol) in 2 ml of dry THF was added to the reaction mixture. The reaction was stirred at 50° C. for 18 h. The solvent was evaporated and the residue was dissolved in $CHCl_3$ and washed with citric acid (10% aq). The organic phase was dried with $Na_2SO_4$, filtered and the solvent was removed by rotary evaporation. The crude product was purified by HPLC on an Ace-5 C8 column (100× 21.2 mm) with a gradient going from 35 to 60% acetonitrile (0.1% TFA) in $H_2O$ (0.1% TFA) over 8 minutes. The product was obtained as a white solid (30 mg, 36%), LRMS (M+H) 722.

$^{13}C$ NMR (CDCl$_3$, 500 MHz) δ 9.7, 15.0, 16.8, 20.8, 24.1, 26.0, 27.7, 32.8, 34.2, 35.4, 36.0, 44.4, 44.8, 47.4, 48.2, 53.3, 56.2, 76.8, 110.0, 112.2, 115.1*, 115.3*, 117.3*, 117.4*, 121.9, 122.1, 124.2, 124.7, 130.0, 133.2, 141.2, 151.5, 158.1, 161.0, 162.3, 166.2, 169.5, 173.6, 180.5. (*=carbon dublets).

Example 163

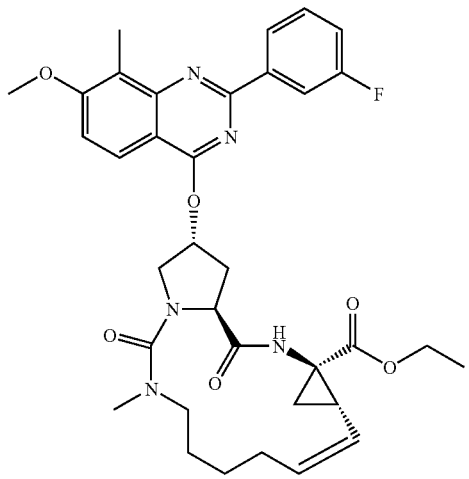

17-[2-(3-Fluoro-phenyl)-7-methoxy-8-methyl-quinazolin-4-yloxy]-13-methyl-2,14-dioxo-3,13,15-triaza-tricyclo[13.3.0.0*4,6*]octadec-7-ene-4-carboxylic acid ethyl ester (163)

PPh$_3$ (415 mg, 1.58 mmol) was added to a stirred solution of the alcohol 51 (300 mg, 0.79 mmol) and the quinazolinol 127 (247 mg, 0.87 mmol) in dry THF (35 mL) and dry DMF 7 mL. The reaction was placed under an inert atmosphere (N$_2$) at room temperature. DIAD (311 µL, 1.58 mmol) was added. The reaction mixture was stirred for 18 h. A precipitation was formed in the flask and more white solid precipitated after addition of 40 mL diethyl ether. The precipitation was filtered off and washed with diethyl ether and dried under vacuum which gave the pure title compound (381 mg, 75%). LRMS (M+H) 646.

Example 164

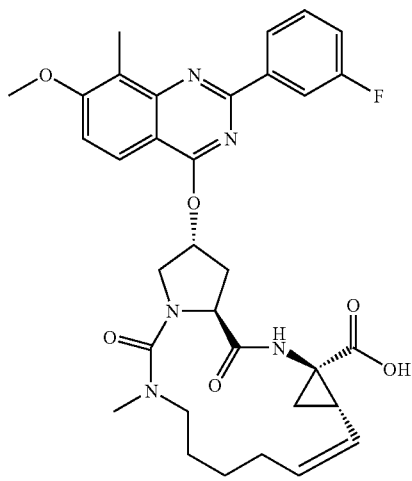

17-[2-(3-Fluoro-phenyl)-7-methoxy-8-methyl-quinazolin-4-yloxy]-13-methyl-2,14-dioxo-3,13,15-triaza-tricyclo[13.3.0.0*4,6*]octadec-7-ene-4-carboxylic acid (164)

The ethyl ester 163 was reacted as described in example 159. Due to solubility problems and a slow reaction the reaction was kept going for 40 h. LC-MS showed that no starting material remained but almost two thirds of the starting material had decomposed. The precipitation which was formed upon acidification was filtered off, washed with water and dried under high vacuum. The yield of the product was estimated to about 35% by weight and HPLC. LRMS (M+H) 618.

Example 165

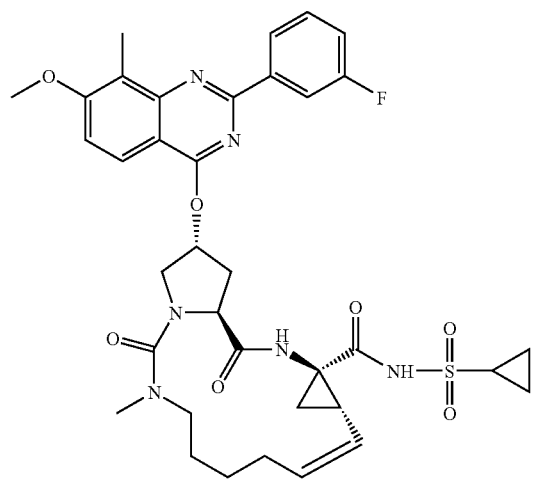

Cyclopropanesulfonic acid {17-[2-(3-fluoro-phenyl)-7-methoxy-8-methyl-quinazolin-4-yloxy]-13-methyl-2,14-dioxo-3,13,15-triaza-tricyclo[13.3.0.0*4, 6*]octadec-7-ene-4-carbonyl}-amide (165)

The acid 164 was reacted according to the procedure described in example 160. The crude product was purified by HPLC on an Ace-5 C8 column (100×21.2 mm) with a gradient going from 35 to 60% acetonitrile in ammonium acetate buffer 5 mM, pH 6.8, 5% acetonitril, over 8 minutes. The title compound was obtained as a white solid in (28 mg, 47%), LRMS (M+H) 721.

$^1$H NMR (CDCl$_3$+ drops of MeOD, 400 MHz) δ 0.95-1.05 (m, 1H), 1.07-1.17 (m, 1H), 1.17-1.26 (m, 1H), 1.27-1.52 (m, 3H), 1.52-1.77 (m, 3H), 1.90 (dd, 1H, J=8.9, 5.8), 1.99 (bs, 1H), 2.33 (bs, 1H), 2.46-2.65 (m, 3H), 2.66 (s, 3H), 2.88 (s, 3H), 2.95 (bs, 1H), 3.10 (bs, 1H), 3.69-3.80 (m, 2H), 4.01 (s, 3H), 4.22 (dd, 1H, J=11.3, 3.8), 4.72 (dd, 1H, J=9.5, 6.6), 5.17 (dd, 1H, J=10.5, 10.5), 5.68-5.77 (m, 1H), 6.10 (bs, 1H), 7.17

(d, 1H, J=7.8), 7.21 (d, 1H, J=8.6), 7.45-7.52 (m, 1H), 7.97 (d, 1H, J=9.3), 8.26 (d, 1H, J=10.7), 8.37 (d, 1H, J=7.8).

Example 166

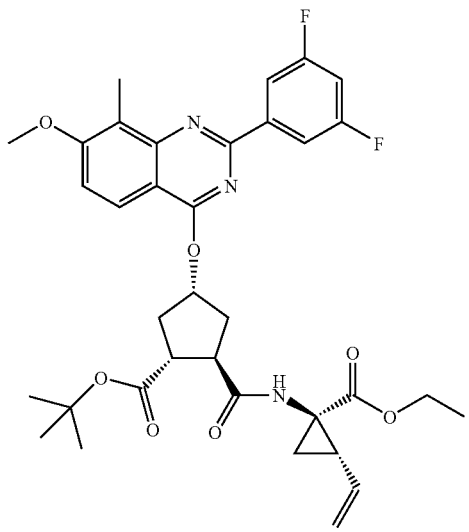

2-(1-Ethoxycarbonyl-2-vinyl-cyclopropylcarbamoyl)-4-[2-(3,5-difluoro-phenyl)-7-methoxy-8-methyl-quinazolin-4-yloxy]-cyclopentanecarboxylic acid tert-butyl ester (166)

The alcohol 15 and the quinazolinol 128 was reacted according to same procedure described in example 155 which gave the title compound as a white solid slightly contaminated by triphenyl phosphine oxide (1.245 g, >100%), LRMS (M+H) 652.

Example 167

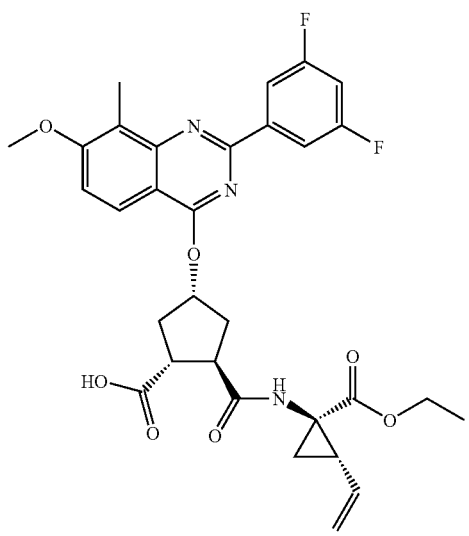

2-(1-Ethoxycarbonyl-2-vinyl-cyclopropylcarbamoyl)-4-[2-(3,5-difluoro-phenyl)-7-methoxy-8-methyl-quinazolin-4-yloxy]-cyclopentanecarboxylic acid (167)

The tert. butyl ester 166 was as described in example 156 which gave the title compound as a white solid (still slightly contaminated with POPH$_3$) in >100% yield. LRMS (M+H) 596.

Example 168

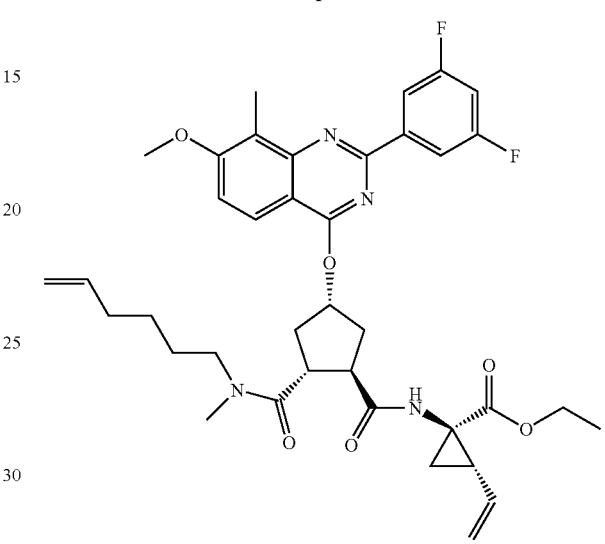

1-{[4-[2-(3,5-Difluoro-phenyl)-7-methoxy-8-methyl-quinazolin-4-yloxy]-2-(hex-5-enyl-methyl-carbamoyl)-cyclopentanecarbonyl]-amino}-2-vinyl-cyclopropane-carboxylic acid ethyl ester (168)

The acid 167 was reacted with hex-5-enyl-methyl-amine hydrochloride as according to the same procedure described in example 157, which gave the title compound (0.838 g, 81%), LRMS (M+H) 691.

Example 169

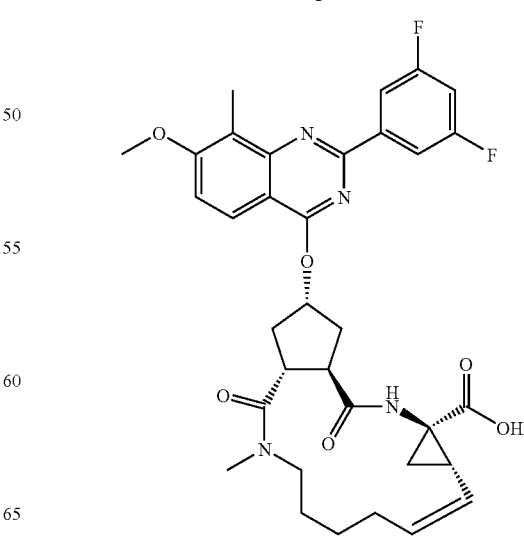

17-[2-(3,5-Difluoro-phenyl)-7-methoxy-8-methyl-quinazolin-4-yloxy]-13-methyl-2,14-dioxo-3,13-diaza-tricyclo[13.3.0.0*4,6*]octadec-7-ene-4-carboxylic acid (169)

A ringclosing metathesis reaction was performed with the diene 168 according to the procedure described in example 158, which gave the title compound slightly contaminated (0.509 g, 66%), LRMS (M+H) 635.

Example 170

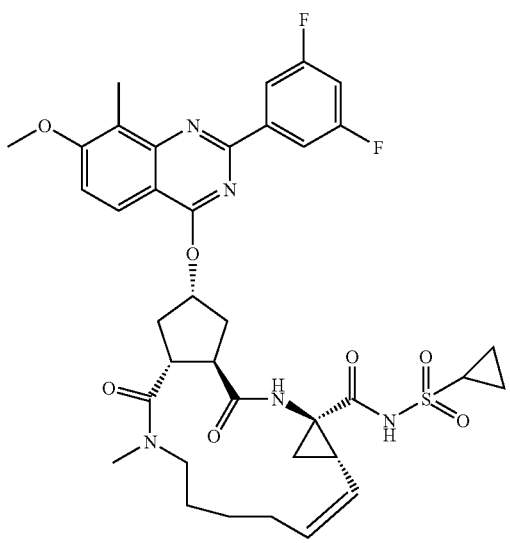

Cyclopropanesulfonic acid {17-[2-(3,5-difluoro-phenyl)-7-methoxy-8-methyl-quinazolin-4-yloxy]-13-methyl-2,14-dioxo-3,13-diaza-tricyclo [13.3.0.0*4,6*]octadec-7-ene-4-carbonyl}-amide. MV065673

Reaction of the acid 169 with cyclopropane sulfonic acid amide according to the procedure described in example 159, followed by purification on HPLC using an Ace-5 C8 column (100×21.2 mm) and an ammonium acetate buffer 5 mM, pH 6.8, 5% acetonitrile, going from 35 to 60% acetonitrile, gave the title compound as a white solid (8 mg, 7%). LRMS (M+H) 738.

$^1$H NMR (CDCl$_3$+drops of MeOD, 500 MHz) δ 0.92-2.57 (m, 8H), 1.71-1.95 (m, 4H), 2.57 (bs, 1H), 2.27-3.35 (m, 3H), 2.63 (s, 3H), 2.82-2.97 (m, 3H), 3.09 (s, 3H), 3.42-3.58 (m, 2H), 4.02 (s, 3H) 4.56 (t, 1H, J=11.7), 5.10 (bs, 1H), 5.61-5.65 (m, 1H), 5.94 (bs, 1H), 6.93 (dd, 1H, J=7.4, 7.4), 7.25 (d, 1H, J=9.4), 8.04 (d, 1H, J=9.0), 8.11 (d, 2H, J=9.0).

Example 171

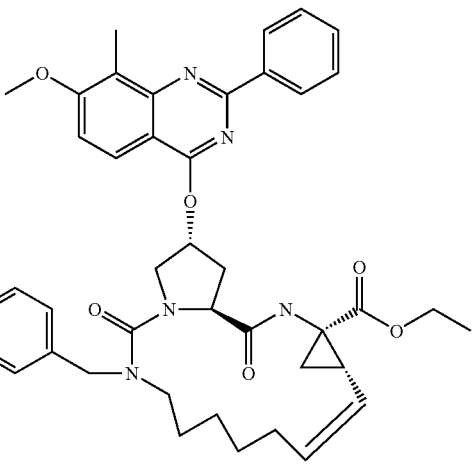

14-(4-Methoxy-benzyl)-1,8-(7-methoxy-8-methyl-2-phenyl-quinazolin-4-yloxy)-2,15-dioxo-3,14,16-triaza-tricyclo[14.3.0.0*4,6*]nonadec-7-ene-4-carboxylic acid ethyl ester (171)

Quinazolinol derivative 83 (352 mg, 0.1.2 mmol) was coupled to the alcohol 100 (600 mg, 1.2 mmol) by using the Mitsunobu conditions described in example 52. The afforded crude product was purified by flash chromatography on silica gel eluted with 1% MeOH in diethyl ether, which gave the title compound (842 mg, 93%).

MS (M+H)$^+$ 748.3

Example 172

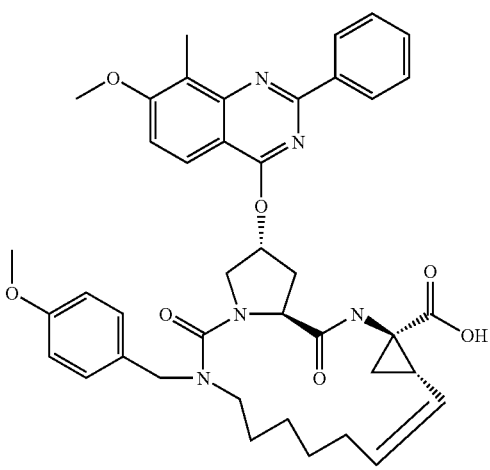

14-(4-Methoxy-benzyl)-1,8-(7-methoxy-8-methyl-2-phenyl-quinazolin-4-yloxy)-2,15-dioxo-3,14,16-triaza-tricyclo[14.3.0.0*4,6*]nonadec-7-ene-4-carboxylic acid ethyl ester (172)

The ethyl ester of compound 171 (842 mg, 1.3 mmol) was hydrolyzed as described in example 20. After 4 h the volume was reduced to half and then doubled with water. Acidification with acetic acid followed by filtration of the precipitated product gave the title compound MSR-489 (688 mg, 85%). MS (M+H)+ 720.3

Example 173

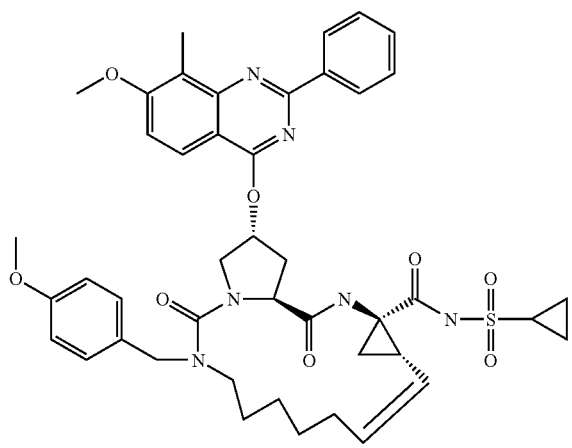

Cyclopropanesulfonic acid [14-(4-methoxy-benzyl)-18-(7-methoxy-8-methyl-2-phenyl-quinazolin-4-yloxy)-2,15-dioxo-3,14,16-triaza-tricyclo[14.3.0.0*4,6*]nonadec-7-ene-4-carbonyl]-amide (173)

Cyclopropanesulfonamide (102 mg, 0.84 mmol) was coupled to the acid 172 (300 mg, 0.42 mmol) as described in example 53. Purification by HPLC gave the title compound (157 mg, 45%), MS (M–H)+ 823.3.

Example 174

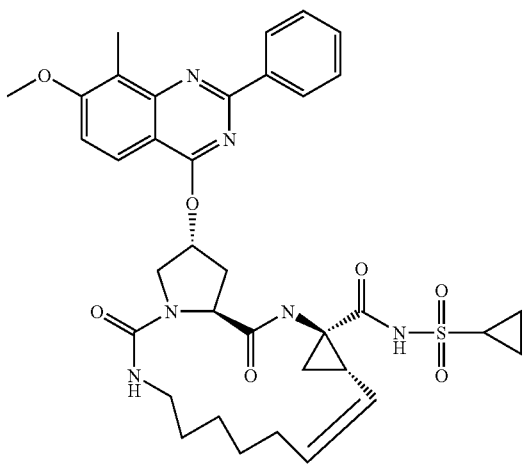

Cyclopropanesulfonic acid [18-(7-methoxy-8-methyl-2-phenyl-quinazolin-4-yloxy)-2,15-dioxo-3,14,16-triaza-tricyclo[14.3.0.0*4,6*]nonadec-7-ene-4-carbonyl]-amide (174)

Compound 173 (150 mg, 0.18 mmol) was stirred for 30 min in a mixture of dichloromethane-trifluoroacetic acid; 2:1. Evaporation and purification by column chromatography (5% methanol in ether) gave the title compound (81 mg, 62%). MS (M–H)+ 703

Example 175

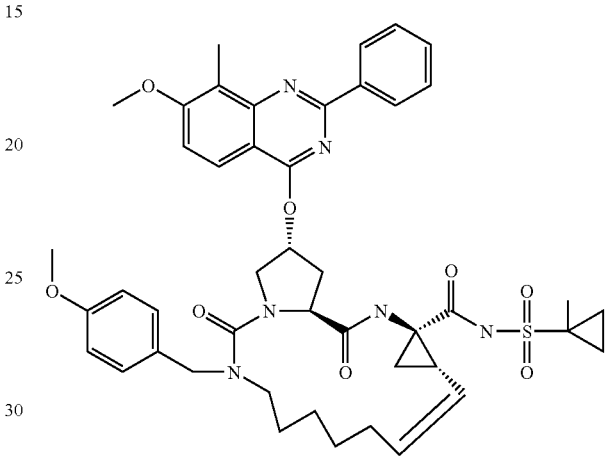

1-Methyl-cyclopropanesulfonic acid [14-(4-methoxy-benzyl)-18-(7-methoxy-8-methyl-2-phenyl-quinazolin-4-yloxy)-2,15-dioxo-3,14,16-triaza-tricyclo[14.3.0.0*4,6]nonadec-7-ene-4-carbonyl]-amide (175)

1-Methyl-cyclopropanesulfonic acid amide (218 mg, 1.62 mmol) was coupled to the acid 172 (388 mg. 0.54 mmol) as described in example 53. Purification by column chromatography gave the title compound (150 mg, 33%), MS (M–H)+ 837.

Example 176

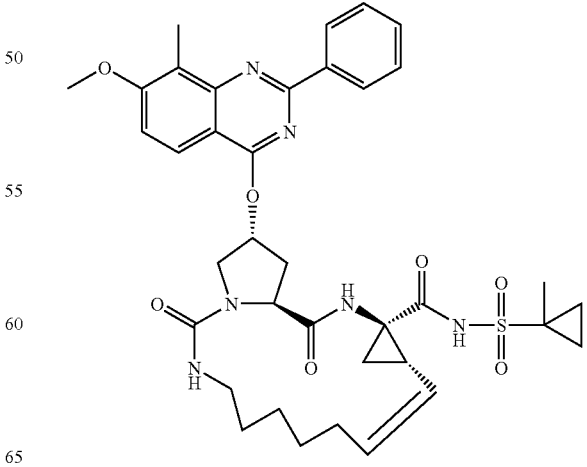

159

1-Methyl-cyclopropanesulfonic acid [18-(7-methoxy-8-methyl-2-phenyl-quinazolin-4-yloxy)-2,15-dioxo-3,14,16-triaza-tricyclo[14.3.0.0*4,6*]nonadec-7-ene-4-carboyl]-amide (176)

Compound 175 (150 mg, 0.18 mmol) was stirred for 30 min in a mixture of dichloromethane-trifluoroacetic acid; 2:1. Evaporation and purification by column chromatography (5% methanol in ether) gave the title compound (74 mg, 57%), MS (M−H)+ 717.3.

Example 177

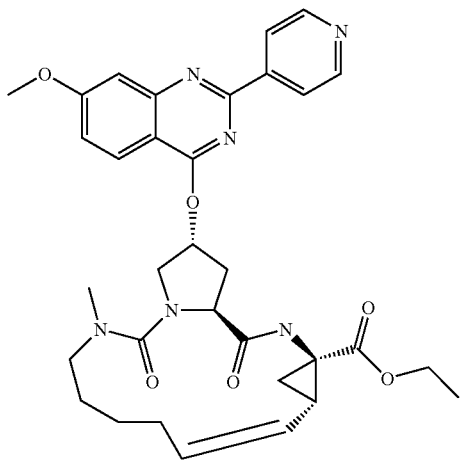

1-Methyl-cyclopropanesulfonic acid [18-(7-methoxy-8-methyl-2-phenyl-quinazolin-4-yloxy)-2,15-dioxo-3,14,16-triaza-tricyclo[14.3.0.0*4,6*]nonadec-7-ene-4-carbonyl]-amide Quinazolinol derivative 123 (155 mg, 0.58 mmol) was coupled to the alcohol 51 (200 mg, 0.53 mmol) by using the Mitsunobu conditions as described in example 52. The desired product precipitated in the reaction mixture and was collected by filtration to give pure title compound (152 mg, 45%), MS (M+H)+ 629.3

Example 178

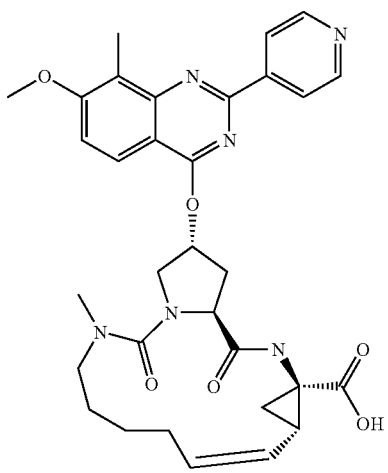

17-(7-Methoxy-8-methyl-2-pyridin-4-yl-quinazolin-4-yloxy)-13-methyl-2,14-dioxo-3,13,15-triaza-tricyclo[13.3.0.0*4,6*]octadec-7-ene-4-carboxylic acid (178)

The ethyl ester of compound 177 (152 mg, 0.24 mmol) was hydrolyzed according to the procedure described for compound 20. The product was partly decomposed during the reaction. Purification by chromatography (0 to 15% methanol in ether+0.1% acetic acid) gave pure title compound (46%), MS (M+H)+ 601.

Example 179

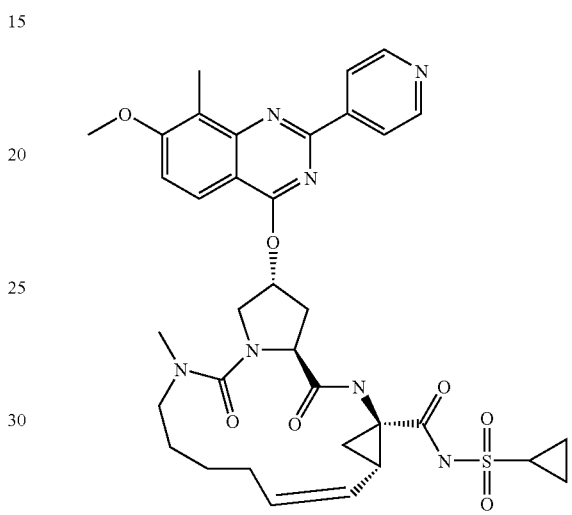

Cyclopropanesulfonic acid [17-(7-methoxy-8-methyl-2-pyridin-4-yl-quinazolin-4-yloxy)-13-methyl-2,14-dioxo-3,13,15-triaza-tricyclo[13.3.0.0*4,6*]octadec-7-ene-4-carbonyl]-amide (179)

The acid 178 (67 mg, 0.11 mmol) and EDAC (26 mg, 0.13 mmol) were dissolved in dichloromethane (3 ml). After stirring at room temperature for 5 h the mixture was diluted with dichloromethane (10 ml) and the organic phase were washed with water and dried (sodium sulphate). The volume was then reduced to 2 ml and cyclopropyl sulphonamide (20 mg, 0.17 mmol) and DBU (36 mg, 2.3 mmol) were added. The mixture was allowed to stir over-night at room temperature and then washed using 5% aqueous citric acid. Purification by chromatography (0 to 2% methanol in dichloromethane gave the title compound (57 mg, 73%), MS (M+H)+ 704.

Biological Example 1

Activity of Compounds of Formula (I)

Replicon Assay

The compounds of formula (I) were examined for activity in the inhibition of HCV RNA replication in a cellular assay. The assay demonstrated that the compounds of formula (I) exhibited activity against HCV replicons functional in a cell culture. The cellular assay was based on a bicistronic expression construct, as described by Lohmann et al. (1999) Science vol. 285 pp. 110-113 with modifications described by Krieger et al. (2001) Journal of Virology 75: 4614-4624, in a multi-target screening strategy. In essence, the method was as follows.

The assay utilized the stably transfected cell line Huh-7 luc/neo (hereafter referred to as Huh-Luc). This cell line harbors an RNA encoding a bicistronic expression construct comprising the wild type NS3-NS5B regions of HCV type 1b translated from an Internal Ribosome Entry Site (IRES) from encephalomyocarditis virus (EMCV), preceded by a reporter portion (FfL-luciferase), and a selectable marker portion (neo$^R$, neomycine phosphotransferase). The construct is bordered by 5' and 3' NTRs (non-translated regions) from HCV type 1b. Continued culture of the replicon cells in the presence of G418 (neo$^R$) is dependent on the replication of the HCV RNA. The stably transfected replicon cells that express HCV RNA, which replicates autonomously and to high levels, encoding inter alia luciferase, are used for screening the antiviral compounds.

The replicon cells were plated in 384 well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of the compound on luciferase activity was monitored on the Huh-Luc cells, enabling a dose-response curve for each test compound. EC50 values were then calculated, which value represents the amount of the compound required to decrease by 50% the level of detected luciferase activity, or more specifically, the ability of the genetically linked HCV replicon RNA to replicate.

Biological Example 2 Activity of Compounds of Formula (I)

Inhibition Assay

The aim of this in vitro assay is to measure the inhibition of HCV NS3/4A protease complexes by the compounds of the present invention. This assay provides an indication of how effective compounds of the present invention would be in inhibiting HCV NS3/4A proteolytic activity.

The inhibition of full-length hepatitis C NS3 protease enzyme was measured essentially as described in Poliakov, 2002 Prot Expression & Purification 25 363 371. Briefly, the hydrolysis of a depsipeptide substrate, Ac-DED(Edans)EEA-buψ[COO]ASK(Dabcyl)-NH$_2$ (AnaSpec, San José, USA), was measured spectrofluorometrically in the presence of a peptide cofactor, KKGSVVIVGRIVLSGK (Åke Engström, Department of Medical Biochemistry and Microbiology, Uppsala University, Sweden). [Landro, 1997 #Biochem 36 9340-9348]. The enzyme (1 nM) was incubated in 50 mM HEPES, pH 7.5, 10 mM DTT, 40% glycerol, 0.1% n-octyl-D-glucoside, with 25 µM NS4A cofactor and inhibitor at 30° C. for 10 min, whereupon the reaction was initiated by addition of 0.5 µM substrate. Inhibitors were dissolved in DMSO, sonicated for 30 sec. and vortexed. The solutions were stored at −20° C. between measurements.

The final concentration of DMSO in the assay sample was adjusted to 3.3%. The rate of hydrolysis was corrected for inner filter effects according to published procedures. [Liu, 1999 Analytical Biochemistry 267 331-335]. Ki values were estimated by non-linear regression analysis (GraFit, Erithacus Software, Staines, MX, UK), using a model for competitive inhibition and a fixed value for Km (0.15 µM). A minimum of two replicates was performed for all measurements.

The following Table 1 lists representative compounds that were prepared according to the above examples. The activities of the compounds tested are also depicted in Table 1. The legend for values A, B, C, D, E, and F is as follows:

value A corresponds to an EC$_{50}$>10 µM;
value B corresponds to an EC$_{50}$ between 10 µM and 1 µM;
value C corresponds to an EC$_{50}$ between 0.99 µM and 200 nM;
value D corresponds to an EC$_{50}$ between 199 nM and 0.5 nM.
value E corresponds to a Ki>1 µM;
value F corresponds to a Ki between 1 µM and 100 nM;
value G corresponds to a Ki between 99.9 nM and 5 nM;
value H corresponds to a Ki between 4.9 nM and 0.1 nM.

| Compound nr. | EC$_{50}$ Replicon assay | Ki Enzymatic assay |
|---|---|---|
| 21 | D | H |
| 31 | D | H |
| 34 | C | G |
| 36 | C | G |
| 44 | D | H |
| 45 | D | H |
| 53 | D | H |
| 70 | A | E |
| 71 | C | H |
| 72 | C | H |
| 73 | A | F |
| 89 | D | H |
| 94 | D | H |
| 98 | D | H |
| 104 | D | H |
| 114 | D | H |
| 119 | D | H |
| 121 | D | H |
| 131 | D | H |
| 132 | D | H |
| 138 | D | H |
| 147 | D | H |
| 150 | D | H |
| 152 | A | E |
| 154 | D | H |
| 160 | D | H |
| 161 | D | H |
| 162 | C | H |
| 165 | D | H |
| 170 | D | G |
| 174 | D | H |
| 176 | D | H |
| 179 | D | H |

The invention claimed is:

1. A compound of the formula I:

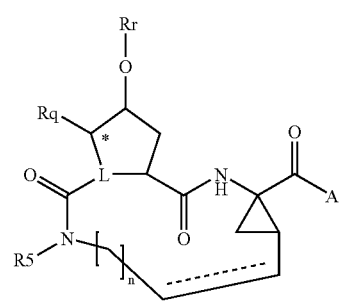

and N-oxides, salts, and stereoisomers thereof wherein

A is $OR^1$, $NHS(=O)_pR^2$; wherein;
- $R^1$ is hydrogen, $C_1$-$C_6$alkyl, $C_0$-$C_3$alkylenecarbocyclyl, $C_0$-$C_3$alkyleneheterocyclyl;
- $R^2$ is $C_1$-$C_6$alkyl, $C_0$-$C_3$alkylenecarbocyclyl, $C_0$-$C_3$alkyleneheterocyclyl;

p is independently 1 or 2;

n is 3, 4, 5 or 6;

----denotes an optional double bond;

L is N or CRz;

Rz is H or forms a double bond with the asterisked carbon;

Rq is H or when L is CRz, Rq can also be $C_1$-$C_6$alkyl;

Rr is quinazolinyl, optionally substituted with one two or three substituents each independently selected from $C_1$-$C_6$alkyl, $C_1$-$C_6$alkoxy, hydroxyl, halo, halo$C_1$-$C_6$alkyl, amino, mono- or dialkylamino, mono- or dialkylaminocarbonyl, $C_1$-$C_6$alkylcarbonylamino, $C_0$-$C_3$alkylenecarbocyclyl and $C_0$-$C_3$ alkyleneheterocyclyl;

$R^5$ is hydrogen, $C_1$-$C_6$alkyl, $C_1$-$C_6$alkoxy$C_1$-$C_6$alkyl or $C_3$-$C_7$cycloalkyl;

and wherein each $C_1$-$C_6$alkyl, $C_0$-$C_3$alkylenecarbocycyl or $C_0$-$C_3$alkyleneheterocyclyl is optionally substituted with 1 to 3 substituents independently selected from the group consisting of halo, oxo, nitrile, azido, nitro, $C_1$-$C_6$alkyl, $C_0$-$C_3$alkylenecarbocyclyl, $C_0$-$C_3$alkyleneheterocyclyl, $NH_2C(=O)$—, Y—NRaRb, Y—O—Rb, Y—C(=O)Rb, Y—(C=O)NRaRb, Y—NRaC(=O)Rb, Y—NHS(=$O_p$)Rb, Y—S(=O)$_p$Rb and Y—S(=O)$_p$NRaRb, Y—C(=O)ORb, Y—NRaC(=O)ORb;

Y is independently a bond or $C_1$-$C_3$alkylene;

Ra is independently H, $C_1$-$C_6$alkoxy, $C_1$-$C_3$alkyl or;
- Rb is independently H, $C_1$-$C_6$alkyl, $C_1$-$C_6$alkoxy, $C_0$-$C_3$alkylenecarbocyclyl or $C_0$-$C_3$alkyleneheterocyclyl;
- or Ra and Rb together with the nitrogen to which they are attached join to form a heterocyclyl group.

2. A compound according to claim 1, with the partial structure:

3. A compound according to claim 1, wherein n is 4 or 5.

4. A compound according to claim 3, wherein ----adjacent the cyclopropyl moiety is a double bond.

5. A compound according to claim 1 wherein $R^5$ is hydrogen or methyl.

6. A compound according to claim 1, wherein A is —OH or —NHS(=O)$_2$-cyclopropyl.

7. A compound according to claim 1, wherein A is NHS(=O)$_2$—$C_1$-$C_6$alkyl substituted cyclopropyl.

8. A compound according to claim 1, with the formula:

I where n, A, L, Rq and $R^5$ are as defined in claim 1, and $R^6$ is hydrogen, $C_1$-$C_6$alkyl, $C_1$-$C_6$alkoxy, $C_0$-$C_3$alkylenecarbocyclyl, $C_0$-$C_3$alkylene-heterocyclyl, hydroxy, bromo, chloro or fluoro;

$R^9$ is hydrogen, $C_1$-$C_6$alkyl, $C_1$-$C_6$alkoxy, NRaRb, $C_0$-$C_3$alkylenecarbocyclyl, $C_0$-$C_3$alkyleneheterocyclyl; wherein said $R^9$ carbocyclyl or heterocyclyl is optionally substituted with $R^{10}$;

$R^{10}$ is $C_1$-$C_6$alkyl, $C_0$-$C_3$alkylenecycloalkyl, $C_0$-$C_3$alkyleneheterocyclyl, $C_1$-$C_6$alkoxy, $C_1$-$C_6$alkoxy$C_1$-$C_6$alkyl, amino, amido, azido, mercapto, cyano, sulfonyl, ($C_1$-$C_3$ alkyl)sulfonyl, nitro, hydroxy, carboxy, mercapto, halo, halo$C_1$-$C_6$alkyl, halo$C_1$-$C_6$alkyloxy;

Ra and Rb are as defined in claim 1;

$R^{11}$ is hydrogen or $C_1$-$C_6$alkoxy.

9. A compound according to claim 8, wherein $R^6$ is $C_1$-$C_3$alkyl, chloro or fluoro, preferably bromo or hydrogen.

10. A compound according to claim 8, wherein $R^{11}$ is hydrogen or methoxy.

11. A compound according to claim 8, wherein $R^9$ is phenyl or heteroaryl, either being optionally substituted with one or two $R^{10}$; wherein $R^{10}$ hydrogen, $C_1$-$C_6$alkyl, $C_3$-$C_7$cycloalkyl, $C_3$-$C_7$heterocyclyl, $C_1$-$C_6$alkoxy, halo, amino optionally mono- or di-substituted with $C_1$-$C_6$alkyl, or amido optionally mono- or di substituted with $C_1$-$C_6$alkyl.

12. A compound according to claim 11, wherein $R^9$ is phenyl, pyridyl, thiazolyl, oxazolyl or pyrazolyl each of which is optionally substituted with $R^{10}$ as defined.

13. A compound according to claim 12, wherein $R^{10}$ is hydrogen, fluoro, difluoro, methyl, ethyl, isopropyl, tert-butyl, $C_1$-$C_6$alkoxy, amino, mono- or di$C_1$-$C_6$alkylamino pyrrolidinyl, piperinyl, piperazinyl, N-methylpiperazinyl, morpholinyl, or mono- or di-$C_1$-$C_6$alkylamido.

14. A compound according to claim 13, wherein $R^{10}$ is hydrogen, fluoro or methoxy.

15. A compound according to claim 12, wherein $R^9$ is selected from

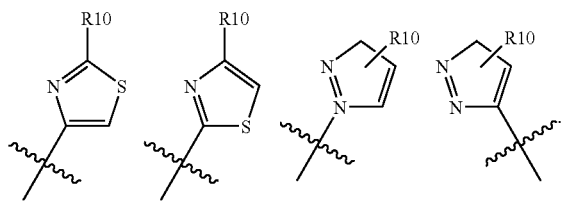
16. A compound according to claim 12, wherein it R⁹ is selected from:
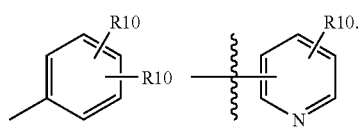
17. A compound having the formula
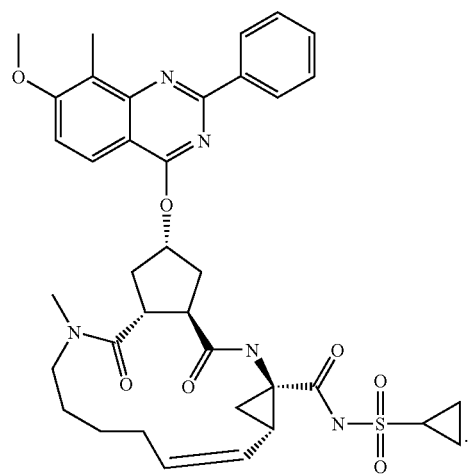
18. A compound having the formula:
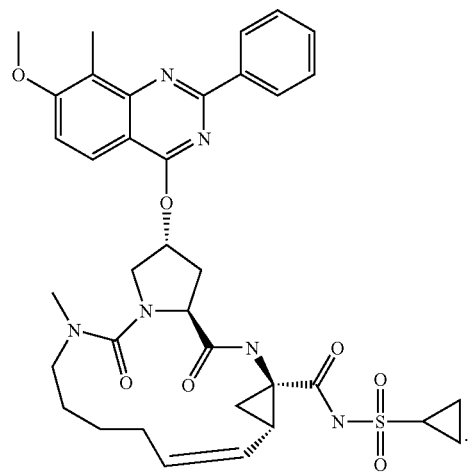
19. A compound having the formula:
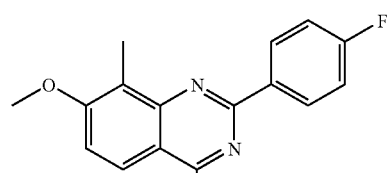
20. A compound having the formula:
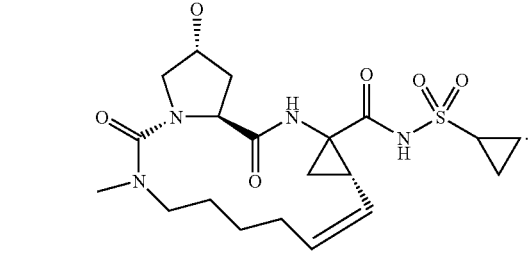
21. A compound having the formula:
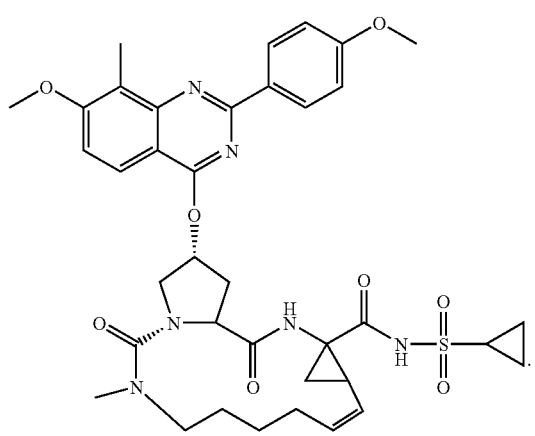
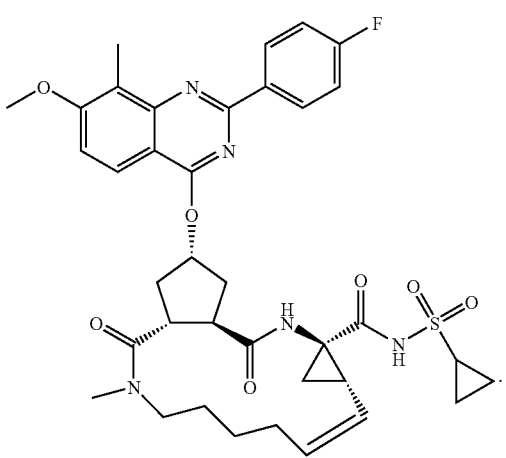

22. A compound having the formula:

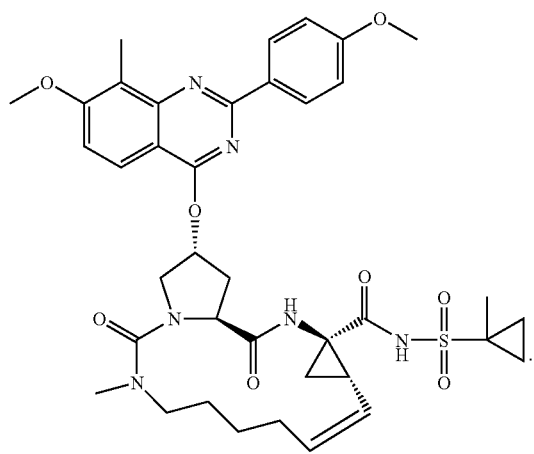

23. A compound having the formula:

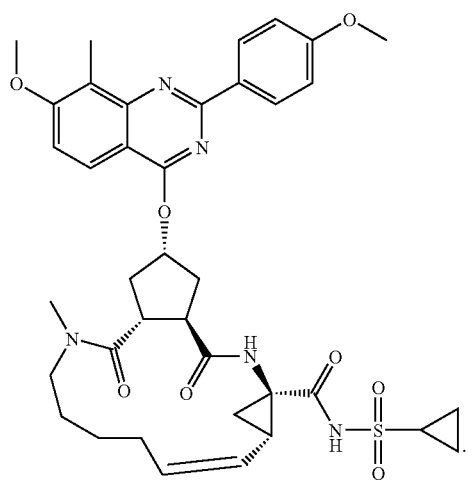

24. A compound having the formula:

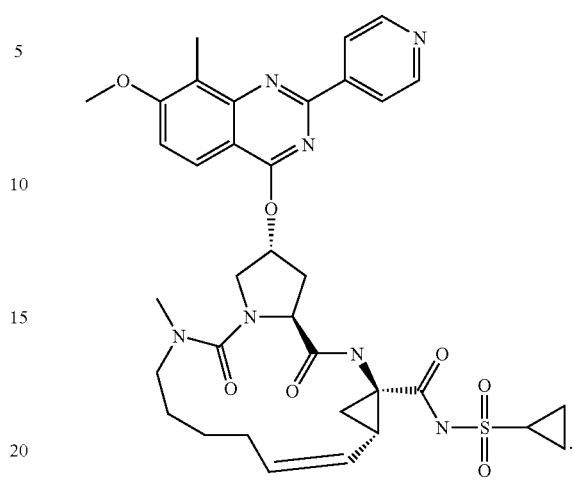

25. A pharmaceutical composition comprising a compound according to claim 20, and a pharmaceutically acceptable carrier.

26. A pharmaceutical composition according to claim 25, further comprising an additional HCV antiviral, selected from nucleoside analogue polymerase inhibitors, protease inhibitors, ribavirin and interferon.

27. A method for treatment of HCV infection comprising the administration of an effective amount of a compound according to any one of claims 1-24 to an individual in need thereof.

28. A pharmaceutical composition comprising a compound according to any one of claims 1-24, and a pharmaceutically acceptable carrier.

* * * * *